United States Patent
Barbosa, Jr. et al.

(10) Patent No.: US 7,601,714 B2
(45) Date of Patent: *Oct. 13, 2009

(54) PYRIMIDINE DERIVATIVES USEFUL AS INHIBITORS OF PKC-THETA

(75) Inventors: Antonio J. M. Barbosa, Jr., Middlebury, CT (US); Steven Richard Brunette, New Milford, CT (US); Eugene Richard Hickey, Danbury, CT (US); Jin Mi Kim, Sandy Hook, CT (US); Michael David Lawlor, Seymour, CT (US); René Marc Lemieux, Plantsville, CT (US); Bryan McKibben, New Milford, CT (US); Matt Aaron Tschantz, Newtown, CT (US); Hui Yu, New Milford, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 199 days.

This patent is subject to a terminal disclaimer.

(21) Appl. No.: 11/175,476

(22) Filed: Jul. 6, 2005

(65) Prior Publication Data

US 2006/0025433 A1 Feb. 2, 2006

Related U.S. Application Data

(60) Provisional application No. 60/586,289, filed on Jul. 8, 2004.

(51) Int. Cl.
*C07D 239/48* (2006.01)
*C07D 403/12* (2006.01)
*A61K 31/505* (2006.01)

(52) U.S. Cl. .............. 514/235.8; 514/255.05; 514/275; 544/122; 544/295; 544/323; 544/324

(58) Field of Classification Search ............ 544/122, 544/295, 323, 324; 514/235.8, 255.05, 275
See application file for complete search history.

(56) References Cited

U.S. PATENT DOCUMENTS

| 6,432,963 B1 | 8/2002 | Hisamichi et al. |
| 2003/0171359 A1 | 9/2003 | Dahmann et al. |
| 2004/0242613 A1 | 12/2004 | Cardozo et al. |

FOREIGN PATENT DOCUMENTS

| WO | WO 97/19065 | 5/1997 |
| WO | WO 00/75113 | 12/2000 |
| WO | WO 01/00213 A1 | 1/2001 |
| WO | WO 02/096887 A1 | 12/2002 |
| WO | WO 02/096888 A1 | 12/2002 |
| WO | WO 03/032997 A1 | 4/2003 |
| WO | WO 03/106451 A1 | 12/2003 |
| WO | WO 2004/067516 A1 | 8/2004 |

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Casanova et al., PubMed Abstract (Rev Neurol 28(9):909-15) May 1999.*
Hayashi et al., Protein Kinase C theta (PKCθ): A key role in T cell life and death, Pharmacological Research 55 (2007), pp. 537-544.*

* cited by examiner

*Primary Examiner*—Deepak Rao
(74) *Attorney, Agent, or Firm*—Michael P. Morris; Mary-Ellen M. Devlin; Philip I. Datlow

(57) ABSTRACT

Disclosed are novel compounds of formula (I):

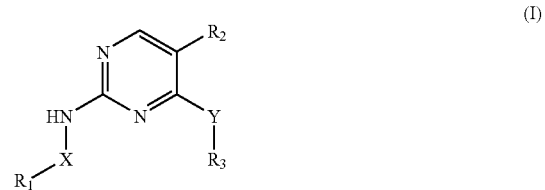

wherein X, Y, $R_1$, $R_2$ and $R_3$ are as defined herein, which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

9 Claims, No Drawings

PYRIMIDINE DERIVATIVES USEFUL AS INHIBITORS OF PKC-THETA

Benefit of U.S. Provisional Application Ser. No. 60/586,289, filed on Jul. 8, 2004 is hereby claimed.

FIELD OF THE INVENTION

This invention relates to substituted pyrimidine derivatives which are useful as inhibitors of PKC-theta and are thus useful for treating a variety of diseases and disorders that are mediated or sustained through the activity of PKC-theta, including immunological disorders and type II diabetes. This invention also relates to pharmaceutical compositions comprising these compounds, methods of using these compounds in the treatment of various diseases and disorders, processes for preparing these compounds and intermediates useful in these processes.

BACKGROUND OF THE INVENTION

The protein kinase C family is a group of serine/threonine kinases that is comprised of twelve related isoenzymes. These kinases are expressed in a wide range of tissues and cell types. Its members are encoded by different genes and are sub-classified according to their requirements for activation. The classical PKC enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKC-theta is a member of the nPKC sub-family. It has a restricted expression pattern, found predominantly in T cells and skeletal muscle. Upon T cell activation, a supramolecular activation complex (SMAC) forms at the site of contact between the T cell and antigen presenting cell (APC). PKC-theta is the only PKC isoform found to localize at the SMAC (C. Monks et al., *Nature*, 1997, 385, 83), placing it in proximity with other signaling enzymes that mediate T cell activation processes. In another study (G. Baier-Bitterlich et al., *Mol. Cell. Biol.*, 1996, 16, 842) the role of PKC-theta in the activation of AP-1, a transcription factor important in the activation of the IL-2 gene, was confirmed. In unstimulated T cells, constitutively active PKC-theta stimulated AP-1 activity while in cells with dominant negative PKC-theta, AP-1 activity was not induced upon activation by PMA. Other studies showed that PKC-theta, via activation of IκB kinase beta, mediates activation of NF-κB induced by T cell receptor/CD28 co-stimulation (N. Coudronniere et al., *Proc. Nat. Acad. Sci. U.S.A.*, 2000, 97, 3394; X. Lin et al., *Moll. Cell. Biol.*, 2000, 20, 2933). Proliferation of peripheral T cells from PKC-theta knockout mice, in response to T cell receptor (TCR)/CD28 stimulation was greatly diminished compared to T cells from wild type mice. In addition, the amount of IL-2 released from the T cells was also greatly reduced (Z. Sun et al., *Nature*, 2000, 404, 402). Otherwise, the PKC-theta knockout mice seemed normal and were fertile.

The studies cited above and other studies confirm the critical role of PKC-theta in T cell activation and subsequent release of cytokines such as IL-2 and T cell proliferation (A. Altman et al., *Immunology Today*, 2000, 21, 567). Thus an inhibitor of PKC-theta would be of therapeutic benefit in treating immunological disorders and other diseases mediated by the inappropriate activation of T cells.

It has been well established that T cells play an important role in regulating the immune response (Powrie and Coffman, *Immunology Today*, 1993, 14, 270). Indeed, activation of T cells is often the initiating event in immunological disorders. Following activation of the TCR, there is an influx of calcium that is required for T cell activation. Upon activation, T cells produce cytokines, including IL-2, leading to T cell proliferation, differentiation, and effector function. Clinical studies with inhibitors of IL-2 have shown that interference with T cell activation and proliferation effectively suppresses immune response in vivo (Waldmann, *Immunology Today*, 1993, 14, 264).

Accordingly, agents that inhibit T lymphocyte activation and subsequent cytokine production are therapeutically useful for selectively suppressing the immune response in a patient in need of such immunosuppression and therefore are useful in treating immunological disorders such as autoimmune and inflammatory diseases.

In addition, PKC theta activation has been shown to be associated with insulin resistance in skeletal muscle (M. E. Griffen et al., *Diabetes*, 1999, 48, 1270). Therefore inhibitors of PKC-theta may also be useful for treating type II diabetes.

Dahmann et al, U.S. application Ser. No. 10/271,763, filed Oct. 16, 2002, (now U.S. Patent Application Publication No. 2003/0171359 A1) discloses pyrimidine derivatives as inhibitors of various protein kinases such as SRC kinase, PLK kinase and particularly cyclin-dependent kinases (CDKs) and Aurora B. WO 00/75113 and U.S. Pat. No. 6,432,963 describe pyrimidine carboxamides as inhibitors of Syk tyrosine kinase. WO 01/00213 discloses heteroaryl substituted pyrimidines as SRC kinase inhibitors. WO 97/19065 describes substituted 2-anilinopyrimidine compounds as inhibitors of certain protein kinases. WO 02/096887 and WO 02/096888 both disclose 2-anilinopyrimidine derivatives as inhibitors of cyclin-dependent kinases. WO 03/106451 discloses certain substituted diaminopyrimidine compounds as inhibitors of PKC-theta.

There is a continuing need in the art for compounds that are potent and selective inhibitors of PKC-theta.

BRIEF SUMMARY OF THE INVENTION

In a general aspect, the present invention is directed to the compounds of the following formula (I):

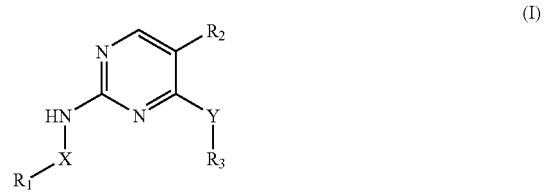

wherein $R_1$, $R_2$ and $R_3$ are as defined herein, as well as the tautomers, pharmaceutically acceptable salts, solvates, and amino-protected derivatives thereof. It has been found that the compounds of formula (I) have valuable pharmacological properties, particularly an inhibiting activity on PKC-theta. Many of the compounds of the invention are not only potent inhibitors of PKC-theta but are also selective for the inhibition of PKC-theta as compared to one or more other protein kinases.

In another aspect, the present invention is directed to a method of inhibiting PKC-theta activity in a patient comprising administering to the patient a compound of the present invention as described above.

In another aspect, the present invention is directed to a method of treating a disease or disorder associated with the activation of T cells comprising administering to a patient in need of such treatment a compound of the present invention as described above.

In another aspect, the present invention is directed to a method of treating an immunological disorder comprising administering to a patient in need of such treatment a compound of the present invention as described above. Examples of such immunological disorders that may be treated include, for example, inflammatory diseases, autoimmune diseases, organ and bone marrow transplant rejection and other disorders associated with T cell mediated immune response, including acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus.

In another aspect, the present invention is directed to a method of treating type II diabetes comprising administering to a patient in need of such treatment a compound of the present invention as described above.

In yet additional aspects, the present invention is directed to pharmaceutical compositions comprising the above-mentioned compounds, processes for preparing the above-mentioned compounds and intermediates used in these processes.

DETAILED DESCRIPTION OF THE INVENTION

Definition of Terms and Conventions Used

Terms not specifically defined herein should be given the meanings that would be given to them by one of skill in the art in light of the disclosure and the context. As used in the present specification and claims, however, unless specified to the contrary, the following terms have the meaning indicated and the following conventions are adhered to.

A. Chemical Nomenclature, Terms, and Conventions

In general, for groups comprising two or more subgroups, the last named group is the radical attachment point, for example, "alkylaryl" means a monovalent radical of the formula Alk-Ar—, while "arylalkyl" means a monovalent radical of the formula Ar—Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

All references to a chemical group being "substituted with" another chemical group shall be understood to mean the first chemical group can be substituted with one or more of the second chemical group, with the exception of any substitution pattern that is not physically or chemically possible or results in a unstable structure or compound. For example, the phrase "$C_{1-6}$ alkyl, which is optionally substituted with halogen" shall mean a $C_{1-6}$ alkyl group having one or multiple halogen substituents being the same or different from each other.

All alkyl groups shall be understood as being branched or unbranched unless otherwise specified. Other more specific definitions are as follows:

The term "halogen" as used in the present specification shall be understood to mean bromine, chlorine, fluorine or iodine.

The term "heteroaryl" refers to a stable 5 or 6 membered, monocyclic aromatic heterocycle radical, wherein the heterocycle radical is optionally fused to either an aryl, e.g. benzene, or to a second 5 or 6 membered, monocyclic aromatic heterocycle to form in each case a bicyclic heteroaryl group. Each heterocycle consists of carbon atoms and from 1 to 3 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl.

The term "aryl" shall be understood to mean a 6-10 membered monocyclic or bicyclic aromatic carbocycle, and includes, for example, phenyl and naphthyl; other terms comprising "aryl" will have the same definition for the aryl component, and examples of these moieties include: arylalkyl, aryloxy or arylthio.

The term "oxo" refers to a double-bonded oxygen group (=O).

The phrases "wherein each of the $C_{1-6}$alkyl groups", "wherein each of the $C_{1-8}$alkyl groups" or "wherein each of the aryl groups" or similar language in a definition is intended to refer to the indicated groups when either alone or as part of another chemical group if such combined groups are provided for in a definition. For example, the language "wherein each of the $C_{1-6}$alkyl groups" refers to $C_{1-6}$alkyl groups as well as $C_{1-6}$alkyl groups when attached to other groups, e.g., the $C_{1-6}$alkyl portion of a $C_{1-6}$alkyloxy or aryl-$C_{1-6}$alkyl group, if such groups are provided for in a definition.

The term "amino protected derivatives" shall be understood to mean compounds of formula (I) wherein one or more of the amine groups are protected by suitable amino protecting groups. Amino protecting groups that may be used include, for example, alkoxycarbonyl groups, such as tert-butyloxycarbonyl (Boc) and ethoxycarbonyl, Mannich bases, Schiff bases and amino acids. As would be understood by a person skilled in the art, such amino protected compounds may be useful as intermediates in the preparation of other compounds of formula (I), e.g., as described in the synthetic processes below, and/or may themselves be useful as pro-drugs that can be administered to a patient to be converted in vivo into a PKC-theta inhibitor having the resulting pharmacologic and therapeutic effects expected from the inhibition of PKC-theta in a patient.

The term "pharmaceutically acceptable salts" include those derived from pharmaceutically acceptable inorganic and organic acids and bases. Examples of suitable acids include hydrochloric, hydrobromic, carbonic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_{1-4}alkyl)_4^+$ salts.

The term "solvate" means a physical association of a compound with one or more solvent molecules or a complex of variable stoichiometry formed by a solute (for example, a compound of Formula (I)) and a solvent, for example, water, EtOH, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, EtOHates, MeOHates, and the like.

The term "hydrate" means a solvate wherein the solvent molecule(s) is/are $H_2O$.

The term "compounds of the invention" and equivalent expressions are meant to embrace compounds of Formula (I) as herein described, including the tautomers, pharmaceutically acceptable salts, solvates, and amino-protected derivatives thereof, where the context so permits. In general, the compounds of the invention and the formulas designating the compounds of the invention are understood to only include the stable compounds thereof and exclude unstable compounds, even if an unstable compound might be considered to be literally embraced by the compound formula.

The term "stable compound" means a compound that is sufficiently robust to survive isolation to a useful degree of purity from a reaction mixture, and formulation into an efficacious therapeutic agent. For example, a compound which would have a "dangling valency" is not a compound contemplated by the invention.

Specific compounds of the present invention may be identified in the present specification by chemical name and/or chemical structure. In the event of any conflict between the chemical name and chemical structure, the chemical structure will control.

B. Isomer Terms and Conventions

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

C. Pharmaceutical Administration Terms and Conventions

The term "patient" includes both human and non-human mammals.

The term "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the state of the art, and this disclosure.

The phrase "disease or disorder associated with the activation of T cells" and similar expressions mean that the activation of T cells is a contributing factor to either the origin or continuation of the disease or disorder in the patient.

EMBODIMENTS OF THE INVENTION

In its broadest generic aspect, the invention provides novel compounds of the formula (I) below

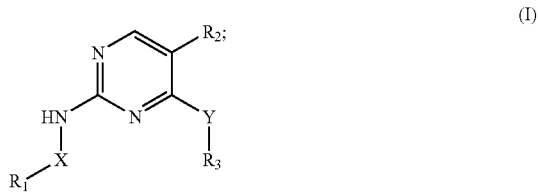

wherein:

X is $C_{1-6}$alkyl wherein one or two of the methylene units can be replaced by an oxygen or sulfur atom, and wherein the $C_{1-6}$alkyl group is optionally and independently substituted with:
  (A) oxo,
  (B) $C_{1-6}$alkyl which is optionally substituted with one or more of the following groups:
    (i) hydroxyl,
    (ii) $C_{1-3}$alkyloxy,
    (iii) halogen,
  (C) $C_{1-6}$alkyloxy,
  (D) $C_{1-6}$alkylthio, (E) aryl
(F) —COR$_6$, wherein R$_6$ is:
  (i) C$_{1-6}$alkyl,
  (ii) C$_{1-6}$alkyloxy,
  (iii) —NR$_7$R$_8$, wherein R$_7$ and R$_8$ are each independently selected from:
    (a) hydrogen,
    (b) C$_{1-6}$alkyl,
    (c) aryl,
    (d) heteroaryl,
  (iv) —OH,
(G) halogen,
(H) —NR$_9$R$_{10}$, wherein R$_9$ and R$_{10}$ are each independently selected from:
  (i) hydrogen,
  (ii) C$_{1-6}$alkyl,
  (iii) C$_{1-6}$alkylcarbonyl,
  (iv) C$_{1-6}$alkylsulfonyl,
  (v) aryl,
  (vi) heteroaryl;

Y is —NH—, —O— or —S—;

R$_1$ is:
(A) aryl or heteroaryl, each optionally and independently substituted with one or more of the following groups:
  (i) C$_{1-6}$alkyl, which is optionally substituted one or more of the following:
    (a) halogen,
    (b) NH$_2$
  (ii) C$_{1-6}$alkoxy, which is optionally substituted with halogen,
  (iii) C$_{1-6}$alkylthio, which is optionally substituted with halogen,
  (iv) C$_{1-6}$alkylsulfonyl,
  (v) cyano,
  (vi) halogen,
  (vii) hydroxyl,
  (viii) nitro,
  (ix) —COR$_{11}$, wherein R$_{11}$ is:
    (a) C$_{1-6}$alkyl,
    (b) C$_{1-6}$alkyloxy,
    (c) —OH,
    (d) —NR$_{12}$R$_{13}$, wherein R$_{12}$ and R$_{13}$ are each independently selected from:
      (I) hydrogen,
      (II) C$_{1-6}$alkyl,
      (III) aryl,
      (IV) heteroaryl,
  (x) —NR$_{14}$R$_{15}$, wherein R$_{14}$ and R$_{15}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
    or wherein R$_{14}$ and R$_{15}$ together constitute an alkylene bridge which together with the nitrogen atom between them forms a five to seven-membered ring,
  (xi) arylthio, arylsulfonyl or aryloxy, each optionally and independently substituted with one or more of the following groups:
    (a) C$_{1-6}$alkyl,
    (b) C$_{1-6}$alkoxy,
    (c) C$_{1-6}$alkylthio,
    (d) C$_{1-6}$alkylsulfonyl,
    (e) cyano,
    (f) halogen,
    (g) nitro,
    (h) —NR$_{16}$R$_{17}$, wherein R$_{16}$ and R$_{17}$ are each independently selected from:
      (I) hydrogen,
      (II) C$_{1-6}$alkyl,
      (III) C$_{1-6}$alkylcarbonyl,
      (IV) C$_{1-6}$alkylsulfonyl,
(B) C$_{3-6}$cycloalkyl which is optionally and independently substituted with one or more of the following groups:
  (i) C$_{1-6}$alkyl, which is optionally substituted with halogen,
  (ii) C$_{1-6}$alkoxy, which is optionally substituted with halogen,
  (iii) C$_{1-6}$alkylthio, which is optionally substituted with halogen,
  (iv) C$_{1-6}$alkylsulfonyl,
  (v) halogen,
  (vi) hydroxyl,
  (vii) —NR$_{18}$R$_{19}$, wherein R$_{18}$ and R$_{19}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
  (viii) —COR$_{20}$, wherein R$_{20}$ is:
    (a) C$_{1-6}$alkyl,
    (b) C$_{1-6}$alkyloxy,
    (c) —OH,
    (d) —NR$_{21}$R$_{22}$, wherein R$_{21}$ and R$_{22}$ are each independently selected from:
      (I) hydrogen,
      (II) C$_{1-6}$alkyl,
(C) —COR$_{23}$, wherein R$_{23}$ is:
  (i) C$_{1-6}$alkyloxy,
  (ii) —NR$_{24}$R$_{25}$, wherein R$_{24}$ and R$_{25}$ are each independently selected from:
    (a) hydrogen,
    (b) C$_{1-6}$alkyl,
  or wherein R$_{24}$ and R$_{25}$ together constitute an alkylene bridge which together with the nitrogen atom between them forms a four to six-membered ring, wherein one of the methylene groups is optionally replaced by an oxygen, sulfur or NH group, and which ring is optionally and independently substituted with one or more of the following groups:
    (a) C$_{1-6}$alkyloxy,
    (b) C$_{1-6}$alkyl, which is optionally substituted with halogen,
    (c) hydroxyl,
    (d) halogen,
    (e) —COR$_{26}$, wherein R$_{26}$ is:
      (I) C$_{1-6}$alkyloxy,
      (II) —NR$_{27}$R$_{28}$, wherein R$_{27}$ and R$_{28}$ are each independently selected from:
        a. hydrogen,
        b. C$_{1-6}$alkyl,
        c. aryl,
        d. heteroaryl,
(D) is:

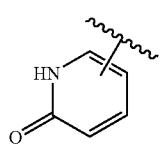

which is optionally substituted with halogen;
(E) is selected from the following:

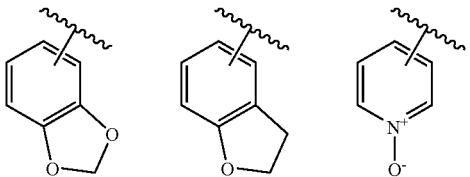

R$_2$ is selected from the following groups:
(A) CF$_3$,
(B) cyano,
(C) halogen,
(D) nitro,
(E) C$_{1-6}$alkylalkynyl,
(F) arylalkynyl which is optionally substituted with one or more of the following groups:
  (i) halogen,
  (ii) C$_{1-6}$alkyl, which is optionally substituted with halogen,
R$_3$ is selected from the following groups:

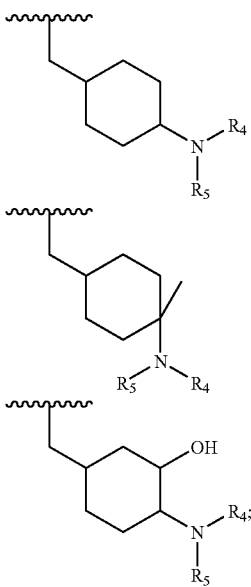

R$_4$ and R$_5$ are each independently selected from:
(A) hydrogen,
(B) C$_{1-6}$alkyl, optionally and independently substituted with one or more of the following groups:
  (i) oxo,
  (ii) C$_{3-6}$cycloalkyl,
  (iii) C$_{1-6}$alkyloxy,
  (iv) C$_{1-6}$alkylthio,
  (v) —COR$_{29}$, wherein R$_{29}$ is:
    (a) C$_{1-6}$alkyl,
    (b) C$_{1-6}$alkyloxy,
    (c) —OH,
  (vi) —CONR$_{30}$R$_{31}$, wherein R$_{30}$ and R$_{31}$ are each independently selected from:
    (a) hydrogen,
    (b) C$_{1-6}$alkyl,
    (c) aryl,
    (d) heteroaryl,
  (vii) halogen,
  (viii) hydroxyl,
  (ix) —NR$_{32}$R$_{33}$, wherein R$_{32}$ and R$_{33}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
    (e) aryl,
    (f) heteroaryl,
  (x) aryl or heteroaryl, each optionally and independently substituted with one or more of the following groups:
    (a) C$_{1-6}$alkyl, which is optionally substituted with halogen,
    (b) C$_{1-6}$alkoxy, which is optionally substituted with halogen,
    (c) C$_{1-6}$alkylthio, which is optionally substituted with halogen,
    (d) C$_{1-6}$alkylsulfonyl,
    (e) cyano,
    (f) halogen,
    (g) nitro,
    (h) —NR$_{34}$R$_{35}$, wherein R$_{34}$ and R$_{35}$ are each independently selected from:
      (I) hydrogen,
      (II) C$_{1-6}$alkyl,
      (III) C$_{1-6}$alkylcarbonyl,
      (IV) C$_{1-6}$alkylsulfonyl,
    (i) —COR$_{36}$, wherein R$_{36}$ is:
      (I) C$_{1-6}$alkyl,
      (II) C$_{1-6}$alkyloxy,
      (III) —OH,
    (j) —CONR$_{37}$R$_{38}$, wherein R$_{37}$ and R$_{38}$ are each independently selected from:
      (I) hydrogen,
      (II) C$_{1-6}$alkyl,
      (III) aryl,
      (IV) heteroaryl,
(C) C$_{1-6}$alkylsulfonyl,
(D) arylsulfonyl,
(E) aryl-C$_{1-6}$alkylsulfonyl,
(F) heteroarylsulfonyl,
(G) C$_{1-6}$alkylcarbonyl,
(H) arylcarbonyl,
(I) aryl-C$_{1-6}$alkylcarbonyl,
(J) heteroarylcarbonyl,
(K) C$_{1-6}$alkylaminocarbonyl, or
(L) heteroaryl,
or wherein R$_4$ and R$_5$ together constitute an alkylene bridge which together with the nitrogen atom between them forms a four- to seven-membered ring, wherein one of the methylene groups is optionally replaced by an oxygen, sulfur or NH group, and which ring is optionally and independently substituted with one or more of the following groups:
(A) C$_{1-6}$alkyl, which is optionally substituted with halogen,
(B) C$_{1-6}$alkoxy, which is optionally substituted with halogen,
(C) C$_{1-6}$alkylthio, which is optionally substituted with halogen,
(D) C$_{1-6}$alkylsulfonyl,
(E) halogen, (F) —NR$_{39}$R$_{40}$, wherein R$_{39}$ and R$_{40}$ are each independently selected from:
  (i) hydrogen,
  (ii) C$_{1-6}$alkyl,
  (iii) C$_{1-6}$alkylcarbonyl,
  (iv) C$_{1-6}$alkylsulfonyl,
  (v) arylcarbonyl,
  (vi) arylsulfonyl
  (vii) heteroarylcarbonyl,
  (viii) heteroarylsulfonyl,
(G) —COR$_{41}$, wherein R$_{41}$ is:
  (i) C$_{1-6}$alkyl,
  (ii) C$_{1-6}$alkyloxy,
  (iii) —NR$_{42}$R$_{43}$, wherein R$_{42}$ and R$_{43}$ are each independently selected from:
    (a) hydrogen,
    (b) C$_{1-6}$alkyl,
    (c) aryl,
    (d) heteroaryl,
  (iv) hydroxyl,
(H) —OR$_{44}$, wherein R$_{44}$ is selected from:
  (i) hydrogen,
  (ii) C$_{1-6}$alkylcarbonyl,
  (iii) C$_{1-6}$alkylsulfonyl
(I) oxo,
or wherein NR$_4$R$_5$ constitutes a 5-membered heteroaryl ring containing a total of 2 nitrogen hetero atoms in the ring; or a tautomer, pharmaceutically acceptable salt, solvate or amino-protected derivative thereof.

In another embodiment there are provided compounds of formula (I) as described above and wherein
X is C$_{1-3}$alkyl, optionally substituted with oxo,
Y is —NH— or —O—;
R$_1$ is:
  (A) aryl or heteroaryl, each optionally and independently substituted with one or more of the following groups:
    (i) C$_{1-3}$alkyl, which is optionally and independently substituted with fluorine,
    (ii) C$_{1-3}$alkoxy, which is optionally and independently substituted with fluorine,
    (iii) C$_{1-3}$alkylthio, which is optionally and independently substituted with fluorine,
    (iv) arylthio, which is optionally substituted with —NH$_2$,
    (v) halogen,
    (vi) hydroxyl,
    (vii) C$_{1-3}$alkylsulfonyl,
    (viii) CONH$_2$,
    (ix) —NR$_{14}$R$_{15}$, wherein R$_{14}$ and R$_{15}$ are each independently selected from:
      (a) hydrogen,
      (b) C$_{1-6}$alkyl
      (c) C$_{1-6}$alkylcarbonyl,
      (d) C$_{1-6}$alkylsulfonyl,
    or wherein R$_{14}$ and R$_{15}$ together constitute an alkylene bridge which together with the nitrogen atom between them forms a five to seven-membered ring,
  (B) cyclohexyl, which is optionally and independently substituted with:
    (i) C$_{1-3}$alkyl,
    (ii) hydroxyl;
  (C) —COR$_{23}$, wherein R$_{23}$ is:
    (i) —NR$_{24}$R$_{25}$, wherein R$_{24}$ and R$_{25}$ are each independently selected from:
      (a) C$_{1-6}$alkyl;
    or wherein R$_{24}$ and R$_{25}$ together constitute a alkylene bridge which together with the nitrogen atom between them forms a five to six-membered ring, wherein one of the methylene groups is optionally replaced by an oxygen atom and which ring is optionally and independently substituted with one or more of the following groups:
      (i) hydroxyl,
      (ii) —CONH$_2$,
(D) is:

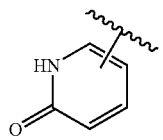

which is optionally substituted with halogen;
(E) is selected from the following:

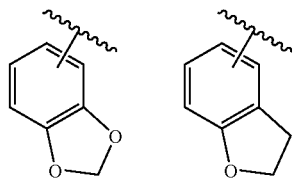

R$_2$ is:
  (A) CF$_3$,
  (B) cyano,
  (C) halogen, or
  (D) nitro,
R$_3$ is selected from the following:

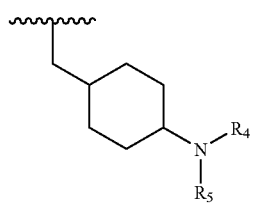

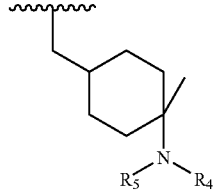

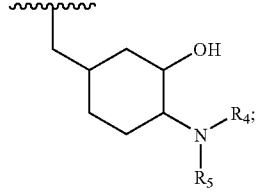

R$_4$ and R$_5$ are each independently selected from:
  (A) hydrogen,
  (B) C$_{1-6}$alkyl, which is optionally and independently substituted with one or more of the following groups:
    (i) oxo,
    (ii) C$_{3-5}$cycloalkyl, (iii) aryl or heteroaryl, each of which is optionally and independently substituted with one or more of the following groups:
  (a) $C_{1-3}$alkyl which is optionally substituted with fluorine,
  (b) —$CO_2H$
  (c) halogen,
(iv) $NH_2$
(v) hydroxyl,
(vi) —$CONH_2$,
(vii) fluorine,
(viii) $NHCOCH_3$
or $R_4$ and $R_5$ together constitute an alkylene bridge which together with the nitrogen atom between them forms a four- to seven-membered ring, wherein one of the methylene groups is optionally replaced by an NH or oxygen atom and which ring is optionally and independently substituted with one or more of the following groups:
(A) —$CONH_2$,
(B) $NR_{39}R_{40}$ wherein $R_{39}$ and $R_{40}$ are optionally and independently selected from:
  (i) $C_{1-5}$alkylcarbonyl
  (ii) $C_{1-5}$alkylsulfonyl
  (iii) arylcarbonyl
  (iv) arylsulfonyl
(C) —$OR_{44}$, wherein $R_{44}$ is selected from:
  (i) hydrogen,
  (ii) $C_{1-5}$alkylcarbonyl
(D) oxo, or
(E) fluorine
or wherein $NR_4R_5$ constitute a 5-membered heteroaryl ring containing a total of 2 nitrogen hetero atoms in the ring, or a tautomer, pharmaceutically acceptable salt, solvate or amino-protected derivative thereof.

In yet another embodiment there are provided compounds are compounds of formula (I) as described above and wherein:
X is —$CH_2$—, —$CH_2CH_2$— or —$CH_2CO$—,
Y is —NH— or —O—;
$R_1$ is:
  (A) phenyl, pyridyl, naphthyl, quinolinyl or benzothienyl, each of which is optionally and independently substituted with one or more of the following groups:
    (i) $C_{1-3}$alkyl, which is optionally substituted with fluorine,
    (ii) $C_{1-3}$alkoxy, which is optionally substituted with fluorine,
    (iii) methylthio, which is optionally substituted with fluorine,
    (iv) arylthio, optionally substituted with $NH_2$,
    (v) F, Cl or Br,
    (vi) hydroxyl,
    (vii) $NH_2$ or $N(CH_3)_2$,
    (viii) $SO_2CH_3$
  (B) cyclohexyl, optionally substituted with hydroxyl,
$R_2$ is:
  (A) $CF_3$,
  (B) cyano,
  (C) F, Cl, Br or
  (D) nitro, $R_3$ is:

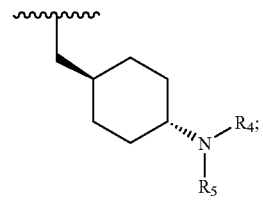

$R_4$, $R_5$ are each independently selected from:
  (A) hydrogen,
  (B) $C_{1-4}$alkyl, which is optionally and independently substituted with one or more of the following groups:
    (i) oxo,
    (ii) cyclopropyl,
    (iii) aryl or heteroaryl selected from phenyl, pyridyl, pyrimidyl, pyrazolyl and oxazolyl, each of which is optionally and independently substituted with one or more of the following groups:
      (a) $C_{1-2}$alkyl,
      (b) fluorine or chlorine,
    (iv) —$CONH_2$
    (v) hydroxyl,
    (vi) fluorine,
    (vii) $NHCOCH_3$
  or $R_4$ and $R_5$ together constitute an alkylene bridge which together with the nitrogen atom between them forms a four- to seven-membered ring, wherein one of the methylene groups is optionally replaced by an NH, and which ring is optionally and independently substituted with one or more of the following groups:
    (A) $CONH_2$,
    (B) hydroxyl,
    (C) $C_{1-5}$alkylcarbonyloxy,
    (D) oxo,
    (E) fluorine,
    (F) $NR_{39}R_{40}$ wherein $R_{39}$ and $R_{40}$ are optionally and independently selected from:
      (i) hydrogen
      (ii) $C_{1-5}$alkylcarbonyl
      (iii) $C_{1-5}$alkylsulfonyl
      (iv) Phenylcarbonyl, or
      (v) phenylsulfonyl,
  or a tautomer, pharmaceutically acceptable salt, solvate or amino-protected derivative thereof.

In a further embodiment there are provided compounds of formula (I) as described above and wherein:
X is —$CH_2$—,
Y is —NH—,
$R_1$ is:
  (A) phenyl or pyridyl optionally and independently substituted with one or more of the following groups:
    (i) methyl,
    (ii) $CF_3$,
    (iii) $OCF_3$,
    (iv) $OCF_2H$
    (v) $OCH_3$,
    (vi) $OCH(CH_3)_2$
    (vii) $SCF_3$,
    (viii) arylthio substituted with $NH_2$,
    (ix) F or Cl,
    (x) $N(CH_3)_2$,
    (xi) $OCH_2CF_3$
    (xii) $SO_2CH_3$ (B) naphthyl,
R$_2$ is:
 (A) cyano,
 (B) Cl, or
 (C) nitro;
R$_3$ is:

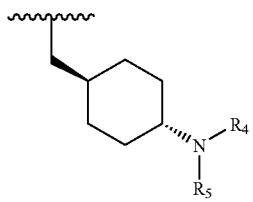

R$_4$ and R$_5$ are each independently selected from:
 (A) hydrogen,
 (B) C$_{1-3}$alkyl, optionally substituted with one or more of the following groups:
  (i) hydroxyl,
  (ii) pyridyl,
  (iii) 1-methyl-1H-pyrazole,
  (iv) 1,5-dimethyl-1H-pyrazole,
  (v) —CONH$_2$,
or R$_4$ and R$_5$ together constitute an alkylene bridge which together with the nitrogen atom between them forms a four or five-membered ring, each optionally and independently substituted with one or more of the following:
 (A) hydroxyl,
 (B) amino
 (C) fluorine
 (D) oxo
 (E) —NHSO$_2$CH$_3$
 (F) —NHCOCH$_3$
 or a tautomer, pharmaceutically acceptable salt, solvate or amino-protected derivative thereof.

In still a further embodiment there are provided compounds of formula (I) as described above and wherein:
X is —CH$_2$—,
Y is —NH—,
R$_1$ is:
 (A) phenyl, optionally and independently substituted with one or more of the following groups:
  (i) methyl,
  (ii) CF$_3$,
  (iii) OCF$_3$,
  (iv) OCH$_3$,
  (v) SCF$_3$,
  (vi) arylthio substituted with NH$_2$,
  (vii) F or Cl;
 (B) naphthyl,
R$_2$ is:
 (A) cyano,
 (B) Cl, or
 (C) nitro;
R$_3$ is:

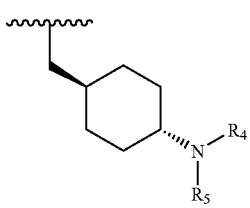

R$_4$ and R$_5$ are each independently selected from:
 (A) hydrogen,
 (B) C$_{1-2}$alkyl, optionally substituted with one or more of the following groups:
  (i) hydroxyl,
  (ii) pyridyl,
  (iii) 1,5-dimethyl-1H-pyrazole,
  (iv) —CONH$_2$,
or R$_4$ and R$_5$ together constitute an alkylene bridge which together with the nitrogen atom between them forms a four or five-membered ring, each optionally and independently substituted with one or more hydroxyl or oxo;
or a tautomer, pharmaceutically acceptable salt, solvate or amino-protected derivative thereof.

In yet a further embodiment there are provided the following compounds:

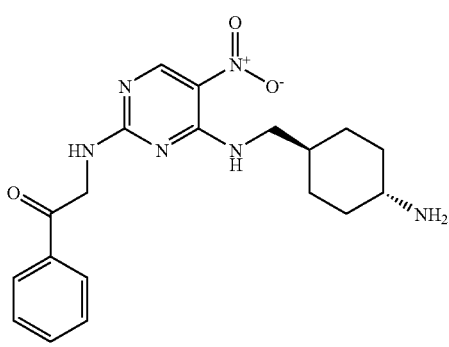

2-[(4-{[(trans-4-aminocyclohexyl)methyl]amino}-5-nitro-pyrimidin-2-yl)amino]-1-phenylethanone -continued

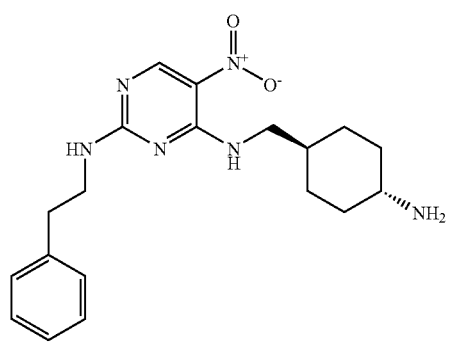

$N^4$-[(trans-4-aminocyclohexyl)methyl]-5-nitro-$N^2$-(2-phenylethyl)pyrimidine-2,4-diamine

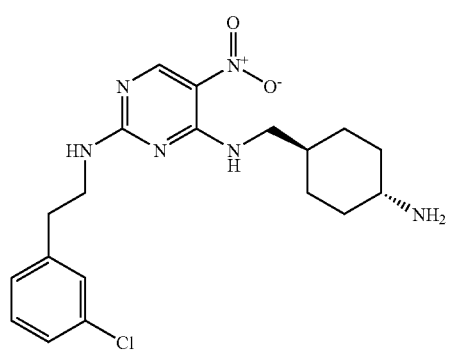

$N^4$-[(trans-4-aminocyclohexyl)methyl]-$N^2$-[2-(3-chlorophenyl)ethyl]-5-nitropyrimidine-2,4-diamine

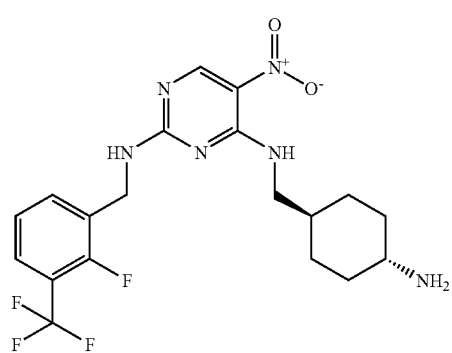

$N^4$-[(trans-4-aminocyclohexyl)methyl]-$N^2$-[2-fluoro-3-(trifluoromethyl)benzyl]-5-nitropyrimidine-2,4-diamine

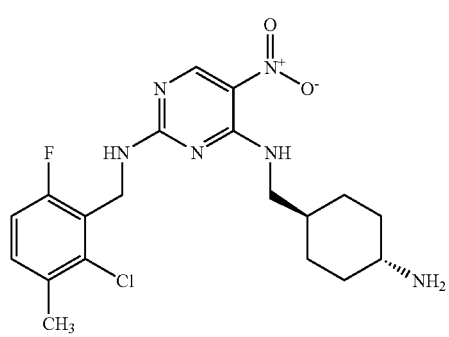

$N^4$-[(trans-4-aminocyclohexyl)methyl]-$N^2$-(2-chloro-6-fluoro-3-methylbenzyl)-5-nitropyrimidine-2,4-diamine -continued
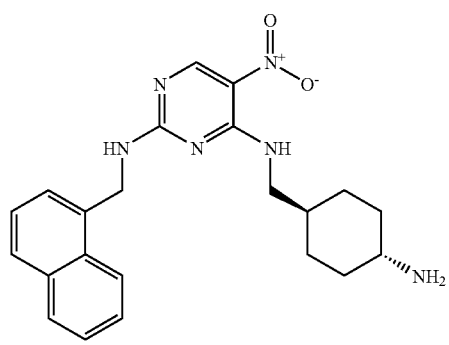
$N^4$-[(trans-4-aminocyclohexyl)methyl]-$N^2$-(1-naphthylmethyl)-5-nitropyrimidine-2,4-diamine
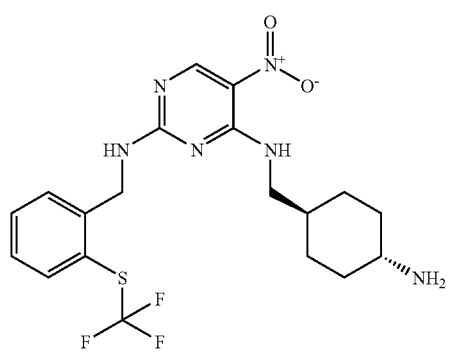
$N^4$-[(trans-4-aminocyclohexyl)methyl]-5-nitro-$N^2$-{2-[(trifluoromethyl)thio]benzyl}pyrimidine-2,4-diamine
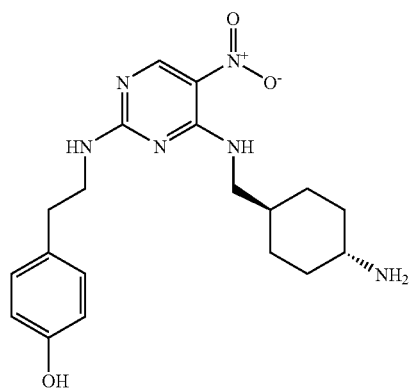
4-{2-[(4-{[(trans-4-aminocyclohexyl)methyl]amino}-5-nitropyrimidin-2-yl)amino]ethyl}phenol
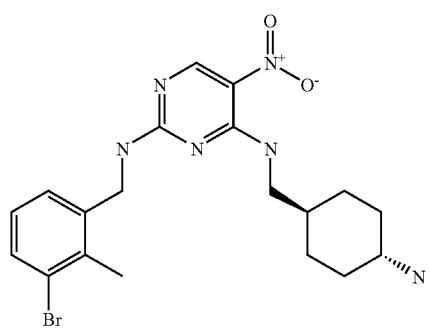
$N^4$-[(trans-4-aminocyclohexyl)methyl]-$N^2$-(3-bromo-2-methylbenzyl)-5-nitropyrimidine-2,4-diamine

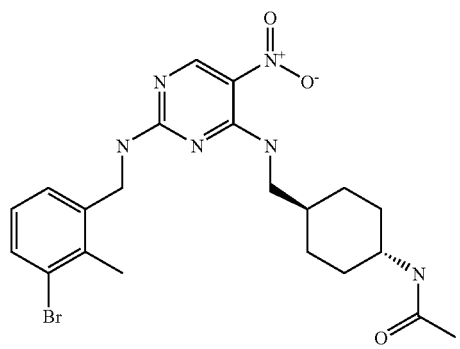
N-{trans-4-[({2-[(3-bromo-2-methylbenzyl)amino]-5-nitropyrimidin-4-yl}amino)methyl]cyclohexyl}acetamide

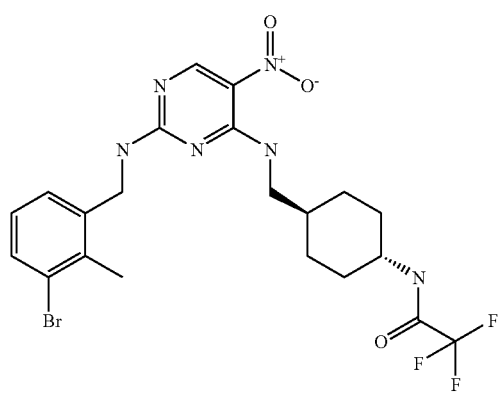
N-{trans-4-[({2-[(3-bromo-2-methylbenzyl)amino]-5-nitropyrimidin-4-yl}amino)methyl]cyclohexyl}-2,2,2-trifluoroacetamide

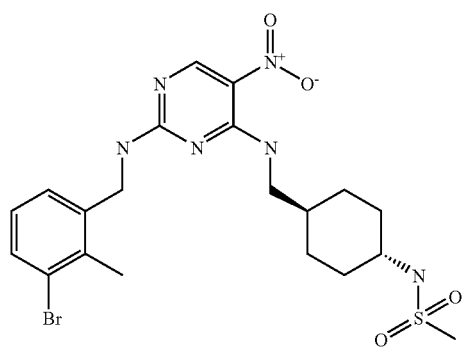
N-{trans-4-[({2-[(3-bromo-2-methylbenzyl)amino]-5-nitropyrimidin-4-yl}amino)methyl]cyclohexyl}methanesulfonamide

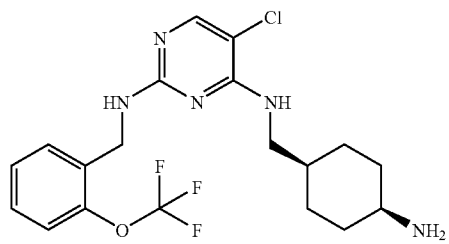
$N^4$-[(cis-4-aminocyclohexyl)methyl]-5-chloro-$N^2$-[2-(trifluoromethoxy)benzyl]pyrimidine-2,4-diamine

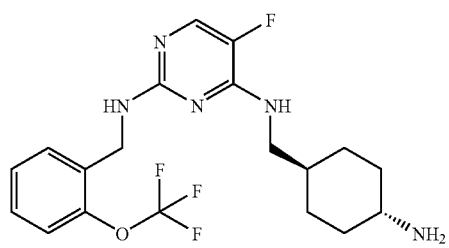
$N^4$-[(trans-4-aminocyclohexyl)methyl]-5-fluoro-$N^2$-[2-(trifluoromethoxy)benzyl]pyrimidine-2,4-diamine -continued

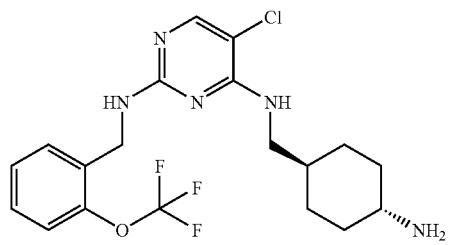

$N^4$-[(trans-4-aminocyclohexyl)methyl]-5-chloro-$N^2$-[2-(trifluoromethoxy)benzyl]pyrimidine-2,4-diamine

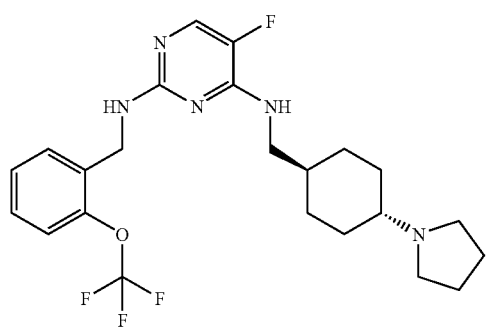

5-fluoro-$N^4$-[(trans-4-pyrrolidin-1-ylcyclohexyl)methyl]-$N^2$-[2-(trifluoromethoxy)benzyl]pyrimidine-2,4-diamine

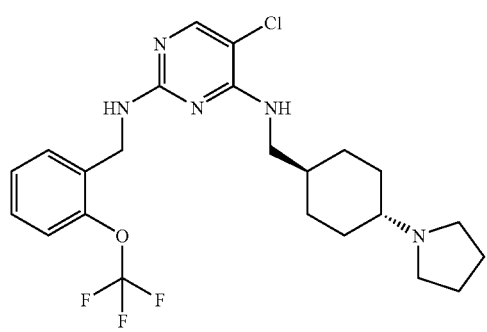

5-chloro-$N^4$-[(trans-4-pyrrolidin-1-ylcyclohexyl)methyl]-$N^2$-[2-(trifluoromethoxy)benzyl]pyrimidine-2,4-diamine

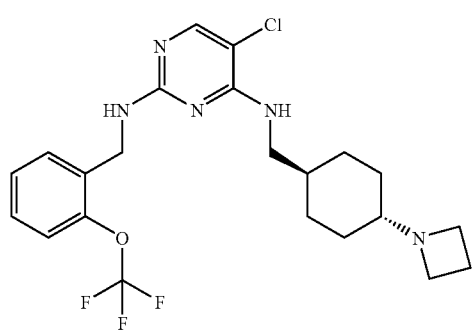

$N^4$-[(trans-4-azetidin-1-ylcyclohexyl)methyl]-5-chloro-$N^2$-[2-(trifluoromethoxy)benzyl]pyrimidine-2,4-diamine

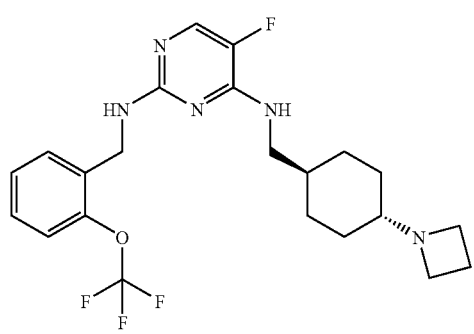

$N^4$-[(trans-4-azetidin-1-ylcyclohexyl)methyl]-5-fluoro-$N^2$-[2-(trifluoromethoxy)benzyl]pyrimidine-2,4-diamine -continued

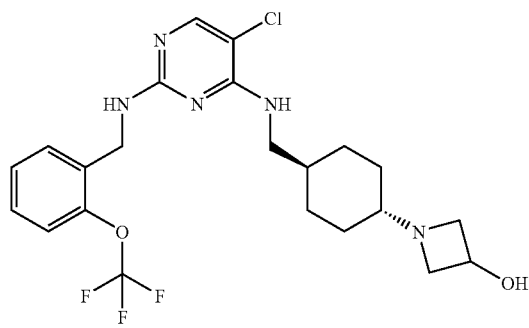

1-(trans-4-{[(5-chloro-2-{[2-(trifluoromethoxy)benzyl]amino}pyrimidin-4-yl)amino]methyl}cyclohexyl)azetidin-3-ol

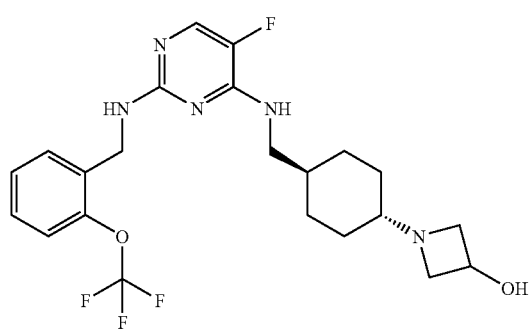

1-(trans-4-{[(5-fluoro-2-{[2-(trifluoromethoxy)benzyl]amino}pyrimidin-4-yl)amino]methyl}cyclohexyl)azetidin-3-ol

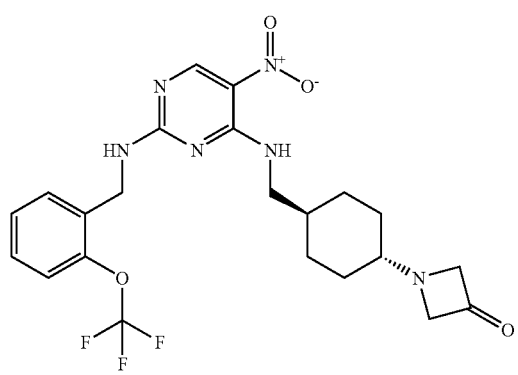

1-(trans-4-{[(5-nitro-2-{[2-(trifluoromethoxy)benzyl]amino}pyrimidin-4-yl)amino]methyl}cyclohexyl)azetidin-3-one

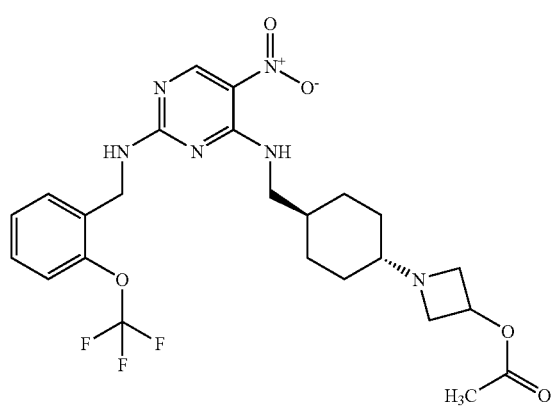

1-(trans-4-{[(5-nitro-2-{[2-(trifluoromethoxy)benzyl]amino}pyrimidin-4-yl)amino]methyl}cyclohexyl)azetidin-3-yl acetate -continued

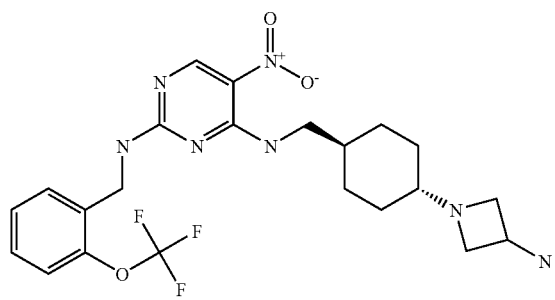

N⁴-{[trans-4-(3-aminoazetidin-1-yl)cyclohexyl]methyl}-5-nitro-N²-[2-(trifluoromethoxy)benzyl]pyrimidine-2,4-diamine

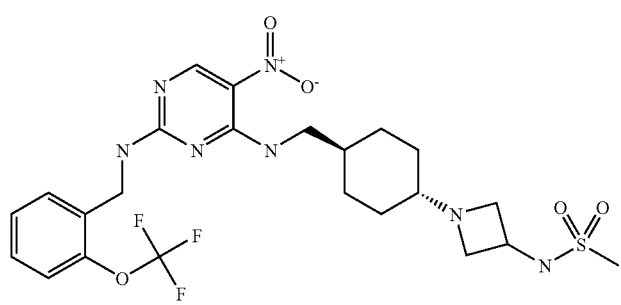

N-[1-(trans-4-{[(5-nitro-2-{[2-(trifluoromethoxy)benzyl]-amino}pyrimidin-4-yl)amino]methyl}cyclohexyl)azetidin-3-yl]methanesulfonamide

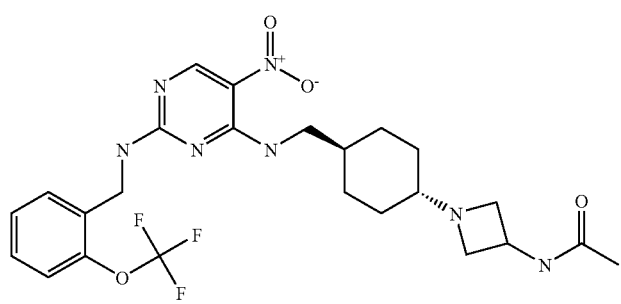

N-[1-(trans-4-{[(5-nitro-2-{[2-(trifluoromethoxy)benzyl]-amino}pyrimidin-4-yl)amino]methyl}cyclohexyl)azetidin-3-yl]acetamide

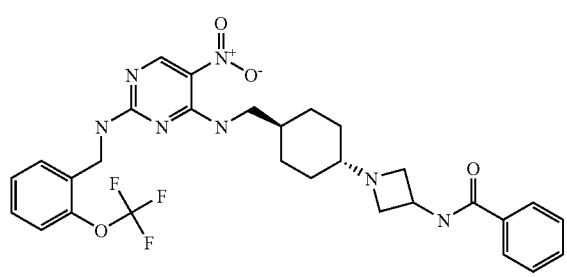

N-[1-(trans-4-{[(5-nitro-2-{[2-(trifluoromethoxy)benzyl]-amino}pyrimidin-4-yl)amino]methyl}cyclohexyl)azetidin-3-yl]benzamide

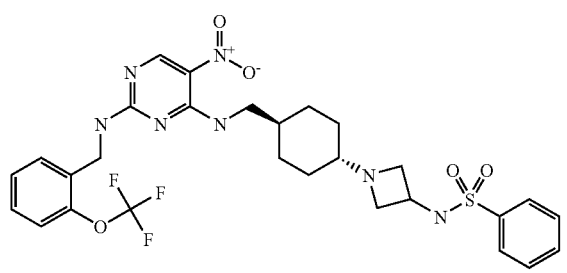

N-[1-(trans-4-{[(5-nitro-2-{[2-(trifluoromethoxy)benzyl]-amino}pyrimidin-4-yl)amino]methyl}cyclohexyl)azetidin-3-yl]benzenesulfonamide -continued

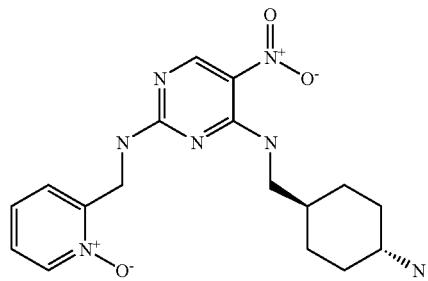

$N^4$-[(trans-4-aminocyclohexyl)methyl]-5-nitro-$N^2$-[(1-oxidopyridin-2-yl)methyl]pyrimidine-2,4-diamine

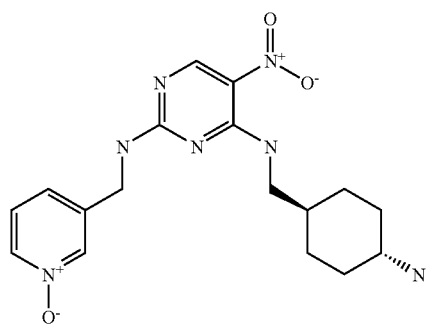

$N^4$-[(trans-4-aminocyclohexyl)methyl]-5-nitro-$N^2$-[(1-oxidopyridin-3-yl)methyl]pyrimidine-2,4-diamine

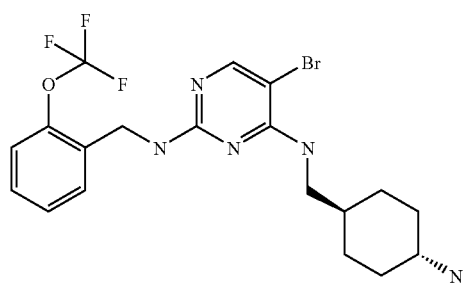

$N^4$-[(trans-4-aminocyclohexyl)methyl]-5-bromo-$N^2$-[2-(trifluoromethoxy)-benzyl]pyrimidine-2,4-diamine

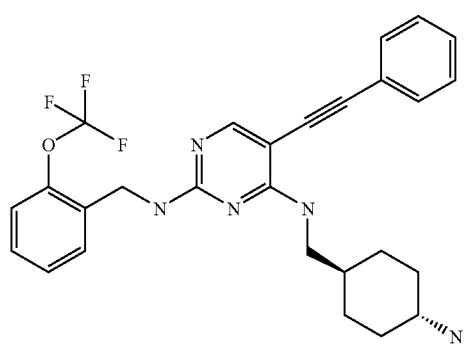

$N^4$-[(trans-4-aminocyclohexyl)methyl]-5-(phenylethynyl)-$N^2$-[2-(trifluoromethoxy)benzyl]pyrimidine-2,4-diamine

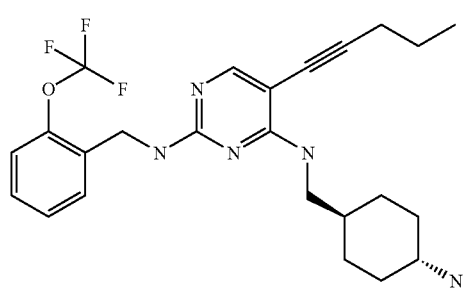

$N^4$-[(trans-4-aminocyclohexyl)methyl]-5-pent-1-yn-1-yl-$N^2$-[2-(trifluoromethoxy)benzyl]pyrimidine-2,4-diamine -continued

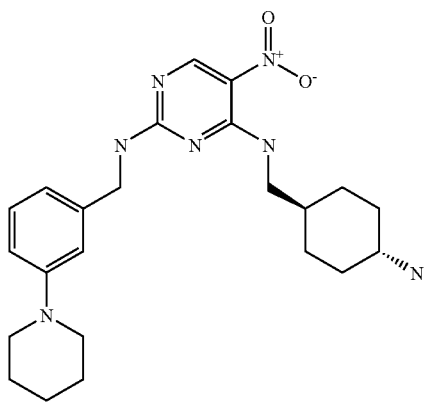

$N^4$-[(trans-4-aminocyclohexyl)methyl]-5-nitro-$N^2$-(3-piperidin-1-ylbenzyl)pyrimidine-2,4-diamine

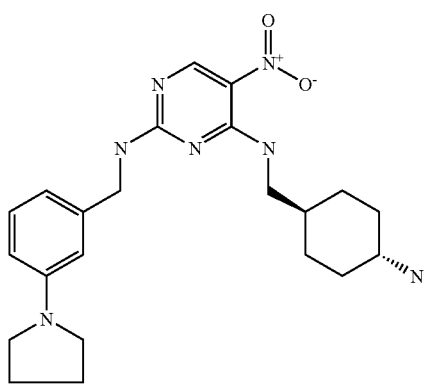

$N^4$-[(trans-4-aminocyclohexyl)methyl]-5-nitro-$N^2$-(3-pyrrolidin-1-ylbenzyl)pyrimidine-2,4-diamine

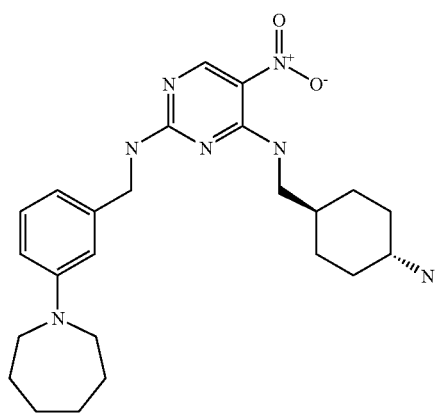

$N^4$-[(trans-4-aminocyclohexyl)methyl]-$N^2$-(3-azepan-1-ylbenzyl)-5-nitropyrimidine-2,4-diamine

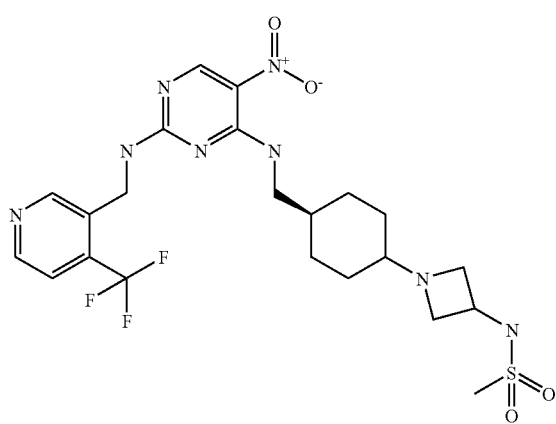

N-{1-[trans-4-({[5-nitro-2-({[4-(trifluoromethyl)pyridin-3-yl]methyl}amino)pyrimidin-4-yl]amino}methyl)-cyclohexyl]azetidin-3-yl}methanesulfonamide

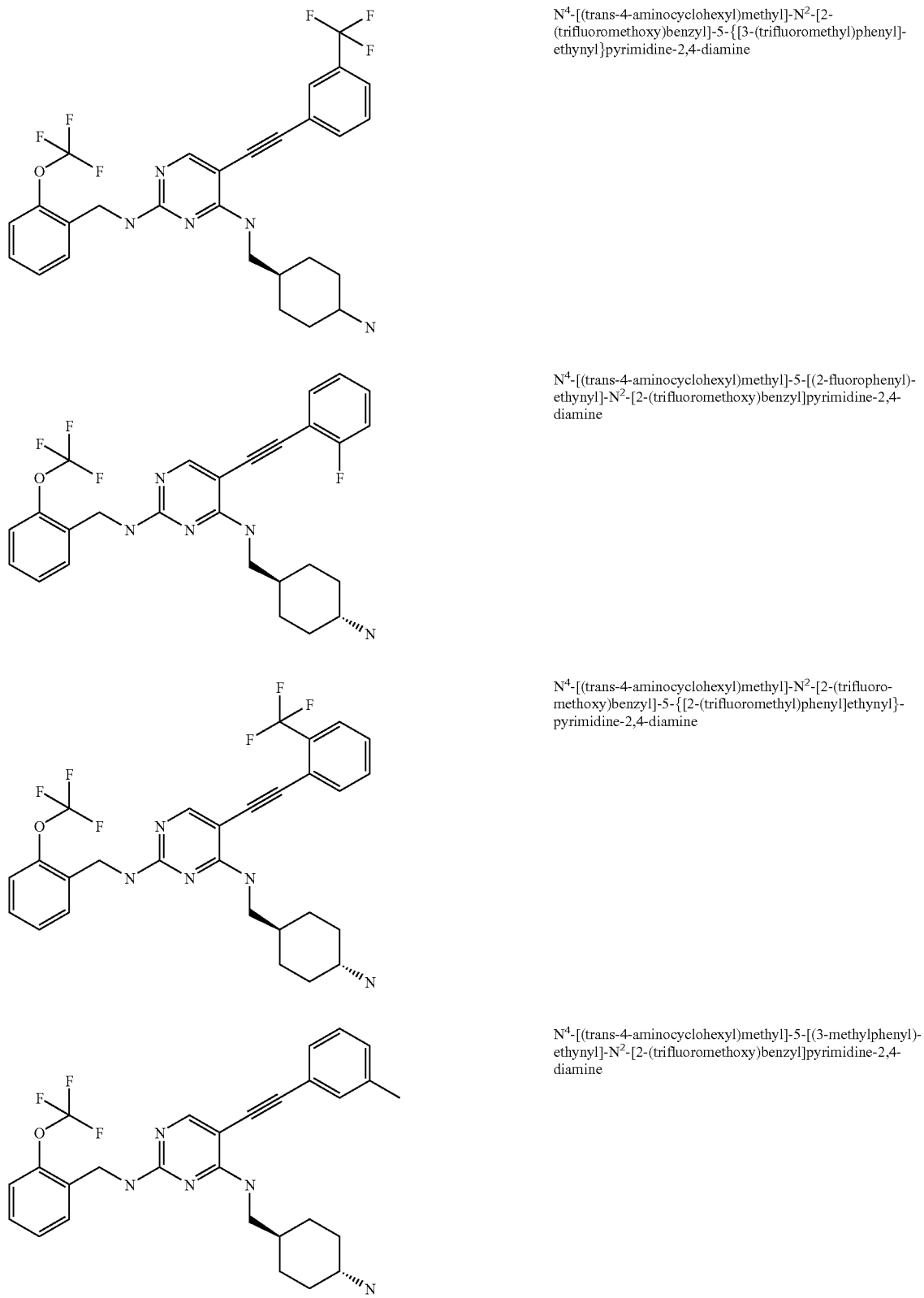

$N^4$-[(trans-4-aminocyclohexyl)methyl]-$N^2$-[2-(trifluoromethoxy)benzyl]-5-{[3-(trifluoromethyl)phenyl]-ethynyl}pyrimidine-2,4-diamine $N^4$-[(trans-4-aminocyclohexyl)methyl]-5-[(2-fluorophenyl)-ethynyl]-$N^2$-[2-(trifluoromethoxy)benzyl]pyrimidine-2,4-diamine $N^4$-[(trans-4-aminocyclohexyl)methyl]-$N^2$-[2-(trifluoromethoxy)benzyl]-5-{[2-(trifluoromethyl)phenyl]ethynyl}-pyrimidine-2,4-diamine $N^4$-[(trans-4-aminocyclohexyl)methyl]-5-[(3-methylphenyl)-ethynyl]-$N^2$-[2-(trifluoromethoxy)benzyl]pyrimidine-2,4-diamine -continued

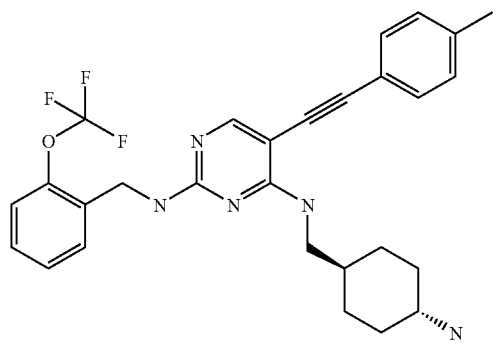

$N^4$-[(trans-4-aminocyclohexyl)methyl]-5-[(4-methylphenyl)ethynyl]-$N^2$-[2-(trifluoromethoxy)benzyl]pyrimidine-2,4-diamine

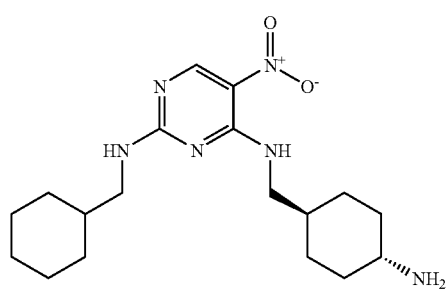

$N^4$-[(trans-4-aminocyclohexyl)methyl]-$N^2$-(cyclohexylmethyl)-5-nitropyrimidine-2,4-diamine

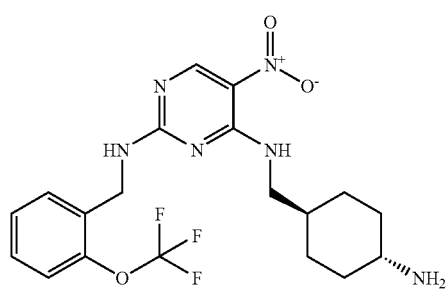

$N^4$-[(trans-4-aminocyclohexyl)methyl]-5-nitro-$N^2$-[2-(trifluoromethoxy)benzyl]pyrimidine-2,4-diamine

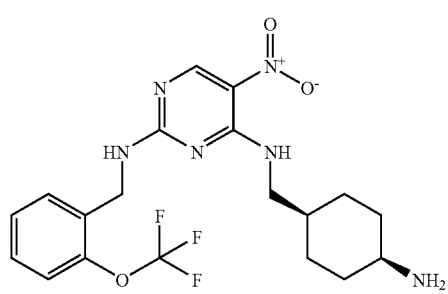

$N^4$-[(cis-4-aminocyclohexyl)methyl]-5-nitro-$N^2$-[2-(trifluoromethoxy)benzyl]pyrimidine-2,4-diamine

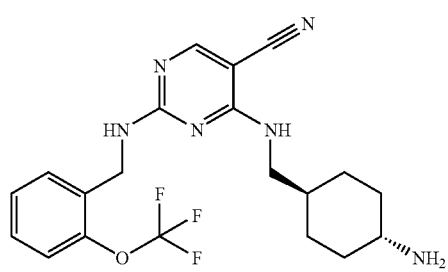

4-{[(trans-4-aminocyclohexyl)methyl]amino}-2-{[2-(trifluoromethoxy)benzyl]amino}pyrimidine-5-carbonitrile

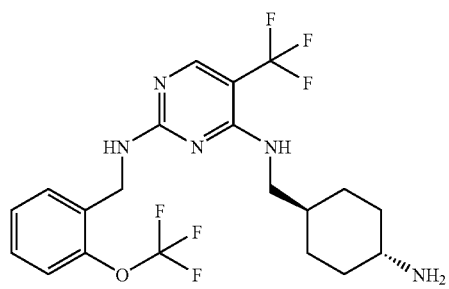

N⁴-[(trans-4-aminocyclohexyl)methyl]-N²-[2-(trifluoromethoxy)benzyl]-5-(trifluoromethyl)pyrimidine-2,4-diamine

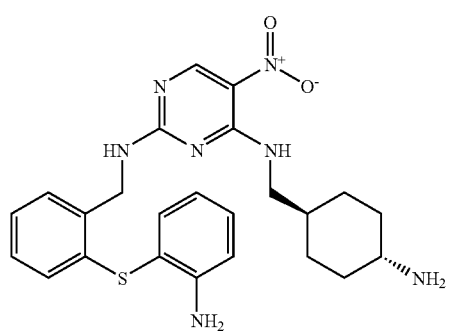

N⁴-[(trans-4-aminocyclohexyl)methyl]-N²-{2-[(2-aminophenyl)thio]benzyl}-5-nitropyrimidine-2,4-diamine

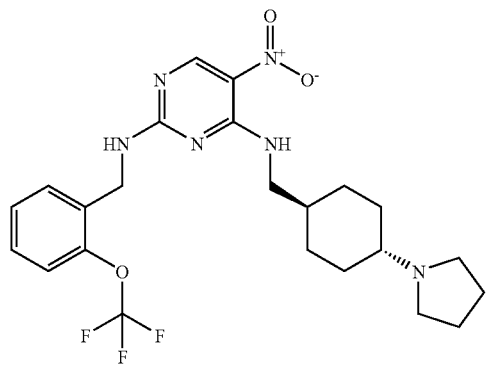

5-nitro-N⁴-[(trans-4-pyrrolidin-1-ylcyclohexyl)methyl]-N²-[2-(trifluoromethoxy)benzyl]pyrimidine-2,4-diamine

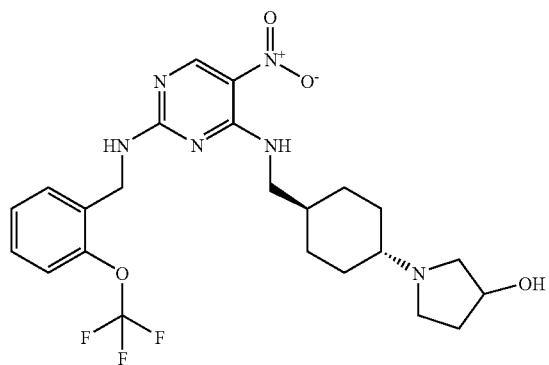

1-(trans-4-{[(5-nitro-2-{[2-(trifluoromethoxy)benzyl]amino}pyrimidin-4-yl)amino]methyl}cyclohexyl)pyrrolidin-3-ol

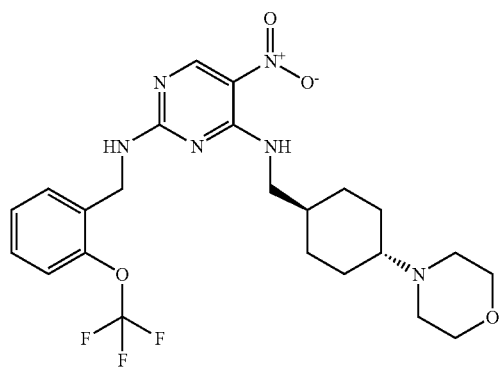

N⁴-[(trans-4-morpholin-4-ylcyclohexyl)methyl]-5-nitro-N²-[2-(trifluoromethoxy)benzyl]pyrimidine-2,4-diamine

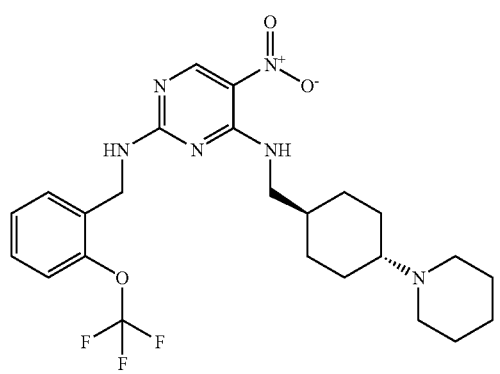

5-nitro-N⁴-[(trans-4-piperidin-1-ylcyclohexyl)methyl]-N²-[2-(trifluoromethoxy)benzyl]pyrimidine-2,4-diamine

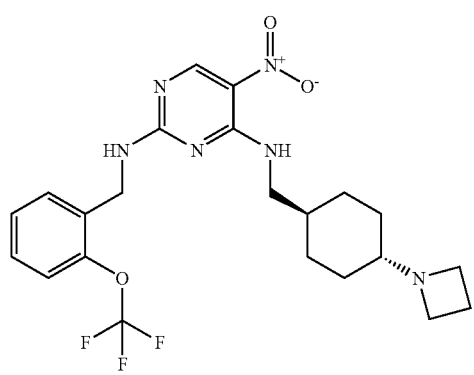

N⁴-[(trans-4-azetidin-1-ylcyclohexyl)methyl]-5-nitro-N²-[2-(trifluoromethoxy)benzyl]pyrimidine-2,4-diamine

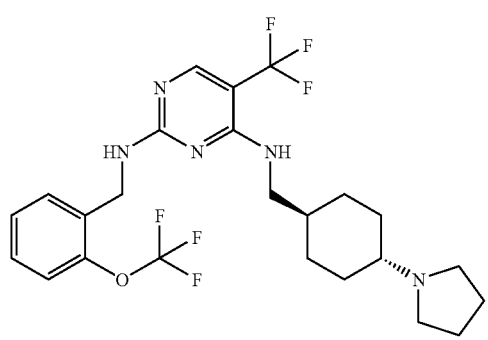

N⁴-[(trans-4-pyrrolidin-1-ylcyclohexyl)methyl]-N²-[2-(trifluoromethoxy)benzyl]-5-(trifluoromethyl)pyrimidine-2,4-diamine

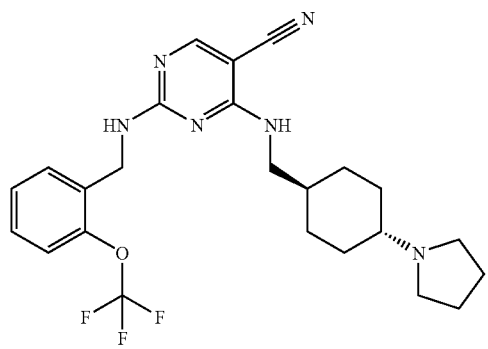

4-{[(trans-4-pyrrolidin-1-ylcyclohexyl)methyl]amino}-2-{[2-(trifluoromethoxy)benzyl]amino}pyrimidine-5-carbonitrile

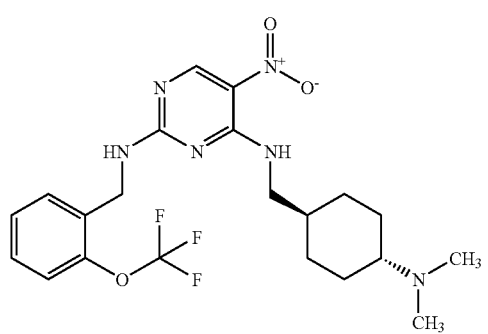

$N^4$-{[trans-4-(dimethylamino)cyclohexyl]methyl}-5-nitro-$N^2$-[2-(trifluoromethoxy)benzyl]pyrimidine-2,4-diamine

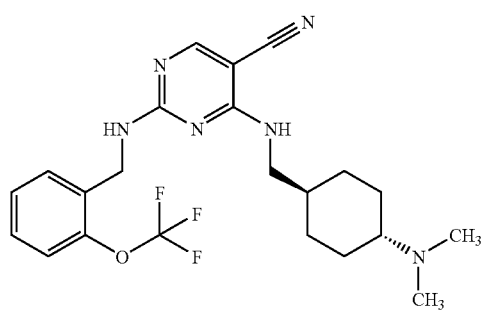

4-({[trans-4-(dimethylamino)cyclohexyl]methyl}amino)-2-{[2-(trifluoromethoxy)benzyl]amino}pyrimidine-5-carbonitrile

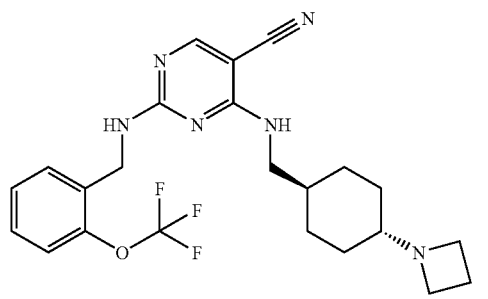

4-{[(trans-4-azetidin-1-ylcyclohexyl)methyl]amino}-2-{[2-(trifluoromethoxy)benzyl]amino}pyrimidine-5-carbonitrile

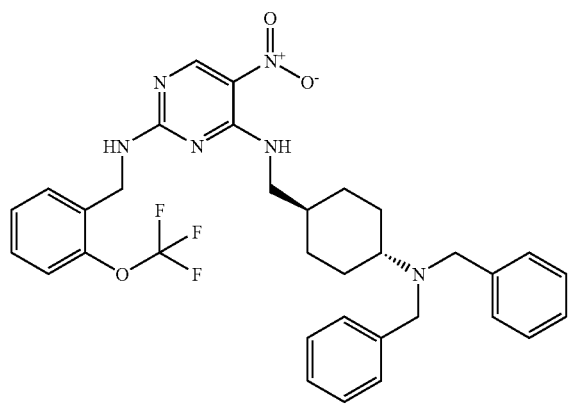

N⁴-{[trans-4-(dibenzylamino)cyclohexyl]methyl}-5-nitro-N²-[2-(trifluoromethoxy)benzyl]pyrimidine-2,4-diamine

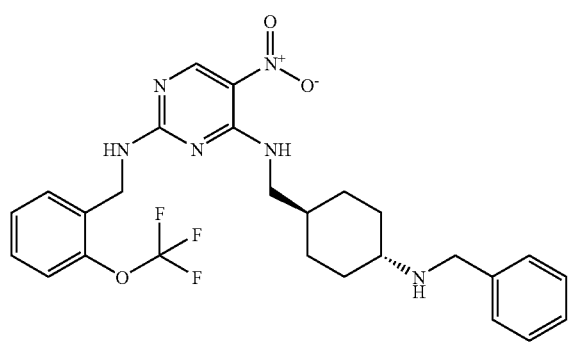

N⁴-{[trans-4-(benzylamino)cyclohexyl]methyl}-5-nitro-N²-[2-(trifluoromethoxy)benzyl]pyrimidine-2,4-diamine

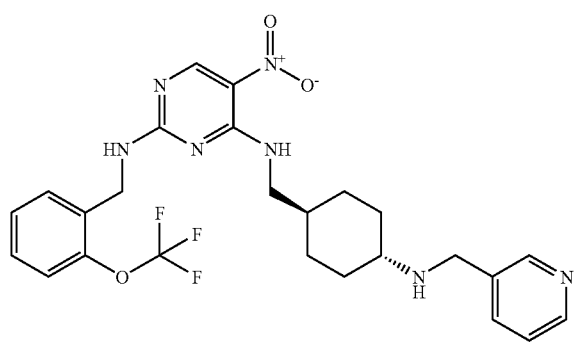

5-nitro-N⁴-({trans-4-[(pyridin-3-ylmethyl)amino]-cyclohexyl}methyl)-N²-[2-(trifluoromethoxy)benzyl]-pyrimidine-2,4-diamine

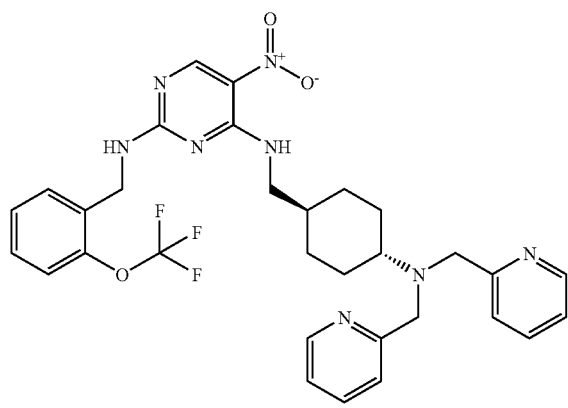

N⁴-({trans-4-[bis(pyridin-2-ylmethyl)amino]cyclohexyl}-methyl)-5-nitro-N²-[2-(trifluoromethoxy)benzyl]pyrimidine-2,4-diamine

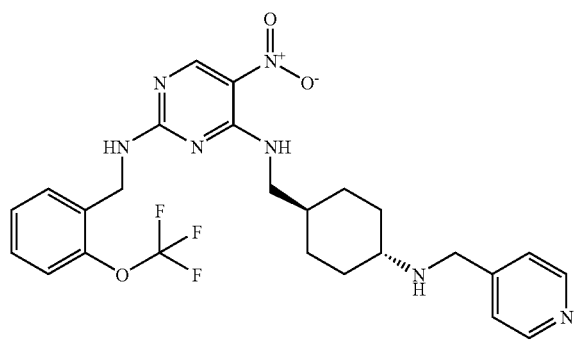

5-nitro-N⁴-({trans-4-[(pyridin-4-ylmethyl)amino]-cyclohexyl}methyl)-N²-[2-(trifluoromethoxy)benzyl]-pyrimidine-2,4-diamine

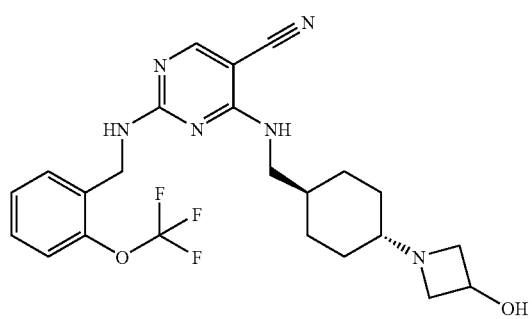

4-({[trans-4-(3-hydroxyazetidin-1-yl)cyclohexyl]methyl}-amino)-2-{[2-(trifluoromethoxy)benzyl]amino}pyrimidine-5-carbonitrile

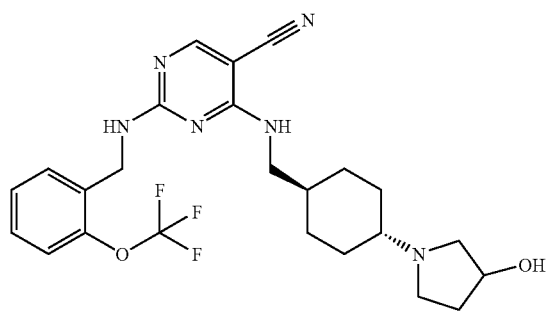

4-({[trans-4-(3-hydroxypyrrolidin-1-yl)cyclohexyl]methyl}-amino)-2-{[2-(trifluoromethoxy)benzyl]amino}pyrimidine-5-carbonitrile

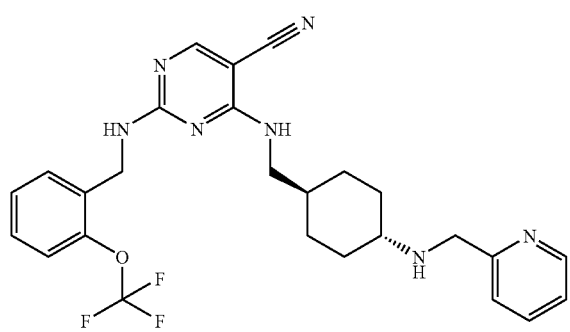

4-[({trans-4-[(pyridin-2-ylmethyl)amino]cyclohexyl}methyl)amino]-2-{[2-(trifluoromethoxy)benzyl]amino}pyrimidine-5-carbonitrile -continued

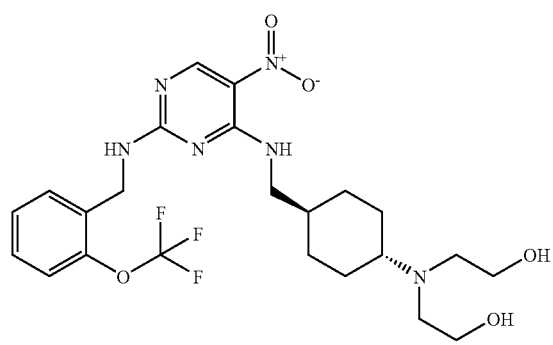

2,2'-[(trans-4-{[(5-nitro-2-{[2-(trifluoromethoxy)benzyl]amino}pyrimidin-4-yl)amino]methyl}cyclohexyl)imino]diethanol

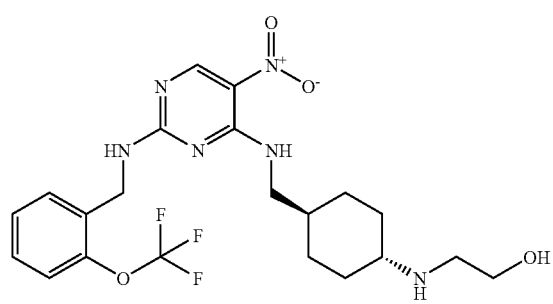

2-[(trans-4-{[(5-nitro-2-{[2-(trifluoromethoxy)benzyl]-amino}pyrimidin-4-yl)amino]methyl}cyclohexyl)-amino]ethanol

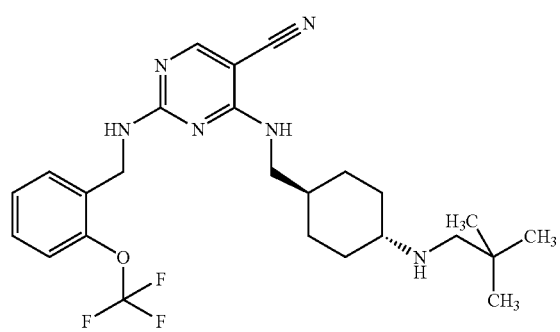

4-[({trans-4-[(2,2-dimethylpropyl)amino]cyclohexyl}-methyl)amino]-2-{[2-(trifluoromethoxy)benzyl]amino}-pyrimidine-5-carbonitrile

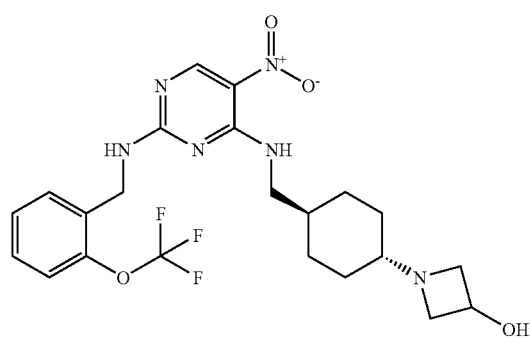

1-(trans-4-{[(5-nitro-2-{[2-(trifluoromethoxy)benzyl]amino}pyrimidin-4-yl)amino]methyl}cyclohexyl)azetidin-3-ol

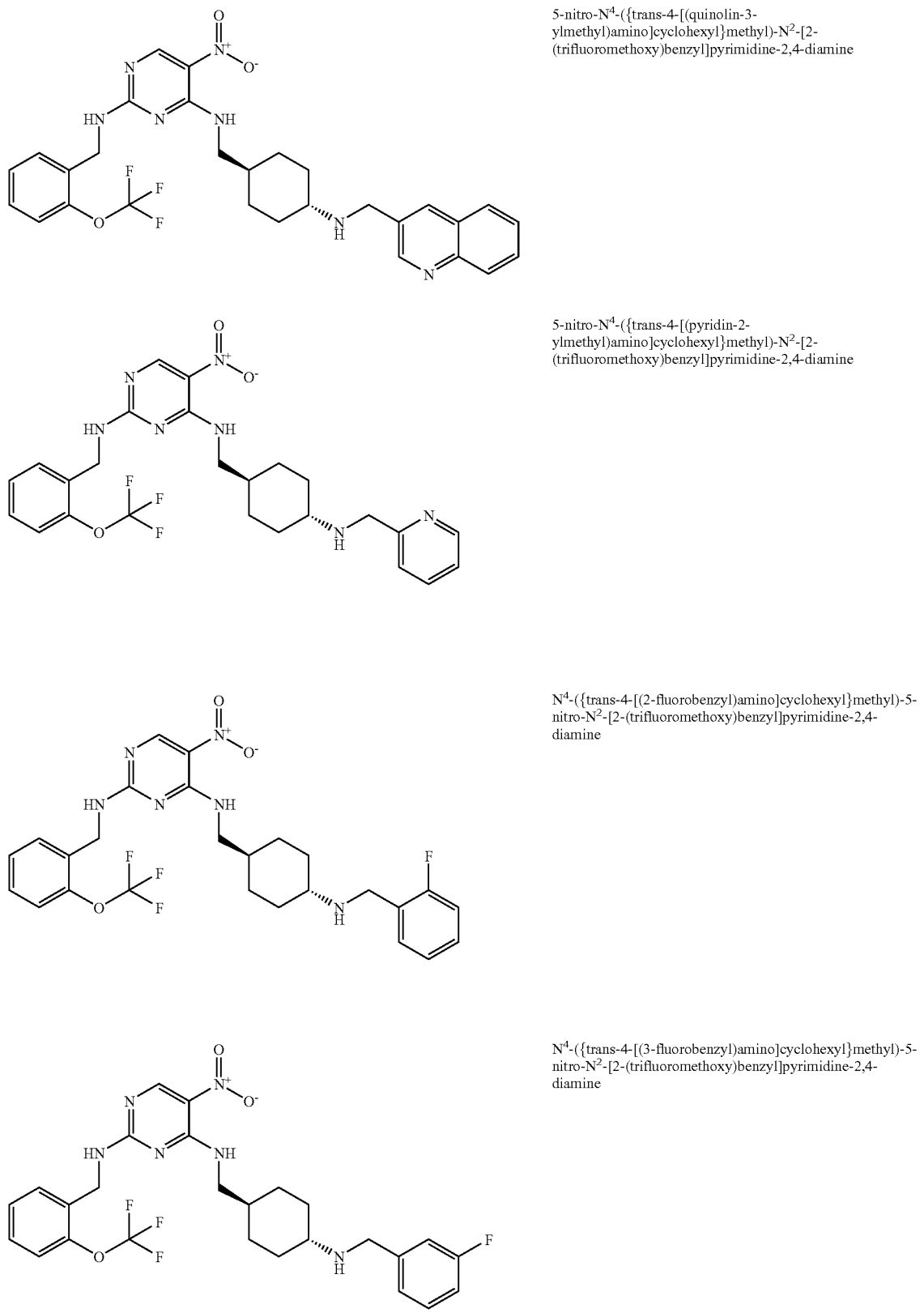

5-nitro-$N^4$-({trans-4-[(quinolin-3-ylmethyl)amino]cyclohexyl}methyl)-$N^2$-[2-(trifluoromethoxy)benzyl]pyrimidine-2,4-diamine 5-nitro-$N^4$-({trans-4-[(pyridin-2-ylmethyl)amino]cyclohexyl}methyl)-$N^2$-[2-(trifluoromethoxy)benzyl]pyrimidine-2,4-diamine $N^4$-({trans-4-[(2-fluorobenzyl)amino]cyclohexyl}methyl)-5-nitro-$N^2$-[2-(trifluoromethoxy)benzyl]pyrimidine-2,4-diamine $N^4$-({trans-4-[(3-fluorobenzyl)amino]cyclohexyl}methyl)-5-nitro-$N^2$-[2-(trifluoromethoxy)benzyl]pyrimidine-2,4-diamine -continued

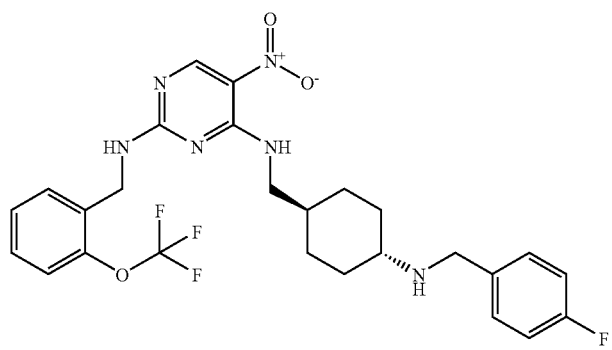

N⁴-({trans-4-[(4-fluorobenzyl)amino]cyclohexyl}methyl)-5-nitro-N²-[2-(trifluoromethoxy)benzyl]pyrimidine-2,4-diamine

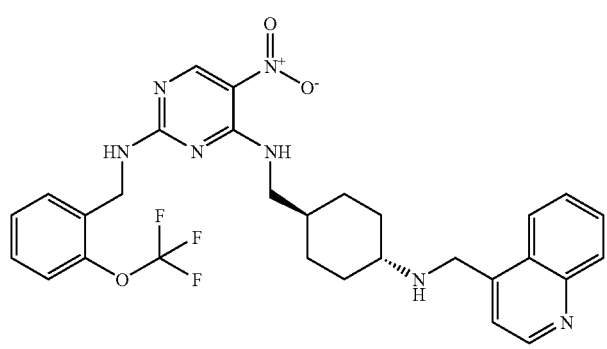

5-nitro-N⁴-({trans-4-[(quinolin-4-ylmethyl)amino]cyclohexyl}methyl)-N²-[2-(trifluoromethoxy)benzyl]pyrimidine-2,4-diamine

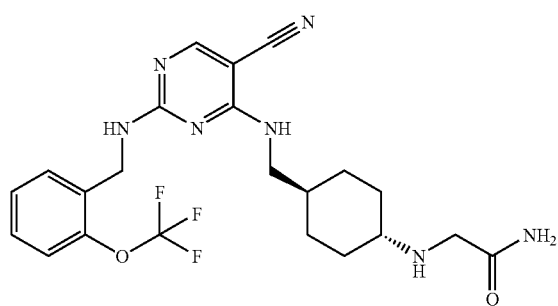

N²-(trans-4-{[(5-cyano-2-{[2-(trifluoromethoxy)benzyl]amino}pyrimidin-4-yl)amino]methyl}cyclohexyl)glycinamide

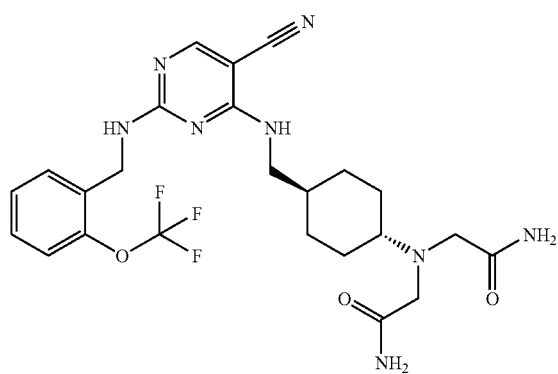

N²-(2-amino-2-oxoethyl)-N²-(trans-4-{[(5-cyano-2-{[2-(trifluoromethoxy)benzyl]amino}pyrimidin-4-yl)amino]methyl}cyclohexyl)glycinamide

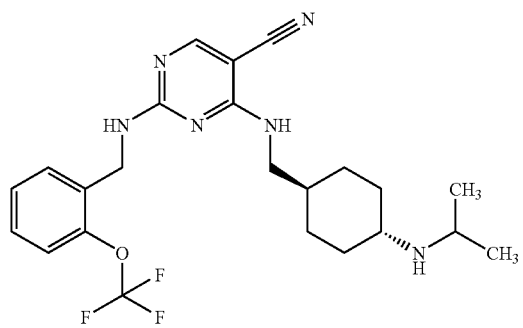

4-({[trans-4-(isopropylamino)cyclohexyl]methyl}amino)-2-{[2-(trifluoromethoxy)benzyl]amino}pyrimidine-5-carbonitrile

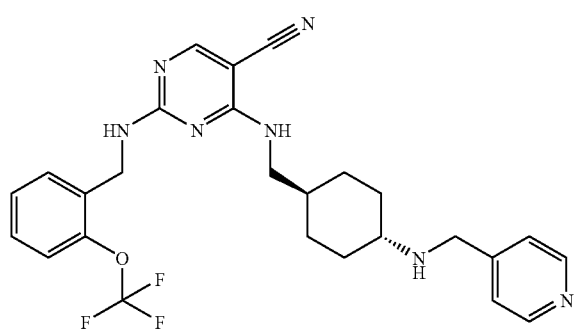

4-[({trans-4-[(pyridin-4-ylmethyl)amino]cyclohexyl}-methyl)amino]-2-{[2-(trifluoromethoxy)benzyl]amino}-pyrimidine-5-carbonitrile

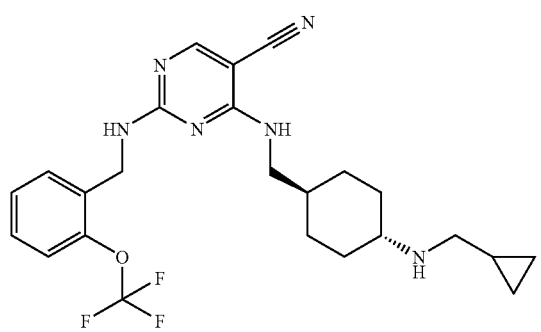

4-[({trans-4-[(cyclopropylmethyl)amino]cyclohexyl}-methyl)amino]-2-{[2-(trifluoromethoxy)benzyl]amino}-pyrimidine-5-carbonitrile

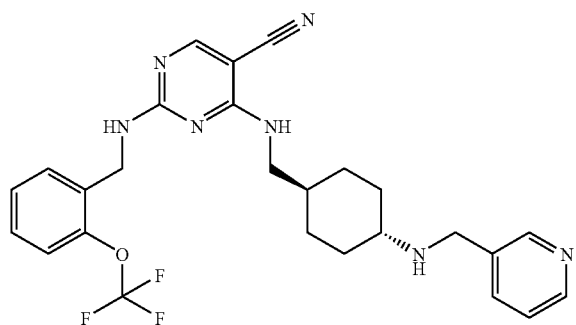

4-[({trans-4-[(pyridin-3-ylmethyl)amino]cyclohexyl}-methyl)amino]-2-{[2-(trifluoromethoxy)benzyl]amino}-pyrimidine-5-carbonitrile

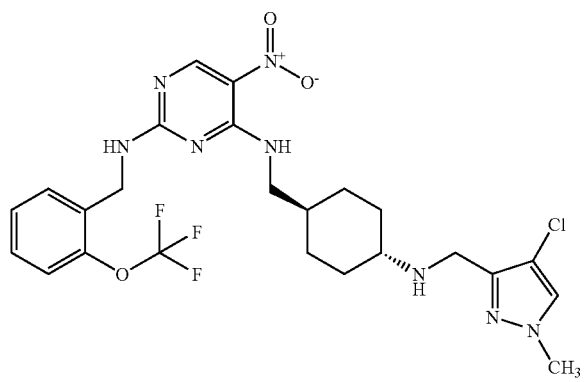

N⁴-[(trans-4-{[(4-chloro-1-methyl-1H-pyrazol-3-yl)methyl]amino}cyclohexyl)methyl]-5-nitro-N²-[2-(trifluoromethoxy)benzyl]pyrimidine-2,4-diamine

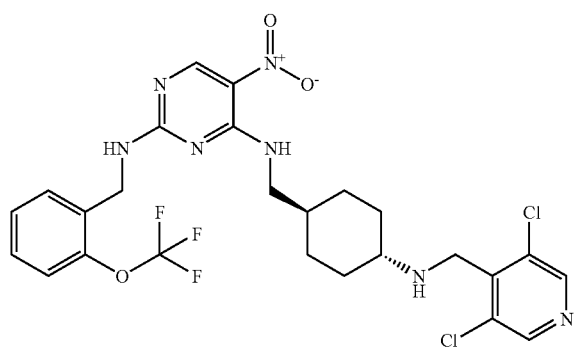

N⁴-[(trans-4-{[(3,5-dichloropyridin-4-yl)methyl]amino}cyclohexyl)methyl]-5-nitro-N²-[2-(trifluoromethoxy)benzyl]pyrimidine-2,4-diamine

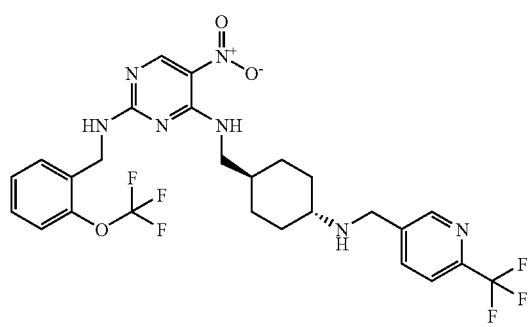

5-nitro-N²-[2-(trifluoromethoxy)benzyl]-N⁴-{[trans-4-({[6-(trifluoromethyl)pyridin-3-yl]methyl}amino)cyclohexyl]-methyl}pyrimidine-2,4-diamine

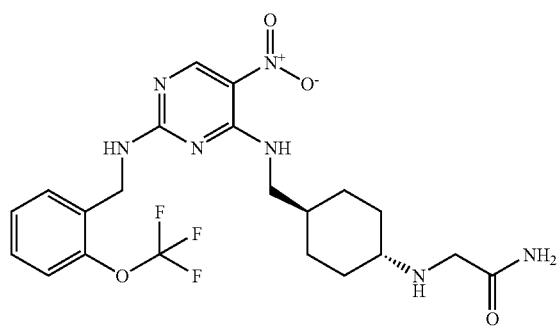

N²-(trans-4-{[(5-nitro-2-{[2-(trifluoromethoxy)benzyl]amino}pyrimidin-4-yl)amino]methyl}cyclohexyl)glycinamide -continued

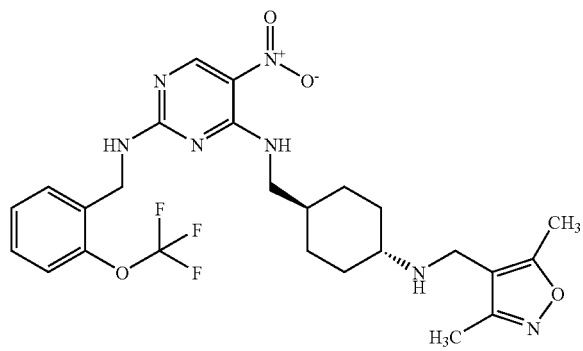

N⁴-[(trans-4-{[(3,5-dimethylisoxazol-4-yl)methyl]amino}cyclohexyl)methyl]-5-nitro-N²-[2-(trifluoromethoxy)benzyl]pyrimidine-2,4-diamine

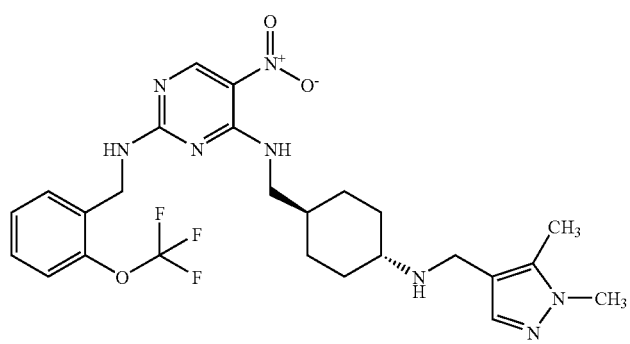

N⁴-[(trans-4-{[(1,5-dimethyl-1H-pyrazol-4-yl)methyl]amino}cyclohexyl)methyl]-5-nitro-N²-[2-(trifluoromethoxy)benzyl]pyrimidine-2,4-diamine

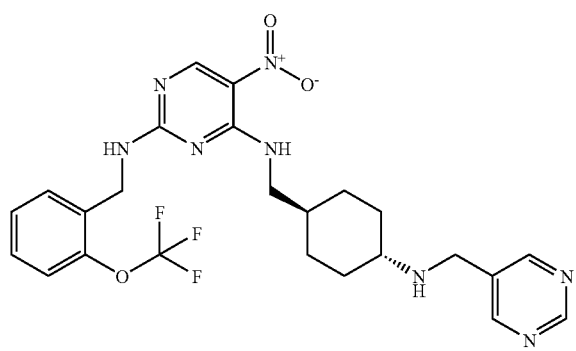

5-nitro-N⁴-({trans-4-[(pyrimidin-5-ylmethyl)amino]cyclohexyl}methyl)-N²-[2-(trifluoromethoxy)benzyl]pyrimidine-2,4-diamine

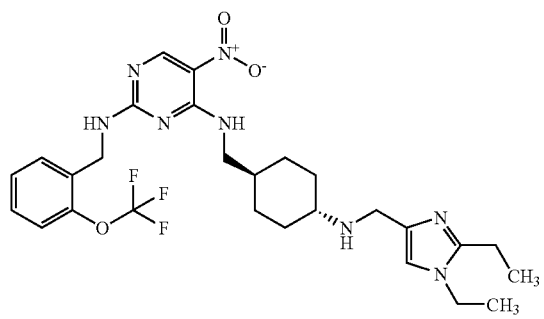

N⁴-[(trans-4-{[(1,2-diethyl-1H-imidazol-4-yl)methyl]amino}cyclohexyl)methyl]-5-nitro-N²-[2-(trifluoromethoxy)benzyl]pyrimidine-2,4-diamine

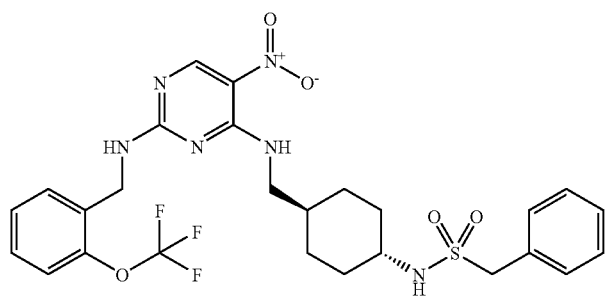

5-(trans-4-{[(5-nitro-2-{[2-(trifluoromethoxy)benzyl]-amino}pyrimidin-4-yl)amino]methyl}cyclohexyl)-1-phenylmethanesulfonamide

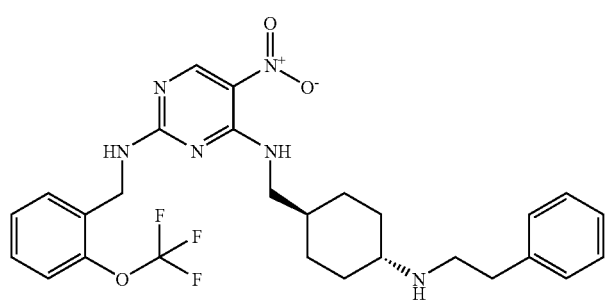

5-nitro-N$^4$-({trans-4-[(2-phenylethyl)amino]cyclohexyl}-methyl)-N$^2$-[2-(trifluoromethoxy)benzyl]pyrimidine-2,4-diamine

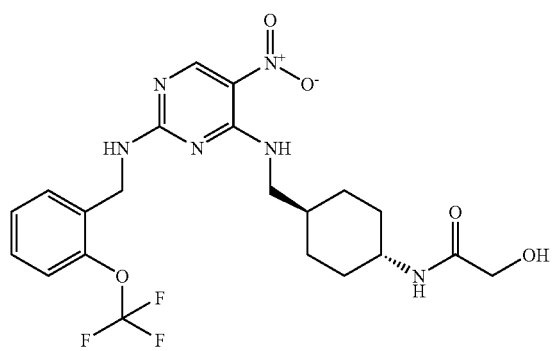

2-hydroxy-N-(trans-4-{[(5-nitro-2-{[2-(trifluoromethoxy)-benzyl]amino}pyrimidin-4-yl)amino]methyl}cyclohexyl)-acetamide

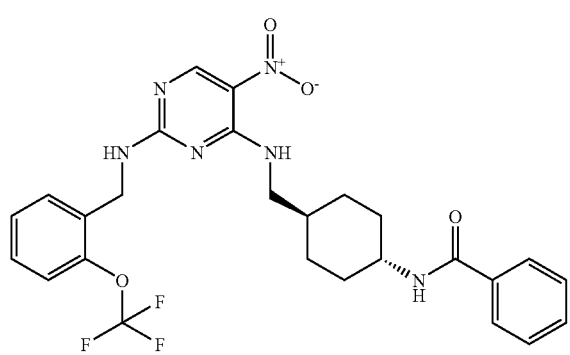

N-(trans-4-{[(5-nitro-2-{[2-(trifluoromethoxy)benzyl]-amino}pyrimidin-4-yl)amino]methyl}cyclohexyl)benzamide

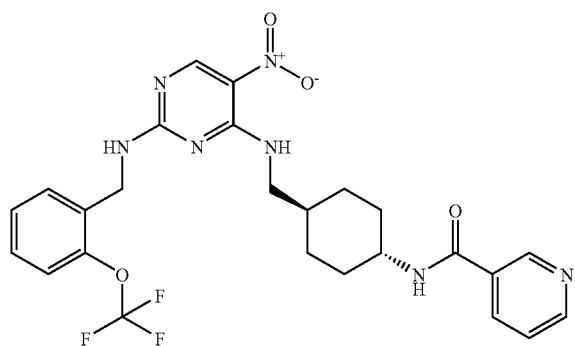

N-(trans-4-{[(5-nitro-2-{[2-(trifluoromethoxy)benzyl]-amino}pyrimidin-4-yl)amino]methyl}cyclohexyl)-nicotinamide

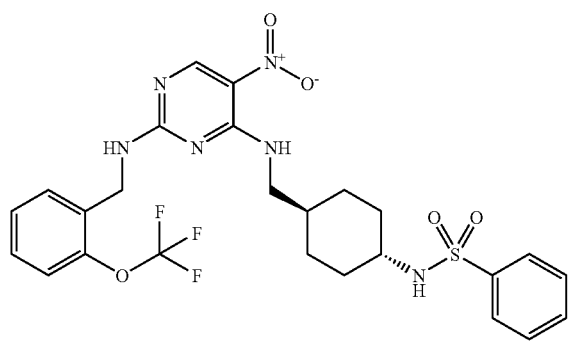

N-(trans-4-{[(5-nitro-2-{[2-(trifluoromethoxy)benzyl]amino}pyrimidin-4-yl)amino]methyl}cyclohexyl)benzenesulfonamide

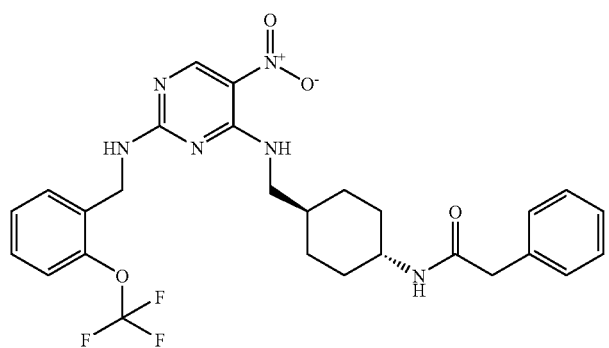

N-(trans-4-{[(5-nitro-2-{[2-(trifluoromethoxy)benzyl]amino}pyrimidin-4-yl)amino]methyl}cyclohexyl)-2-phenylacetamide

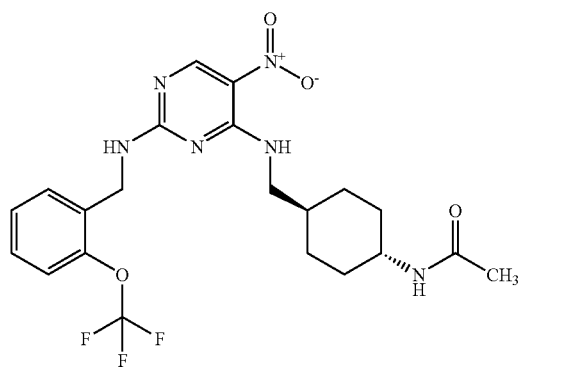

N-(trans-4-{[(5-nitro-2-{[2-(trifluoromethoxy)benzyl]amino}pyrimidin-4-yl)amino]methyl}cyclohexyl)acetamide

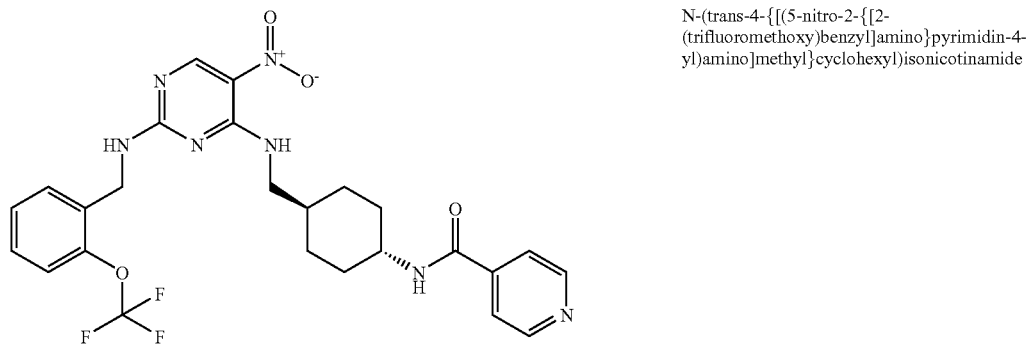

N-(trans-4-{[(5-nitro-2-{[2-(trifluoromethoxy)benzyl]amino}pyrimidin-4-yl)amino]methyl}cyclohexyl)isonicotinamide

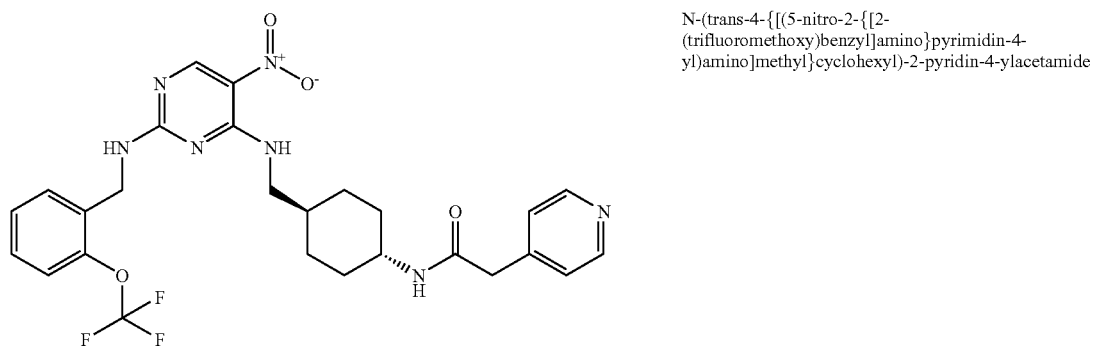

N-(trans-4-{[(5-nitro-2-{[2-(trifluoromethoxy)benzyl]amino}pyrimidin-4-yl)amino]methyl}cyclohexyl)-2-pyridin-4-ylacetamide

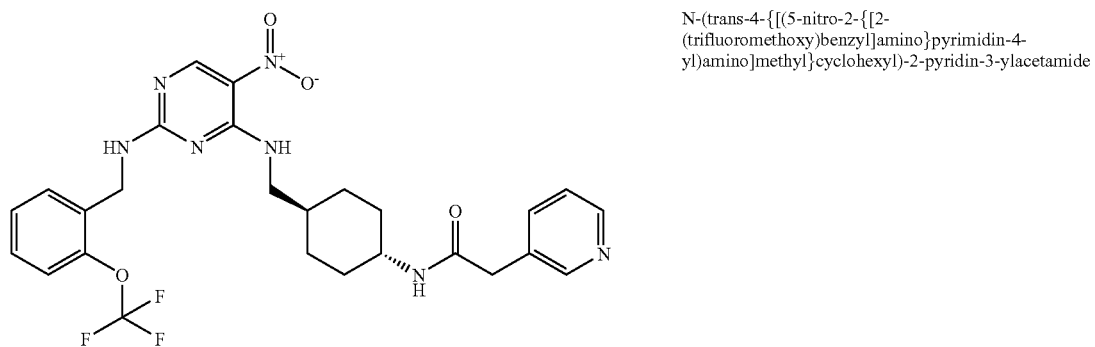

N-(trans-4-{[(5-nitro-2-{[2-(trifluoromethoxy)benzyl]amino}pyrimidin-4-yl)amino]methyl}cyclohexyl)-2-pyridin-3-ylacetamide

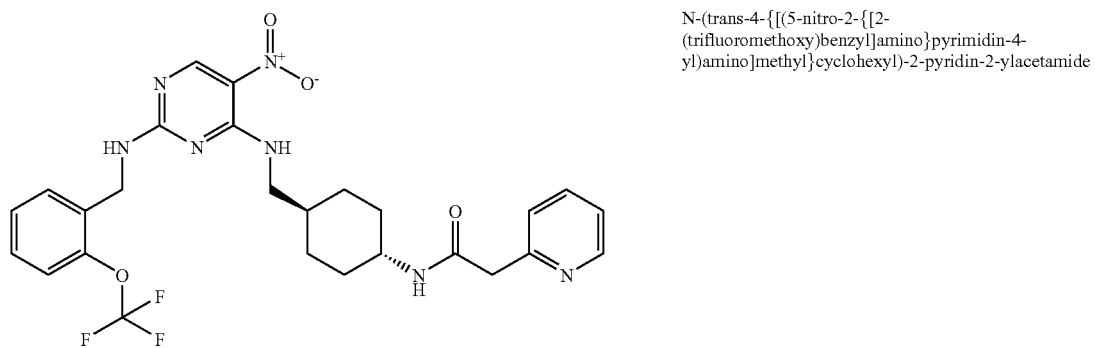

N-(trans-4-{[(5-nitro-2-{[2-(trifluoromethoxy)benzyl]amino}pyrimidin-4-yl)amino]methyl}cyclohexyl)-2-pyridin-2-ylacetamide

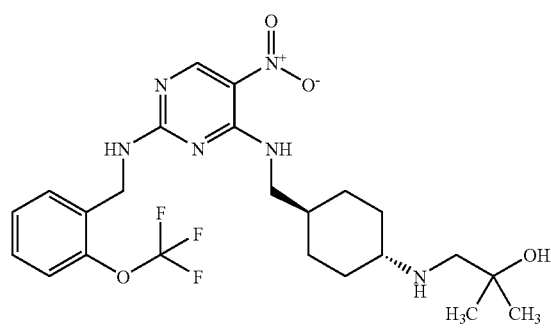

2-methyl-1-[(trans-4-{[(5-nitro-2-{[2-(trifluoromethoxy)benzyl]amino}pyrimidin-4-yl)amino]methyl}cyclohexyl)amino]propan-2-ol

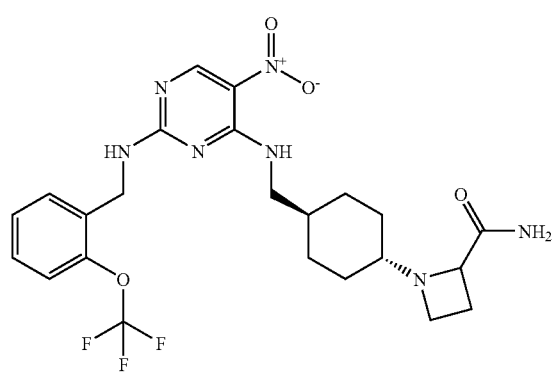

1-(trans-4-{[(5-nitro-2-{[2-(trifluoromethoxy)benzyl]amino}pyrimidin-4-yl)amino]methyl}cyclohexyl)azetidine-2-carboxamide

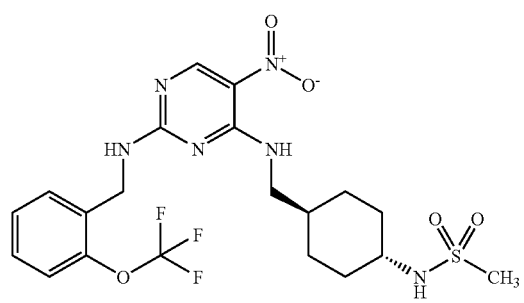

N-(trans-4-{[(5-nitro-2-{[2-(trifluoromethoxy)benzyl]amino}pyrimidin-4-yl)amino]methyl}cyclohexyl)methanesulfonamide

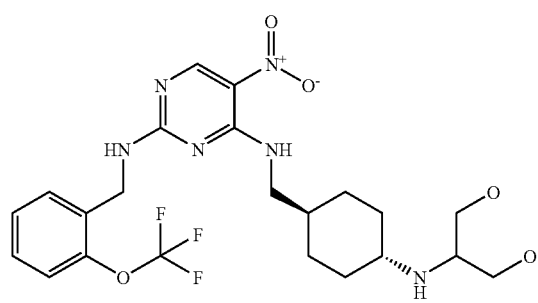

2-[(trans-4-{[(5-nitro-2-{[2-(trifluoromethoxy)benzyl]amino}pyrimidin-4-yl)amino]methyl}cyclohexyl)amino]propane-1,3-diol -continued
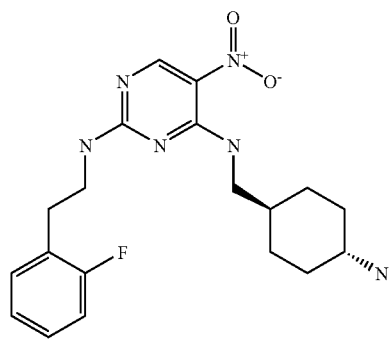
N⁴-[(trans-4-aminocyclohexyl)methyl]-N²-[2-(2-fluorophenyl)ethyl]-5-nitropyrimidine-2,4-diamine
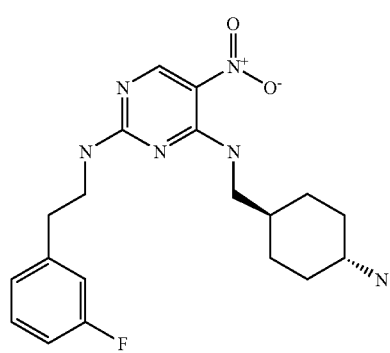
N⁴-[(trans-4-aminocyclohexyl)methyl]-N²-[2-(3-fluorophenyl)ethyl]-5-nitropyrimidine-2,4-diamine
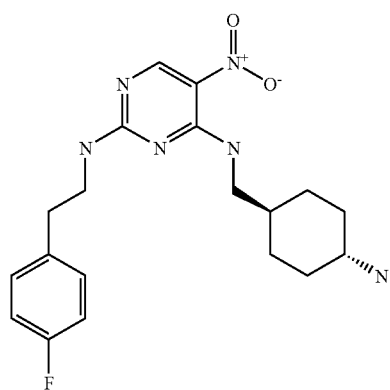
N⁴-[(trans-4-aminocyclohexyl)methyl]-N²-[2-(4-fluorophenyl)ethyl]-5-nitropyrimidine-2,4-diamine
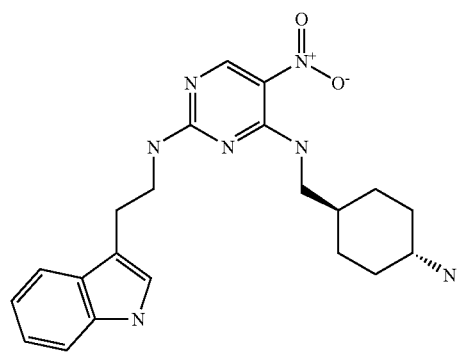
N⁴-[(trans-4-aminocyclohexyl)methyl]-N²-[2-(1H-indol-3-yl)ethyl]-5-nitropyrimidine-2,4-diamine

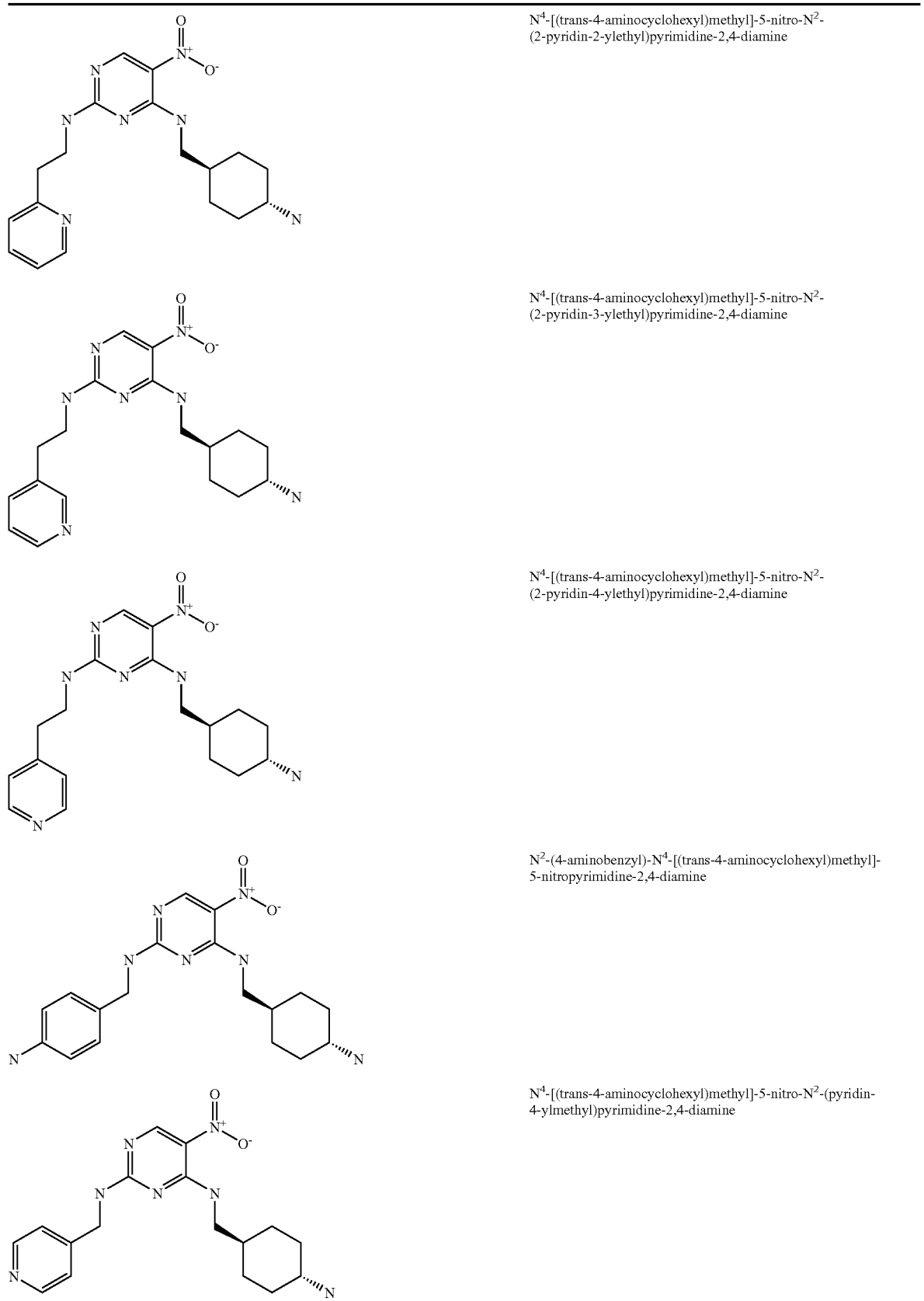

$N^4$-[(trans-4-aminocyclohexyl)methyl]-5-nitro-$N^2$-(2-pyridin-2-ylethyl)pyrimidine-2,4-diamine $N^4$-[(trans-4-aminocyclohexyl)methyl]-5-nitro-$N^2$-(2-pyridin-3-ylethyl)pyrimidine-2,4-diamine $N^4$-[(trans-4-aminocyclohexyl)methyl]-5-nitro-$N^2$-(2-pyridin-4-ylethyl)pyrimidine-2,4-diamine $N^2$-(4-aminobenzyl)-$N^4$-[(trans-4-aminocyclohexyl)methyl]-5-nitropyrimidine-2,4-diamine $N^4$-[(trans-4-aminocyclohexyl)methyl]-5-nitro-$N^2$-(pyridin-4-ylmethyl)pyrimidine-2,4-diamine -continued

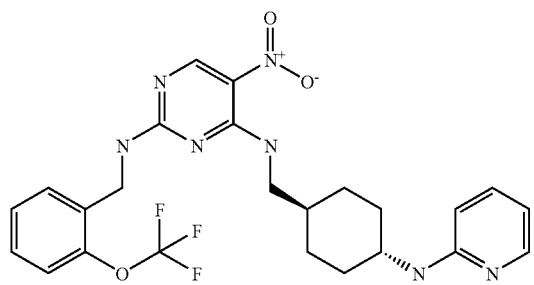

5-nitro-N$^4$-{[trans-4-(pyridin-2-ylamino)cyclohexyl]-methyl}-N$^2$-[2-(trifluoromethoxy)benzyl]pyrimidine-2,4-diamine

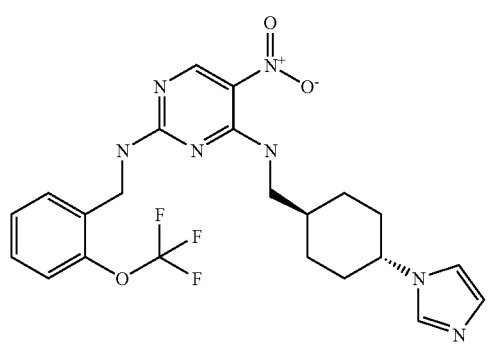

N$^4$-{[trans-4-(1H-imidazol-1-yl)cyclohexyl]methyl}-5-nitro-N$^2$-[2-(trifluoromethoxy)benzyl]pyrimidine-2,4-diamine

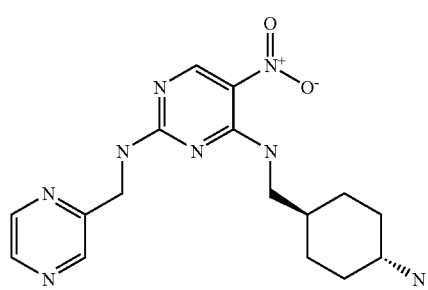

N$^4$-[(trans-4-aminocyclohexyl)methyl]-5-nitro-N$^2$-(pyrazin-2-ylmethyl)pyrimidine-2,4-diamine

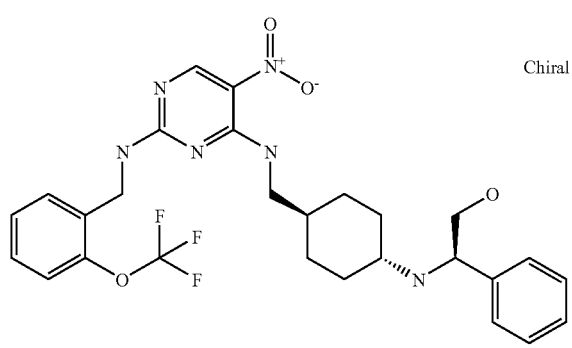

Chiral (2R)-2-[(trans-4-{[(5-nitro-2-{[2-(trifluoromethoxy)benzyl]amino}pyrimidin-4-yl)amino]methyl}cyclohexyl)amino]-2-phenylethanol

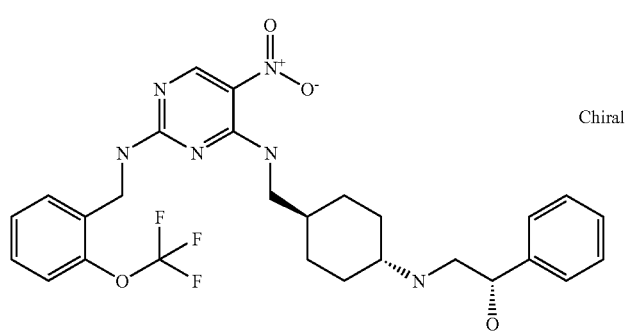

Chiral (1S)-2-[(trans-4-{[(5-nitro-2-{[2-(trifluoromethoxy)benzyl]amino}pyrimidin-4-yl)amino]methyl}cyclohexyl)amino]-1-phenylethanol -continued

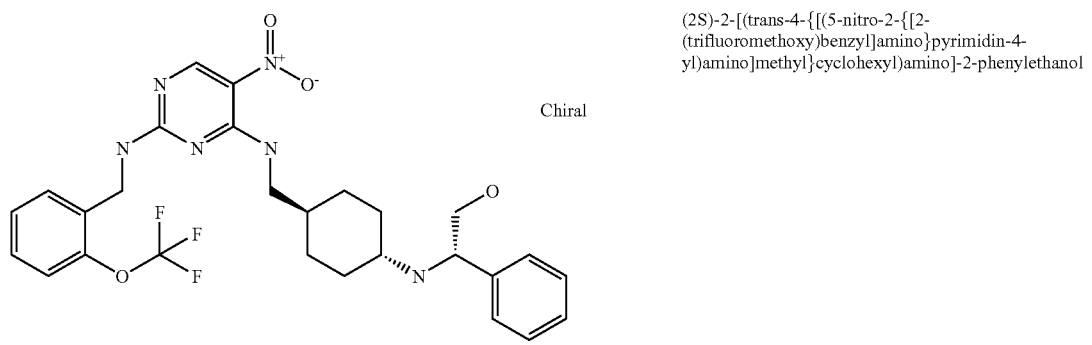

Chiral (2S)-2-[(trans-4-{[(5-nitro-2-{[2-(trifluoromethoxy)benzyl]amino}pyrimidin-4-yl)amino]methyl}cyclohexyl)amino]-2-phenylethanol

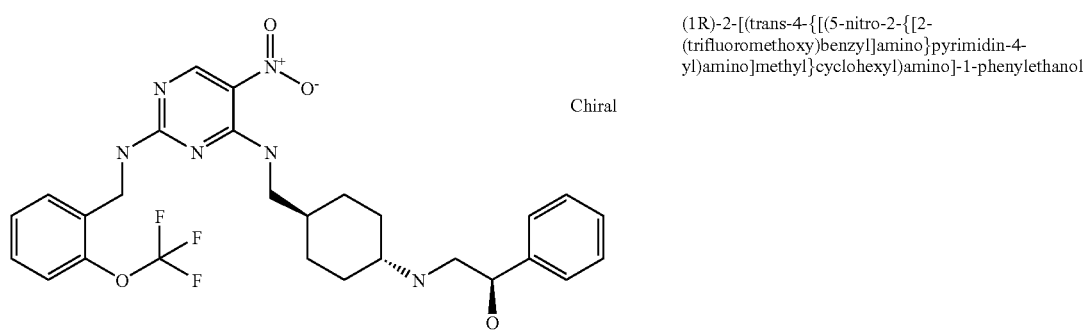

Chiral (1R)-2-[(trans-4-{[(5-nitro-2-{[2-(trifluoromethoxy)benzyl]amino}pyrimidin-4-yl)amino]methyl}cyclohexyl)amino]-1-phenylethanol

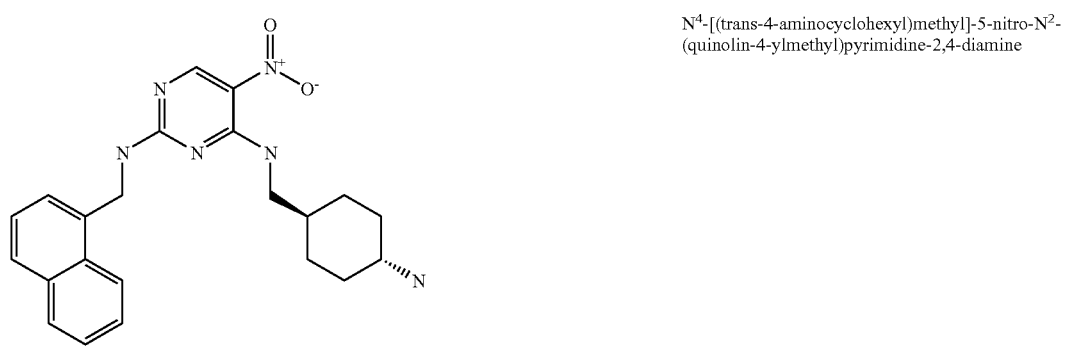

$N^4$-[(trans-4-aminocyclohexyl)methyl]-5-nitro-$N^2$-(quinolin-4-ylmethyl)pyrimidine-2,4-diamine

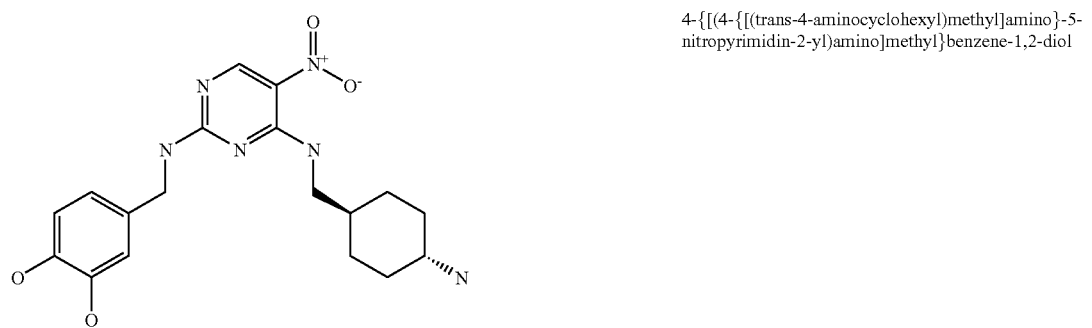

4-{[(4-{[(trans-4-aminocyclohexyl)methyl]amino}-5-nitropyrimidin-2-yl)amino]methyl}benzene-1,2-diol -continued

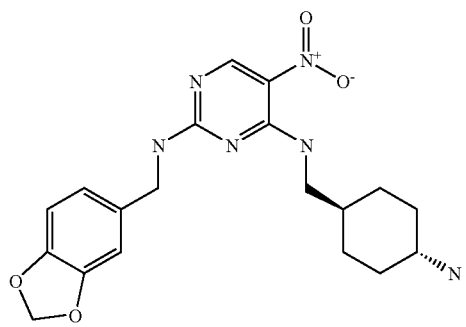

$N^4$-[(trans-4-aminocyclohexyl)methyl]-$N^2$-(1,3-benzodioxol-5-ylmethyl)-5-nitropyrimidine-2,4-diamine

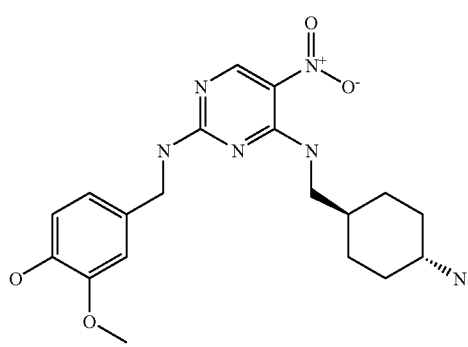

4-{[(4-{[(trans-4-aminocyclohexyl)methyl]amino}-5-nitropyrimidin-2-yl)amino]methyl}-2-methoxyphenol

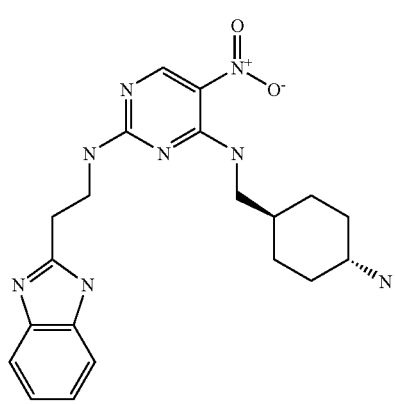

$N^4$-[(trans-4-aminocyclohexyl)methyl]-$N^2$-[2-(1H-benzimidazol-2-yl)ethyl]-5-nitropyrimidine-2,4-diamine

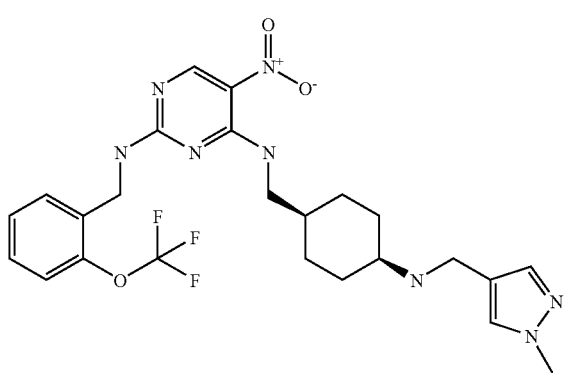

$N^4$-[(trans-4-{[(1-methyl-1H-pyrazol-4-yl)methyl]amino}cyclohexyl)methyl]-5-nitro-$N^2$-[2-(trifluoromethoxy)benzyl]pyrimidine-2,4-diamine -continued

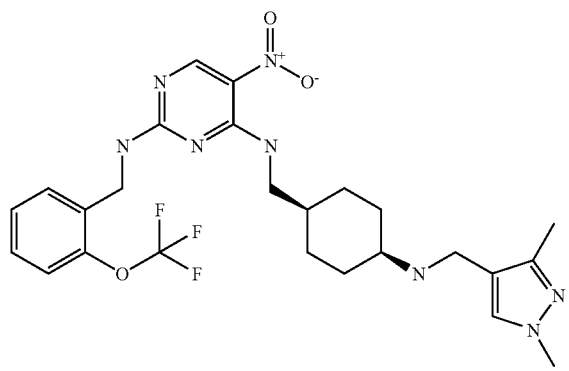

N4-[(trans-4-{[(1,3-dimethyl-1H-pyrazol-4-yl)methyl]amino}cyclohexyl)methyl]-5-nitro-N2-[2-(trifluoromethoxy)benzyl]pyrimidine-2,4-diamine

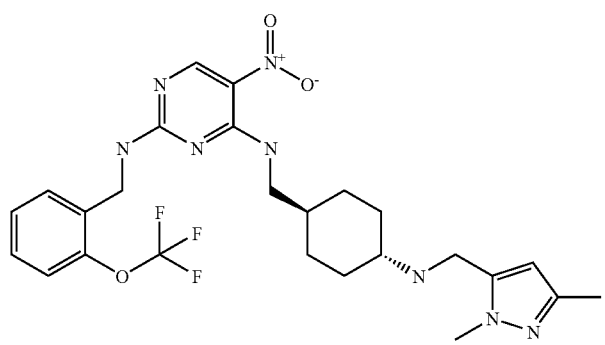

N4-[(trans-4-{[(1,3-dimethyl-1H-pyrazol-5-yl)methyl]amino}cyclohexyl)methyl]-5-nitro-N2-[2-(trifluoromethoxy)benzyl]pyrimidine-2,4-diamine

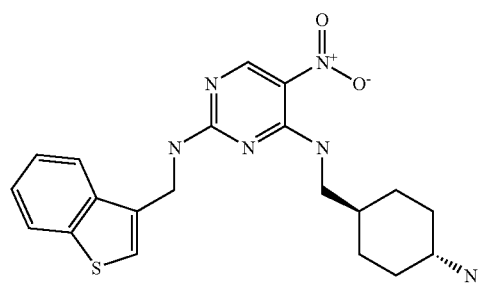

N4-[(trans-4-aminocyclohexyl)methyl]-N2-(1-benzothien-3-ylmethyl)-5-nitropyrimidine-2,4-diamine

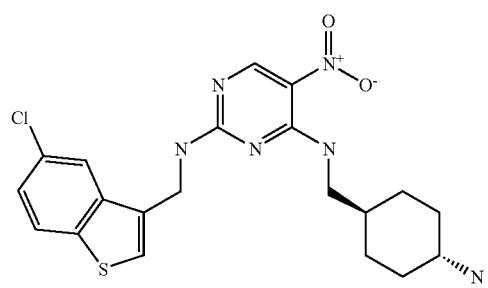

N4-[(trans-4-aminocyclohexyl)methyl]-N2-[(5-chloro-1-benzothien-3-yl)methyl]-5-nitropyrimidine-2,4-diamine

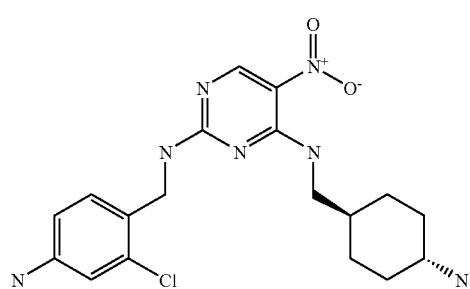

N2-(4-amino-2-chlorobenzyl)-N4-[(trans-4-aminocyclohexyl)methyl]-5-nitropyrimidine-2,4-diamine -continued

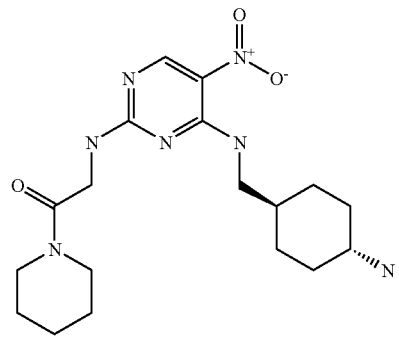

$N^4$-[(trans-4-aminocyclohexyl)methyl]-5-nitro-$N^2$-(2-oxo-2-piperidin-1-ylethyl)pyrimidine-2,4-diamine

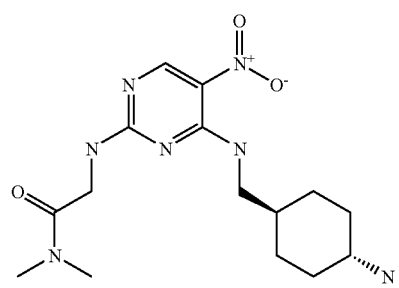

$N^2$-(4-{[(trans-4-aminocyclohexyl)methyl]amino}-5-nitropyrimidin-2-yl)-N,N-dimethylglycinamide

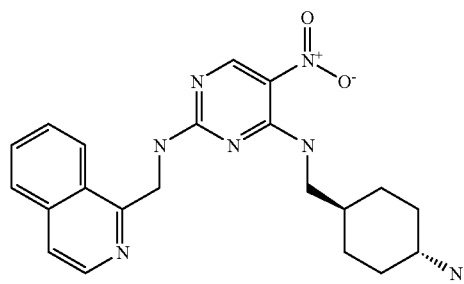

$N^4$-[(trans-4-aminocyclohexyl)methyl]-$N^2$-(isoquinolin-1-ylmethyl)-5-nitropyrimidine-2,4-diamine

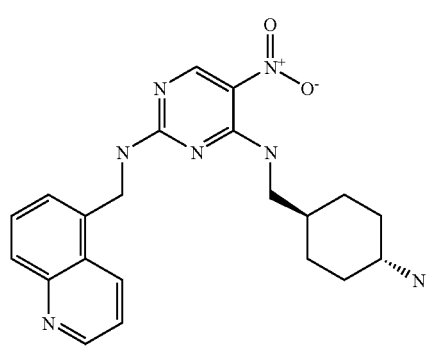

$N^4$-[(trans-4-aminocyclohexyl)methyl]-5-nitro-$N^2$-(quinolin-5-ylmethyl)pyrimidine-2,4-diamine

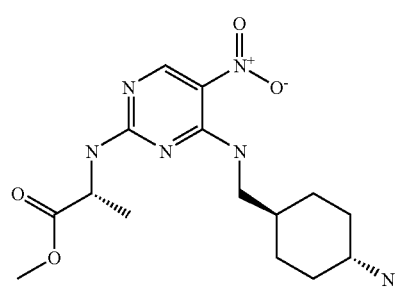

methyl N-(4-{[(trans-4-aminocyclohexyl)methyl]amino}-5-nitropyrimidin-2-yl)-L-alaninate -continued

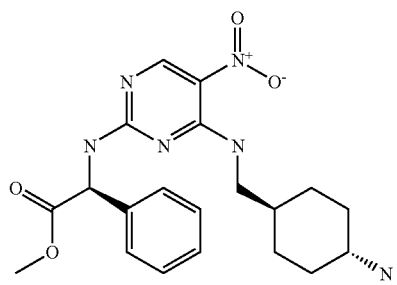

methyl (2S)-[(4-{[(trans-4-aminocyclohexyl)methyl]-amino]-5-nitropyrimidin-2-yl)amino](phenyl)acetate

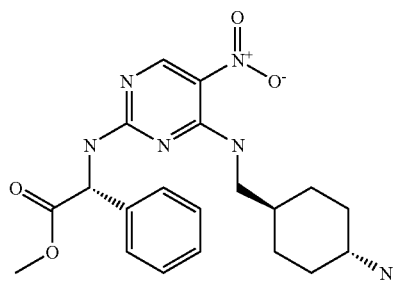

methyl (2R)-[(4-{[(trans-4-aminocyclohexyl)methyl]-amino}-5-nitropyrimidin-2-yl)amino](phenyl)acetate

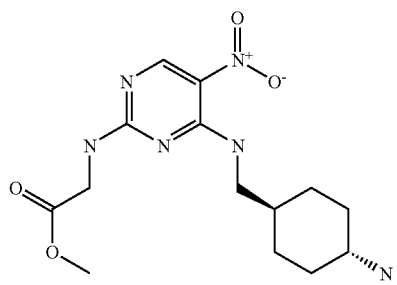

methyl N-(4-{[(trans-4-aminocyclohexyl)methyl]amino}-5-nitropyrimidin-2-yl)glycinate Chiral

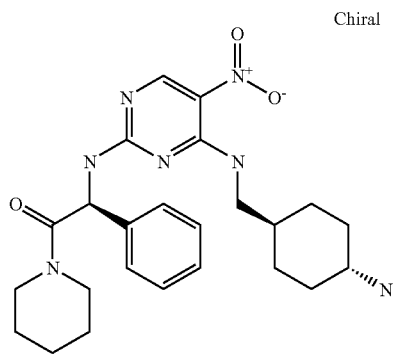

$N^4$-[(trans-4-aminocyclohexyl)methyl]-5-nitro-$N^2$-[(1S)-2-oxo-1-phenyl-2-piperidin-1-ylethyl]pyrimidine-2,4-diamine Chiral

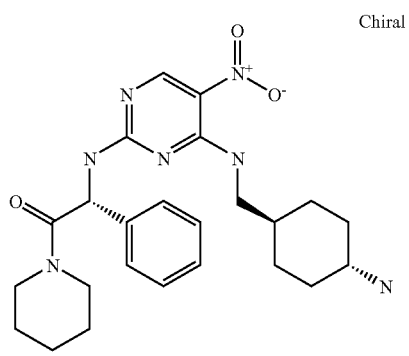

$N^4$-[(trans-4-aminocyclohexyl)methyl]-5-nitro-$N^2$-[(1R)-2-oxo-1-phenyl-2-piperidin-1-ylethyl]pyrimidine-2,4-diamine

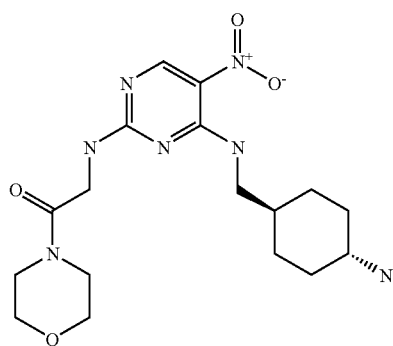
$N^4$-[(trans-4-aminocyclohexyl)methyl]-$N^2$-(2-morpholin-4-yl-2-oxoethyl)-5-nitropyrimidine-2,4-diamine
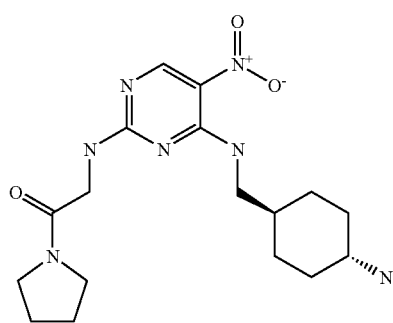
$N^4$-[(trans-4-aminocyclohexyl)methyl]-5-nitro-$N^2$-(2-oxo-2-pyrrolidin-1-ylethyl)pyrimidine-2,4-diamine
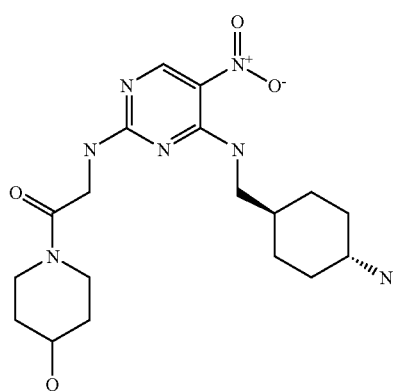
1-[N-(4-{[(trans-4-aminocyclohexyl)methyl]amino}-5-nitropyrimidin-2-yl)glycyl]piperidin-4-ol
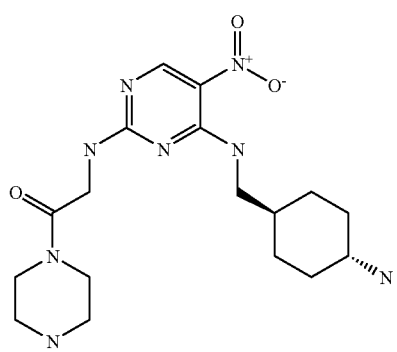
$N^4$-[(trans-4-aminocyclohexyl)methyl]-5-nitro-$N^2$-(2-oxo-2-piperazin-1-ylethyl)pyrimidine-2,4-diamine

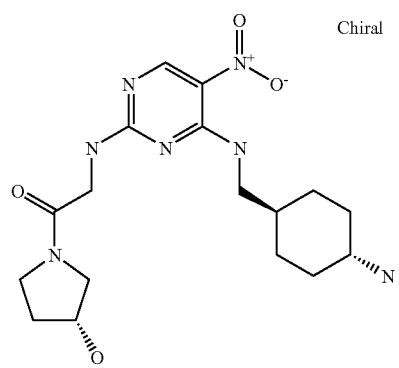 Chiral
(3R)-1-[N-(4-{[(trans-4-aminocyclohexyl)methyl]amino}-5-nitropyrimidin-2-yl)glycyl]pyrrolidin-3-ol
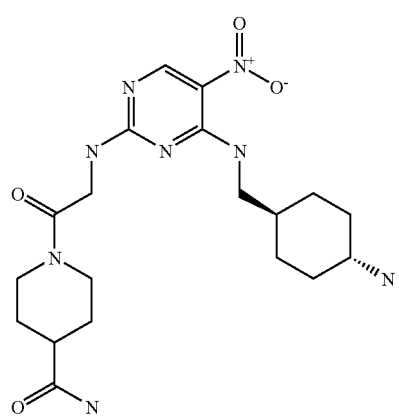
1-[N-(4-{[(trans-4-aminocyclohexyl)methyl]amino}-5-nitropyrimidin-2-yl)glycyl]piperidine-4-carboxamide
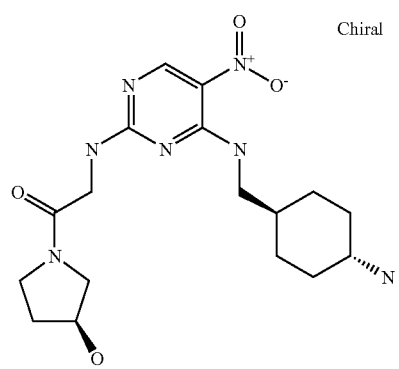 Chiral
(3S)-1-[N-(4-{[(trans-4-aminocyclohexyl)methyl]amino}-5-nitropyrimidin-2-yl)glycyl]pyrrolidin-3-ol
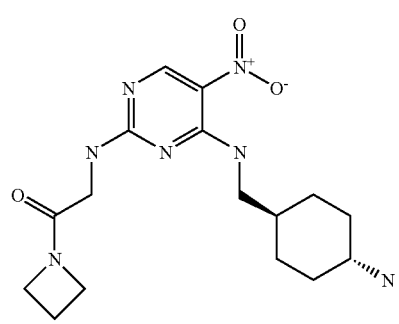
$N^4$-[(trans-4-aminocyclohexyl)methyl]-$N^2$-(2-azetidin-1-yl-2-oxoethyl)-5-nitropyrimidine-2,4-diamine

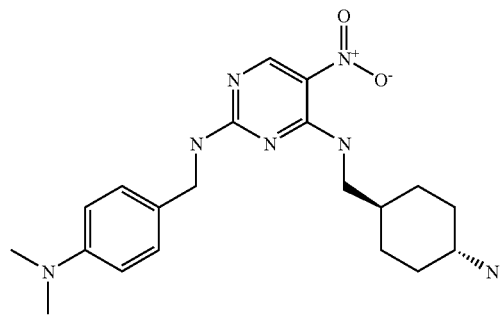

$N^4$-[(trans-4-aminocyclohexyl)methyl]-$N^2$-[4-(dimethylamino)benzyl]-5-nitropyrimidine-2,4-diamine

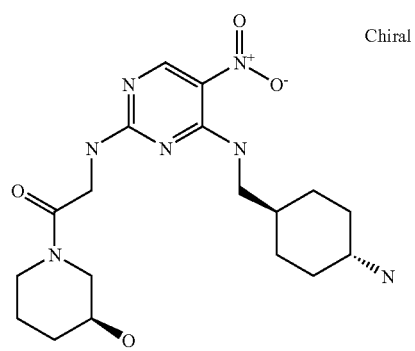

Chiral (3R)-1-[N-(4-{[(trans-4-aminocyclohexyl)methyl]amino}-5-nitropyrimidin-2-yl)glycyl]piperidin-3-ol

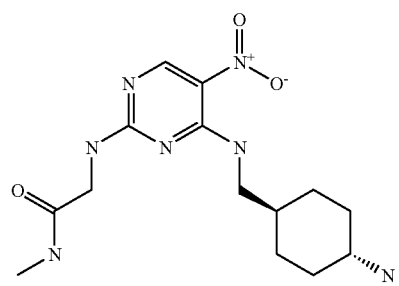

$N^2$-(4-{[(trans-4-aminocyclohexyl)methyl]amino}-5-nitropyrimidin-2-yl)-N-methylglycinamide

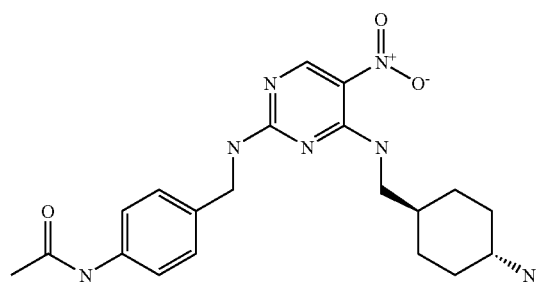

N-(4-{[(4-{[(trans-4-aminocyclohexyl)methyl]amino}-5-nitropyrimidin-2-yl)amino]methyl}phenyl)acetamide

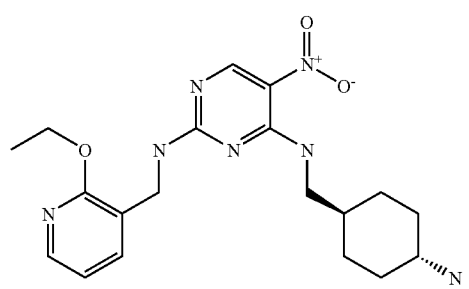

$N^4$-[(trans-4-aminocyclohexyl)methyl]-$N^2$-[(2-ethoxypyridin-3-yl)methyl]-5-nitropyrimidine-2,4-diamine -continued

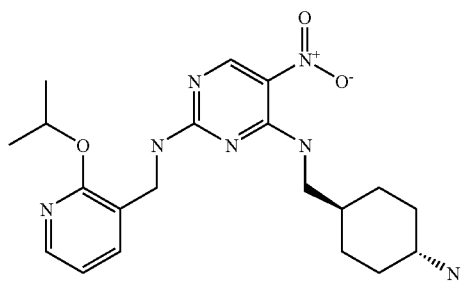

$N^4$-[(trans-4-aminocyclohexyl)methyl]-$N^2$-[(2-isopropoxypyridin-3-yl)methyl]-5-nitropyrimidine-2,4-diamine

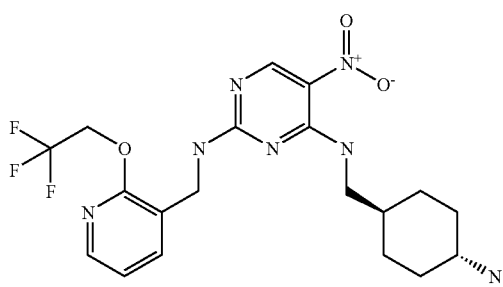

$N^4$-[(trans-4-aminocyclohexyl)methyl]-5-nitro-$N^2$-{[2-(2,2,2-trifluoroethoxy)pyridin-3-yl]methyl}pyrimidine-2,4-diamine

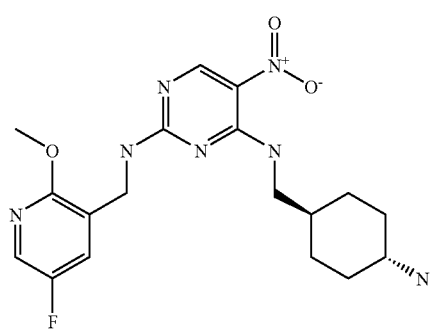

$N^4$-[(trans-4-aminocyclohexyl)methyl]-$N^2$-[(5-fluoro-2-methoxypyridin-3-yl)methyl]-5-nitropyrimidine-2,4-diamine

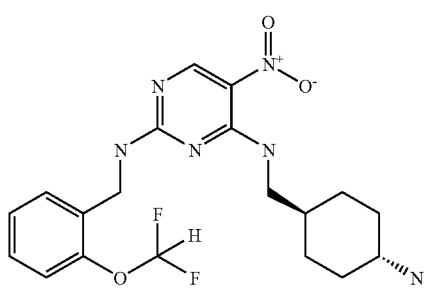

$N^4$-[(trans-4-aminocyclohexyl)methyl]-$N^2$-[2-(difluoromethoxy)benzyl]-5-nitropyrimidine-2,4-diamine

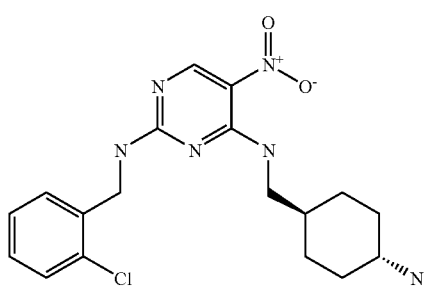

$N^4$-[(trans-4-aminocyclohexyl)methyl]-$N^2$-(2-chlorobenzyl)-5-nitropyrimidine-2,4-diamine -continued

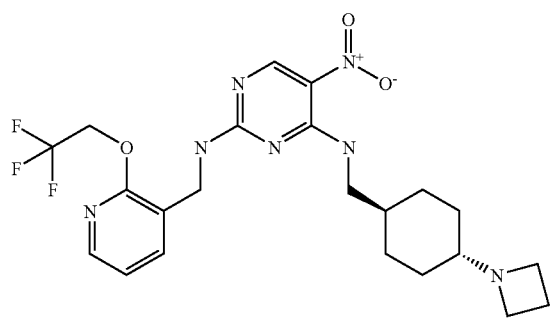

$N^4$-[(trans-4-azetidin-1-ylcyclohexyl)methyl]-5-nitro-$N^2$-{[2-(2,2,2-trifluoroethoxy)pyridin-3-yl]methyl}pyrimidine-2,4-diamine

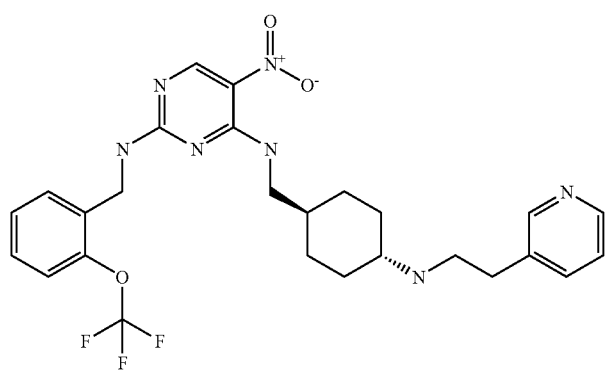

5-nitro-$N^4$-({trans-4-[(2-pyridin-3-ylethyl)amino]cyclohexyl}methyl)-$N^2$-[2-(trifluoromethoxy)benzyl]pyrimidine-2,4-diamine

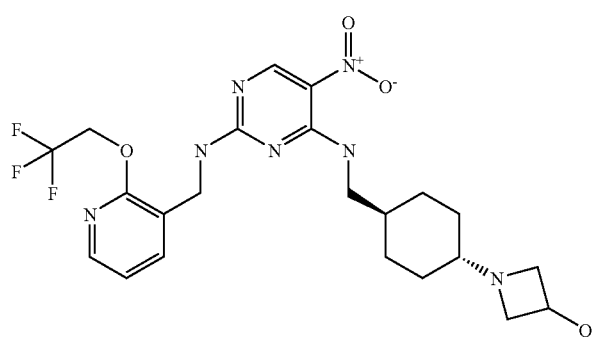

1-[trans-4-({[5-nitro-2-({[2-(2,2,2-trifluoroethoxy)pyridin-3-yl]methyl}amino)pyrimidin-4-yl]amino}methyl)cyclohexyl]azetidin-3-ol

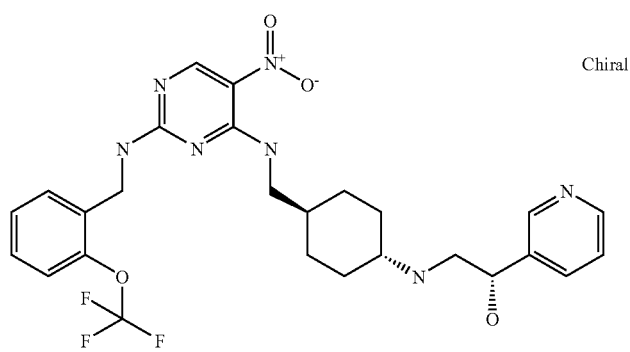

Chiral (1S)-2-[(trans-4-{[(5-nitro-2-{[2-(trifluoromethoxy)benzyl]amino}pyrimidin-4-yl)amino]methyl}cyclohexyl)amino]-1-pyridin-3-ylethanol -continued

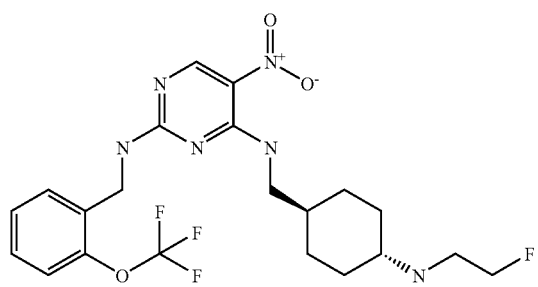

N⁴-({trans-4-[(2-fluoroethyl)amino]cyclohexyl}methyl)-5-nitro-N²-[2-(trifluoromethoxy)benzyl]pyrimidine-2,4-diamine

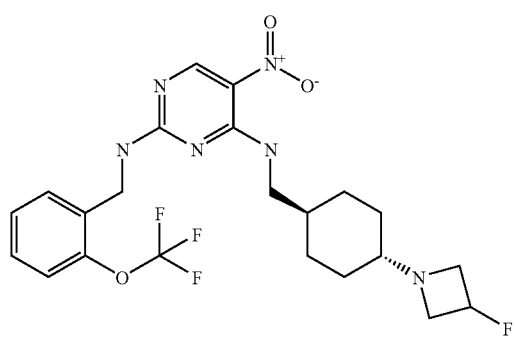

N⁴-{[trans-4-(3-fluoroazetidin-1-yl)cyclohexyl]methyl}-5-nitro-N²-[2-(trifluoromethoxy)benzyl]pyrimidine-2,4-diamine

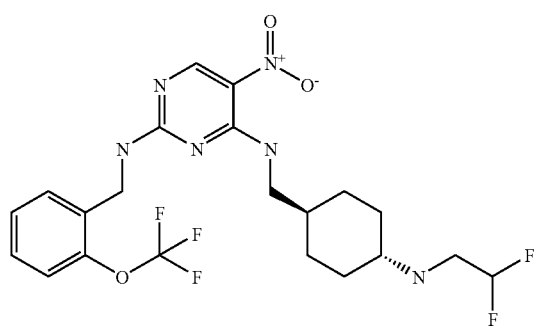

N⁴-({trans-4-[(2,2-difluoroethyl)amino]cyclohexyl}methyl)-5-nitro-N²-[2-(trifluoromethoxy)benzyl]pyrimidine-2,4-diamine

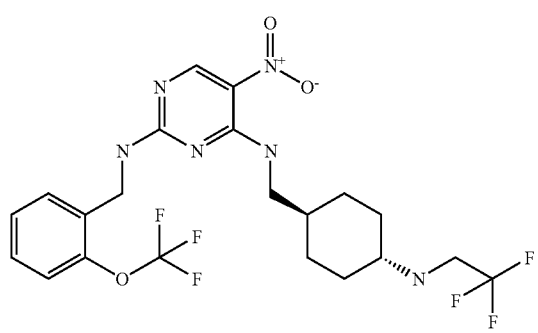

5-nitro-N⁴-({trans-4-[(2,2,2-trifluoroethyl)amino]cyclohexyl}methyl)-N²-[2-(trifluoromethoxy)benzyl]-pyrimidine-2,4-diamine

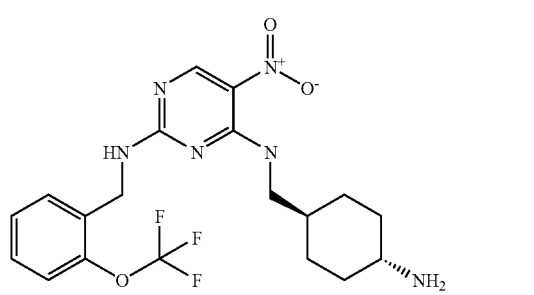

4-[(trans-4-aminocyclohexyl)methoxy]-5-nitro-N-[2-(trifluoromethoxy)benzyl]pyrimidin-2-amine -continued

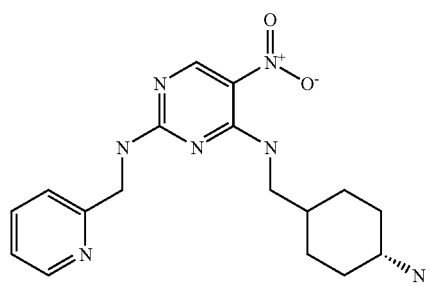

$N^4$-[(trans-4-aminocyclohexyl)methyl]-5-nitro-$N^2$-(pyridin-2-ylmethyl)pyrimidine-2,4-diamine

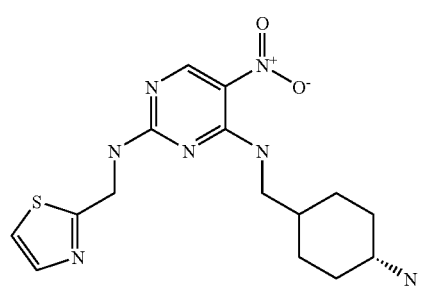

$N^4$-[(trans-4-aminocyclohexyl)methyl]-5-nitro-$N^2$-(1,3-thiazol-2-ylmethyl)pyrimidine-2,4-diamine

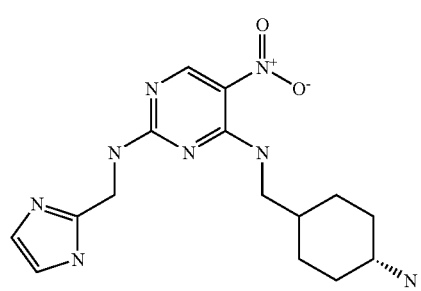

$N^4$-[(trans-4-aminocyclohexyl)methyl]-$N^2$-(1H-imidazol-2-ylmethyl)-5-nitropyrimidine-2,4-diamine

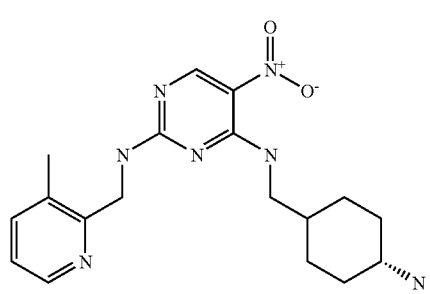

$N^4$-[(trans-4-aminocyclohexyl)methyl]-$N^2$-[(3-methylpyridin-2-yl)methyl]-5-nitropyrimidine-2,4-diamine

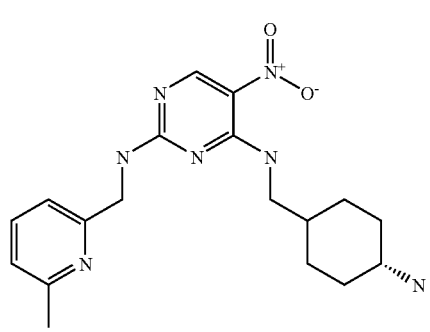

$N^4$-[(trans-4-aminocyclohexyl)methyl]-$N^2$-[(6-methylpyridin-2-yl)methyl]-5-nitropyrimidine-2,4-diamine

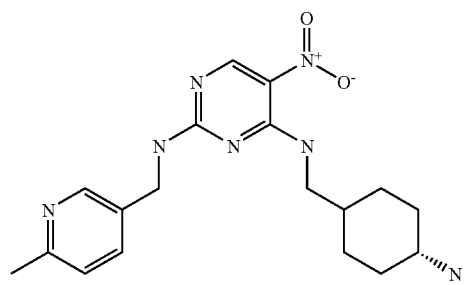

N[4]-[(trans-4-aminocyclohexyl)methyl]-N[2]-[(6-methylpyridin-3-yl)methyl]-5-nitropyrimidine-2,4-diamine

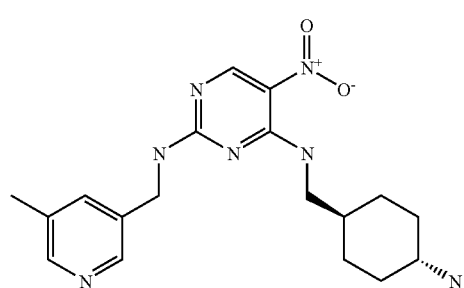

N[4]-[(trans-4-aminocyclohexyl)methyl]-N[2]-[(5-methylpyridin-3-yl)methyl]-5-nitropyrimidine-2,4-diamine

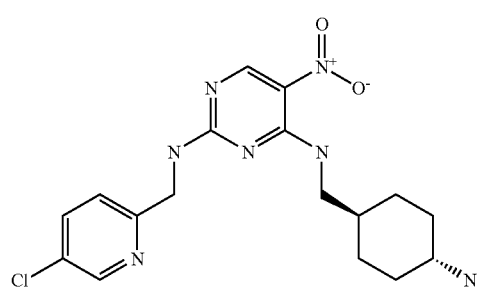

N[4]-[(trans-4-aminocyclohexyl)methyl]-N[2]-[(5-chloropyridin-2-yl)methyl]-5-nitropyrimidine-2,4-diamine

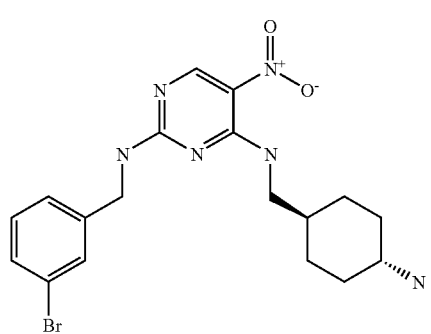

N[4]-[(trans-4-aminocyclohexyl)methyl]-N[2]-(3-bromobenzyl)-5-nitropyrimidine-2,4-diamine

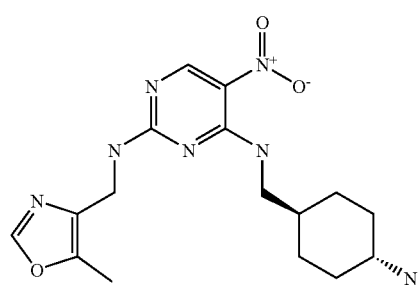

N[4]-[(trans-4-aminocyclohexyl)methyl]-N[2]-[(5-methyl-1,3-oxazol-4-yl)methyl]-5-nitropyrimidine-2,4-diamine -continued

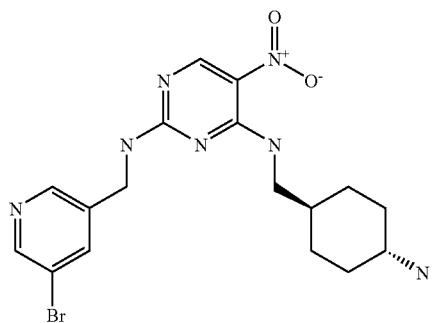

$N^4$-[(trans-4-aminocyclohexyl)methyl]-$N^2$-[(5-bromopyridin-3-yl)methyl]-5-nitropyrimidine-2,4-diamine

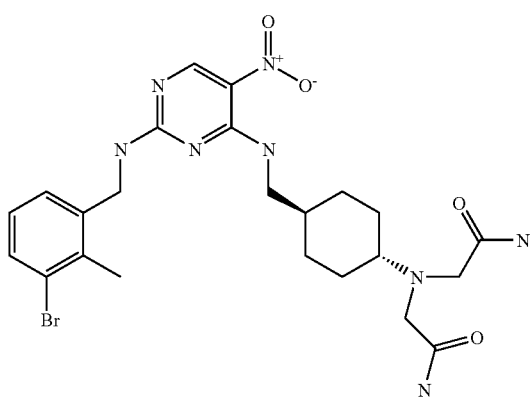

2,2'-({trans-4-[({2-[(3-bromo-2-methylbenzyl)amino]-5-nitropyrimidin-4-yl}amino)methyl]cyclohexyl}-imino)diacetamide

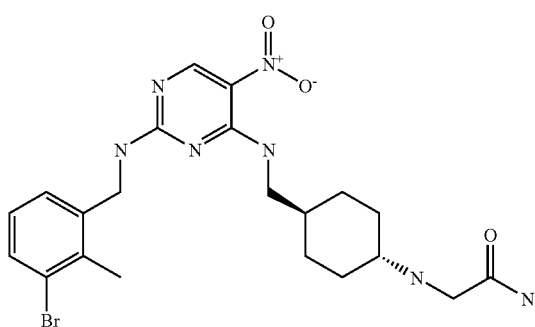

$N^2$-{trans-4-[({2-[(3-bromo-2-methylbenzyl)amino]-5-nitropyrimidin-4-yl}amino)methyl]cyclohexyl}glycinamide

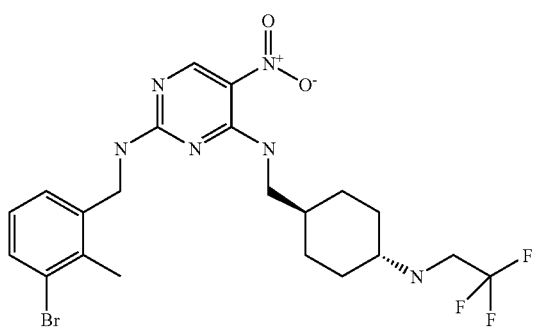

$N^2$-(3-bromo-2-methylbenzyl)-5-nitro-$N^4$-({trans-4-[(2,2,2-trifluoroethyl)amino]cyclohexyl}methyl)pyrimidine-2,4-diamine

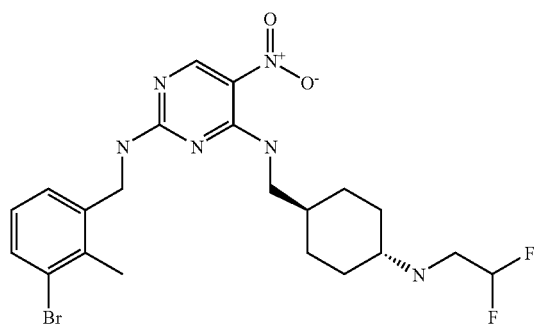

$N^2$-(3-bromo-2-methylbenzyl)-$N^4$-({trans-4-[(2,2-difluoroethyl)amino]cyclohexyl}methyl)-5-nitropyrimidine-2,4-diamine

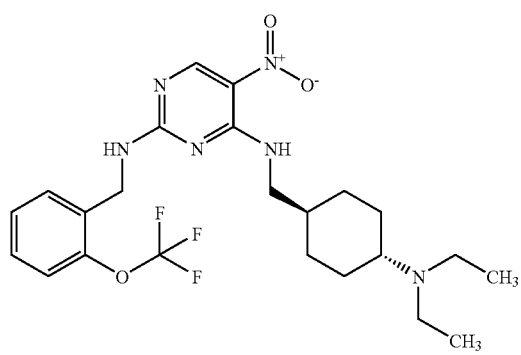

$N^4$-{[trans-4-(diethylamino)cyclohexyl]methyl}-5-nitro-$N^2$-[2-(trifluoromethoxy)benzyl]pyrimidine-2,4-diamine

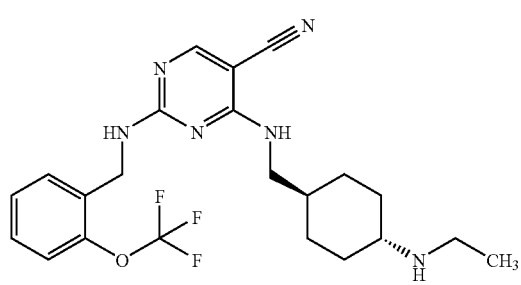

4-({[trans-4-(ethylamino)cyclohexyl]methyl}amino)-2-{[2-(trifluoromethoxy)benzyl]amino}pyrimidine-5-carbonitrile

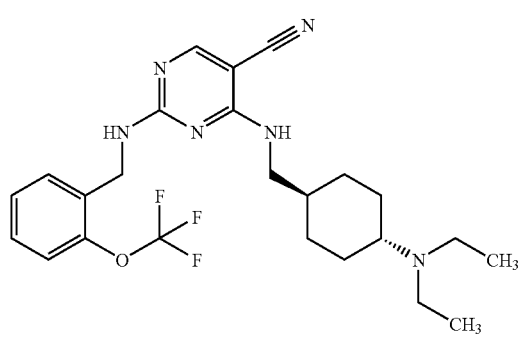

4-({[trans-4-(diethylamino)cyclohexyl]methyl}amino)-2-{[2-(trifluoromethoxy)benzyl]amino}pyrimidine-5-carbonitrile

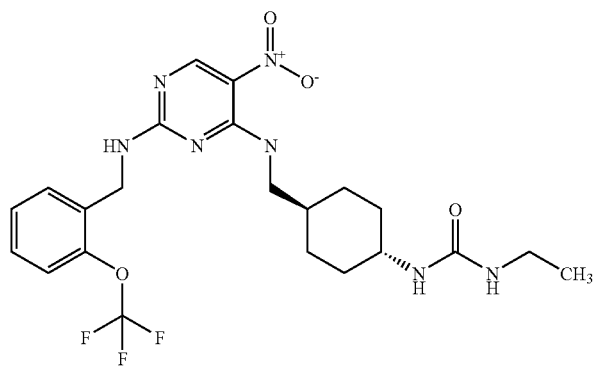

N-ethyl-N'-(trans-4-{[(5-nitro-2-{[2-(trifluoromethoxy)benzyl]amino}pyrimidin-4-yl)amino]methyl}cyclohexyl)urea

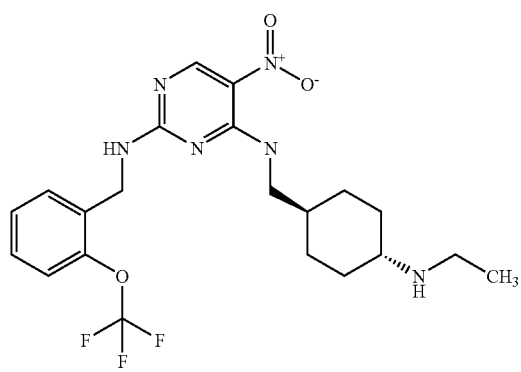

N$^4$-{[trans-4-(ethylamino)cyclohexyl]methyl}-5-nitro-N$^2$-[2-(trifluoromethoxy)benzyl]pyrimidine-2,4-diamine

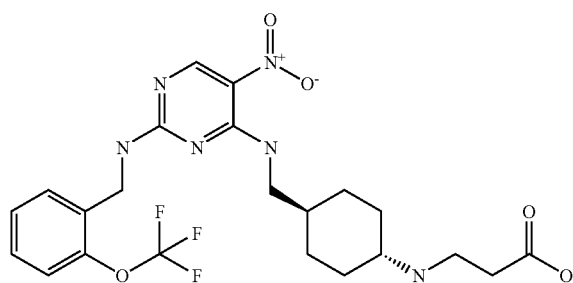

N-(trans-4-{[(5-nitro-2-{[2-(trifluoromethoxy)benzyl]-amino}pyrimidin-4-yl)amino]methyl}cyclohexyl)glycine

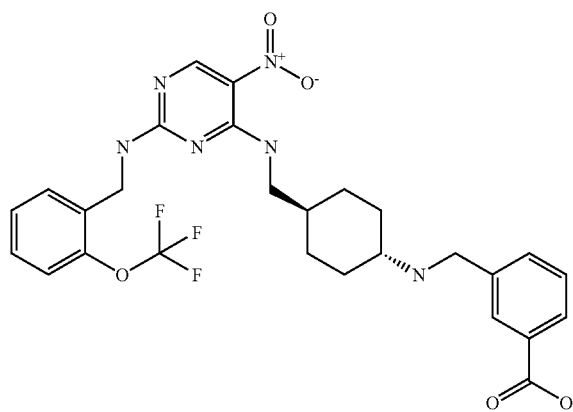

N-(trans-4-{[(5-nitro-2-{[2-(trifluoromethoxy)benzyl]-amino}pyrimidin-4-yl)amino]methyl}cyclohexyl)-beta-alanine

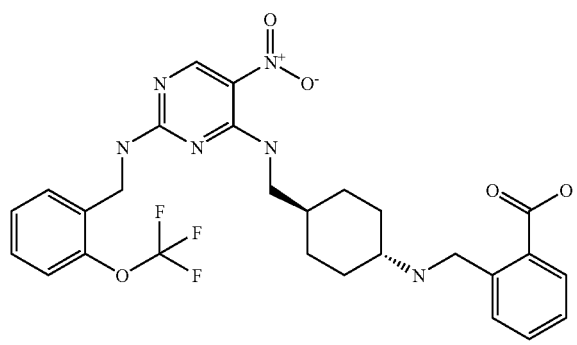

3-{[(trans-4-{[(5-nitro-2-{[2-(trifluoromethoxy)benzyl]amino}pyrimidin-4-yl)amino]methyl}cyclohexyl)amino]methyl}benzoic acid

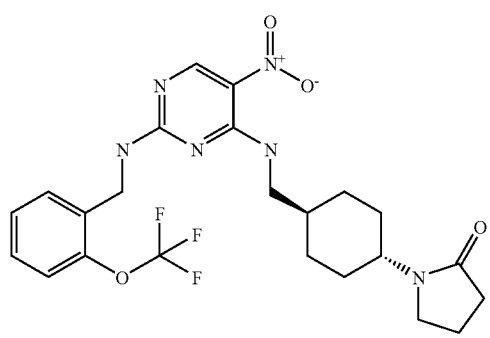

2-{[(trans-4-{[(5-nitro-2-{[2-(trifluoromethoxy)benzyl]amino}pyrimidin-4-yl)amino]methyl}cyclohexyl)amino]methyl}benzoic acid

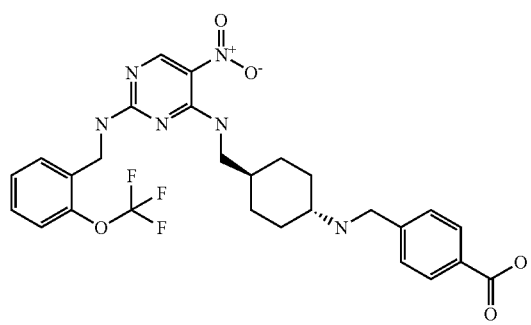

1-(trans-4-{[(5-nitro-2-{[2-(trifluoromethoxy)benzyl]-amino}pyrimidin-4-yl)amino]methyl}cyclohexyl)pyrrolidin-2-one

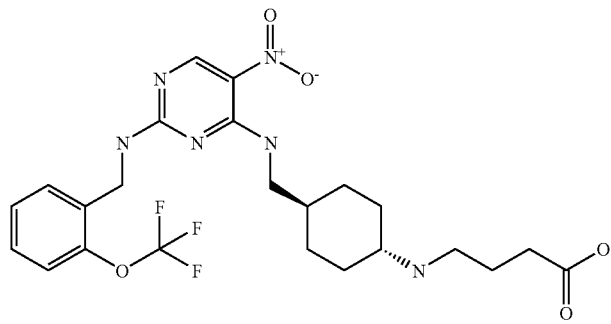

4-{[(trans-4-{[(5-nitro-2-{[2-(trifluoromethoxy)benzyl]-amino}pyrimidin-4-yl)amino]methyl}cyclohexyl)amino]-methyl}benzoic acid -continued

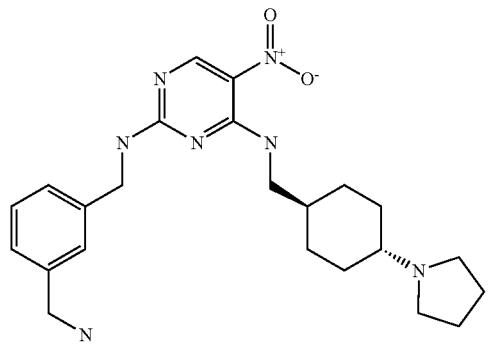

4-[(trans-4-{[(5-nitro-2-{[2-(trifluoromethoxy)benzyl]-amino}pyrimidin-4-yl)amino]methyl}cyclohexyl)amino]-butanoic acid

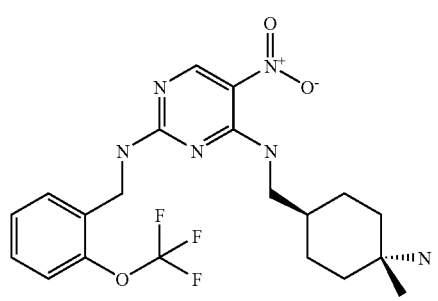

N²-[3-(aminomethyl)benzyl]-5-nitro-N⁴-[(trans-4-pyrrolidin-1-ylcyclohexyl)methyl]pyrimidine-2,4-diamine

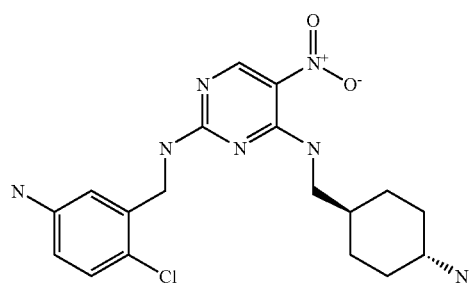

N⁴-[(trans-4-amino-4-methylcyclohexyl)methyl]-5-nitro-N²-[2-(trifluoromethoxy)benzyl]pyrimidine-2,4-diamine

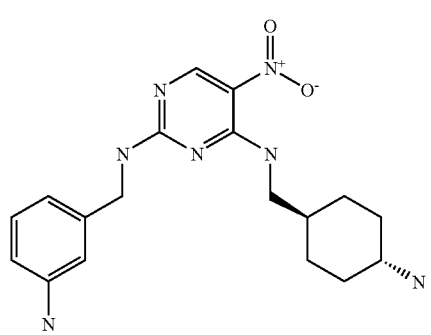

N²-(5-amino-2-chlorobenzyl)-N⁴-[(trans-4-aminocyclohexyl)methyl]-5-nitropyrimidine-2,4-diamine

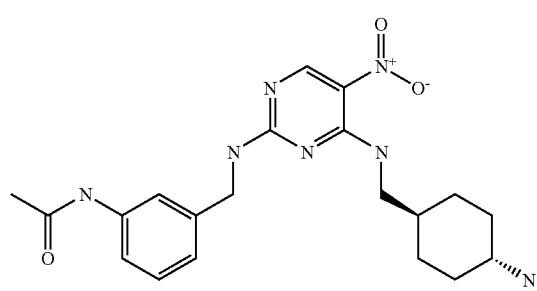

N²-(3-aminobenzyl)-N⁴-[(trans-4-aminocyclohexyl)methyl]-5-nitropyrimidine-2,4-diamine -continued

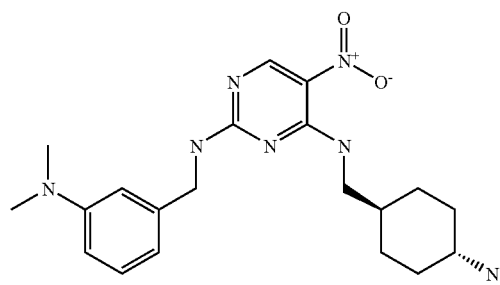

N-(3-{[(4-{[(trans-4-aminocyclohexyl)methyl]amino}-5-nitropyrimidin-2-yl)amino]methyl}phenyl)acetamide

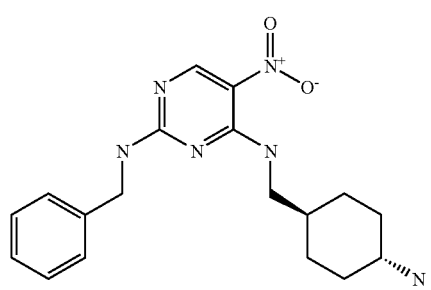

$N^4$-[(trans-4-aminocyclohexyl)methyl]-$N^2$-[3-(dimethylamino)benzyl]-5-nitropyrimidine-2,4-diamine

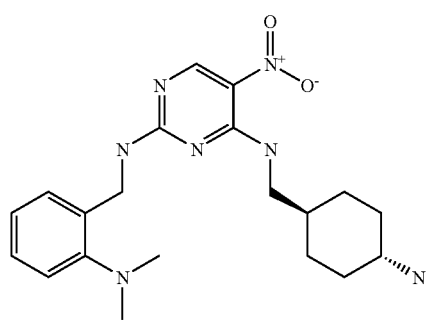

$N^4$-[(trans-4-aminocyclohexyl)methyl]-$N^2$-benzyl-5-nitropyrimidine-2,4-diamine

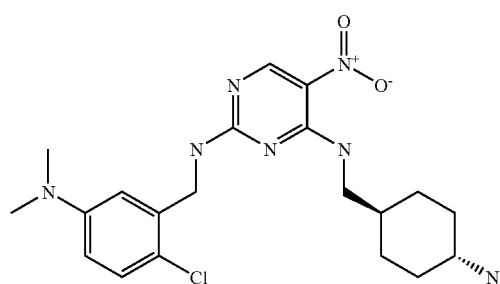

$N^4$-[(trans-4-aminocyclohexyl)methyl]-$N^2$-[2-(dimethylamino)benzyl]-5-nitropyrimidine-2,4-diamine

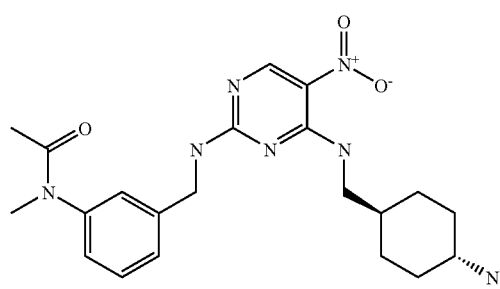

$N^4$-[(trans-4-aminocyclohexyl)methyl]-$N^2$-[2-chloro-5-(dimethylamino)benzyl]-5-nitropyrimidine-2,4-diamine -continued

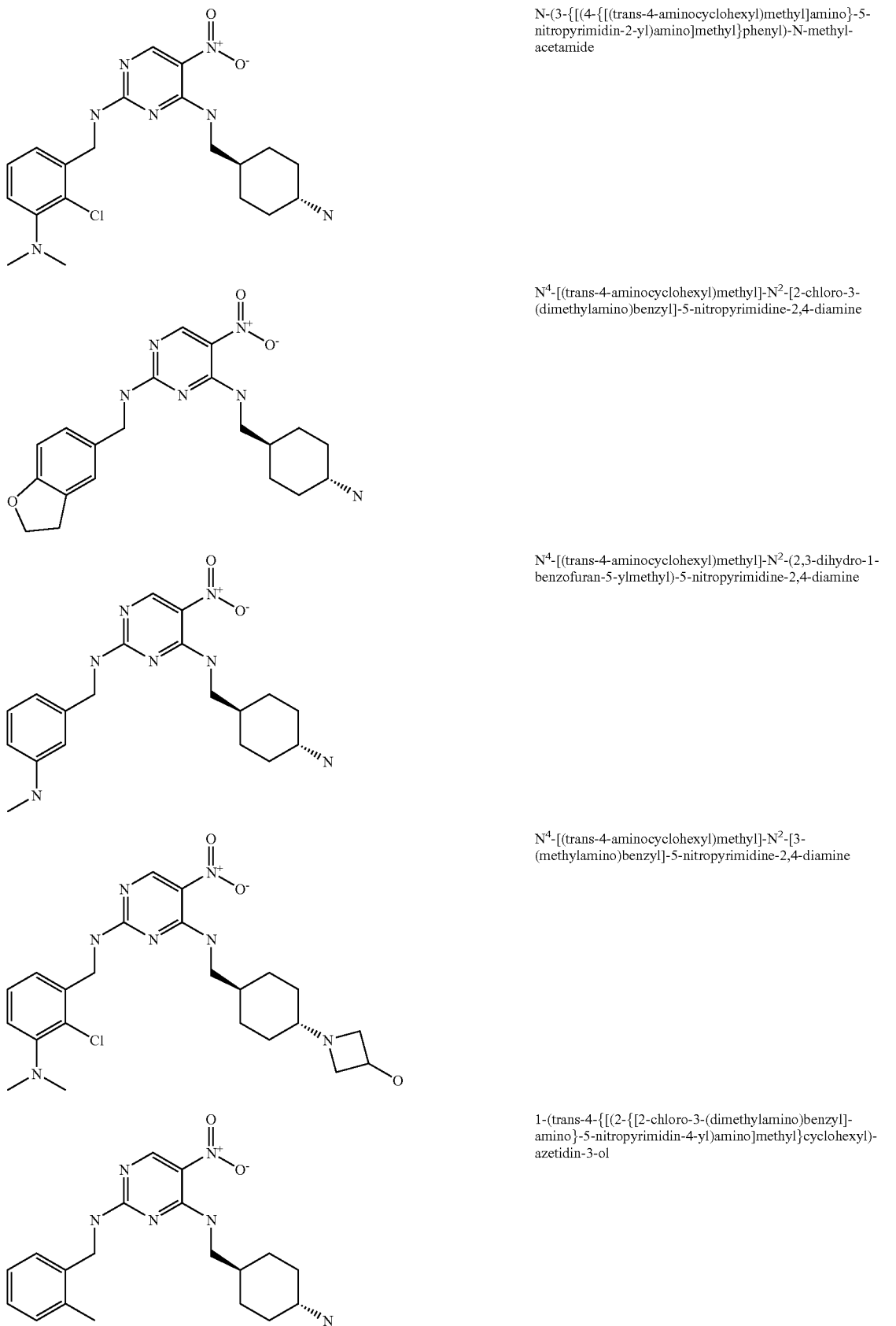

N-(3-{[(4-{[(trans-4-aminocyclohexyl)methyl]amino}-5-nitropyrimidin-2-yl)amino]methyl}phenyl)-N-methyl-acetamide $N^4$-[(trans-4-aminocyclohexyl)methyl]-$N^2$-[2-chloro-3-(dimethylamino)benzyl]-5-nitropyrimidine-2,4-diamine $N^4$-[(trans-4-aminocyclohexyl)methyl]-$N^2$-(2,3-dihydro-1-benzofuran-5-ylmethyl)-5-nitropyrimidine-2,4-diamine $N^4$-[(trans-4-aminocyclohexyl)methyl]-$N^2$-[3-(methylamino)benzyl]-5-nitropyrimidine-2,4-diamine 1-(trans-4-{[(2-{[2-chloro-3-(dimethylamino)benzyl]amino}-5-nitropyrimidin-4-yl)amino]methyl}cyclohexyl)-azetidin-3-ol

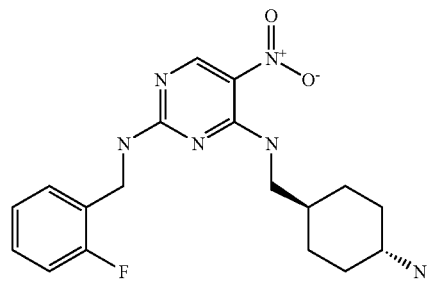
N⁴-[(trans-4-aminocyclohexyl)methyl]-N²-(2-methyl-benzyl)-5-nitropyrimidine-2,4-diamine
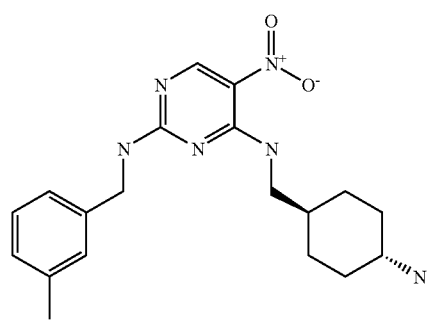
N⁴-[(trans-4-aminocyclohexyl)methyl]-N²-(2-fluorobenzyl)-5-nitropyrimidine-2,4-diamine
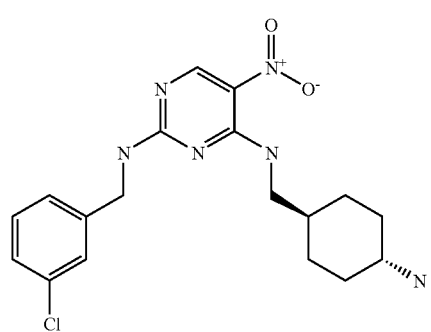
N⁴-[(trans-4-aminocyclohexyl)methyl]-N²-(3-methyl-benzyl)-5-nitropyrimidine-2,4-diamine
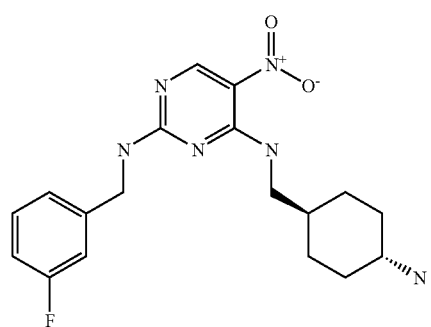
N⁴-[(trans-4-aminocyclohexyl)methyl]-N²-(3-chlorobenzyl)-5-nitropyrimidine-2,4-diamine -continued
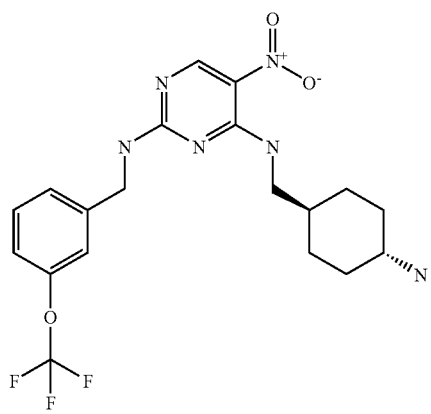
N⁴-[(trans-4-aminocyclohexyl)methyl]-N²-(3-fluorobenzyl)-5-nitropyrimidine-2,4-diamine
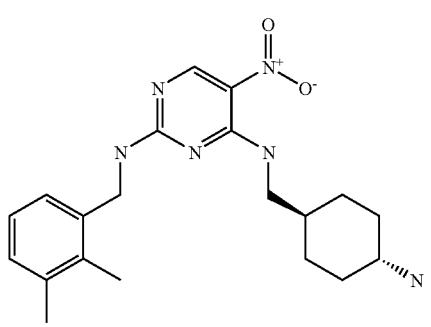
N⁴-[(trans-4-aminocyclohexyl)methyl]-5-nitro-N²-[3-(trifluoromethoxy)benzyl]pyrimidine-2,4-diamine
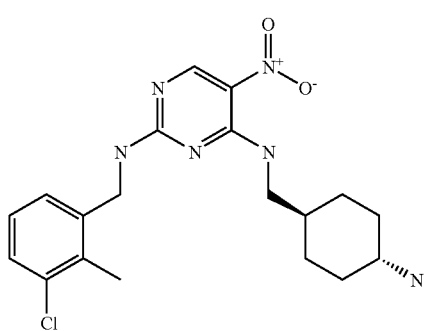
N⁴-[(trans-4-aminocyclohexyl)methyl]-N²-(2,3-dimethylbenzyl)-5-nitropyrimidine-2,4-diamine
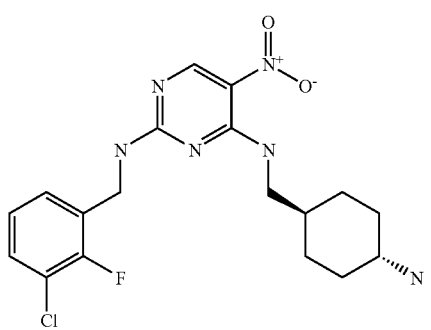
N⁴-[(trans-4-aminocyclohexyl)methyl]-N²-(3-chloro-2-methylbenzyl)-5-nitropyrimidine-2,4-diamine -continued

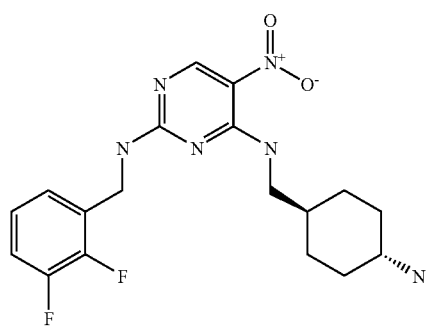

$N^4$-[(trans-4-aminocyclohexyl)methyl]-$N^2$-(3-chloro-2-fluorobenzyl)-5-nitropyrimidine-2,4-diamine

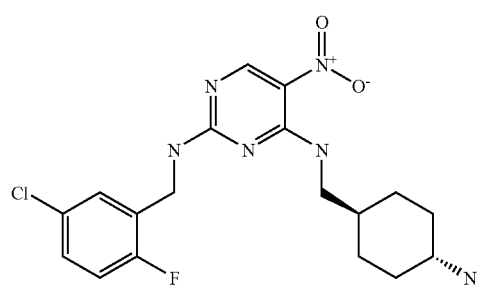

$N^4$-[(trans-4-aminocyclohexyl)methyl]-$N^2$-(2,3-difluorobenzyl)-5-nitropyrimidine-2,4-diamine

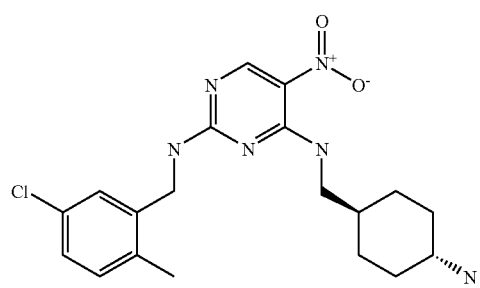

$N^4$-[(trans-4-aminocyclohexyl)methyl]-$N^2$-(5-chloro-2-fluorobenzyl)-5-nitropyrimidine-2,4-diamine

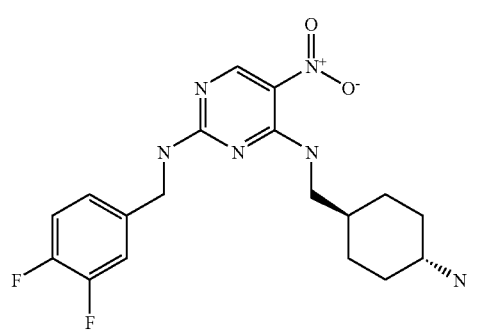

$N^4$-[(trans-4-aminocyclohexyl)methyl]-$N^2$-(5-chloro-2-methylbenzyl)-5-nitropyrimidine-2,4-diamine

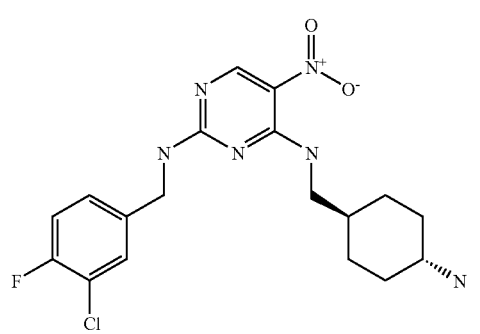

$N^4$-[(trans-4-aminocyclohexyl)methyl]-$N^2$-(3,4-difluorobenzyl)-5-nitropyrimidine-2,4-diamine -continued

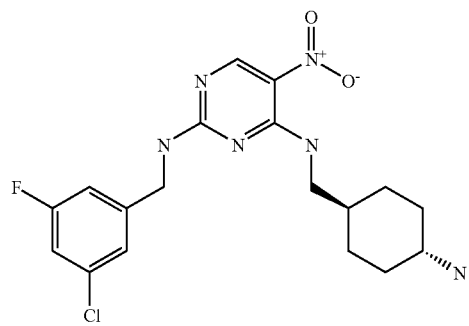

$N^4$-[(trans-4-aminocyclohexyl)methyl]-$N^2$-(3-chloro-4-fluorobenzyl)-5-nitropyrimidine-2,4-diamine

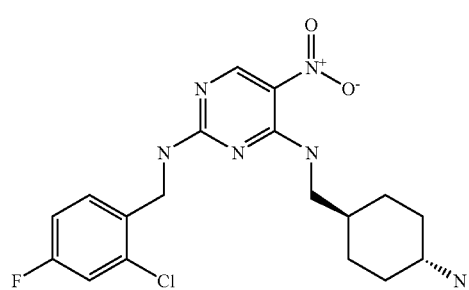

$N^4$-[(trans-4-aminocyclohexyl)methyl]-$N^2$-(3,5-difluorobenzyl)-5-nitropyrimidine-2,4-diamine

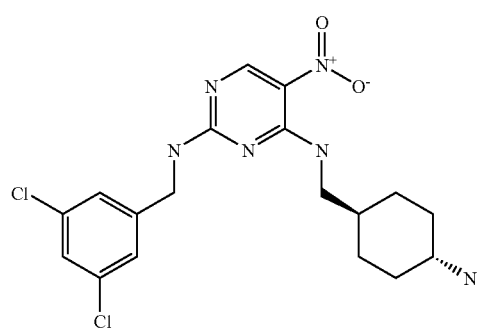

$N^4$-[(trans-4-aminocyclohexyl)methyl]-$N^2$-(2-chloro-4-fluorobenzyl)-5-nitropyrimidine-2,4-diamine

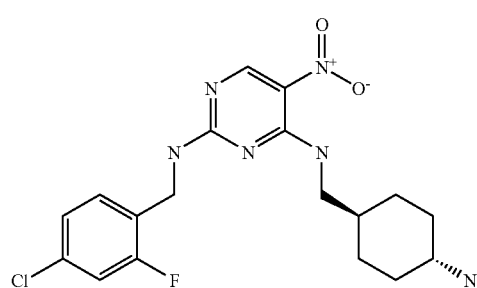

$N^4$-[(trans-4-aminocyclohexyl)methyl]-$N^2$-(3,5-dichlorobenzyl)-5-nitropyrimidine-2,4-diamine

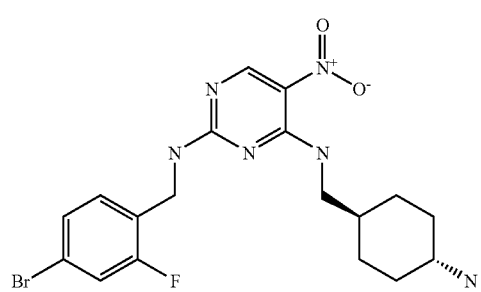

$N^4$-[(trans-4-aminocyclohexyl)methyl]-$N^2$-(4-chloro-2-fluorobenzyl)-5-nitropyrimidine-2,4-diamine

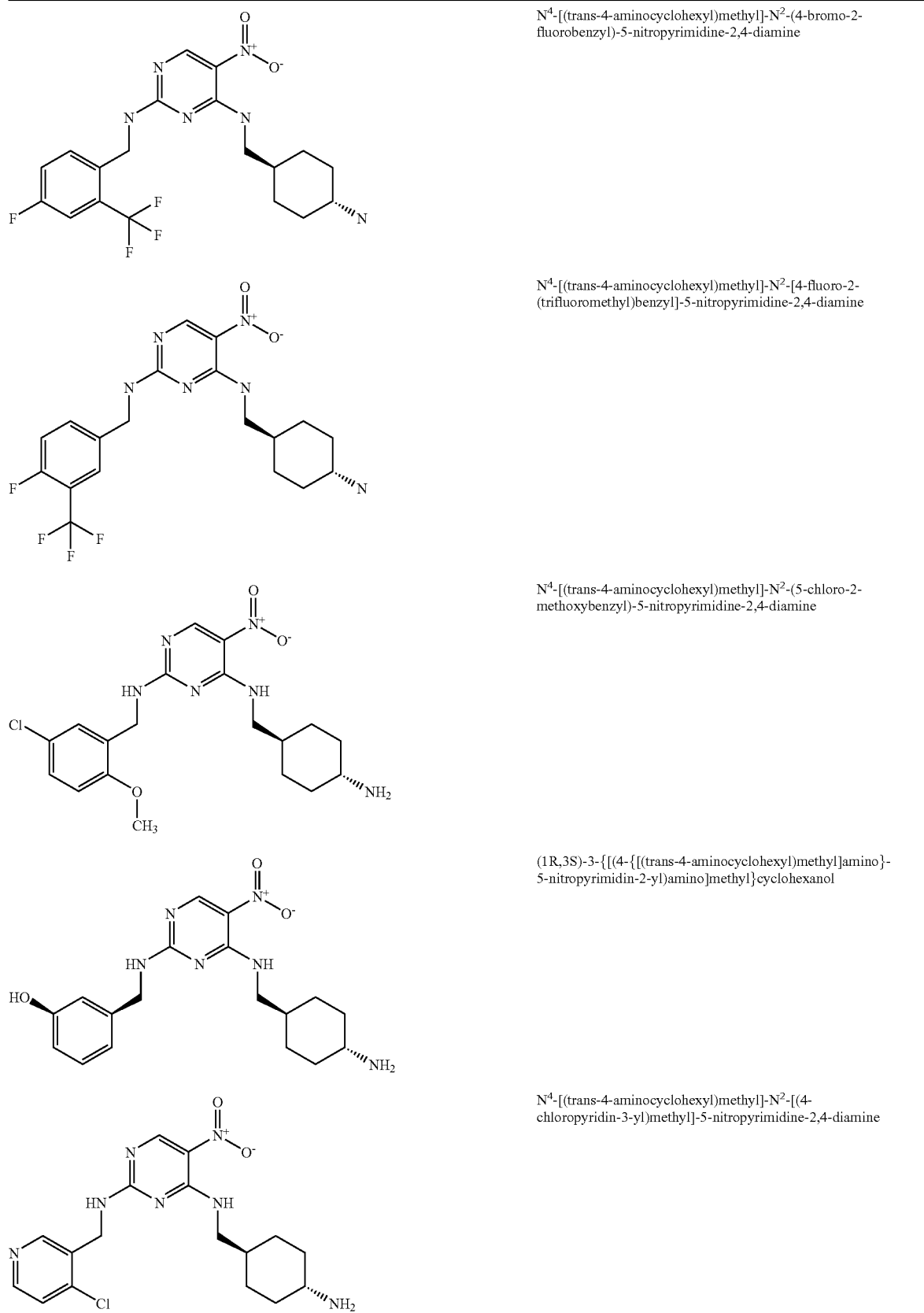

N4-[(trans-4-aminocyclohexyl)methyl]-N2-(4-bromo-2-fluorobenzyl)-5-nitropyrimidine-2,4-diamine N4-[(trans-4-aminocyclohexyl)methyl]-N2-[4-fluoro-2-(trifluoromethyl)benzyl]-5-nitropyrimidine-2,4-diamine N4-[(trans-4-aminocyclohexyl)methyl]-N2-(5-chloro-2-methoxybenzyl)-5-nitropyrimidine-2,4-diamine (1R,3S)-3-{[(4-{[(trans-4-aminocyclohexyl)methyl]amino}-5-nitropyrimidin-2-yl)amino]methyl}cyclohexanol N4-[(trans-4-aminocyclohexyl)methyl]-N2-[(4-chloropyridin-3-yl)methyl]-5-nitropyrimidine-2,4-diamine -continued

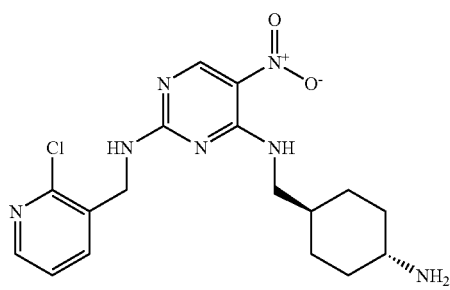

$N^4$-[(trans-4-aminocyclohexyl)methyl]-$N^2$-[(2-chloropyridin-3-yl)methyl]-5-nitropyrimidine-2,4-diamine

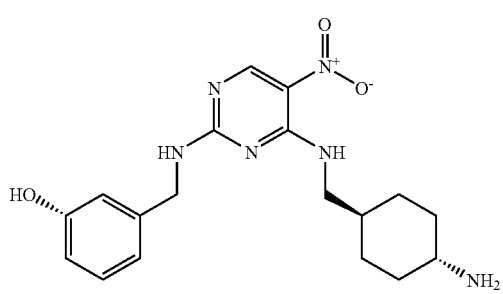

(1S,3S)-3-{[(4-{[(trans-4-aminocyclohexyl)methyl]amino}-5-nitropyrimidin-2-yl)amino]methyl}cyclohexanol

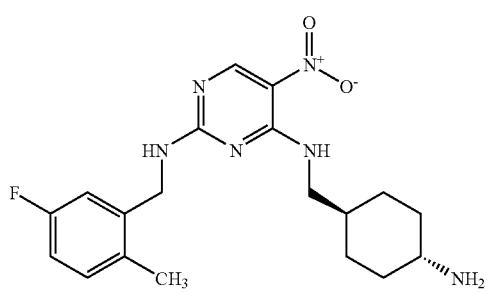

$N^4$-[(trans-4-aminocyclohexyl)methyl]-$N^2$-(5-fluoro-2-methylbenzyl)-5-nitropyrimidine-2,4-diamine

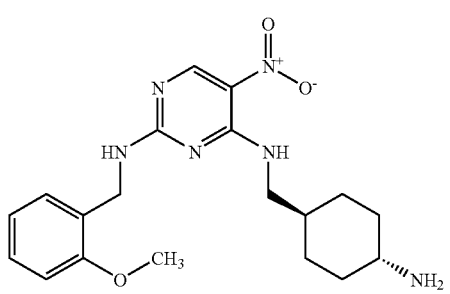

$N^4$-[(trans-4-aminocyclohexyl)methyl]-$N^2$-(2-methoxybenzyl)-5-nitropyrimidine-2,4-diamine

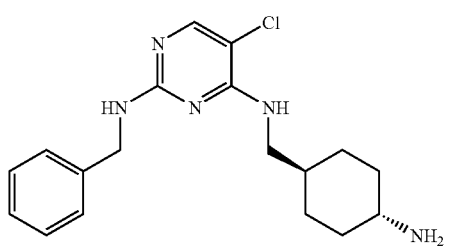

$N^4$-[(trans-4-aminocyclohexyl)methyl]-$N^2$-benzyl-5-chloropyrimidine-2,4-diamine

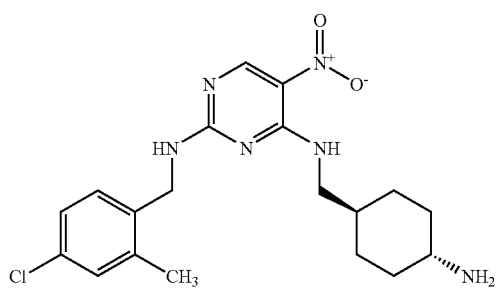

N4-[(trans-4-aminocyclohexyl)methyl]-N2-(4-chloro-2-methylbenzyl)-5-nitropyrimidine-2,4-diamine

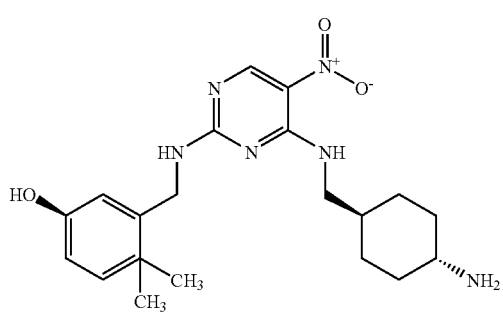

(1R,3R)-3-{[(4-{[(trans-4-aminocyclohexyl)methyl]amino}-5-nitropyrimidin-2-yl)amino]methyl}-4,4-dimethyl-cyclohexanol

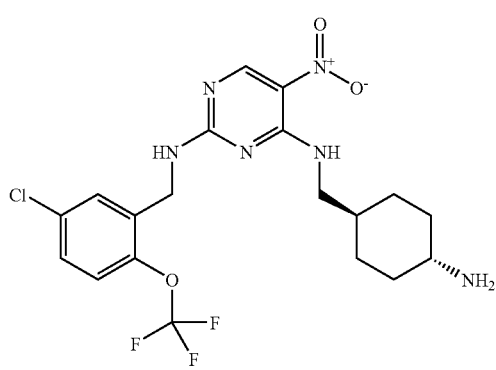

N4-[(trans-4-aminocyclohexyl)methyl]-N2-[5-chloro-2-(trifluoromethoxy)benzyl]-5-nitropyrimidine-2,4-diamine

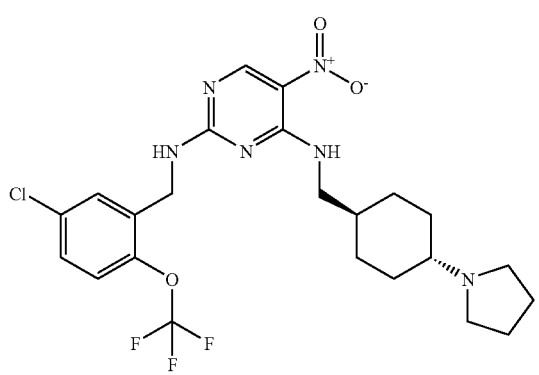

N2-[5-chloro-2-(trifluoromethoxy)benzyl]-5-nitro-N4-[(trans-4-pyrrolidin-1-ylcyclohexyl)methyl]pyrimidine-2,4-diamine -continued

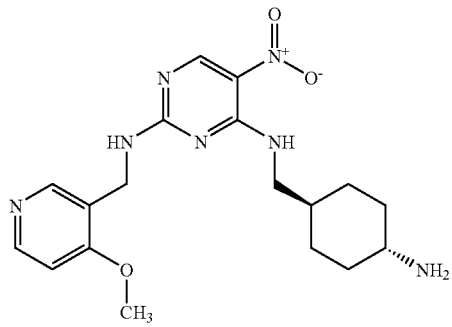 N⁴-[(trans-4-aminocyclohexyl)methyl]-N²-[(4-methoxypyridin-3-yl)methyl]-5-nitropyrimidine-2,4-diamine

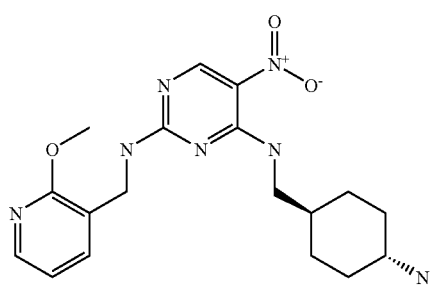 N⁴-[(trans-4-aminocyclohexyl)methyl]-N²-[(2-methoxypyridin-3-yl)methyl]-5-nitropyrimidine-2,4-diamine

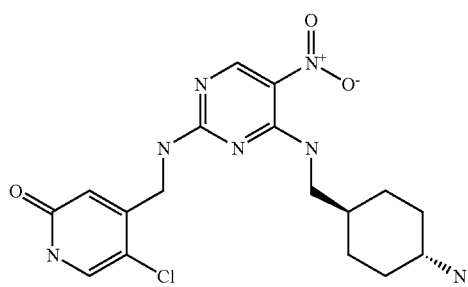 4-{[(4-{[(trans-4-aminocyclohexyl)methyl]amino}-5-nitro-pyrimidin-2-yl)amino]methyl}-5-chloropyridin-2(1H)-one

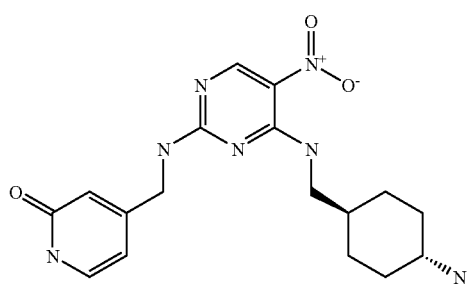 4-{[(4-{[(trans-4-aminocyclohexyl)methyl]amino}-5-nitropyrimidin-2-yl)amino]methyl}pyridin-2(1H)-one

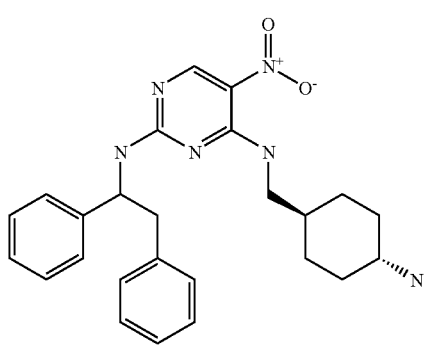 N⁴-[(trans-4-aminocyclohexyl)methyl]-N²-(1,2-diphenylethyl)-5-nitropyrimidine-2,4-diamine -continued

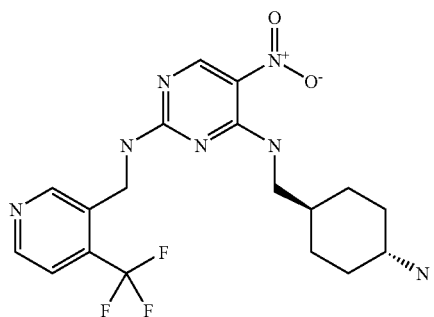

N⁴-[(trans-4-aminocyclohexyl)methyl]-5-nitro-N²-{[4-(trifluoromethyl)pyridin-3-yl]methyl}pyrimidine-2,4-diamine

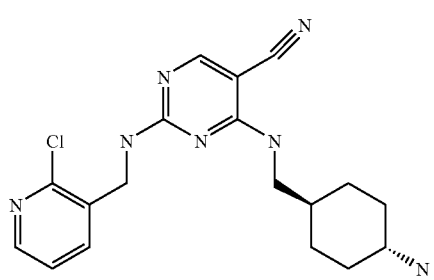

4-{[(trans-4-aminocyclohexyl)methyl]amino}-2-{[(2-chloropyridin-3-yl)methyl]amino}pyrimidine-5-carbonitrile

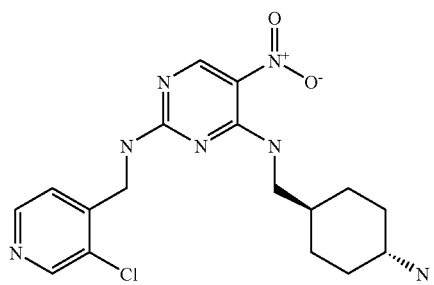

N⁴-[(trans-4-aminocyclohexyl)methyl]-N²-[(3-chloropyridin-4-yl)methyl]-5-nitropyrimidine-2,4-diamine

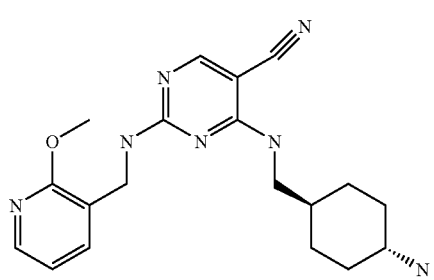

4-{[(trans-4-aminocyclohexyl)methyl]amino}-2-{[(2-methoxypyridin-3-yl)methyl]amino}pyrimidine-5-carbonitrile

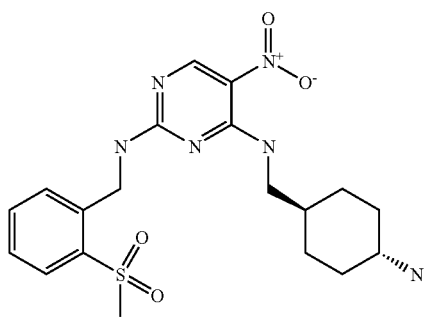

N⁴-[(trans-4-aminocyclohexyl)methyl]-N²-[2-(methylsulfonyl)benzyl]-5-nitropyrimidine-2,4-diamine -continued

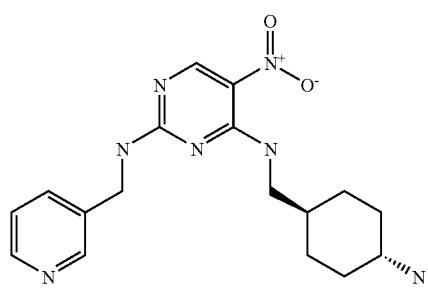

$N^4$-[(trans-4-aminocyclohexyl)methyl]-5-nitro-$N^2$-(pyridin-3-ylmethyl)pyrimidine-2,4-diamine

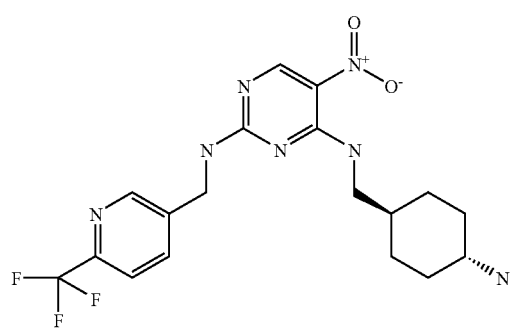

$N^4$-[(trans-4-aminocyclohexyl)methyl]-5-nitro-$N^2$-{[6-(trifluoromethyl)pyridin-3-yl]methyl}pyrimidine-2,4-diamine

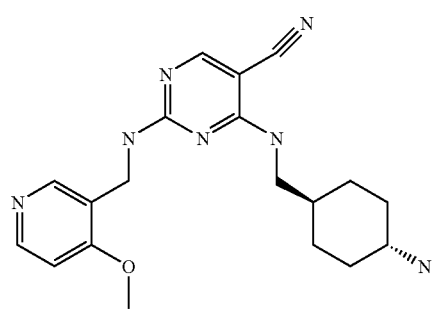

4-{[(trans-4-aminocyclohexyl)methyl]amino}-2-{[(4-methoxypyridin-3-yl)methyl]amino}pyrimidine-5-carbonitrile

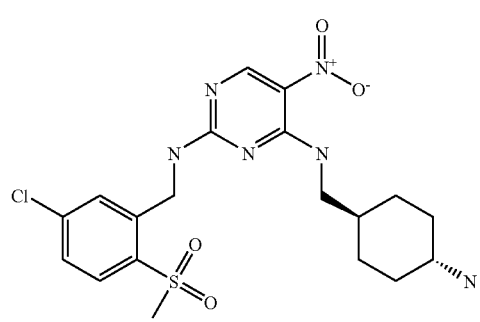

$N^4$-[(trans-4-aminocyclohexyl)methyl]-$N^2$-[5-chloro-2-(methylsulfonyl)benzyl]-5-nitropyrimidine-2,4-diamine

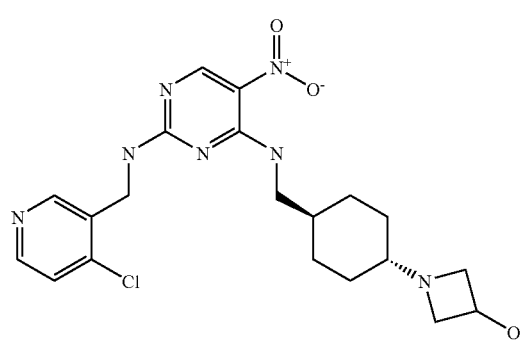

1-(trans-4-{[(2-{[(4-chloropyridin-3-yl)methyl]amino}-5-nitropyrimidin-4-yl)amino]methyl}cyclohexyl)azetidin-3-ol -continued

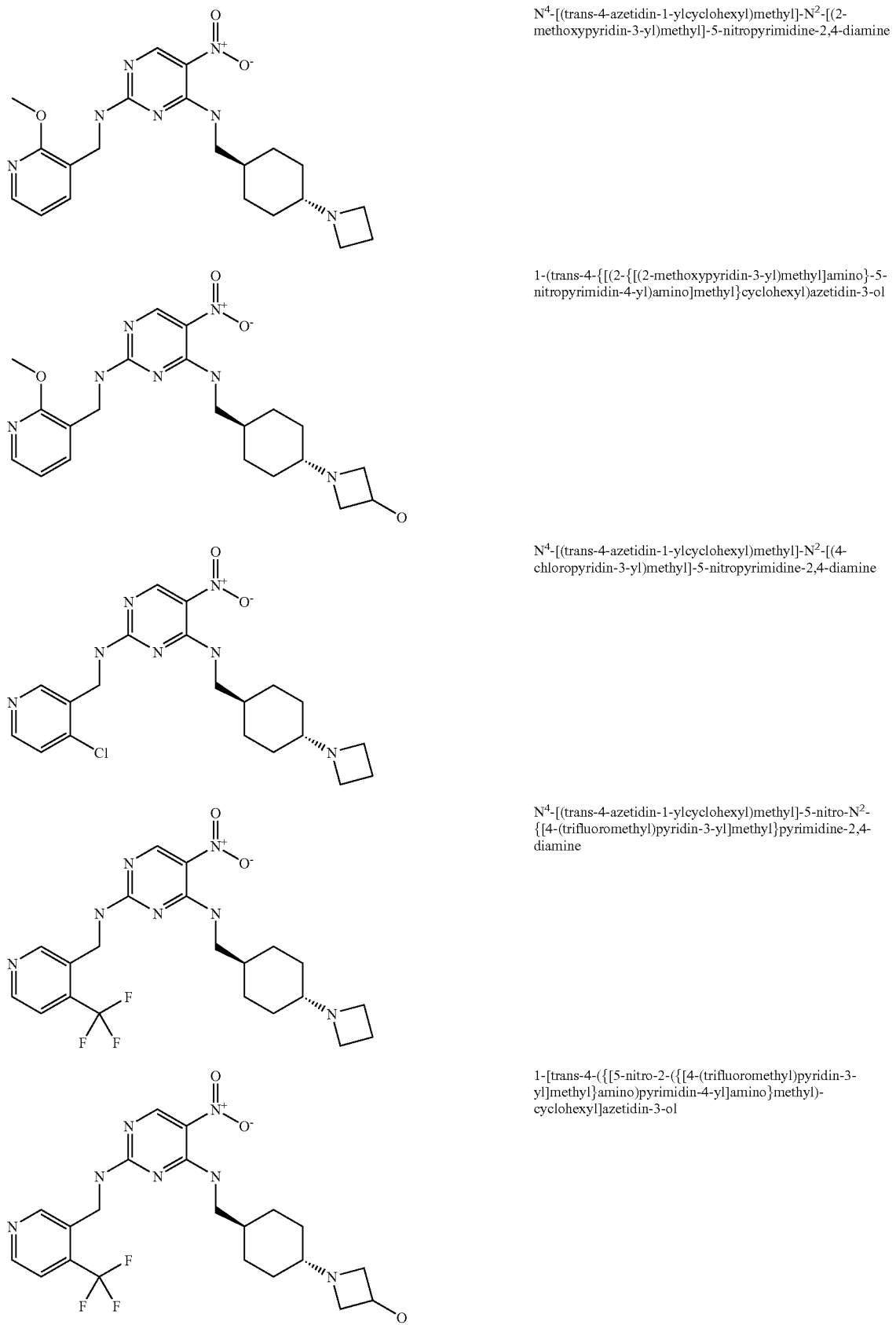

N4-[(trans-4-azetidin-1-ylcyclohexyl)methyl]-N2-[(2-methoxypyridin-3-yl)methyl]-5-nitropyrimidine-2,4-diamine 1-(trans-4-{[(2-{[(2-methoxypyridin-3-yl)methyl]amino}-5-nitropyrimidin-4-yl)amino]methyl}cyclohexyl)azetidin-3-ol N4-[(trans-4-azetidin-1-ylcyclohexyl)methyl]-N2-[(4-chloropyridin-3-yl)methyl]-5-nitropyrimidine-2,4-diamine N4-[(trans-4-azetidin-1-ylcyclohexyl)methyl]-5-nitro-N2-{[4-(trifluoromethyl)pyridin-3-yl]methyl}pyrimidine-2,4-diamine 1-[trans-4-({[5-nitro-2-({[4-(trifluoromethyl)pyridin-3-yl]methyl}amino)pyrimidin-4-yl]amino}methyl)-cyclohexyl]azetidin-3-ol -continued

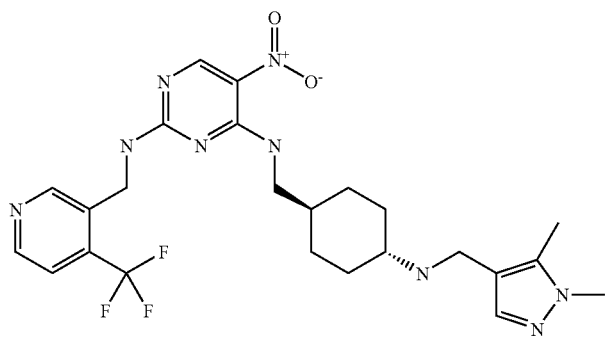

N⁴-[(trans-4-{[(1,5-dimethyl-1H-pyrazol-4-yl)methyl]-amino}cyclohexyl)methyl]-5-nitro-N²-{[4-(trifluoromethyl)-pyridin-3-yl]methyl}pyrimidine-2,4-diamine

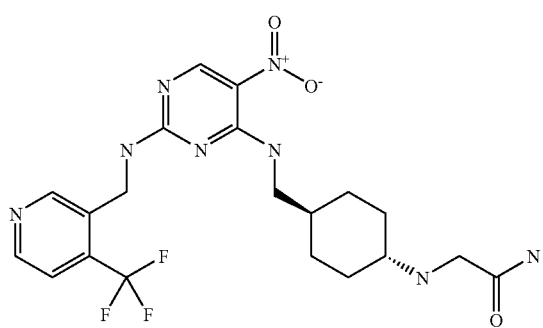

N²-[trans-4-({[5-nitro-2-({[4-(trifluoromethyl)pyridin-3-yl]methyl}amino)pyrimidin-4-yl]amino}methyl)-cyclohexyl]glycinamide

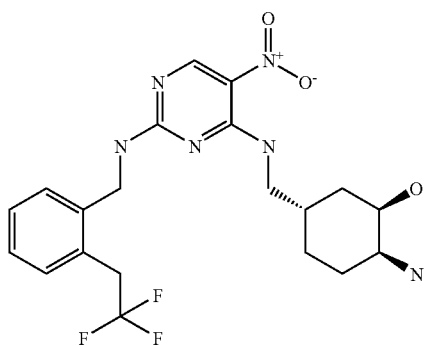

cis-2-amino-trans-5-{[(5-nitro-2-{[2-(trifluoromethoxy)-benzyl]amino}pyrimidin-4-yl)amino]methyl}cyclohexanol

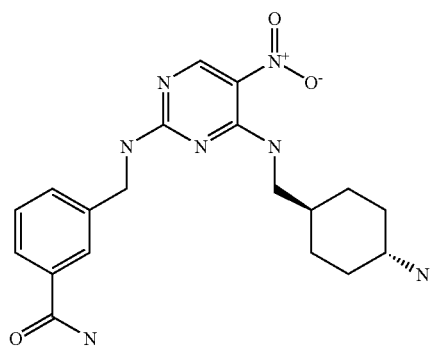

3-{[(4-{[(trans-4-aminocyclohexyl)methyl]amino}-5-nitropyrimidin-2-yl)amino]methyl}benzamide -continued

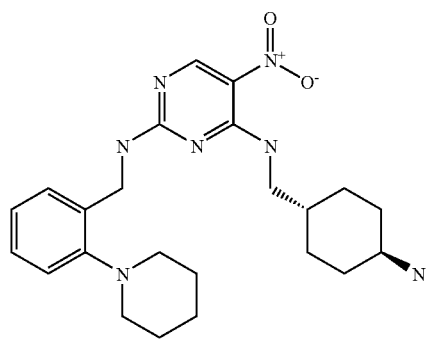

N4-[(trans-4-aminocyclohexyl)methyl]-5-nitro-N2-(2-piperidin-1-ylbenzyl)pyrimidine-2,4-diamine

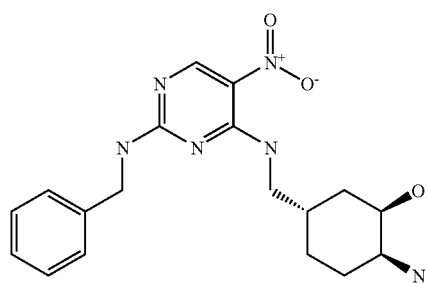

cis-2-amino-trans-5-({[2-(benzylamino)-5-nitropyrimidin-4-yl]amino}methyl)cyclohexanol

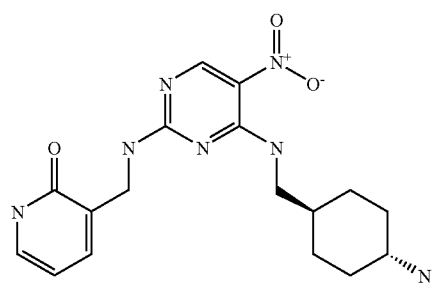

3-{[(4-{[(trans-4-aminocyclohexyl)methyl]amino}-5-nitropyrimidin-2-yl)amino]methyl}pyridin-2(1H)-one

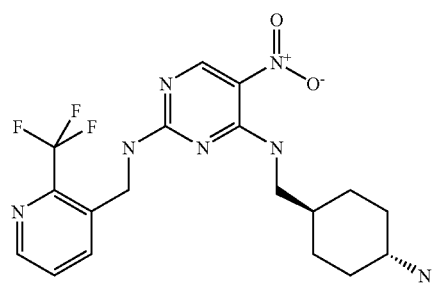

N4-[(trans-4-aminocyclohexyl)methyl]-5-nitro-N2-{[2-(trifluoromethyl)pyridin-3-yl]methyl}pyrimidine-2,4-diamine

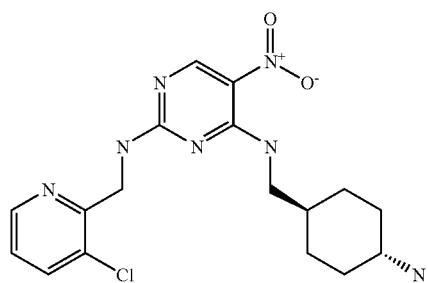

N4-[(trans-4-aminocyclohexyl)methyl]-N2-[(3-chloropyridin-2-yl)methyl]-5-nitropyrimidine-2,4-diamine

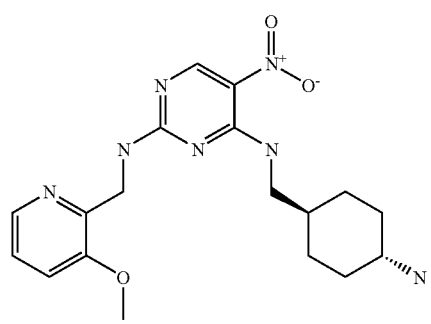

N[4]-[(trans-4-aminocyclohexyl)methyl]-N[2]-[(3-methoxypyridin-2-yl)methyl]-5-nitropyrimidine-2,4-diamine

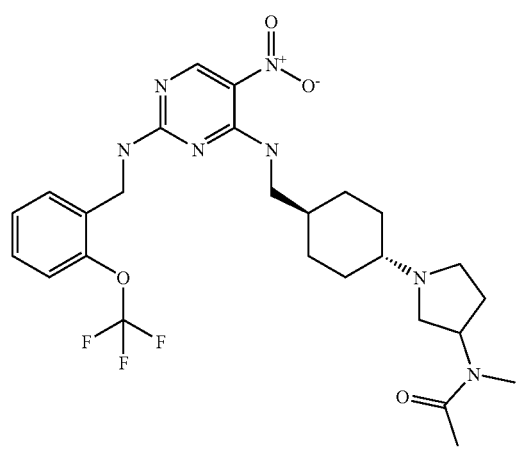

N-methyl-N-[1-(trans-4-{[(5-nitro-2-{[2-(trifluoromethoxy)benzyl]amino}pyrimidin-4-yl)amino]methyl}cyclohexyl)pyrrolidin-3-yl]acetamide

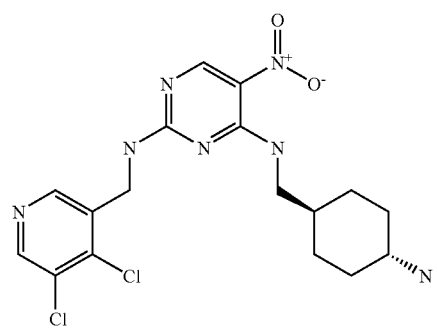

N[4]-[(trans-4-aminocyclohexyl)methyl]-N[2]-[(4,5-dichloropyridin-3-yl)methyl]-5-nitropyrimidine-2,4-diamine

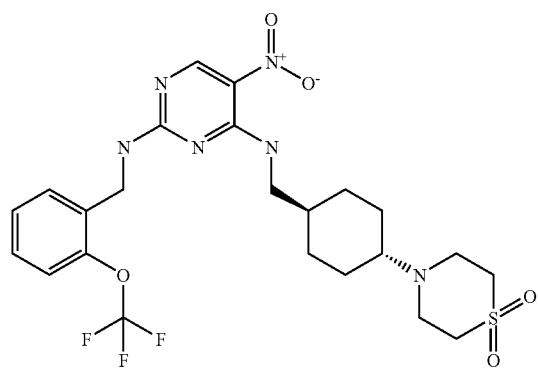

N[4]-{[trans-4-(1,1-dioxidothiomorpholin-4-yl)cyclohexyl]methyl}-5-nitro-N[2]-[2-(trifluoromethoxy)benzyl]pyrimidine-2,4-diamine

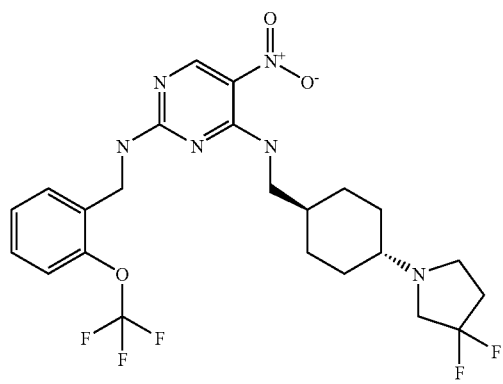

N$^4$-{[trans-4-(3,3-difluoropyrrolidin-1-yl)cyclohexyl]-methyl}-5-nitro-N$^2$-[2-(trifluoromethoxy)benzyl]-pyrimidine-2,4-diamine

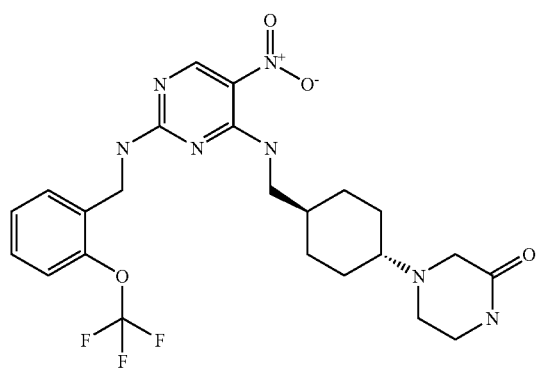

4-(trans-4-{[(5-nitro-2-{[2-(trifluoromethoxy)benzyl]-amino}pyrimidin-4-yl)amino]methyl}cyclohexyl)-piperazin-2-one

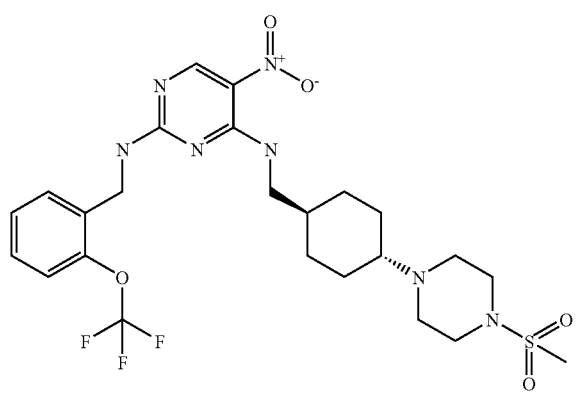

N$^4$-({trans-4-[4-(methylsulfonyl)piperazin-1-yl]cyclohexyl}-methyl)-5-nitro-N-[2-(trifluoromethoxy)benzyl]pyrimidine-2,4-diamine

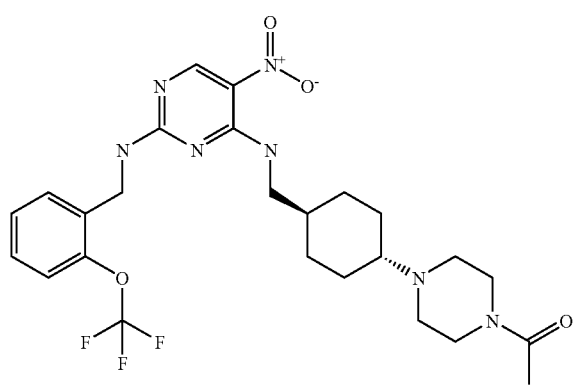

N$^4$-{[trans-4-(4-acetylpiperazin-1-yl)cyclohexyl]methyl}-5-nitro-N$^2$-[2-(trifluoromethoxy)benzyl]pyrimidine-2,4-diamine

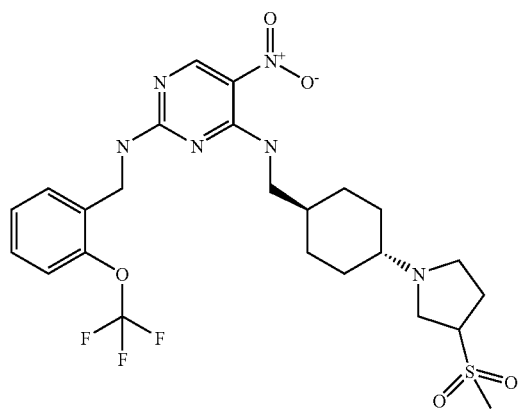
N$^4$-({trans-4-[3-(methylsulfonyl)pyrrolidin-1-yl]-cyclohexyl}methyl)-5-nitro-N$^2$-[2-(trifluoromethoxy)-benzyl]pyrimidine-2,4-diamine
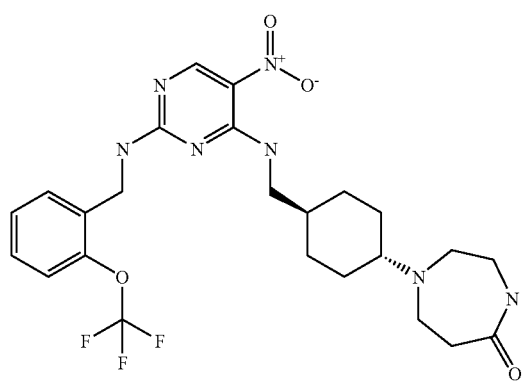
1-(trans-4-{[(5-nitro-2-{[2-(trifluoromethoxy)benzyl]-amino}pyrimidin-4-yl)amino]methyl}cyclohexyl)-1,4-diazepan-5-one
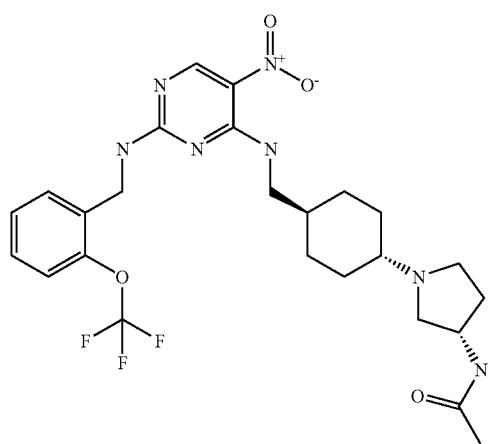
N-[(3S)-1-(trans-4-{[(5-nitro-2-{[2-(trifluoromethoxy)-benzyl]amino}pyrimidin-4-yl)amino]methyl}cyclohexyl)-pyrrolidin-3-yl]acetamide

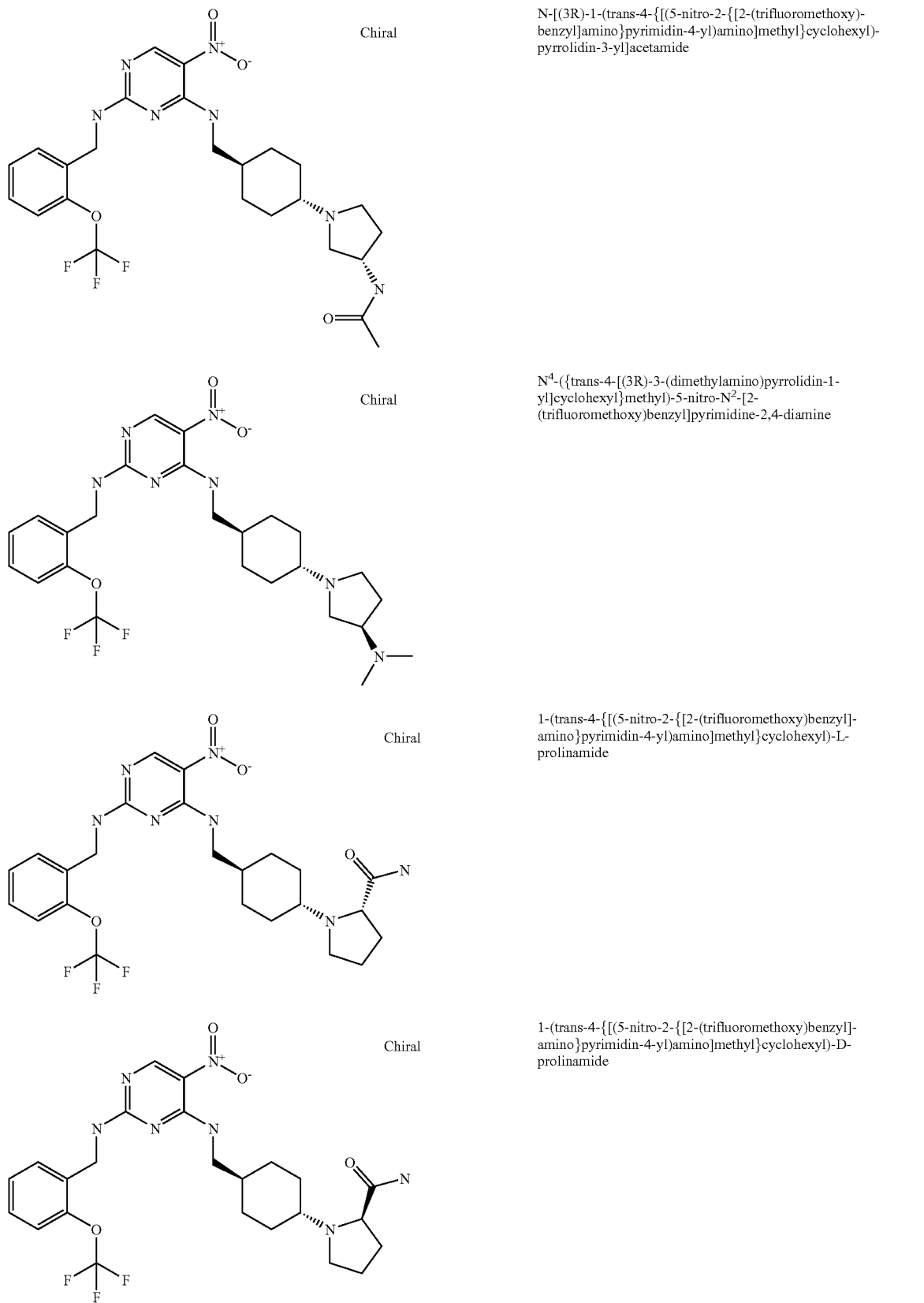

| | |
|---|---|
| Chiral | N-[(3R)-1-(trans-4-{[(5-nitro-2-{[2-(trifluoromethoxy)-benzyl]amino}pyrimidin-4-yl)amino]methyl}cyclohexyl)-pyrrolidin-3-yl]acetamide |
| Chiral | N$^4$-({trans-4-[(3R)-3-(dimethylamino)pyrrolidin-1-yl]cyclohexyl}methyl)-5-nitro-N$^2$-[2-(trifluoromethoxy)benzyl]pyrimidine-2,4-diamine |
| Chiral | 1-(trans-4-{[(5-nitro-2-{[2-(trifluoromethoxy)benzyl]-amino}pyrimidin-4-yl)amino]methyl}cyclohexyl)-L-prolinamide |
| Chiral | 1-(trans-4-{[(5-nitro-2-{[2-(trifluoromethoxy)benzyl]-amino}pyrimidin-4-yl)amino]methyl}cyclohexyl)-D-prolinamide |

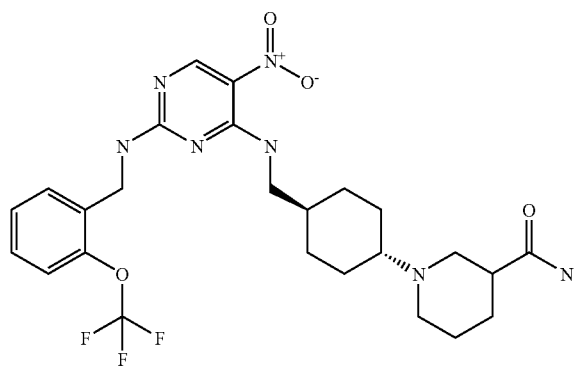

1-(trans-4-{[(5-nitro-2-{[2-(trifluoromethoxy)benzyl]-amino}pyrimidin-4-yl)amino]methyl}cyclohexyl)piperidine-3-carboxamide

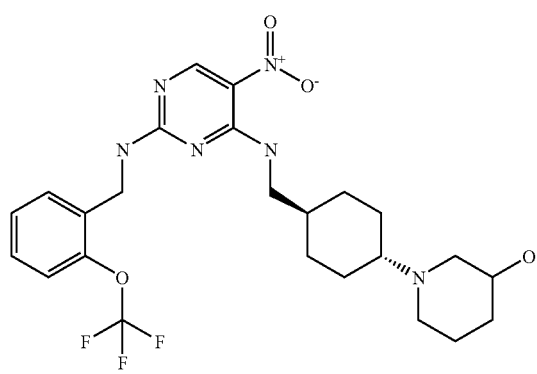

1-(trans-4-{[(5-nitro-2-{[2-(trifluoromethoxy)benzyl]-amino}pyrimidin-4-yl)amino]methyl}cyclohexyl)piperidin-3-ol

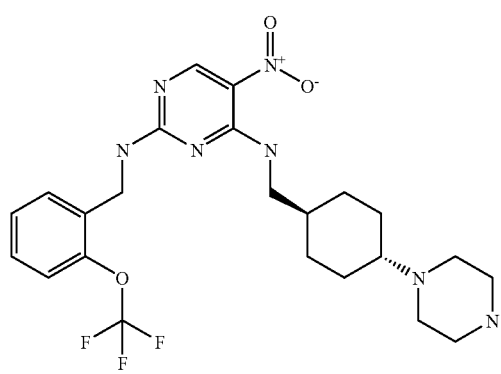

5-nitro-$N^4$-[(trans-4-piperazin-1-ylcyclohexyl)methyl]-$N^2$-[2-(trifluoromethoxy)benzyl]pyrimidine-2,4-diamine

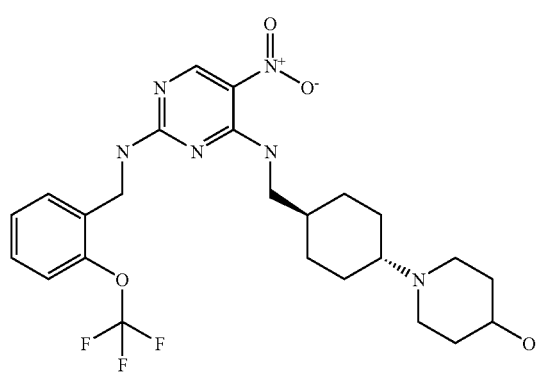

1-(trans-4-{[(5-nitro-2-{[2-(trifluoromethoxy)benzyl]-amino}pyrimidin-4-yl)amino]methyl}cyclohexyl)piperidin-4-ol

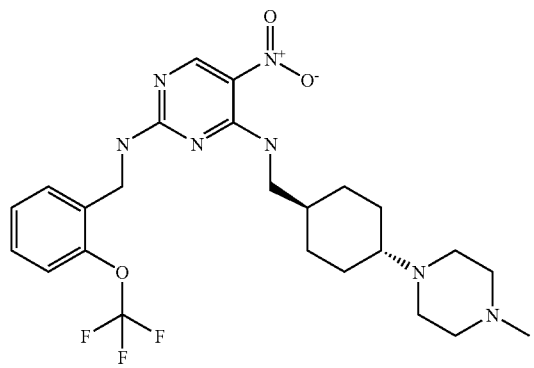

N⁴-{[trans-4-(4-methylpiperazin-1-yl)cyclohexyl]methyl}-5-nitro-N²-[2-(trifluoromethoxy)benzyl]pyrimidine-2,4-diamine

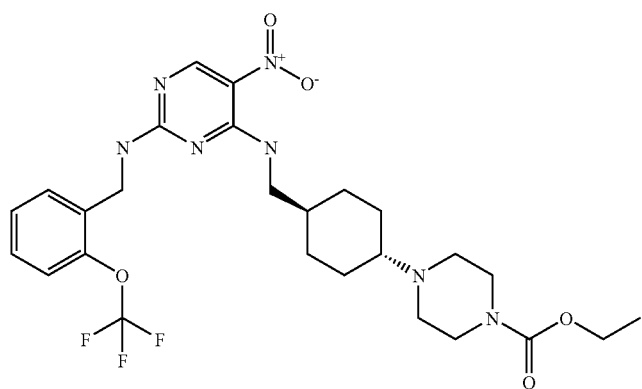

ethyl 4-(trans-4-{[(5-nitro-2-{[2-(trifluoromethoxy)benzyl]amino}pyrimidin-4-yl)amino]methyl}cyclohexyl)piperazine-1-carboxylate

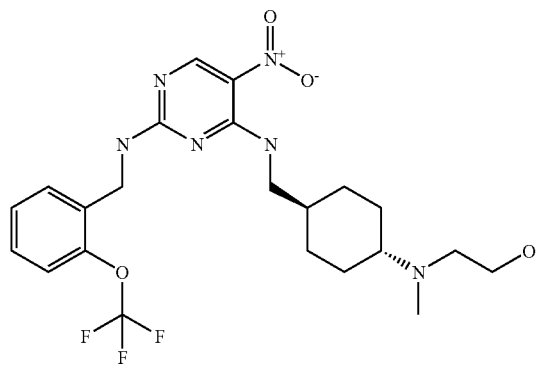

2-[methyl(trans-4-{[(5-nitro-{2-[2-(trifluoromethoxy)-benzyl]amino}pyrimidin-4-yl)amino]methyl}cyclohexyl)-amino]ethanol

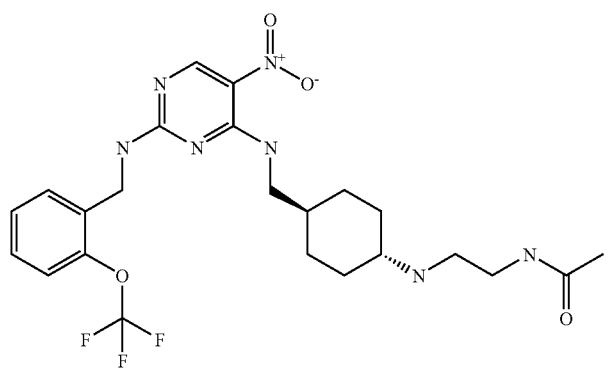

N-{2-[(trans-4-{[(5-nitro-2-{[2-(trifluoromethoxy)benzyl]-amino}pyrimidin-4-yl)amino]methyl}cyclohexyl)amino]-ethyl}acetamide

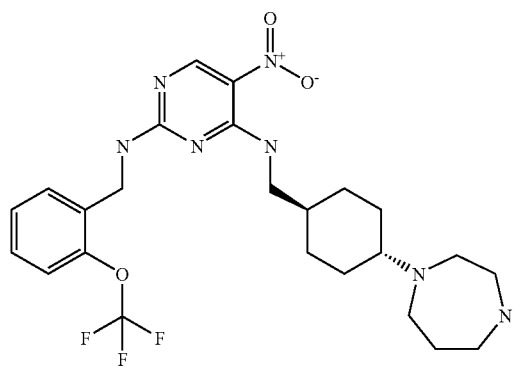

N⁴-{[trans-4-(1,4-diazepan-1-yl)cyclohexyl]methyl}-5-nitro-N²-[2-(trifluoromethoxy)benzyl]pyrimidine-2,4-diamine

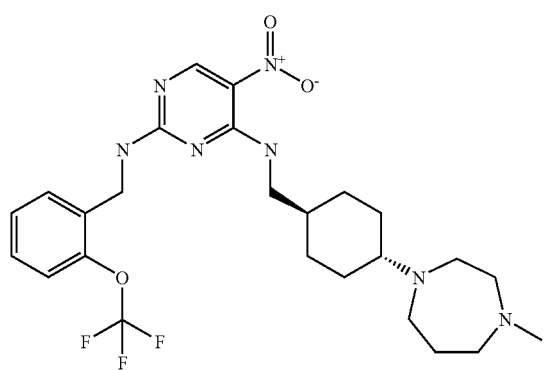

N⁴-{[trans-4-(4-methyl-1,4-diazepan-1-yl)cyclohexyl]methyl}-5-nitro-N²-[2-(trifluoromethoxy)benzyl]pyrimidine-2,4-diamine

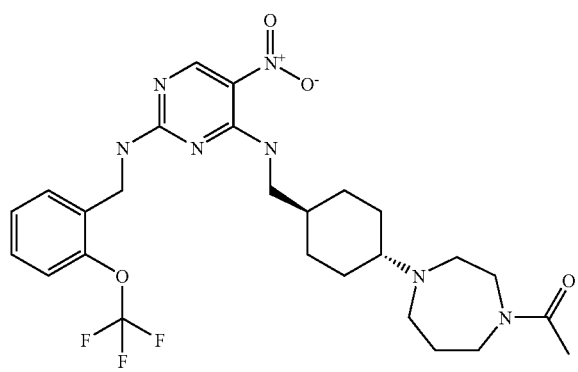

N⁴-{[trans-4-(4-acetyl-1,4-diazepan-1-yl)cyclohexyl]methyl}-5-nitro-N²-[2-(trifluoromethoxy)benzyl]pyrimidine-2,4-diamine

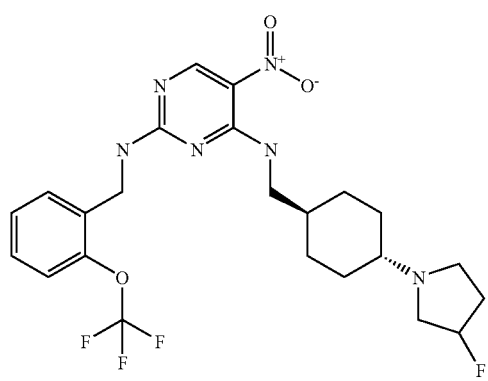

N⁴-{[trans-4-(3-fluoropyrrolidin-1-yl)cyclohexyl]methyl}-5-nitro-N²-[2-(trifluoromethoxy)benzyl]pyrimidine-2,4-diamine -continued

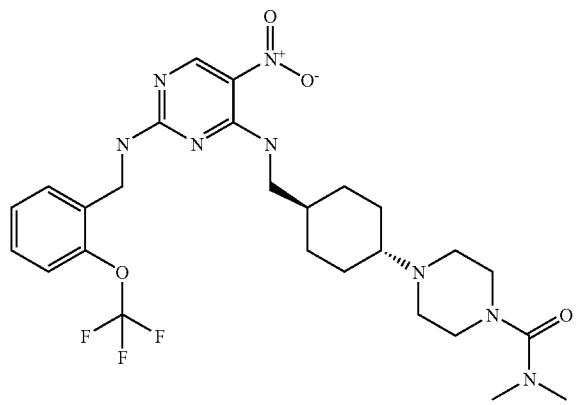

N,N-dimethyl-4-(trans-4-{[(5-nitro-2-{[2-(trifluoromethoxy)benzyl]amino}pyrimidin-4-yl)amino]methyl}cyclohexyl)piperazine-1-carboxamide

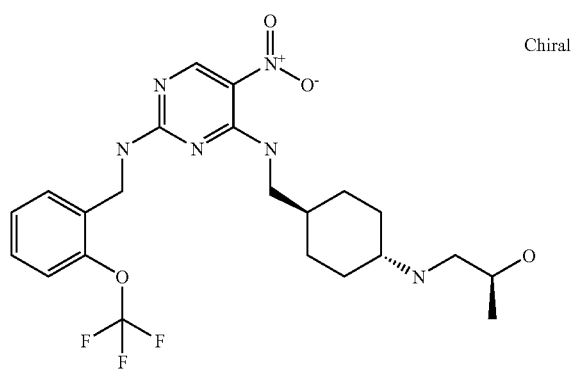

Chiral (2R)-1-[(trans-4-{[(5-nitro-2-{[2-(trifluoromethoxy)-benzyl]amino}pyrimidin-4-yl)amino]methyl}cyclohexyl)-amino]propan-2-ol

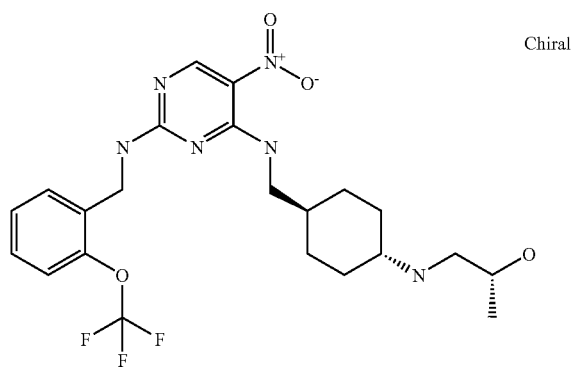

Chiral (2S)-1-[(trans-4-{[(5-nitro-2-{[2-(trifluoromethoxy)-benzyl]amino}pyrimidin-4-yl)amino]methyl}cyclohexyl)-amino]propan-2-ol

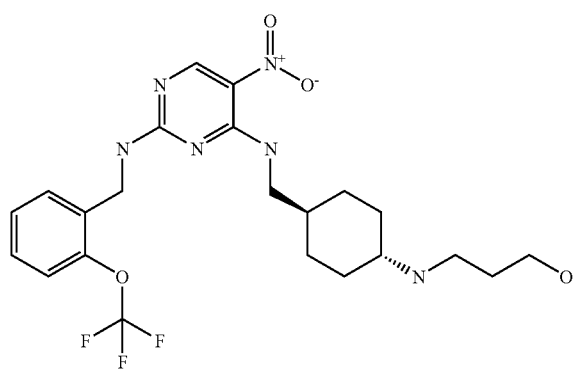

3-[(trans-4-{[(5-nitro-2-{[2-(trifluoromethoxy)benzyl]-amino}pyrimidin-4-yl)amino]methyl}cyclohexyl)-amino]propan-1-ol

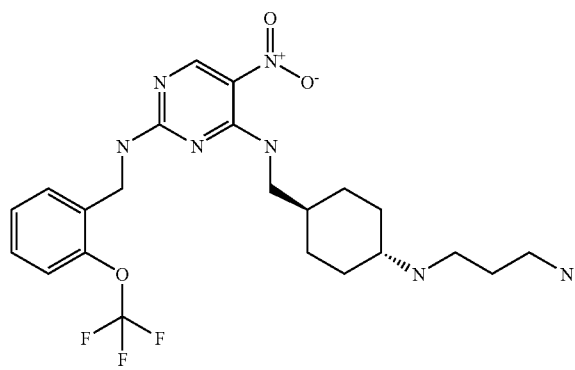

N⁴-({trans-4-[(3-aminopropyl)amino]cyclohexyl}methyl)-5-nitro-N-[2-(trifluoromethoxy)benzyl]pyrimidine-2,4-diamine

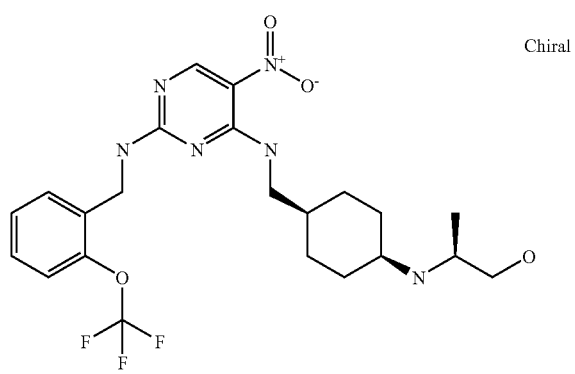

Chiral (2R)-2-[(trans-4-{[(5-nitro-2-{[2-(trifluoromethoxy)-benzyl]amino}pyrimidin-4-yl)amino]methyl}cyclohexyl)-amino]propan-1-ol

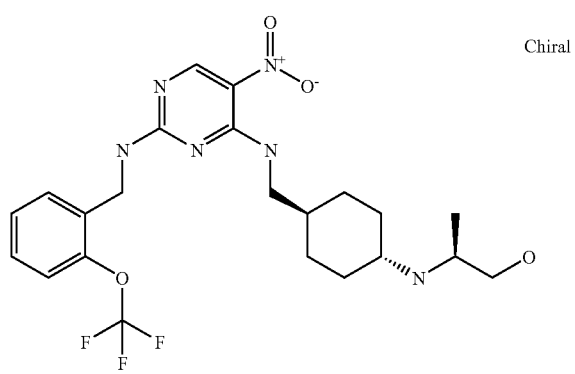

Chiral (2S)-2-[(trans-4-{[(5-nitro-2-{[2-(trifluoromethoxy)benzyl]amino}pyrimidin-4-yl)amino]methyl}cyclohexyl)amino]propan-1-ol

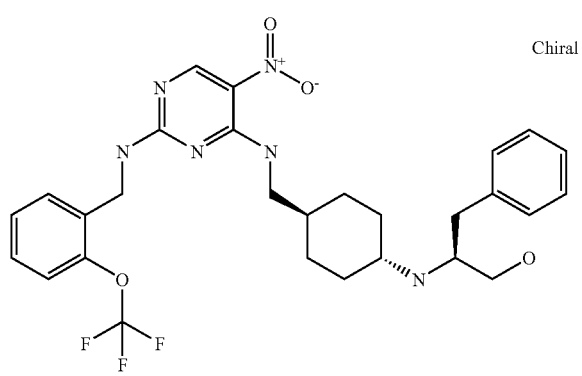

Chiral (2R)-2-[(trans-4-{[(5-nitro-2-{[2-(trifluoromethoxy)-benzyl]amino}pyrimidin-4-yl)amino]methyl}cyclohexyl)-amino]-3-phenylpropan-1-ol -continued

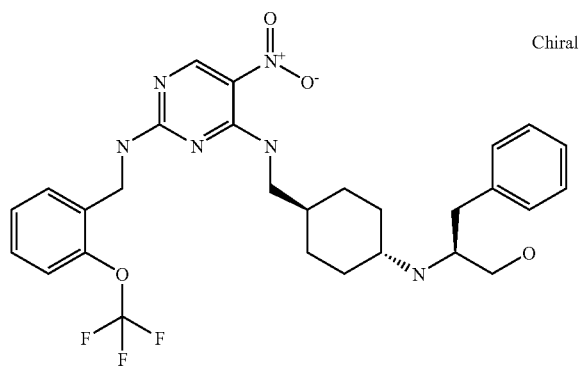 Chiral (2S)-2-[(trans-4-{[(5-nitro-2-{[2-(trifluoromethoxy)benzyl]-amino}pyrimidin-4-yl)amino]methyl}cyclohexyl)amino]-3-phenylpropan-1-ol

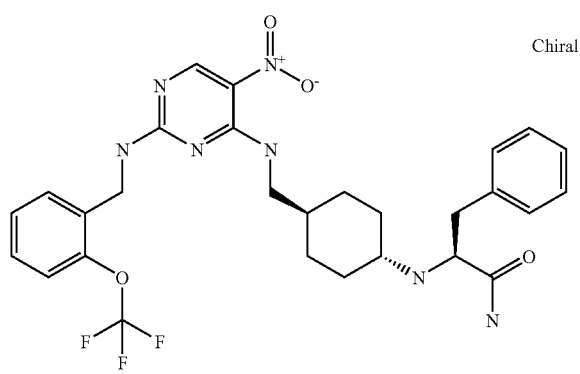 Chiral

Nα-(trans-4-{[(5-nitro-2-{[2-(trifluoromethoxy)benzyl]-amino}pyrimidin-4-yl)amino]methyl}cyclohexyl)-L-phenylalaninamide

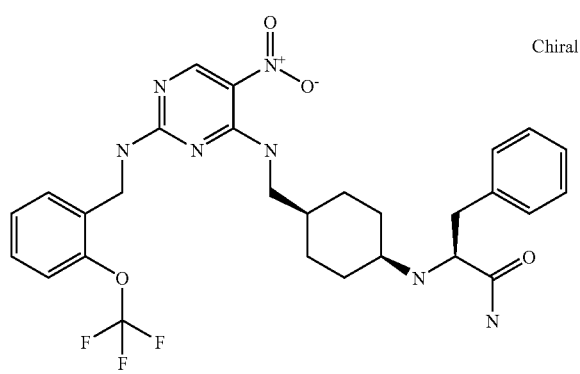 Chiral

Nα-(trans-4-{[(5-nitro-2-{[2-(trifluoromethoxy)benzyl]-amino}pyrimidin-4-yl)amino]methyl}cyclohexyl)-D-phenylalaninamide

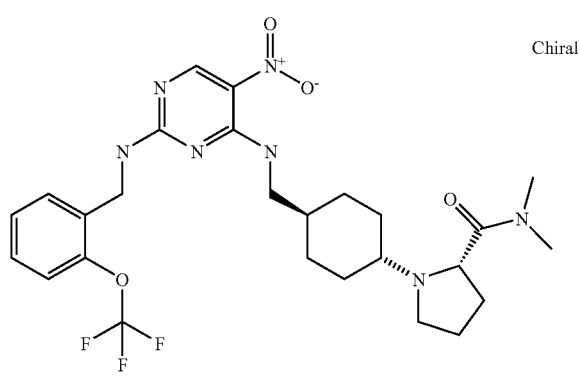 Chiral

N,N-dimethyl-1-(trans-4-{[(5-nitro-2-{[2-(trifluoromethoxy)benzyl]amino}pyrimidin-4-yl)amino]methyl}cyclohexyl)-L-prolinamide

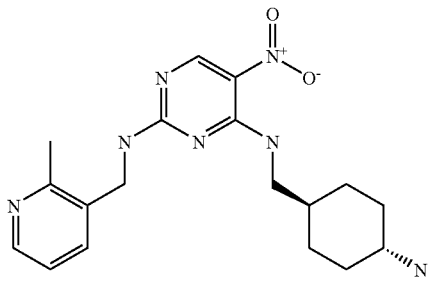

$N^4$-[(trans-4-aminocyclohexyl)methyl]-$N^2$-[(2-methylpyridin-3-yl)methyl]-5-nitropyrimidine-2,4-diamine In still an even further embodiment there are provided the following compounds:

$N^4$-[(trans-4-aminocyclohexyl)methyl]-$N^2$-[2-fluoro-3-(trifluoromethyl)benzyl]-5-nitropyrimidine-2,4-diamine;

$N^4$-[(trans-4-aminocyclohexyl)methyl]-$N^2$-(2-chloro-6-fluoro-3-methylbenzyl)-5-nitropyrimidine-2,4-diamine;

$N^4$-[(trans-4-aminocyclohexyl)methyl]-$N^2$-(1-naphthylmethyl)-5-nitropyrimidine-2,4-diamine;

$N^4$-[(trans-4-aminocyclohexyl)methyl]-5-nitro-$N^2$-{2-[(trifluoromethyl)thio]benzyl}pyrimidine-2,4-diamine;

$N^4$-[(trans-4-aminocyclohexyl)methyl]-5-chloro-$N^2$-[2-(trifluoromethoxy)benzyl]pyrimidine-2,4-diamine;

1-(trans-4-{[(5-nitro-2-{[2-(trifluoromethoxy)benzyl]amino}pyrimidin-4-yl)amino]methyl}-cyclohexyl)azetidin-3-one;

$N^4$-{[trans-4-(3-aminoazetidin-1-yl)cyclohexyl]methyl}-5-nitro-$N^2$-[2-(trifluoromethoxy)benzyl]-pyrimidine-2,4-diamine;

N-[1-(trans-4-{[(5-nitro-2-{[2-(trifluoromethoxy)benzyl]amino}pyrimidin-4-yl)amino]methyl}-cyclohexyl)azetidin-3-yl]methanesulfonamide;

N-[1-(trans-4-{[(5-nitro-2-{[2-(trifluoromethoxy)benzyl]amino}pyrimidin-4-yl)amino]methyl}-cyclohexyl)azetidin-3-yl]acetamide;

$N^4$-[(trans-4-aminocyclohexyl)methyl]-5-nitro-$N^2$-[2-(trifluoromethoxy)benzyl]pyrimidine-2,4-diamine;

4-{[(trans-4-aminocyclohexyl)methyl]amino}-2-{[2-(trifluoromethoxy)benzyl]amino}pyrimidine-5-carbonitrile;

$N^4$-[(trans-4-aminocyclohexyl)methyl]-$N^2$-{2-[(2-aminophenyl)thio]benzyl}-5-nitropyrimidine-2,4-diamine;

5-nitro-$N^4$-[(trans-4-pyrrolidin-1-ylcyclohexyl)methyl]-$N^2$-[2-(trifluoromethoxy)benzyl]pyrimidine-2,4-diamine;

1-(trans-4-{[(5-nitro-2-{[2-(trifluoromethoxy)benzyl]amino}pyrimidin-4-yl)amino]methyl}-cyclohexyl)pyrrolidin-3-ol;

$N^4$-[(trans-4-azetidin-1-ylcyclohexyl)methyl]-5-nitro-$N^2$-[2-(trifluoromethoxy)benzyl]pyrimidine-2,4-diamine;

$N^4$-{[trans-4-(dimethylamino)cyclohexyl]methyl}-5-nitro-$N^2$-[2-(trifluoromethoxy)benzyl]pyrimidine-2,4-diamine;

4-({[trans-4-(dimethylamino)cyclohexyl]methyl}amino)-2-{[2-(trifluoromethoxy)benzyl]amino}-pyrimidine-5-carbonitrile;

5-nitro-$N^4$-({trans-4-[(pyridin-3-ylmethyl)amino]cyclohexyl}methyl)-$N^2$-[2-(trifluoromethoxy)-benzyl]pyrimidine-2,4-diamine;

5-nitro-$N^4$-({trans-4-[(pyridin-4-ylmethyl)amino]cyclohexyl}methyl)-$N^2$-[2-(trifluoromethoxy)-benzyl]pyrimidine-2,4-diamine;

2-[(trans-4-{[(5-nitro-2-{[2-(trifluoromethoxy)benzyl]amino}pyrimidin-4-yl)amino]methyl}cyclohexyl)amino]ethanol;

1-(trans-4-{[(5-nitro-2-{[2-(trifluoromethoxy)benzyl]amino}pyrimidin-4-yl)amino]methyl}-cyclohexyl)azetidin-3-ol;

5-nitro-$N^4$-({trans-4-[(pyridin-2-ylmethyl)amino]cyclohexyl}methyl)-$N^2$-[2-(trifluoromethoxy)-benzyl]pyrimidine-2,4-diamine;

$N^2$-(trans-4-{[(5-nitro-2-{[2-(trifluoromethoxy)benzyl]amino}pyrimidin-4-yl)amino]methyl}-cyclohexyl)glycinamide;

$N^4$-[(trans-4-{[(1,5-dimethyl-1H-pyrazol-4-yl)methyl]amino}cyclohexyl)methyl]-5-nitro-$N^2$-[2-(trifluoromethoxy)benzyl]pyrimidine-2,4-diamine;

$N^4$-[(trans-4-{[(1-methyl-1H-pyrazol-4-yl)methyl]amino}cyclohexyl)methyl]-5-nitro-$N^2$-[2-(trifluoromethoxy)benzyl]pyrimidine-2,4-diamine;

$N^4$-[(trans-4-aminocyclohexyl)methyl]-$N^2$-[(2-isopropoxypyridin-3-yl)methyl]-5-nitropyrimidine-2,4-diamine;

$N^4$-[(trans-4-aminocyclohexyl)methyl]-5-nitro-$N^2$-{[2-(2,2,2-trifluoroethoxy)pyridin-3-yl]methyl}pyrimidine-2,4-diamine;

$N^4$-[(trans-4-aminocyclohexyl)methyl]-$N^2$-[(5-fluoro-2-methoxypyridin-3-yl)methyl]-5-nitropyrimidine-2,4-diamine;

$N^4$-[(trans-4-aminocyclohexyl)methyl]-$N^2$-[2-(difluoromethoxy)benzyl]-5-nitropyrimidine-2,4-diamine;

$N^4$-[(trans-4-aminocyclohexyl)methyl]-$N^2$-(2-chlorobenzyl)-5-nitropyrimidine-2,4-diamine;

$N^4$-[(trans-4-azetidin-1-ylcyclohexyl)methyl]-5-nitro-$N^2$-{[2-(2,2,2-trifluoroethoxy)pyridin-3-yl]methyl}pyrimidine-2,4-diamine;

$N^4$-{[trans-4-(3-fluoroazetidin-1-yl)cyclohexyl]methyl}-5-nitro-$N^2$-[2-(trifluoromethoxy)benzyl]pyrimidine-2,4-diamine;

$N^4$-{[trans-4-(ethylamino)cyclohexyl]methyl}-5-nitro-$N^2$-[2-(trifluoromethoxy)benzyl]pyrimidine-2,4-diamine;

$N^4$-[(trans-4-aminocyclohexyl)methyl]-$N^2$-[2-chloro-3-(dimethylamino)benzyl]-5-nitropyrimidine-2,4-diamine;

1-(trans-4-{[(2-{[2-chloro-3-(dimethylamino)benzyl]amino}-5-nitropyrimidin-4-yl)amino]methyl}cyclohexyl)azetidin-3-ol;

$N^4$-[(trans-4-aminocyclohexyl)methyl]-$N^2$-(5-chloro-2-methoxybenzyl)-5-nitropyrimidine-2,4-diamine;

$N^4$-[(trans-4-aminocyclohexyl)methyl]-$N^2$-(2-methoxybenzyl)-5-nitropyrimidine-2,4-diamine;

$N^4$-[(trans-4-aminocyclohexyl)methyl]-$N^2$-[5-chloro-2-(trifluoromethoxy)benzyl]-5-nitropyrimidine-2,4-diamine;

$N^2$-[5-chloro-2-(trifluoromethoxy)benzyl]-5-nitro-$N^4$-[(trans-4-pyrrolidin-1-ylcyclohexyl)-5 methyl]pyrimidine-2,4-diamine;

$N^4$-[(trans-4-aminocyclohexyl)methyl]-$N^2$-[(2-methoxypyridin-3-yl)methyl]-5-nitropyrimidine-2,4-diamine;

N⁴-[(trans-4-aminocyclohexyl)methyl]-5-nitro-N²-{[4-(trifluoromethyl)pyridin-3-yl]methyl}pyrimidine-2,4-diamine;

N⁴-[(trans-4-aminocyclohexyl)methyl]-N²-[5-chloro-2-(methylsulfonyl)benzyl]-5-nitropyrimidine-2,4-diamine;

N⁴-[(trans-4-azetidin-1-ylcyclohexyl)methyl]-N²-[(4-chloropyridin-3-yl)methyl]-5-nitropyrimidine-2,4-diamine;

N⁴-[(trans-4-azetidin-1-ylcyclohexyl)methyl]-5-nitro-N²-{[4-(trifluoromethyl)pyridin-3-yl]methyl}pyrimidine-2,4-diamine;

1-[trans-4-({[5-nitro-2-({[4-(trifluoromethyl)pyridin-3-yl]methyl}amino)pyrimidin-4-yl]amino}methyl)cyclohexyl]azetidin-3-ol;

(2R)-1-[(trans-4-{[(5-nitro-2-{[2-(trifluoromethoxy)benzyl]amino}pyrimidin-4-yl)amino]methyl}cyclohexyl)amino]propan-2-ol;

(2S)-1-[(trans-4-{[(5-nitro-2-{[2-(trifluoromethoxy)benzyl]amino}pyrimidin-4-yl)amino]methyl}cyclohexyl)amino]propan-2-ol;

3-[(trans-4-{[(5-nitro-2-{[2-(trifluoromethoxy)benzyl]amino}pyrimidin-4-yl)amino]methyl}cyclohexyl)amino]propan-1-ol;

(2R)-2-[(trans-4-{[(5-nitro-2-{[2-(trifluoromethoxy)benzyl]amino}pyrimidin-4-yl)amino]methyl}cyclohexyl)amino]propan-1-ol (2S)-2-[(trans-4-{[(5-nitro-2-{[2-(trifluoromethoxy)benzyl]amino}pyrimidin-4-yl)amino]methyl}cyclohexyl)amino]propan-1-ol;

General Synthetic Methods

The compounds of the invention may be prepared by the methods described below. In each of the schemes below, the groups $R_1$, $R_2$ and $R_3$ are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art from commercially available materials using methods described in the chemical literature.

Compounds of formula (I) may be prepared as illustrated in Scheme I and described below.

Scheme I

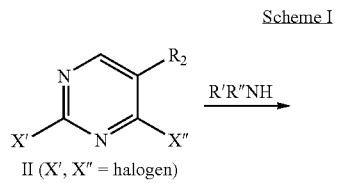

II (X', X" = halogen)

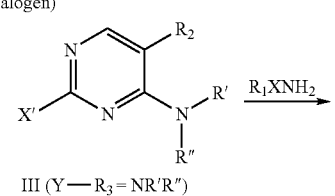

III (Y—R₃ = NR'R")

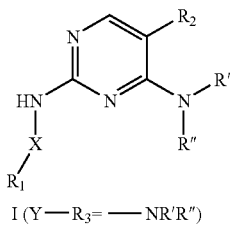

I (Y—R₃= ——NR'R")

As illustrated above, a 2,4-dihalopyrimidine (II), preferably a 2,4-dichloropyrimidine, is reacted with about one equivalent of an amine (R'R"NH) in the presence of a base, such as triethylamine, in a suitable solvent, such as ETOH, to provide intermediate III. The reaction is carried out preferably at about 0° C. to about room temperature. Intermediate III is then reacted with a second amine $R_1XNH_2$ in a suitable solvent, such as EtOH, to provide the desired I. The reaction is preferably heated to about the reflux temperature of the solvent. For intermediates III having $R_2$ groups that are less electron withdrawing than $NO_2$, such as $R_2$=F, Cl, CN or $CO_2Et$, the reaction is preferably carried out in a sealed vessel in a microwave reactor at about 140° C.

If $R_3$ contains a second amine group, (i.e., in the R' and/or R" groups in Scheme I above) the second amine is preferably protected with a suitable amino-protecting group, for example with a Boc-group, prior to reaction with intermediate II, and the amine is deprotected after reaction of the pyrimidine intermediate III with $R_1XNH_2$. For example, in the case of 1-amino 4-aminomethylcyclohexane as illustrated in Scheme II, the mono-Boc-protected diamine is reacted with II as described above. The resulting intermediate IV is then reacted with $R_1XNH_2$ as described above, and the Boc-protected intermediate V is then deprotected by treatment with acid to provide the desired compound of formula (I). The free amino group is then reacted with suitable reagents, such as alkylating agents or, under reductive conditions, carbonyl compounds, to provide the N-monoalkylated or N-dialkylated product of formula (I)

Scheme II

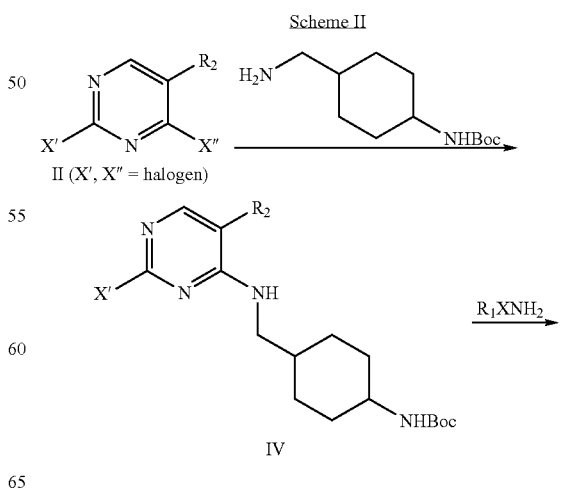

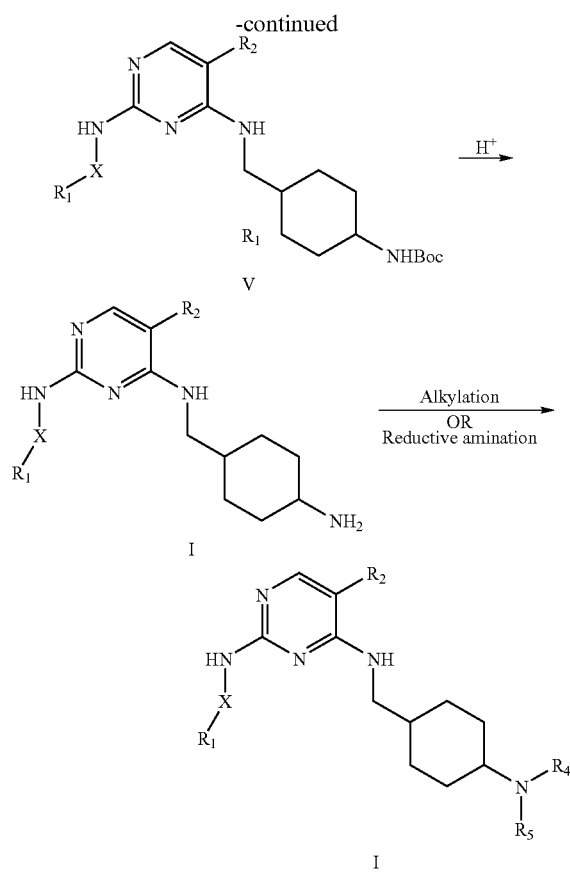

In a variation illustrated in Scheme III, if $R_2$ is $NO_2$, intermediate II may be reacted with a thiocyanate salt, such as potassium thiocyanate, in a suitable solvent, such as EtOH, to produce VI. Intermediate VI is reacted with $R_1XNH_2$ in a suitable solvent, such as EtOH, and in the presence of a base, such as triethylamine, to provide VII. Intermediate VII may then be reacted with an amine R'R"NH in a suitable solvent, such as EtOH or methylene chloride, to provide the desired compound of formula I Substituents $R_1$, $R_2$ and $R_3$ may be further modified by methods known in the art to obtain additional compounds of formula (I). Some of these modifications are illustrated in the synthetic examples below.

Compounds of formula (I) having Y=O or S may be prepared by reacting VII with the desired R'OH or R'SH in the presence of a suitable base such as sodium hydride in a suitable solvent such as THF or DMF to obtain I (Y—$R_3$=—OR' or —SR' respectively).

In order that this invention be more fully understood, the following examples are set forth. These examples are for the purpose of illustrating embodiments of this invention, and are not to be construed as limiting the scope of the invention in any way. Starting materials used are either commercially available or easily prepared from commercially available materials by those skilled in the art.

EXPERIMENTAL SECTION

Example 1

$N^4$-[(trans-4-aminocyclohexyl)methyl]-$N^2$-(cyclohexylmethyl)-5-nitropyrimidine-2,4-diamine

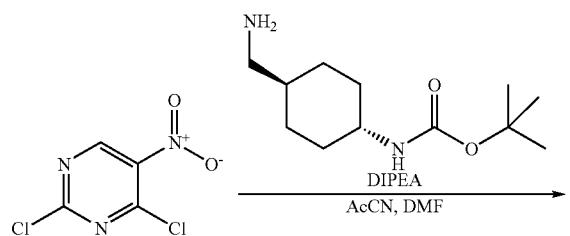

-continued

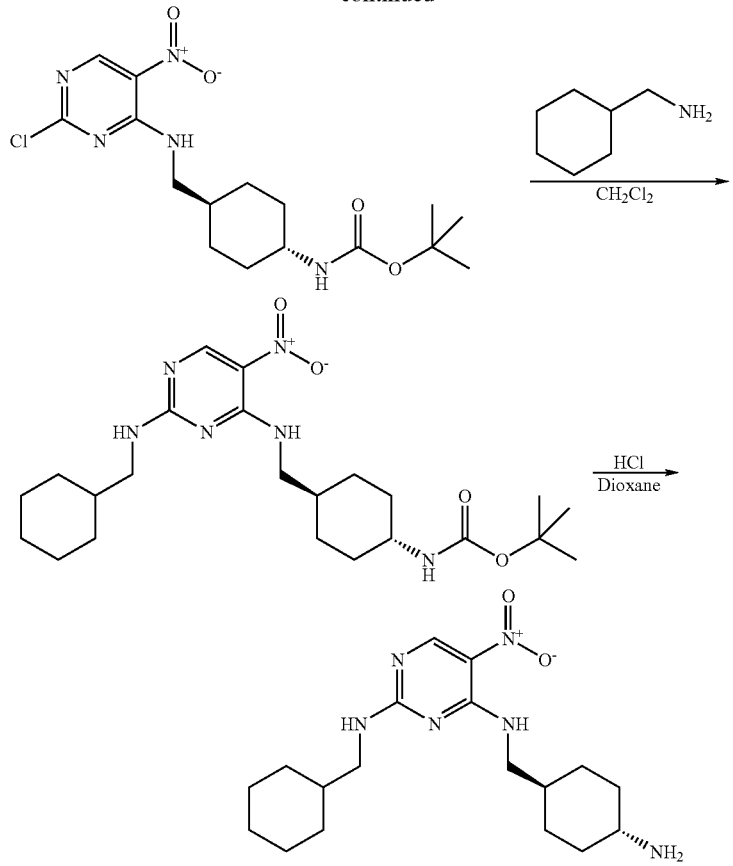

To a solution of 2,4-dichloro-5-nitropyrimidine (1.77 g, 9.11 mmol) in a mixture of AcCN (75 mL) and DMF (8 mL), were added tert-butyl trans-4-aminomethylcyclohexylcarbamate (2.08 g, 9.11 mmol) and diisopropylethylamine (DIPEA) (1.59 mL, 9.11 mmol). The reaction mixture was stirred at room temperature for 1 h. The reaction mixture was diluted with EtOAc and washed with water (×4). The organic phase was dried over anhydrous $Na_2SO_4$ and concentrated in vacuo. The resulting residue was purified by silica gel column chromatography using 9:1 EtOAc:hexanes as an eluent to afford 2.21 g (63%) of the desired product as a yellowish solid.

To a solution of the above {4-[(2-chloro-5-nitro-pyrimidin-4-ylamino)-methyl]-cyclohexyl}-carbamic acid tert-butyl ester (50.2 mg, 0.13 mmol) in $CH_2Cl_2$ (0.8 mL) was added cyclohexylmethylamine (44.1 mg, 0.39 mmol). The reaction mixture was stirred at room temperature for 3 h and then purified by silica gel column chromatography using 50:1 $CH_2Cl_2$:MeOH as an eluent to afford 32 mg (54%) of the desired product as a pale yellow solid.

The above (4-{[2-(cyclohexylmethylamino)-5-nitro-pyrimidin-4-ylamino]-methyl}-cyclohexyl)-carbamic acid tert-butyl ester (32 mg, 0.07 mmol) was dissolved in dioxane (0.6 mL) and treated with 4M HCl in dioxane (0.25 mL). The reaction mixture was concentrated in vacuo and the resulting residue was purified by silica gel preparative TLC to afford 9 mg (35%) of the title compound, m/z 363.4 [M+1]$^+$.

The following compounds were prepared using similar procedures as described above:

$N^4$-[(trans-4-aminocyclohexyl)methyl]-$N^2$-(5-fluoro-2-methylbenzyl)-5-nitropyrimidine-2,4-diamine, m/z 389.4 [M+1]$^+$ $N^4$-[(trans-4-aminocyclohexyl)methyl]-$N^2$-(2-methoxybenzyl)-5-nitropyrimidine-2,4-diamine, m/z 387.4 [M+1]$^+$ $N^4$-[(trans-4-aminocyclohexyl)methyl]-N2-(4-chloro-2-methylbenzyl)-5-nitropyrimidine-2,4-diamine, m/z 405.4 [M+1]$^+$ $N^4$-[(trans-4-aminocyclohexyl)methyl]-$N^2$-[2-fluoro-3-(trifluoromethyl)benzyl]-5-nitropyrimidine-2,4-diamine, m/z 443.6 [M+1]$^+$ $N^4$-[(trans-4-aminocyclohexyl)methyl]-$N^2$-(2-chloro-6-fluoro-3-methylbenzyl)-5-nitropyrimidine-2,4-diamine, m/z 423.6 [M+1]$^+$ $N^4$-[(trans-4-aminocyclohexyl)methyl]-$N^2$-(1-naphthylmethyl)-5-nitropyrimidine-2,4-diamine, m/z 407.6 [M+1]$^+$ $N^4$-[(trans-4-aminocyclohexyl)methyl]-5-nitro-$N^2$-{2-[(trifluoromethyl)thio]benzyl}pyrimidine-2,4-diamine, m/z 457.6 [M+1]$^+$ $N^4$-[(trans-4-aminocyclohexyl)methyl]-$N^2$-[2-(2-fluorophenyl)ethyl]-5-nitropyrimidine-2,4-diamine, m/z 389.8 [M+1]$^+$.

$N^4$-[(trans-4-aminocyclohexyl)methyl]-N~2~-[2-(3-fluorophenyl)ethyl]-5-nitropyrimidine-2,4-diamine, m/z 389.8 [M+1]$^+$.

$N^4$-[(trans-4-aminocyclohexyl)methyl]-$N^2$-[2-(4-fluorophenyl)ethyl]-5-nitropyrimidine-2,4-diamine, m/z 389.8 [M+1]$^+$.

N⁴-[(trans-4-aminocyclohexyl)methyl]-N²-[2-(1H-indol-3-yl)ethyl]-5-nitropyrimidine-2,4-diamine, m/z 408.7 [M–1]⁺.

N⁴-[(trans-4-aminocyclohexyl)methyl]-5-nitro-N²-(2-pyridin-2-ylethyl)pyrimidine-2,4-diamine, m/z 372.8 [M+1]⁺.

N⁴-[(trans-4-aminocyclohexyl)methyl]-5-nitro-N²-(2-pyridin-3-ylethyl)pyrimidine-2,4-diamine, m/z 372.8 [M+1]⁺.

N⁴-[(trans-4-aminocyclohexyl)methyl]-5-nitro-N²-(2-pyridin-4-ylethyl)pyrimidine-2,4-diamine, m/z 372.9 [M+1]⁺.

N²-(4-aminobenzyl)-N⁴-[(trans-4-aminocyclohexyl)methyl]-5-nitropyrimidine-2,4-diamine, m/z 372.9 [M+1]⁺.

N⁴-[(trans-4-aminocyclohexyl)methyl]-5-nitro-N²-(pyridin-4-ylmethyl)pyrimidine-2,4-diamine, m/z 358.9 [M+1]⁺.

N⁴-[(trans-4-aminocyclohexyl)methyl]-5-nitro-N²-(quinolin-4-ylmethyl)pyrimidine-2,4-diamine, m/z 408.3 [M+1]⁺.

4-{[(4-{[(trans-4-aminocyclohexyl)methyl]amino}-5-nitropyrimidin-2-yl)amino]methyl}benzene-1,2-diol, m/z 389.6 [M+1]⁺.

N⁴-[(trans-4-aminocyclohexyl)methyl]-N²-(1,3-benzodioxol-5-ylmethyl)-5-nitropyrimidine-2,4-diamine, m/z 401.6 [M+1]⁺.

4-{[(4-{[(trans-4-aminocyclohexyl)methyl]amino}-5-nitropyrimidin-2-yl)amino]methyl}-2-methoxyphenol, m/z 403.4 [M+1]⁺.

N⁴-[(trans-4-aminocyclohexyl)methyl]-N²-[2-(1H-benzimidazol-2-yl)ethyl]-5-nitropyrimidine-2,4-diamine, m/z 411.6 [M+1]⁺.

N⁴-[(trans-4-aminocyclohexyl)methyl]-N²-(1-benzothien-3-ylmethyl)-5-nitropyrimidine-2,4-diamine, m/z 413.3 [M+1]⁺.

N⁴-[(trans-4-aminocyclohexyl)methyl]-N²-[(5-chloro-1-benzothien-3-yl)methyl]-5-nitropyrimidine-2,4-diamine, m/z 447.3 [M+1]⁺.

N⁴-[(trans-4-aminocyclohexyl)methyl]-N²-[4-(dimethylamino)benzyl]-5-nitropyrimidine-2,4-diamine, m/z 398.4 [M–1]⁺.

N⁴-[(trans-4-aminocyclohexyl)methyl]-N²-[2-(difluoromethoxy)benzyl]-5-nitropyrimidine-2,4-diamine, m/z 423.4 [M+1]⁺.

N⁴-[(trans-4-aminocyclohexyl)methyl]-N²-(2-chlorobenzyl)-5-nitropyrimidine-2,4-diamine, m/z 391.2 [M+1]⁺.

N²-(4-{[(trans-4-aminocyclohexyl)methyl]amino}-5-nitropyrimidin-2-yl)-N,N-dimethylglycinamide, m/z 352.6 [M+1]⁺.

N²-(4-{[(trans-4-aminocyclohexyl)methyl]amino}-5-nitropyrimidin-2-yl)-N-methylglycinamide, m/z 338.5 [M+1]⁺.

Methyl N-(4-{[(trans-4-aminocyclohexyl)methyl]amino}-5-nitropyrimidin-2-yl)glycinate, m/z 339.4 [M+1]⁺.

methyl N-(4-{[(trans-4-aminocyclohexyl)methyl]amino}-5-nitropyrimidin-2-yl)-L-alaninate, m/z 353.4 [M+1]⁺.

Methyl (2S)-[(4-{[(trans-4-aminocyclohexyl)methyl]amino}-5-nitropyrimidin-2-yl)amino](phenyl)acetate, m/z 415.4 [M+1]⁺.

Methyl (2R)-[(4-{[(trans-4-aminocyclohexyl)methyl]amino}-5-nitropyrimidin-2-yl)amino](phenyl)acetate, m/z 415.4 [M+1]⁺.

N⁴-[(trans-4-aminocyclohexyl)methyl]-N²-(3-bromobenzyl)-5-nitropyrimidine-2,4-diamine, m/z 435.5 [M+1]⁺.

N⁴-(4-Amino-cyclohexylmethyl)-N²-(3-bromo-2-methylbenzyl)-5-nitro-pyrimidine-2,4-diamine, m/z 450.4 [M+1]⁺

N²-(5-amino-2-chlorobenzyl)-N⁴-[(trans-4-aminocyclohexyl)methyl]-5-nitropyrimidine-2,4-diamine, m/z 406.4 [M+1]⁺

N²-(3-aminobenzyl)-N⁴-[(trans-4-aminocyclohexyl)methyl]-5-nitropyrimidine-2,4-diamine, m/z 372.5 [M+1]⁺

N-(3-{[(4-{[(trans-4-aminocyclohexyl)methyl]amino}-5-nitropyrimidin-2-yl)amino]methyl}phenyl)acetamide, m/z 414.6 [M+1]⁺

N⁴-[(trans-4-aminocyclohexyl)methyl]-N²-[3-(dimethylamino)benzyl]-5-nitropyrimidine-2,4-diamine, m/z 400.5 [M+1]⁺

N⁴-[(trans-4-aminocyclohexyl)methyl]-N²-benzyl-5-nitropyrimidine-2,4-diamine, m/z 357.6 [M+1]⁺

N⁴-[(trans-4-aminocyclohexyl)methyl]-N²-[2-(dimethylamino)benzyl]-5-nitropyrimidine-2,4-diamine, m/z 371.6 [M+1]⁺

N-(3-{[(4-{[(trans-4-aminocyclohexyl)methyl]amino}-5-nitropyrimidin-2-yl)amino]methyl}phenyl)-N-methylacetamide, m/z 428.6 [M+1]⁺

N⁴-[(trans-4-aminocyclohexyl)methyl]-N²-(2,3-dihydro-1-benzofuran-5-ylmethyl)-5-nitropyrimidine-2,4-diamine, m/z 399.5 [M+1]⁺

N⁴-[(trans-4-aminocyclohexyl)methyl]-N²-[3-(methylamino)benzyl]-5-nitropyrimidine-2,4-diamine, m/z 386.7 [M+1]⁺

N⁴-[(trans-4-aminocyclohexyl)methyl]-N²-(2-methylbenzyl)-5-nitropyrimidine-2,4-diamine, m/z 371.6 [M+1]⁺

N⁴-[(trans-4-aminocyclohexyl)methyl]-N²-(2-fluorobenzyl)-5-nitropyrimidine-2,4-diamine, m/z 375.6 [M+1]⁺

N⁴-[(trans-4-aminocyclohexyl)methyl]-N²-(3-methylbenzyl)-5-nitropyrimidine-2,4-diamine, m/z 371.7 [M+1]⁺

N⁴-[(trans-4-aminocyclohexyl)methyl]-N²-(3-chlorobenzyl)-5-nitropyrimidine-2,4-diamine, m/z 390.8 [M+1]⁺

N⁴-[(trans-4-aminocyclohexyl)methyl]-N²-(3-fluorobenzyl)-5-nitropyrimidine-2,4-diamine, m/z 375.6 [M+1]⁺

N⁴-[(trans-4-aminocyclohexyl)methyl]-5-nitro-N²-[3-(trifluoromethoxy)benzyl]pyrimidine-2,4-diamine, m/z 441.6 [M+1]⁺

N⁴-[(trans-4-aminocyclohexyl)methyl]-N²-(2,3-dimethylbenzyl)-5-nitropyrimidine-2,4-diamine, m/z 385.7 [M+1]⁺

N⁴-[(trans-4-aminocyclohexyl)methyl]-N²-(3-chloro-2-methylbenzyl)-5-nitropyrimidine-2,4-diamine, m/z 405.6 [M+1]⁺

N⁴-[(trans-4-aminocyclohexyl)methyl]-N²-(3-chloro-2-fluorobenzyl)-5-nitropyrimidine-2,4-diamine, m/z 409.6 [M+1]⁺

N⁴-[(trans-4-aminocyclohexyl)methyl]-N²-(2,3-difluorobenzyl)-5-nitropyrimidine-2,4-diamine, m/z 393.6 [M+1]⁺

N⁴-[(trans-4-aminocyclohexyl)methyl]-N²-(5-chloro-2-fluorobenzyl)-5-nitropyrimidine-2,4-diamine m/z 410.5 [M+1]⁺

N⁴-[(trans-4-aminocyclohexyl)methyl]-N²-(5-chloro-2-methylbenzyl)-5-nitropyrimidine-2,4-diamine m/z 407.2 [M+1]⁺

N⁴-[(trans-4-aminocyclohexyl)methyl]-N²-(3,4-difluorobenzyl)-5-nitropyrimidine-2,4-diamine, m/z 392.9 [M+1]⁺

N⁴-[(trans-4-aminocyclohexyl)methyl]-N²-(3-chloro-4-fluorobenzyl)-5-nitropyrimidine-2,4-diamine, m/z 410.0 [M+1]⁺

N⁴-[(trans-4-aminocyclohexyl)methyl]-N²-(3,5-difluorobenzyl)-5-nitropyrimidine-2,4-diamine, m/z 392.9 [M+1]⁺

N⁴-[(trans-4-aminocyclohexyl)methyl]-N²-(2-chloro-4-fluorobenzyl)-5-nitropyrimidine-2,4-diamine, m/z 410.3 [M+1]⁺

$N^4$-[(trans-4-aminocyclohexyl)methyl]-$N^2$-(3,5-dichlorobenzyl)-5-nitropyrimidine-2,4-diamine, m/z 425.5 [M+1]$^+$ $N^4$-[(trans-4-aminocyclohexyl)methyl]-$N^2$-(4-chloro-2-fluorobenzyl)-5-nitropyrimidine-2,4-diamine, m/z 409.6 [M+1]$^+$ $N^4$-[(trans-4-aminocyclohexyl)methyl]-$N^2$-(4-bromo-2-fluorobenzyl)-5-nitropyrimidine-2,4-diamine, m/z 455.5 [M+1]$^+$ $N^4$-[(trans-4-aminocyclohexyl)methyl]-$N^2$-[4-fluoro-2-(trifluoromethyl)benzyl]-5-nitropyrimidine-2,4-diamine, m/z 443.6 [M+1]$^+$ $N^4$-[(trans-4-aminocyclohexyl)methyl]-$N^2$-[4-fluoro-3-(trifluoromethyl)benzyl]-5-nitropyrimidine-2,4-diamine, m/z 443.6 [M+1]$^+$ $N^4$-[(trans-4-aminocyclohexyl)methyl]-$N^2$-[2-chloro-5-(dimethylamino)benzyl]-5-nitropyrimidine-2,4-diamine, m/z 434.5 [M+1]$^+$ $N^4$-[(trans-4-aminocyclohexyl)methyl]-$N^2$-[2-chloro-3-(dimethylamino)benzyl]-5-nitropyrimidine-2,4-diamine, m/z 434.8 [M+1]$^+$ 3-{[(4-{[(trans-4-aminocyclohexyl)methyl]amino}-5-nitropyrimidin-2-yl)amino]methyl}benzamide, m/z 400.4 [M+1]$^+$ $N^4$-[(trans-4-aminocyclohexyl)methyl]-5-nitro-$N^2$-(pyridin-3-ylmethyl)pyrimidine-2,4-diamine m/z 358.5 [M+1]$^+$.

$N^4$-[(trans-4-aminocyclohexyl)methyl]-5-nitro-$N^2$-{[6-(trifluoromethyl)pyridin-3-yl]methyl}pyrimidine-2,4-diamine m/z 426.5 [M+1]$^+$ $N^4$-[(trans-4-aminocyclohexyl)methyl]-$N^2$-[(3-chloropyridin-2-yl)methyl]-5-nitropyrimidine-2,4-diamine m/z 392.4 [M+1]$^+$ $N^4$-[(trans-4-aminocyclohexyl)methyl]-$N^2$-[(2-methoxypyridin-3-yl)methyl]-5-nitropyrimidine-2,4-diamine m/z 388.5 [M+1]$^+$ $N^4$-[(trans-4-aminocyclohexyl)methyl]-5-nitro-$N^2$-{[2-(trifluoromethyl)pyridin-3-yl]methyl}pyrimidine-2,4-diamine m/z 426.4 [M+1]$^+$ $N^4$-[(trans-4-aminocyclohexyl)methyl]-$N^2$-[(4,5-dichloropyridin-3-yl)methyl]-5-nitropyrimidine-2,4-diamine m/z 426.5 [M+1]$^+$ $N^4$-[(trans-4-aminocyclohexyl)methyl]-$N^2$-[(3-methoxypyridin-2-yl)methyl]-5-nitropyrimidine-2,4-diamine m/z 388.7 [M+1]$^+$ $N^4$-[(trans-4-aminocyclohexyl)methyl]-5-nitro-$N^2$-(pyrazin-2-ylmethyl)pyrimidine-2,4-diamine, m/z 359 [M+1]$^+$.

(3-Aminomethyl-2-chloro-phenyl)-dimethyl-amine intermediate was synthesized according to the following procedure:

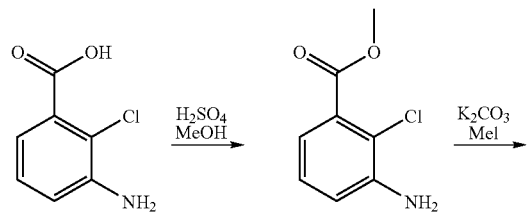

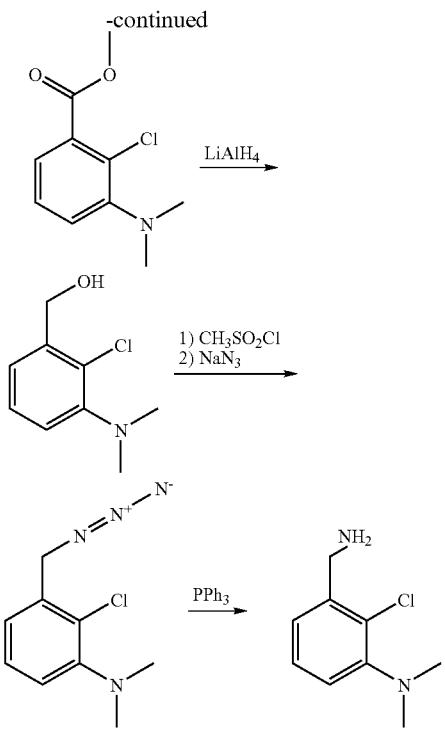

A 100 mL round bottomed flask was charged with 2-chloro-3-aminobenzoic acid (1.00 g, 5.38 mmol) methanol (50 mL) and sulfuric acid (0.1 mL). The reaction was heated to reflux for 12 h. The reaction was cooled, and the solvent was removed. The residual material was taken up in ethyl acetate (35 mL) and washed with water (4×20 mL). The organics were dried (MgSO4), concentrated, then purified by column chromatography using hexanes/ethyl acetate (4:1) to yield 2-chloro-3-amino-benzoic acid methyl ester (990 mg, 86%)

2-Chloro-3-amino-benzoic acid methyl ester (1.20 g, 6.47 mmol) was placed in a round bottomed flask with DMF (5 mL), Potassium carbonate (1.97 g, 14.2 mmol) and methyl iodide (0.89 mL, 14.22 mmol) were added. A reflux condenser was fitted and the reaction was heated to 60° C. for 12 h. The reaction was cooled to rt, diluted with water (20 mL) and extracted with ethyl acetate (3×20 mL). The organics were dried (MgSO4), concentrated, then purified by column chromatography using hexanes/ethyl acetate (1:1) to afford 2-chloro-3-dimethylamino-benzoic acid methyl ester (1.04 g, 75%)

2-Chloro-3-dimethylamino-benzoic acid methyl ester (0.85 g, 3.98 mmol) was placed in a round bottomed flask with tetrahydrofuran (50 mL) and cooled to 0° C. Lithium aluminum hydride (0.30 g, 7.96 mmol) was added in portions and after all the LAH was added, the reaction was allowed to warm and stir at rt for 14. The reaction was quenched by the addition of ice, then water (10 mL) was added. The organics were extracted into ethyl acetate (3×15 mL), dried (MgSO4) and concentrated down to afford (2-chloro-3-dimethylaminophenyl)-methanol which was taken onward without further purification.

(2-Chloro-3-dimethylamino-phenyl)-methanol (0.50 g, 2.69 mmol) was placed in a round bottomed flask with dichloromethane (10 mL) and cooled to 0° C. Triethylamine (0.68 g, 6.73 mmol), methanesulfonylchloride (0.23 mL, 2.97 mmol), and dimethylaminopyridine (0.02 g) were added and the reaction was allowed to warm and stir at rt over 3 h. The reaction was diluted with dichloromethane (20 mL) and washed with 1N Hydrochloric acid (10 mL), 10% aqueous sodium bicarbonate (10 mL), and water (10 mL). The organics were dried (MgSO4) and concentrated to afford methanesulfonic acid 2-chloro-3-dimethylamino-benzyl ester.

Methanesulfonic acid 2-chloro-3-dimethylamino-benzyl ester was placed in a round bottomed flask with DMF (8 mL). Sodium azide (0.35 g, 5.38 mmol) was added and the reaction was heated to 60° C. for 3 h. The reaction was cooled to rt, and the solvent was removed in vacuo. The residual crude material was purified by column chromatography using hexanes/ethyl acetate (1:1) as eluent to afford (3-azidomethyl-2-chloro-phenyl)-dimethyl-amine (3-Azidomethyl-2-chloro-phenyl)-dimethyl-amine (0.25 g, 1.19 mmol) was placed in a round bottomed flask with tetrahydrofuran (25 mL). Triphenylphosphine (0.78 g, 2.97 mmol) was added and the reaction was allowed to stir for 3 h at rt. The resulting precipitate was filtered off and set adise. The filtrate was concentrated down, then purified by column chromatography using methanol/methylene chloride/ammonium hydroxide (5:95:0.1) to afford the desired intermediate.

The following amine intermediates were prepared using similar procedures as described above:
(3-Aminomethyl-4-chloro-phenyl)-dimethylamine
(2-Methoxy-pyridin-3-yl)-methylamine
(2-trifluoromethyl-pyridin-3-yl)-methylamine
(4,5-Dichloro-pyridin-3-yl)-methylamine
(3-Methoxy-pyridin-2-yl)-methylamine
Pyrazin-2-yl-methylamine (2-Methoxy-pyridin-3-yl)-methanol intermediate was prepared according to the following procedure:

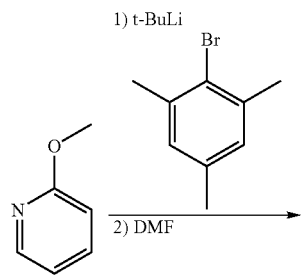

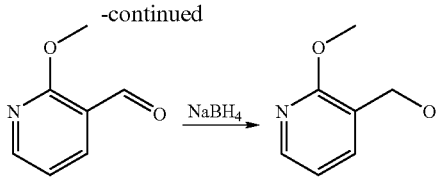

To a stirred solution of 1.7M t-butyl lithium in THF (35.0 mL, 59.6 mmol, 2.60 equiv.) with THF (150 mL) at −78 degrees was added dropwise 2-bromomesitylene (4.56 mL, 29.8 mmol, 1.30 equiv.). After stirring for 1 h, 2-methoxy-pyridine (2.5 g, 22.9 mmol) was added dropwise. This solution was warmed to −23 degrees and stirred for 3 h and then cooled to −78 degrees again. DMF (2.66 mL, 34.4 mmol, 1.5 equiv.) was added, the solution was stirred at −78 degrees for 1 h. The reaction was quenched at this temperature with brine (150 mL) and extracted with ether. The combined ether was dried over $K_2CO_3$ and evaporated on vacuo. The residue was chromatographed with 50%-80% EtOAc/Hexanes to give 2-methoxy-pyridine-3-carbaldehyde (2.34 g, 17.1 mmol, 74.5%) as a yellow solid.

To a solution of 2-methoxy-pyridine-3-carbaldehyde (2.05 g, 14.9 mmol) in MeOH (70 mL) cooled to 0° C. was added sodium borohydride (670 mg, 17.7 mmol, 1.18 equiv.) as a solid in one portion. The reaction was allowed to slowly warm to room temperature and stirred for 2 h. Excess hydride was consumed by the addition of $H_2O$ and the reaction mixture was concentrated under reduced pressure. The residue was taken back up in EtOAc and washed with $H_2O$. The aqueous phase was back extracted with EtOAc and the combine organic phase was washed with brine, dried over anhydrous $Na_2SO_4$ and concentrated under reduced pressure. The crude residue was purified by flash silica gel chromatography using a 5% MeOH/DCM to provide, after concentration of the eluent, to give (2-methoxy-pyridin-3-yl)-methanol (1.65 g, 11.9 mmol, 81.3 %) as a white solid.

The following intermediates were made using similar procedures described above:
(2-Trifluoromethyl-pyridin-3-yl)-methanol
(4,5-Dichloro-pyridin-3-yl)-methanol
(3-Methoxy-pyridin-2-yl)-methanol Example 2

$N^4$-[(trans-4-aminocyclohexyl)methyl]-5-nitro-$N^2$-[2-(trifluoromethoxy)benzyl]pyrimidine-2,4-diamine

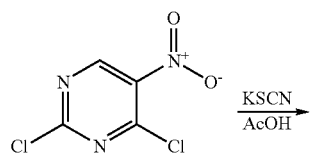

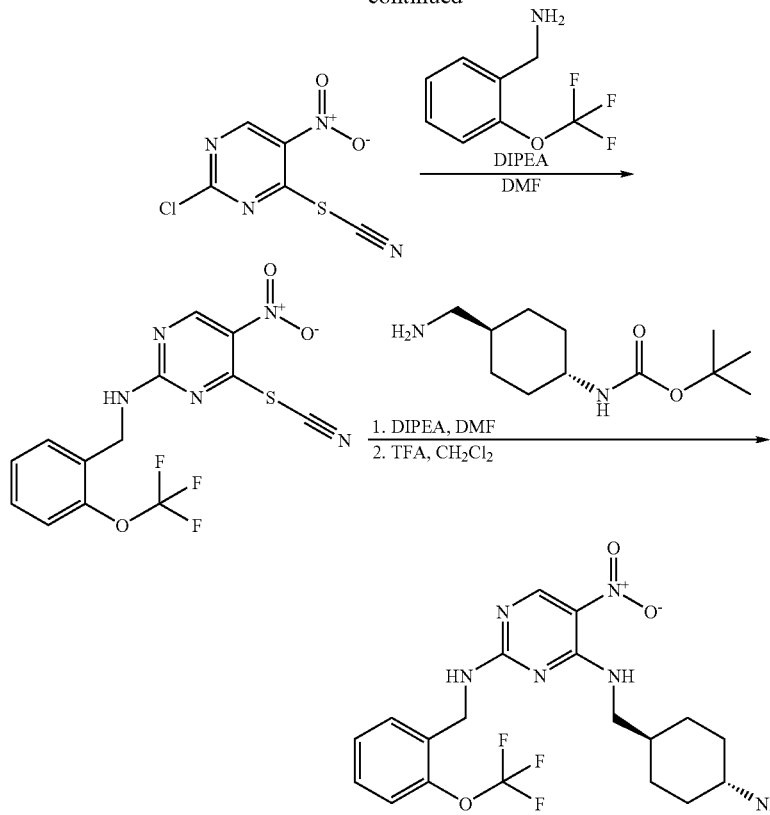

2,4-Dichloro-5-nitropyrimidine (12 g) was dissolved in AcOH (70 mL) and cooled to 0° C. Potassium thiocyanate (6.31 g) was added portion-wise to the solution over 2 h. The reaction was diluted with water and filtered. The filter cake was washed with cold ether to afford the desired 2-chloro-5-nitro-4-thiocyanatopyrimidine (9.5 g, 71%).

To a solution of 2-chloro-5-nitro-4-thiocyanatopyrimidine (1 g, 4.6 mmol) in DMF (5 mL) was added 2-(trifluoromethoxy)benzylamine (883 mg, 4.6 mmol) followed by DIPEA (804 μL, 4.6 mmol). The reaction mixture was stirred at room temperature for 30 min and diluted with EtOAc. The solution was washed with water (×4). The organic phase was dried over anhydrous $Na_2SO_4$ and then concentrated in vacuo. The resulting residue was purified by silica gel prep TLC using $CH_2Cl_2$ as an eluent to afford 727 mg (42%) of the desired product as a yellowish solid.

To a solution of the above product (50 mg, 0.135 mmol) in DMF (1 mL) were added tert-butyl trans-4-aminomethylcyclohexylcarbamate (61 mg, 0.27 mmol) and DIPEA (47 mL, 0.27 mmol). The reaction mixture was stirred at room temperature for 2 h. The reaction mixture was diluted with EtOAc (20 mL) and washed with water (×3). The organic phase was dried over anhydrous Na2SO4 and concentrated in vacuo. The resulting residue was purified by silica gel prep TLC using 95:5 $CH_2Cl_2$:MeOH as an eluent to afford the 71.8 mg (99%) of the desired product.

The above substituted diamino product (70 mg, 0.13 mmol) was dissolved in $CH_2Cl_2$ (10 mL) and TFA (0.7 mL) was added. The reaction mixture was stirred at room temperature for 40 min. until all the starting material was consumed. The mixture was then treated with a mixture of saturated $NaHCO_3$ and 1M $Na_2CO_3$ until pH 9-10. The mixture was extracted with $CH_2Cl_2$ (×2). MeOH was added to the organic phase during work-up to solubilize the product. The combined organic phase was dried over anhydrous $Na_2SO_4$ and concentrated in vacuo. The resulting residue was purified by silica gel preparative TLC using $CH_2Cl_2$:MeOH:$NH_4OH$ (10:1:0.1) as an eluent to afford 39 mg (69%) of the title compound, m/z 438.8 [M−1]$^+$.

The following compound was prepared using similar procedures as described above:

$N^4$-[(cis-4-aminocyclohexyl)methyl]-5-nitro-$N^2$-[2-(trifluoromethoxy)benzyl]pyrimidine-2,4-diamine, m/z 441.3 [M+1]$^+$ Example 3

$N^4$-[trans-4-aminocyclohexyl)methyl]-$N^2$-[(4-chloropyridin-3-yl)methyl]-5-nitropyrimidine-2,4-diamine

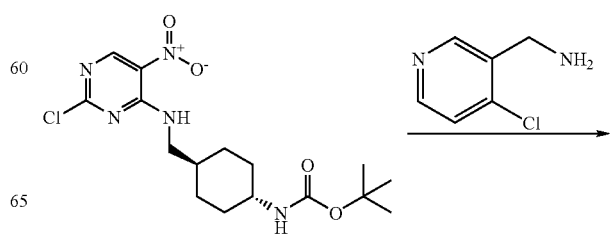

-continued

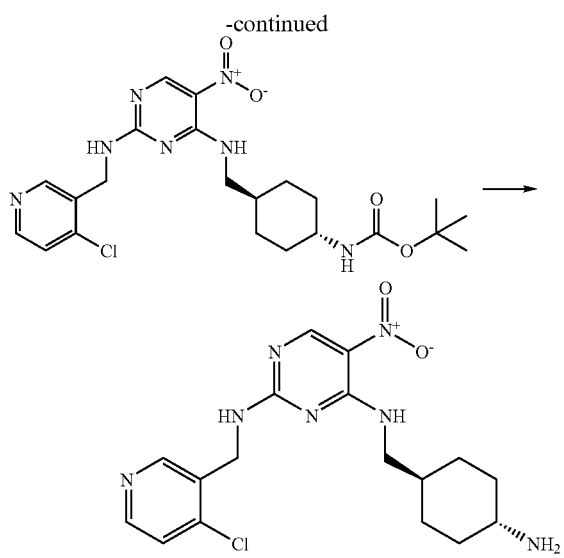

To a solution of {4-[(2-chloro-5-nitro-pyrimidin-4-ylamino)-methyl]-cyclohexyl}-carbamic acid tert-butyl ester (48.2 mg, 0.13 mmol) in CH$_2$Cl$_2$ (0.8 mL) was added 3-aminomethyl-4-chloropyridine (53.5 mg, 0.38 mmol). The reaction mixture was stirred at room temperature for 3 h. The mixture was then purified by silica gel column chromatography using 50:1 CH$_2$Cl$_2$:MeOH as an eluent to afford 20.6 mg (34%) of the desired product as a pale yellow solid.

The above [4-({2-[(4-chloro-pyridin-3-ylmethyl)-amino]-5-nitro-pyrimidin-4-ylamino}-methyl)-cyclohexyl]-carbamic acid tert-butyl ester (20.6 mg, 0.042 mmol) was dissolved in dioxane (0.5 mL) and 4 M HCl in dioxane (200 μL) was added to the solution. The reaction mixture was stirred at room temperature for 4 h and concentrated in vacuo. The resulting residue was purified by silica gel column chromatography using a mixture of 10% 2M NH$_3$ in MeOH and CH$_2$Cl$_2$ as an eluent to afford 5.5 mg (34%) of the desired product, m/z 392.3 [M+1]$^+$.

Preparation of 3-aminomethyl-4-chloropyridine intermediate:

To a solution of 4-chloro-nicotinic acid (2.5 g, 15.9 mmol) in DMF (26 mL)), were added Dicyclo-hexylcarbodiimide (DCC) (7.75 g, 37.5 mmol), 4-dimethylaminopyridine (DMAP) (0.286 g, 2.1 mmol) and EtOH (2.6 mL, 46.8 mmol). The reaction mixture was stirred at room temperature for 4 h. The mixture was then distilled (0.1 mmHg) to afford 1.5 g (51%) of 4-chloro-nicotinic acid ethyl ester as a colorless oil.

To a solution of 4-chloro-nicotinic acid ethyl ester (1.5 g, 8.1 mmol) in ether (15 mL) was added lithium aluminum hydride (0.31 g, 8.2 mmol) in ether (10 mL) over 10 min while cooling. The reaction mixture was stirred for 1 h and quenched with water (2 mL) and 15% NaOH (0.5 mL). The reaction mixture was filtered and the residue on the filter was washed with ether. The combined filtrate was dried over anhydrous Na$_2$SO$_4$ and concentrated in vacuo to afford 0.75 g of (4-chloro-pyridin-3-yl)-MeOH as a yellowish solid.

1,8-Diazabicyclo[5.4.0]undec-7-ene (DBU) (0.69 mL, 4.5 mmol) was added to a solution of the above (4-chloro-pyridin-3-yl)-MeOH (0.51 g, 3.6 mmol) and diphenylphosphoryl azide (DPPA) (0.92 mL, 4.3 mmol) in toluene (8 mL). The reaction mixture was stirred at room temperature for 3 h and then concentrated in vacuo. The resulting residue was purified by silica gel column chromatography using 1:4 EtOAc:hexanes to afford 0.47 g (79%) of 3-azidomethyl-4-chloro-pyridine.

Triphenylphosphine (0.81 g, 3.1 mmol) was added to a solution of the above 3-azidomethyl-4-chloro-pyridine (0.47 g, 3.1 mmol) in anhydrous THF (10 mL) at 0° C. The reaction mixture was warmed to room temperature and stirred for 18 h. The reaction mixture was then diluted with NH$_4$OH (3 mL) and stirred for another 3 h. 3M NaOH was then added to the reaction mixture and stirred for 1 h. The mixture was acidified to pH 2 by adding 4M HCl solution. The mixture was diluted with ether and the layers were separated. The aqueous layer was extracted with ether and then basified with 2M NaOH solution. The aqueous solution was extracted with CH$_2$Cl$_2$ (×3). The combined organic phase was dried over MgSO$_4$ and concentrated in vacuo to afford a pale yellow oily solid. This product was diluted with ether and filtered. The filtrated was concentrated in vacuo to afford a pale yellow oil. The crude product was purified by silica gel column chromatography using 20:1 CH$_2$Cl$_2$:MeOH as an eluent to afford 0.21 g (53%) of 3-aminomethyl-4-chloropyridine as a colorless oil.

The following compounds were prepared using similar procedures as described above:

N$^4$-[(trans-4-aminocyclohexyl)methyl]-N$^2$-[(2-chloropyridin-3-yl)methyl]-5-nitropyrimidine-2,4-diamine, m/z 392.4 [M+1]$^+$ Preparation of 3-aminomethyl-2-chloropyridine intermediate:

A mixture of 2-chloronicotinic acid (5.0 g, 31.7 mmol) and thionyl chloride (20 mL) was heated at reflux for 1.5 h. The reaction mixture was concentrated in vacuo to remove an excess thionyl chloride. The resulting solid was added in portions to a solution of sodium borohydride (4.3 g, 114 mmol) in water at 10° C. The reaction was maintained at 10-15° C. during the addition to NaBH$_4$. The reaction mixture was then warmed to room temperature. The mixture was saturated with NaCl and extracted with ether (30 mL×3). The combined organic layer was dried over MgSO$_4$ and concentrated in vacuo to afford 4.1 g (90%) of (2-chloro-pyridin-3-yl)-methanol.

To a solution of the above (2-chloro-pyridin-3-yl)-methanol (2.2 g, 15.1 mmol) and DPPA (3.9 mL, 18.2 mmol) in toluene (30 mL) was added DBU (2.9 mL, 18.2 mmol) at room temperature and stirred for 3 h. The reaction was diluted with 3M HCl (30 mL) and Et$_2$O (75 mL). The layers were separated and the aqueous layer was extracted with Et$_2$O (75 mL). The combined organic layers were washed with water (50 mL), brine and dried over MgSO$_4$. The solution was filtered and concentrated in vacuo to yield a yellow oil. Silica gel column chromatography using 95:5 hexanes:EtOAc afforded 2.0 g (77%) of 3-azidomethyl-2-chloro-pyridine as a colorless oil.

Triphenylphosphine (2.5 g, 9.5 mmol) was added to a solution of the above 3-azidomethyl-2-chloro-pyridine (1.4 g, 8.5 mmol) in anhydrous THF (30 mL) at 0° C. The reaction mixture was warmed to room temperature and stirred for 18 h. The reaction mixture was diluted with NH$_4$OH (3 mL) and stirred for another 3 h. The mixture was then treated with 3M NaOH and stirred for 1 h. The mixture was acidified to pH 2 by adding 4M HCl solution. The mixture was diluted with ether and the layers were separated. The aqueous layer was extracted with ether and then basified with 2M NaOH solution. The aqueous solution was extracted with CH$_2$Cl$_2$ (×3). The combined organic phase was dried over MgSO$_4$ and concentrated in vacuo to afford a pale yellow oily solid. This product was diluted with ether and filtered. The filtrated was concentrated to afford a pale yellow oil. The crude product was purified by silica gel column chromatography using 20:1 CH$_2$Cl$_2$:MeOH as an eluent to afford 0.88 g (73%) of 3-aminomethyl-2-chloropyridine as a colorless oil.

N$^4$-[(trans-4-aminocyclohexyl)methyl]-N$^2$-(5-chloro-2-methoxybenzyl)-5-nitropyrimidine-2,4-diamine, m/z 421.3 [M+1]$^+$ Preparation of 5-chloro-2-methoxy-benzylamine intermediate:

A mixture of methyl 5-chloro-2-methoxybenzoate (2.5 g, 12.5 mmol) and 7 M NH$_3$ (25 mL) in MeOH was heated to 120° C. in a sealed tube for 72 h. The reaction mixture was cooled to room temperature and nitrogen was bubbled through the solution for 15 min. The solution was then concentrated in vacuo to yield a tan solid. The crude product was recrystallized from MeOH (10 mL). The crystals were filtered and washed with cold MeOH to afford 1.4 g (60%) of 2-chloro-2-methoxy-benzamide.

To a solution of the above 2-chloro-2-methoxy-benzamide (1.0 g, 5.4 mmol) in anhydrous THF (10 mL) was added dropwise 1M BH$_3$-THF complex (12.8 mL, 12.8 mmol) at 0° C. After 10 min. of stirring at 0° C., the reaction mixture was heated at 65° C. for 4 h. MeOH (approximately 10 mL) was then added to the cooled reaction mixture at 0° C. The reaction was warmed to room temperature and stirred for 10 min. The reaction solution was concentrated in vacuo to yield an oily product. The product was dissolved in 50% THF/MeOH (10 mL) and 4M HCl (10 mL) was added slowly to the solution. After 10 min. the mixture was partitioned between water (10 mL) and CH$_2$Cl$_2$ (20 mL). The aqueous layer was extracted with CH$_2$Cl$_2$ (10 mL) and the organic layers were discarded. The aqueous layer was basified to pH 9 with 5M NaOH solution. The solution was extracted with CH$_2$Cl$_2$ (3×20 mL). The combined organic layers were washed with brine, dried over MgSO$_4$, and concentrated in vacuo to afford 0.36 g (39%) of 5-chloro-2-methoxy-benzylamine as a white solid.

(1R,3S)-3-{[(4-{[(trans-4-aminocyclohexyl)methyl]amino}-5-nitropyrimidin-2-yl)amino]methyl}-cyclohexanol, m/z 379.4 [M+1]$^+$ Preparation of cis-3-aminomethyl-cyclohexanol intermediate:

To a solution of 2-cyclohexen-1-one (6 mL, 62 mmol) in hexanes (100 mL) was added 1M Et$_2$AlCN (160 mL) in toluene with cooling at −15° C. After stirring for 30 min, the reaction mixture was poured into an ice-cold 2M HCl solution and extracted with CH$_2$Cl$_2$. The extracts were washed with cold 2M NaOH and water, dried and concentrated in vacuo. Distillation of the product yielded 1.7 g (22%) of 3-oxo-cyclohexanecarbonitrile, b.p. 145-146° C. (16 mmHg).

To a solution of the above 3-oxo-cyclohexanecarbonitrile (0.31 g, 2.5 mmol) in MeOH (10 mL) was added NaBH$_4$ (0.11 g, 2.9 mmol) at 0° C. in one portion. The reaction mixture was allowed to slowly warm to room temperature and stirred for 2 h. Excess hydride was consumed by the addition of H$_2$O. The reaction mixture was then concentrated under reduced pressure. The resulting residue was diluted with EtOAc and the solution was washed with water. The organic phase was washed with brine, dried over anhydrous Na$_2$SO$_4$ and concentrated under reduced pressure. The crude residue was purified by silica gel chromatography using a 0-40% gradient of EtOAc and hexanes as an eluent to provide 0.2 g (64%) of cis-3-hydrocy-cyclohexanecarbonitrile as a colorless oil.

To a 2 N solution of NH$_3$ in MeOH (15 mL) in a high pressure Parr bottle was added cis-3-hydroxy-cyclohexanecarbonitrile (0.2 g, 1.6 mmol) and W-7 Raney Nickel (0.35 g, 6.0 mmol). The mixture was placed under 45 psi H$_2$ and shaken for 15 h. The pressure was released and the reaction filtered through a pad of diatomaceous earth. The filter pad was washed with MeOH and the filtrate was concentrated under reduced pressure to provide 0.16 g (64%) of cis-3-aminomethyl-cyclohexanol as a white solid (1S,3S)-3-{[(4-{[(trans-4-aminocyclohexyl)methyl]amino}-5-nitropyrimidin-2-yl)amino]methyl}-cyclohexanol, m/z 379.5 [M+1]$^+$ Preparation of trans-3-aminomethyl-cyclohexanol intermediate:

To a solution of benzoic acid (1.1 g, 8.8 mmol) and PS-triphenylphosphine (6.7 g, 15.5 mmol) in anhydrous THF (40 mL) was added cis-3-hydroxy-cyclohexanecarbonitrile (1.1 g, 8.8 mmol) in anhydrous THF (20 mL). The reaction mixture was cooled while diethyl azodicarboxylate (DEAD) (1.9 mL, 12.3 mmol) was added by syringe over 3 min. The reaction was shaken for 12 h. The mixture was filtered and the resin was washed with ether. The filtrate was concentrated in vacuo to afford an oily solid. Silica gel column chromatography using 95:5 hexanes:EtOAc as an eluent afforded 0.29 g (14%) of benzoic acid trans-3-cyano-cyclohexyl ester as a white solid.

A mixture of the above benzoic acid trans-3-cyano-cyclohexyl ester (0.29 g, 1.3 mmol) and 0.5M NaOCH$_3$ (0.13 mL, 0.065 mmol) in MeOH (1 mL) was stirred at room temperature for 12 h. The reaction mixture was concentrated in vacuo and the resulting residue was purified by silica gel column chromatography using 3:2 hexanes:EtOAc as an eluent to afford 0.12 g (78%) of trans-3-hydroxy-cyclohexanecarbonitrile as a colorless oil.

To a 2 N solution of NH$_3$ in MeOH (15 mL) in a high pressure Parr bottle was added trans-3-hydroxy-cyclohexanecarbonitrile (0.12 g, 1.0 mmol) and W-7 Raney Nickel (0.2 g, 3.4 mmol). The mixture was placed under 45 psi H$_2$ and shaken for 15 h. The pressure was released and the reaction filtered through a pad of diatomaceous earth. The filter pad was washed with MeOH and the filtrate was concentrated under reduced pressure to provide 0.1 g (79%) of trans-3-aminomethyl-cyclohexanol as a white solid.

2-[(4-{[(trans-4-aminocyclohexyl)methyl]amino}-5-nitropyrimidin-2-yl)amino]-1-phenylethanone, m/z 385.3 [M+1]$^+$ N$^4$-[(trans-4-aminocyclohexyl)methyl]-N$^2$-[5-chloro-2-(trifluoromethoxy)benzyl]-5-nitropyrimidine-2,4-diamine, m/z 475.5 [M+1]$^+$ Preparation of 5-chloro-2-trifluoromethoxy-benzylamine intermediate:

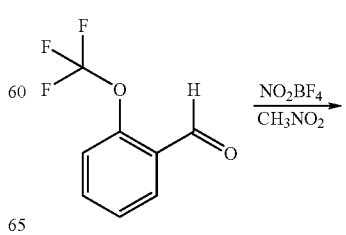

-continued

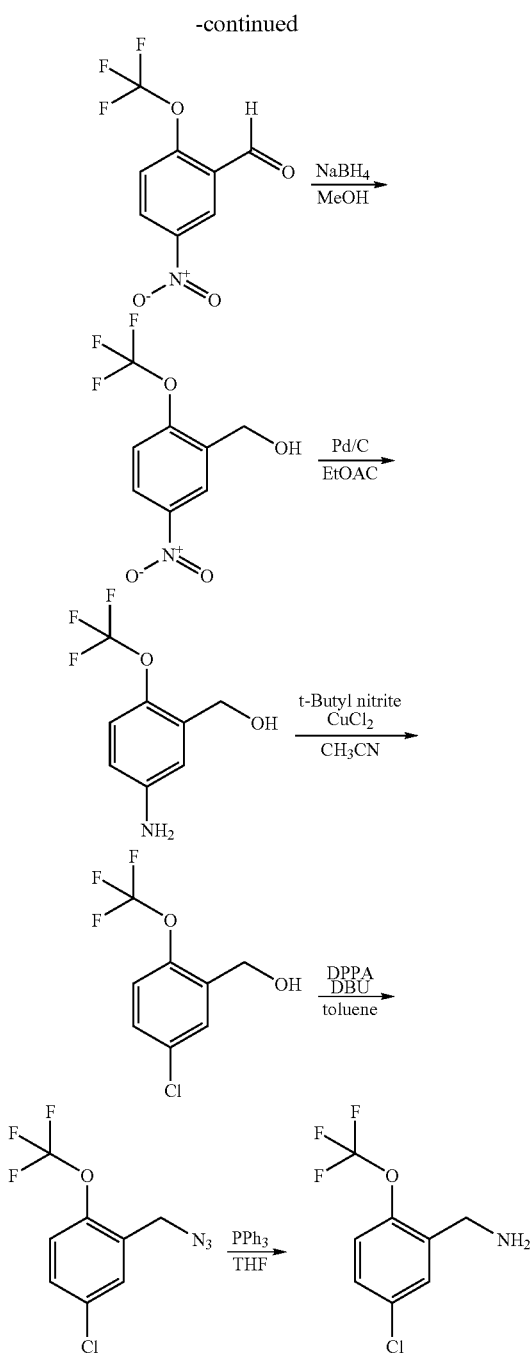

Nitronium tetrafluoroborate (14.0 g, 105 mmol) was added to a solution of 2-trifluoromethoxy-benzaldehyde (10.0 g, 52.6 mmol) in nitromethane (30 mL) at room temperature. The mixture was stirred for 2 h and was then quenched with ice water and extracted with ether (100 mL). The organic layer was separated, washed with water, dried over MgSO$_4$ and chromatographed with 5% EtOAc/hexanes to afford 7.52 g of 5-nitro-2-trifluoromethoxy-benzaldehyde (60.8%) as a pale yellow solid.

To a solution of 5-nitro-2-trifluoromethoxy-benzaldehyde (2.33 g, 9.91 mmol) in MeOH (30 mL) cooled to 0° C. was added sodium borohydride (440 mg, 11.7 mmol) as a solid in one portion. The reaction was allowed to slowly warm to room temperature and stirred for 2 h. Excess hydride was consumed by the addition of water and the reaction mixture was concentrated under reduced pressure. The residue was taken back up in EtOAc and washed with water. The aqueous phase was back extracted with EtOAc and the combine organic phase was washed with brine, dried over anhydrous Na$_2$SO$_4$ and concentrated under reduced pressure. The crude residue was purified by flash silica gel chromatography using a 0-40% gradient of EtOAc:hexanes to provide, after concentration of the eluent, 1.89 g (80%) of (5-nitro-2-trifluoromethoxy-phenyl)-methanol as a white solid.

(5-Nitro-2-trifluoromethoxy-phenyl)-methanol (2 g, 8.4 mmol) was dissolved in EtOAc (50 mL) and was degassed. Pd/C (200 mg) was then added and the mixture was degassed again. The solution was hydrogenated with a balloon for 3 h. After the reaction was complete, the solution was filtered through diatomaceous earth and the residue was chromatographed with 95:5 CH$_2$Cl$_2$:MeOH as an eluent to give 1.67 g (96%) of (5-amino-2-trifluoromethoxy-phenyl)-methanol as a yellow solid.

t-Butyl nitrite (2.49 g, 24.2 mmol), copper (II) chloride (2.71 g, 20.2 mmol), and acetonitrile (100 mL) were added to a round-bottom flask. The resulting mixture was cooled to 0° C. (5-Amino-2-trifluoromethoxy-phenyl)-methanol (1.67 g, 8.1 mmol) in acetonitrile (10 mL) was slowly added to the reaction over a period of 5 min. The reaction was warmed up to room temperature and stirred overnight. The mixture was then poured into 20% HCl (100 mL) and extracted with ether (100 mL). The organic layer was washed with 20% HCl (100 mL) and dried over MgSO$_4$. The ether was removed in vacuo and the residue was chromatographed with 4:1 hexanes:EtOAC to give 1.2 g (66%) of (5-chloro-2-trifluoromethoxy-phenyl)-methanol as a yellow solid.

DBU (1.0 mL, 6.7 mmol) was added to a solution of (5-chloro-2-trifluoromethoxy-phenyl)-methanol (1.2 g, 5.3 mmol) and DPPA (1.4 mL, 6.4 mmol) in toluene (30 mL) at room temperature. After 3 h, the reaction was concentrated in vacuo to yield an yellow oil. Silica gel column chromatography using 95:5 hexanes:EtOAc yielded 0.86g (65%) of 2-azidomethyl-4-chloro-1-trifluoromethoxy-benzene as a colorless oil.

Triphenylphosphine (0.99 g, 3.8 mmol) was added to a solution of the azide (0.86 g, 3.4 mmol) in THF (25 mL) at 0° C. After 5 min, the mixture was warmed to room temperature. After 18 h, the reaction was diluted with ammonium hydroxide (10 mL). After 3 h, the reaction was diluted with 3 M NaOH and stirred for 1 h. The reaction was acidified to pH 2 with 4 N HCl. The solution was then diluted with Et$_2$O and the layers were separated. The aqueous layer was extracted with Et$_2$O and then basified with 2 N NaOH. The basic aqueous solution was extracted with CH$_2$Cl$_2$ (3×50 mL). The combined organic layers were dried over MgSO$_4$, filtered and concentrated to yield an oily solid. The crude solid was diluted with Et$_2$O (50 mL) and filtered. The filtrate was concentrated in vacuo to yield a pale yellow oil. Silica gel column chromatography using 20:1 CH$_2$Cl$_2$:MeOH as an eluent yielded 0.64 g (83%) of 5-chloro-2-trifluoromethoxy-benzylamine as a colorless oil. The product was not stable at room temperature and was used for the next step immediately.

$N^4$-[(trans-4-aminocyclohexyl)methyl]-$N^2$-[(4-methoxypyridin-3-yl)methyl]-5-nitropyrimidine-2,4-diamine, m/z 388.9 [M+1]$^+$ Preparation of (4-methoxy-pyridin-3-yl)-methylamine intermediate:

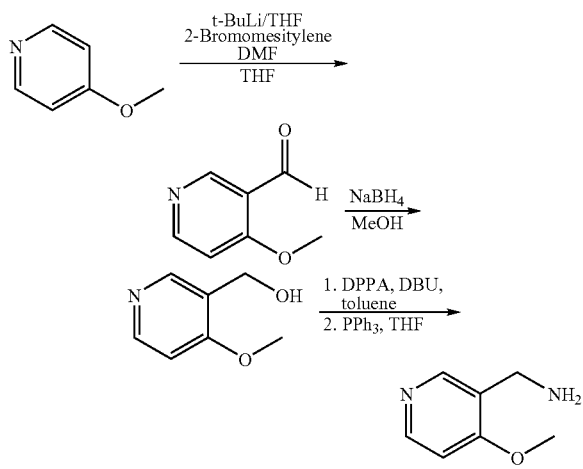

To a stirred solution of 1.7 M t-butyl lithium in THF (35.0 mL, 59.6 mmol) with THF (150 mL) at −78° C. was added dropwise 2-bromomesitylene (4.6 mL, 29.8 mmol). After stirring for 1 h, 4-methoxy-pyridine (2.5 g, 22.9 mmol) was added dropwise. This solution was warmed to −23° C. and stirred for 3 h and then cooled to −78° C. again. DMF (2.7 mL, 34.4 mmol) was added and the solution was stirred at −78° C. for 1 h. The reaction was quenched at this temperature with brine (150 mL) and extracted with ether. The combined ether was dried over $K_2CO_3$ and evaporated in vacuo. The residue was chromatographed with 50%-80% EtOAc/hexanes to give 2.1 g (65%) of 4-methoxy-pyridine-3-carbaldehyde as a yellow solid.

To a solution of 4-methoxy-pyridine-3-carbaldehyde (2.1 g, 14.9 mmol) in MeOH (70 mL) cooled to 0° C. was added sodium borohydride (0.67 g, 17.7 mmol) as a solid in one portion. The reaction was allowed to slowly warm to room temperature and stirred for 2 h. Excess hydride was consumed by the addition of water and the reaction mixture was concentrated under reduced pressure. The residue was taken back up in EtOAc and washed with water. The aqueous phase was back extracted with EtOAc and the combined organic phase was washed with brine, dried over anhydrous $Na_2SO_4$ and concentrated under reduced pressure. The crude residue was purified by flash silica gel chromatography using a 95:5 $CH_2Cl_2$:MeOH as an eluent to provide, after concentration, to give 1.1 g (55%) of (4-methoxy-pyridin-3-yl)-methanol as a white solid.

(4-Methoxy-pyridin-3-yl)-methanol was then converted to C-(4-methoxy-pyridin-3-yl)-methylamine through standard procedures as described in the previous compound.

(1R,3R)-3-{[(4-{[(trans-4-aminocyclohexyl)methyl]amino}-5-nitropyrimidin-2-yl)amino]methyl}-4,4-dimethylcyclohexanol, m/z 407.6 $[M+1]^+$.

Preparation of (1R,3R)-3-aminomethyl-4,4-dimethyl-cyclohexanol

To a solution of 4,4'-dimethyl-2-cyclohexene-1-one and acetic acid in 95% EtOH (70 mL) warmed to 40° C. was added a solution of potassium cyanide in $H_2O$ (10 mL). The reaction was stirred at 40° C. for 4 h. The reaction was cooled to room temperature and filtered through a pad of silica gel. The filter pad was washed with EtOAc and the mixture was concentrated under reduced pressure. The residue was taken back up into $H_2O$ and washed with EtOAc. The combined organic phase was washed with brine, dried over anhydrous $Na_2SO_4$ and concentrated under reduced pressure. The crude reaction product was purified by flash silica gel chromatography using a 0-20% gradient of EtOAc to hexanes to provide, after concentration of the eluent, 1.03 g of 2,2-dimethyl-5-oxo-cyclohexanecarbonitrile as a clear oil.

To a solution of 2,2-dimethyl-5-oxo-cyclohexanecarbonitrile in MeOH (15 mL) cooled to 0° C. was added $NaBH_4$ as a solid in one portion. The reaction was allowed to slowly warm to room temperature and stirred for 2 h. Excess hydride was consumed by the addition of $H_2O$ and the reaction mixture was concentrated under reduced pressure. The residue was taken back up in EtOAc and washed with $H_2O$. The aqueous phase was back extracted with EtOAc and the combine organic phase was washed with brine, dried over anhydrous $Na_2SO_4$ and concentrated under reduced pressure. The crude residue was purified by flash silica gel chromatography using a 0-40% gradient of A (EtOAc) to B (hexanes) to provide, after concentration of the eluent, 400 mg of (1R,5R)-5-hydroxy-2,2-dimethyl-cyclohexanecarbonitrile as a clear oil. $^1$H-NMR indicates only a single diastereomer was isolated.

To a 2 N solution of $NH_3$ in MeOH (15 mL) in a high pressure Parr bottle was added (1R,5R)-5-hydroxy-2,2-dimethyl-cyclohexanecarbonitrile and Ni. The mixture was placed under 45 psi $H_2$ and shaken for 15 h. The pressure was released and the reaction filtered through a pad of diatomaceous earth. The filter pad was washed with MeOH and the mixture was concentrated under reduced pressure to provide 260 mg of a colorless oil. 1H-NMR showed a mixture of (1R,3R)-3-aminomethyl-4,4-dimethyl-cyclohexanol (major) with a minor impurity of (1R,5R)-5-hydroxy-2,2-dimethyl-cyclohexanecarbonitrile. The crude reaction product was used without further purification.

$N^4$-[(trans-4-aminocyclohexyl)methyl]-$N^2$-[(5-bromopyridin-3-yl)methyl]-5-nitropyrimidine-2,4-diamine, m/z 437.9 $[M+1]^+$.

Preparation of (5-Bromo-pyridin-3-yl)-methylamine

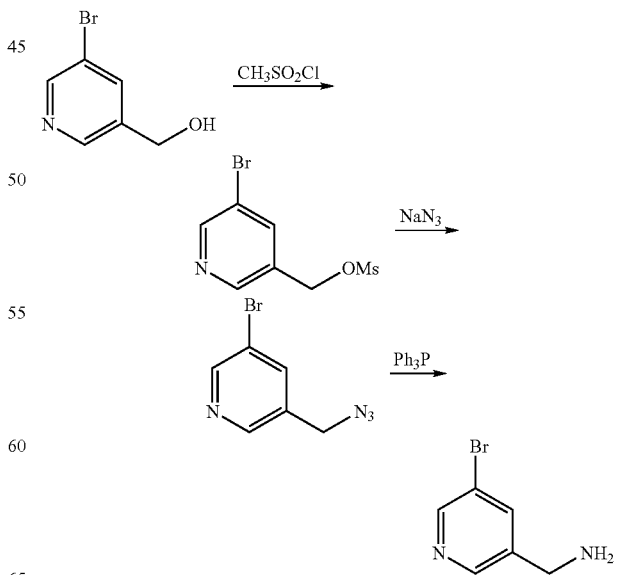

To a solution of (5-bromo-pyridin-3-yl)-methanol (2.75 g, 14.6 mmol) and Et$_3$N (3.10 mL, 22.2 mmol) in DCM (75 mL) at −20° C. under N$_2$ was added methanesulfonyl chloride (1.70 mL, 22.2 mmol) dropwise. After 45 min the reaction was allowed to warm to room temperature and diluted with DCM (75 mL). The reaction mixture was washed with water (75 mL), sat. NaHCO$_3$ (2×75 mL) and brine before drying over Na$_2$SO$_4$. Concentration in vacuo afforded crude methanesulfonic acid 5-bromo-pyridin-3-ylmethyl ester (4.21 g) as an oil. The crude material was used in the next step without purification.

To a solution of crude methanesulfonic acid 5-bromo-pyridin-3-ylmethyl ester (4.20 g) in DMF (60 mL) was added NaN$_3$ (10.0 g, 153.8 mmol). The mixture was stirred under N$_2$ overnight then diluted with water. The mixture was extracted with EtOAc (2×300 mL) and the combined organic layers washed with water before drying over Na$_2$SO$_4$. The solution was concentrated in vacuo to afford crude 3-azidomethyl-5-bromo-pyridine (2.04 g) as a dark brown oil. This crude material was used directly in the next step.

To a solution of crude 3-azidomethyl-5-bromo-pyridine (2.04 g) in THF (50 mL) and water (1 mL) was added triphenylphosphine (5.02 g, 19.1 mmol). The mixture was heated at reflux under N$_2$ for 2 h before cooling to room temperature and concentrating in vacuo. The residue was purified by column chromatography using an ISCO combi-flash cartridge (silica gel, 100:0 to 30:70 DCM/10% NH$_4$OH in MeOH) to afford (5-bromo-pyridin-3-yl)-methylamine (0.97 g)

N$^4$-[(trans-4-aminocyclohexyl)methyl]-5-nitro-N$^2$-(pyridin-2-ylmethyl)pyrimidine-2,4-diamine m/z 358.4 [M+1]$^+$ N$^4$-[(trans-4-aminocyclohexyl)methyl]-5-nitro-N$^2$-(1,3-thiazol-2-ylmethyl)pyrimidine-2,4-diamine m/z 364.3 [M+1]$^+$ N$^4$-[(trans-4-aminocyclohexyl)methyl]-5-nitro-N$^2$-(1,3-thiazol-2-ylmethyl)pyrimidine-2,4-diamine m/z 347.6 [M+1]$^+$ Preparation of (1H-Imidazol-2-yl)-methylamine intermediate was synthesized as described in literature. (Gebert, U; Von Kerekjarto, B. Liebigs Ann. Chem. 1968 249-259; Bastiaansen, L. A. M.; Godefroi, E. F. J. Org. Chem. 1978 1603-1604.)

N$^4$-[(trans-4-aminocyclohexyl)methyl]-N$^2$-[(3-methylpyridin-2-yl)methyl]-5-nitropyrimidine-2,4-diamine m/z 372.4 [M+1]$^+$ N$^4$-[(trans-4-aminocyclohexyl)methyl]-N$^2$-[(6-methylpyridin-2-yl)methyl]-5-nitropyrimidine-2,4-diamine m/z 372.4 [M+1]$^+$ N$^4$-[(trans-4-aminocyclohexyl)methyl]-N$^2$-[(5-methylpyridin-3-yl)methyl]-5-nitropyrimidine-2,4-diamine m/z 372.5 [M+1]$^+$ Preparation of (5-Methyl-pyridin-2-yl)-methylamine intermediate:

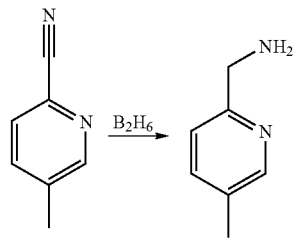

To a solution of 5-methyl-pyridine-2-carbonitrile (0.20 g, 1.69 mmol) in THF (10 mL) was added Borane-THF solution (1.0 M solution in THF, 8.47 mL, 8.47 mmol) rapidly via syringe at room temperature. The reaction mixture was stirred at room temperature for 15 min then heated at reflux for 3.5 h. The reaction mixture was cooled to 0° C., and MeOH (3 mL) was added to the reaction mixture slowly. After the rxn mixture was stirred for 10 min, the mixture was then concentrated to a white solid residue using reduced pressure. The residue was then suspended in 5 mL of 1:1 THF/MeOH and treated with 2 mL of 4 M HCl, stirred at room temperature for 10 min, then neutralized to basic pH by the addition of 2.5 M NaOH. The mixture was extracted with CH$_2$Cl$_2$. the combined organic layers were washed with brine, dried over MgSO$_4$, filtered and concentrated to afford 0.10 g of (5-methyl-pyridin-2-yl)-methylamine as a colorless oil. The crude reaction product was used without further purification.

The following two intermediates were prepared using similar procedures as described above:
(6-Methyl-pyridin-3-yl)-methylamine
(5-Methyl-pyridin-3-yl)-methylamine N$^4$-[(trans-4-aminocyclohexyl)methyl]-N$^2$-[(5-chloropyridin-2-yl)methyl]-5-nitropyrimidine-2,4-diamine m/z 372.5 [M+1]$^+$ N$^4$-[(trans-4-aminocyclohexyl)methyl]-N$^2$-[(6-methylpyridin-3-yl)methyl]-5-nitropyrimidine-2,4-diamine m/z 372.6 [M+1]$^+$ N$^4$-[(trans-4-aminocyclohexyl)methyl]-N$^2$-[(5-methyl-1,3-oxazol-4-yl)methyl]-5-nitropyrimidine-2,4-diamine m/z 362.3 [M+1]$^+$ (5-Methyl-oxazol-4-yl)-methylamine was synthesized from the (5-methyl-oxazol-4-yl)-methanol using the method described in the synthesis of 5-chloro-2-trifluoromethoxybenzylamine

Example 4

N⁴-[(trans-4-aminocyclohexyl)methyl]-5-nitro-N²-(2-phenylethyl)pyrimidine-2,4-diamine

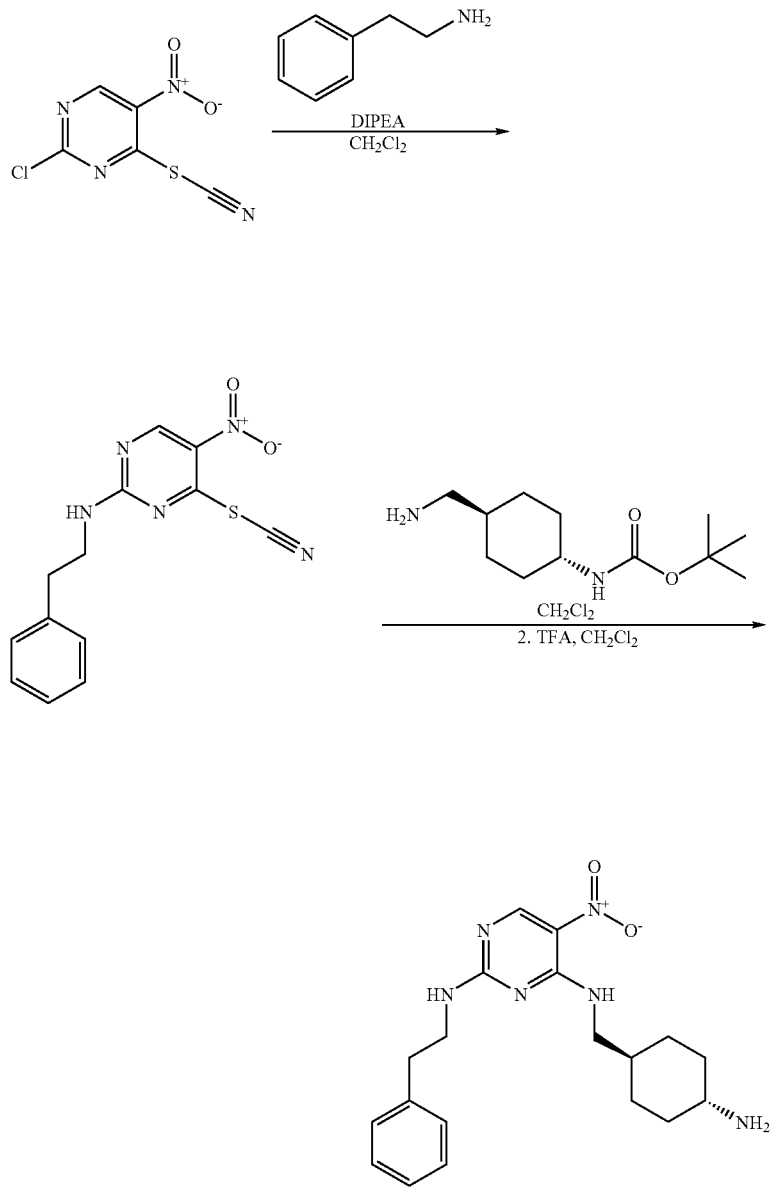

To a solution of 2-chloro-5-nitro-4-thiocyanato-pyrimidine (54 mg, 0.25 mmol) in CH$_2$Cl$_2$ were added 2-phenethylamine (30 mg, 0.25 mmol) and DIPEA (130 mL, 0.75 mmol). The reaction mixture was stirred at room temperature for 16 h until the reaction was complete. The reaction mixture was then used for the next reaction without purification.

To a solution of the above (5-nitro-4-thiocyanato-pyrimidin-2-yl)-phenethyl-amine (75 mg, 0.25 mmol) in CH$_2$Cl$_2$ was added tert-butyl trans-4-aminomethylcyclohexylcarbamate (114 mg, 0.5 mmol). The reaction mixture was stirred at room temperature for 16 h and concentrated in vacuo. The resulting residue was then diluted with CH$_2$Cl$_2$ (1 mL) and TFA (0.5 mL) was added. The mixture was stirred at room temperature for 4 h and concentrated in vacuo. The resulting residue was purified by preparative LCMS to afford 36 mg (39%) of the title compound, m/z 371.6 [M+1]⁺.

The following compound was prepared using similar procedures as described above:

N⁴-[(trans-4-aminocyclohexyl)methyl]-N²-[2-(3-chlorophenyl)ethyl]-5-nitropyrimidine-2,4-diamine, m/z 405.6 [M+1]⁺

4-{2-[(4-{[(trans-4-aminocyclohexyl)methyl]amino}-5-nitropyrimidin-2-yl)amino]ethyl}phenol, m/z 387.4 [M+1]⁺

Example 5

N⁴-[(trans-4-aminocyclohexyl)methyl]-N²-[2-(trifluoromethoxy)benzyl]-5-(trifluoromethyl)pyrimidine-2,4-diamine

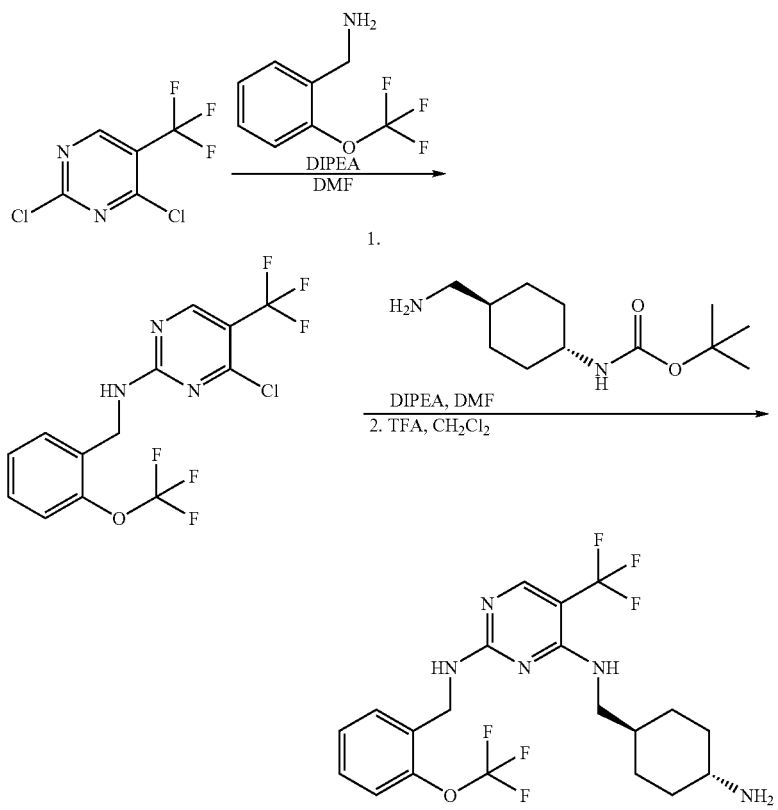

To a solution of 5-(trifluoromethyl)-2,4-di-chloropyrimidine (0.5 g, 2.3 mmol) in DMF (8 mL) were added a solution of 2-(trifluoromethoxy)benzylamine (0.44g, 2.3 mmol) in DMF (2 mL) followed by DIPEA (0.44 mL, 2.3 mmol) at −20° C. The reaction mixture was stirred at that temperature for 20 min. When the starting material was all consumed, the mixture was diluted with EtOAc and washed with water (×4). The organic phase was dried over anhydrous $Na_2SO_4$ and concentrated in vacuo. The resulting residue was purified by silica gel preparative TLC using 100% $CH_2Cl_2$ as an eluent to afford 0.44 g (52%) of (4-chloro-5-trifluoromethyl-pyrimidin-2-yl)-(2-trifluoromethoxy-benzyl)-amine as a white foam.

To a solution of the above (4-chloro-5-trifluoromethyl-pyrimidin-2-yl)-(2-trifluoromethoxy-benzyl)-amine (80 mg, 0.22 mmol) in DMF (2 mL) was added the Boc-protected cyclohexyl amine (74 mg, 0.33 mmol) followed by DIPEA (37 μL, 0.22 mmol). The reaction mixture was stirred at 70° C. for 3 h. When the reaction was complete, the reaction mixture was diluted with EtOAc and washed with water (×4). The organic phase was dried over anhydrous $Na_2SO_4$ and concentrated in vacuo. The resulting residue was purified by silica gel preparative TLC using 95:5 $CH_2Cl_2$:MeOH as an eluent. The resulting residue was then re-dissolved in $CH_2Cl_2$ (10 mL) and TFA (1 mL) was added. The reaction mixture was stirred at room temperature for 2 h and treated with saturated $NaHCO_3$. The product was extracted with $CH_2Cl_2$ and dried over anhydrous $Na_2SO_4$. Silica gel preparative TLC using $CH_2Cl_2$:MeOH:$NH_4OH$ 10:1:0.2 as an eluent afforded 56 mg (56%) of the title compound as a white solid, m/z 462.4 [M−1]⁺.

Example 6

N⁴-[(trans-4-pyrrolidin-1-ylcyclohexyl)methyl]-N²-[2-(trifluoromethoxy)benzyl]-5-(trifluoromethyl)pyrimidine-2,4-diamine -continued

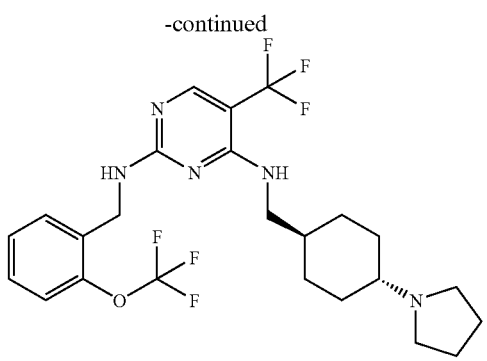

To a solution of N⁴-[(trans-4-aminocyclohexyl)methyl]-N²-[2-(trifluoromethoxy)benzyl]-5-(trifluoromethyl)pyrimidine-2,4-diamine (100 mg, 0.22 mmol) in DMF (2 mL) were added 1,4-dibromobutane (140 mg, 0.65 mmol) and DIPEA (113 μL, 0.65 mmol). The reaction mixture was stirred at room temperature for 16 h and then heated at 65° C. for another 2 h. The reaction mixture was then diluted with EtOAc and washed with water (×4). The organic phase was dried over anhydrous Na₂SO₄ and concentrated in vacuo. The resulting residue was purified by silica gel preparative TLC using 10:1 CH₂Cl₂:MeOH as an eluent to afford 49 mg of the title compound as a while solid, m/z 518.6 [M+1]⁺.

The following compounds were prepared using similar procedures as described above:

2,2'-({trans-4-[({2-[(3-bromo-2-methylbenzyl)amino]-5-nitropyrimidin-4-yl}amino)methyl]cyclohexyl}imino)diacetamide, m/z 565.0 [M+1]⁺

N²-{trans-4-[({2-[(3-bromo-2-methylbenzyl)amino]-5-nitropyrimidin-4-yl}amino)methyl] cyclohexyl}glycinamide, m/z 508.9 [M+2]⁺

N²-(3-bromo-2-methylbenzyl)-5-nitro-N⁴-({trans-4-[(2,2,2-trifluoroethyl)amino]cyclohexyl}methyl)pyrimidine-2,4-diamine, m/z 532.9 [M+1]⁺

N²-(3-bromo-2-methylbenzyl)-N⁴-({trans-4-[(2,2-difluoroethyl)amino]cyclohexyl}-methyl)-5-nitropyrimidine-2,4-diamine, m/z 514.9 [M+1]⁺

N⁴-({trans-4-[(2-fluoroethyl)amino]cyclohexyl}methyl)-5-nitro-N²-[2-(trifluoromethoxy)benzyl]pyrimidine-2,4-diamine, m/z 487.0 (M+1)⁺.

N⁴-({trans-4-[(2,2-difluoroethyl)amino] cyclohexyl}methyl)-5-nitro-N²-[2-(trifluoromethoxy) benzyl]pyrimidine-2,4-diamine, m/z 505.0 (M+1)⁺.

5-Nitro-N⁴-({trans-4-[(2-pyridin-3-ylethyl)amino] cyclohexyl}methyl)-N²-[2-(trifluoromethoxy)benzyl]pyrimidine-2,4-diamine, m/z 546.6 (M+1)⁺.

Preparation of 3-(2-bromo-ethyl)-pyridine:

A solution of 2-(3-pyridyl)ethan-1-ol (100 mg, 0.79 mmol) and CBr₄ (314 mg, 0.95 mmol) in THF (2 mL) was cooled to 0° C. and PPh₃ (313 mg, 1.18 mmol) was added portionwise. The ice-bath was removed and the reaction mixture was stirred at room temperature for 16 h. The mixture was concentrated and diluted with CH₂Cl₂. The mixture was basified using saturated NaHCO₃ and the organic phase was separated. The aqueous phase was re-extracted with CH₂Cl₂ and the combined organic phase was dried over Na₂SO₄ and concentrated. Silica gel prep TLC using 95:5 CH₂Cl₂:MeOH as an eluent afforded 3-(2-bromo-ethyl)-pyridine.

Example 7

5-nitro-N⁴-[(trans-4-pyrrolidin-1-ylcyclohexyl)methyl]-N²-[2-(trifluoromethoxy)benzyl]pyrimidine-2,4-diamine

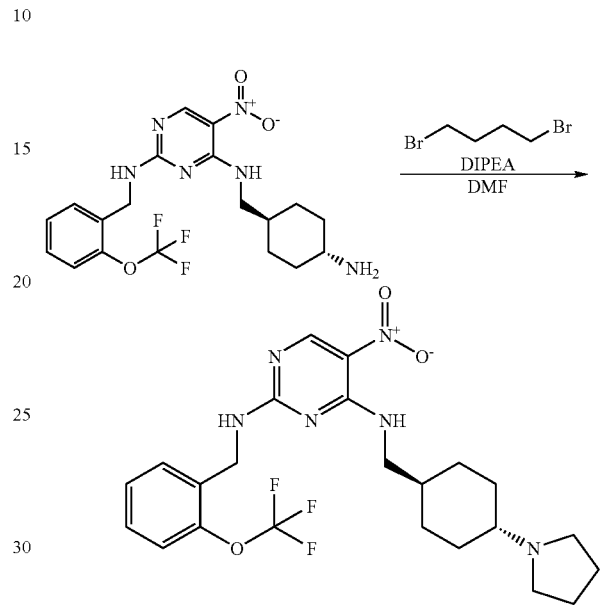

To a solution of N⁴-[(trans-4-aminocyclohexyl)methyl]-5-nitro-N²-[2-(trifluoromethoxy)benzyl]-pyrimidine-2,4-diamine (86 mg, 0.2 mmol) in DMF (1 mL) were added 1,4-dibromobutane (710 μL, 0.59 mmol) and DIPEA (103 μL, 0.59 mmol). The reaction mixture was stirred at 65° C. for 4 h. The reaction mixture was then diluted with EtOAc and washed with saturated NaHCO₃ and water (×4). The organic phase was dried over anhydrous Na₂SO₄ and concentrated in vacuo. The resulting residue was purified by silica gel preparative TLC using 10:1:0.05 CH₂Cl₂:MeOH:NH₄OH as an eluent to afford 60 mg (62%) of the title compound as an off-white solid, m/z 493.3 [M−1]⁺.

The following compounds were prepared following similar procedures as described above:

1-(trans-4-{[(5-nitro-2-{[2-(trifluoromethoxy)benzyl] amino}pyrimidin-4-yl)amino]methyl}-cyclohexyl)pyrrolidin-3-ol, m/z 509.3 [M−1]⁺

N⁴-[(trans-4-morpholin-4-ylcyclohexyl)methyl]-5-nitro-N²-[2-(trifluoromethoxy)benzyl]pyrimidine-2,4-diamine, m/z 511.7 [M+1]⁺

5-nitro-N⁴-[(trans-4-piperidin-1-ylcyclohexyl)methyl]-N²-[2-(trifluoromethoxy)benzyl]pyrimidine-2,4-diamine, m/z 509.7 [M+1]⁺

N⁴-[(trans-4-azetidin-1-ylcyclohexyl)methyl]-5-nitro-N²-[2-(trifluoromethoxy)benzyl]pyrimidine-2,4-diamine, m/z 479.5 [M−1]⁺

1-(trans-4-{[(5-nitro-2-{[2-(trifluoromethoxy)benzyl] amino}pyrimidin-4-yl)amino]methyl}-cyclohexyl)azetidin-3-ol, m/z 497.6 [M+1]⁺

1-(trans-4-{[(2-{[2-chloro-3-(dimethylamino)benzyl] amino}-5-nitropyrimidin-4-yl)amino] methyl}cyclohexyl)azetidin-3-ol, m/z 490.6 [M+1]⁺.

1-(trans-4-{[(2-{[(4-chloropyridin-3-yl)methyl]amino}-5-nitropyrimidin-4-yl)amino]methyl}cyclohexyl)azetidin-3-ol, m/z 448.5 [M+1]$^+$ $N^4$-[(trans-4-azetidin-1-ylcyclohexyl)methyl]-$N^2$-[(2-methoxypyridin-3-yl)methyl]-5-nitropyrimidine-2,4-diamine m/z 428.6 [M+1]$^+$ 1-(trans-4-{[(2-{[(2-methoxypyridin-3-yl)methyl]amino}-5-nitropyrimidin-4-yl)amino]methyl}cyclohexyl)azetidin-3-ol, m/z 444.5 [M+1]$^+$ $N^4$-[(trans-4-azetidin-1-ylcyclohexyl)methyl]-$N^2$-[(4-chloropyridin-3-yl)methyl]-5-nitropyrimidine-2,4-diamine m/z 432.5 [M+1]$^+$ $N^4$-[(trans-4-azetidin-1-ylcyclohexyl)methyl]-5-nitro-$N^2$-{[4-(trifluoromethyl)pyridin-3-yl]methyl}pyrimidine-2,4-diamine m/z 466.5 [M+1]$^+$ 1-[trans-4-({[5-nitro-2-({[4-(trifluoromethyl)pyridin-3-yl]methyl}amino)pyrimidin-4-yl]amino}methyl)cyclohexyl]azetidin-3-ol m/z 482.5 [M+1]$^+$

Example 8

$N^4$-{[trans-4-(dimethylamino)cyclohexyl]methyl}-5-nitro-$N^2$-[2-(trifluoromethoxy)benzyl]pyrimidine-2,4-diamine

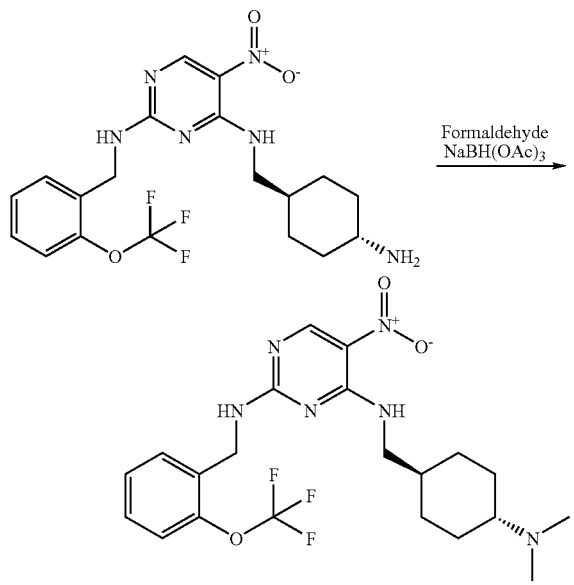

To a solution of $N^4$-[(trans-4-aminocyclohexyl)methyl]-5-nitro-$N^2$-[2-(trifluoromethoxy)benzyl]-pyrimidine-2,4-diamine (100 mg, 0.23 mmol) in dichloroethane (2 mL) were added 37% formaldehyde (74 mg, 0.91 mmol) and sodium triacetoxyborohydride (144 mg, 0.68 mmol). The reaction mixture was stirred at room temperature for 2 h. The reaction mixture was treated with a mixture of saturated NaHCO$_3$ and 1M Na$_2$CO$_3$ until pH 9 and extracted with CH$_2$Cl$_2$ (×2). The combined organic phase was dried over anhydrous Na$_2$SO$_4$ and concentrated in vacuo. The resulting residue was purified by silica gel preparative TLC using 10:1:0.2 CH$_2$Cl$_2$:MeOH:NH$_4$OH as an eluent to afford 59 mg of the title compound as a yellowish solid, m/z 469.7 [M+1]$^+$.

The following compound was prepared following similar procedures as described above:

$N^4$-{[trans-4-(diethylamino)cyclohexyl]methyl}-5-nitro-$N^2$-[2-(trifluoromethoxy)benzyl]pyrimidine-2,4-diamine, m/z 497.8 [M+1]$^+$ $N^4$-{[trans-4-(ethylamino)cyclohexyl]methyl}-5-nitro-$N^2$-[2-(trifluoromethoxy)benzyl]pyrimidine-2,4-diamine, m/z 469.4 [M+1]$^+$

Example 9

$N^4$-{[trans-4-(benzylamino)cyclohexyl]methyl}-5-nitro-$N^2$-[2-(trifluoromethoxy)benzyl]pyrimidine-2,4-diamine

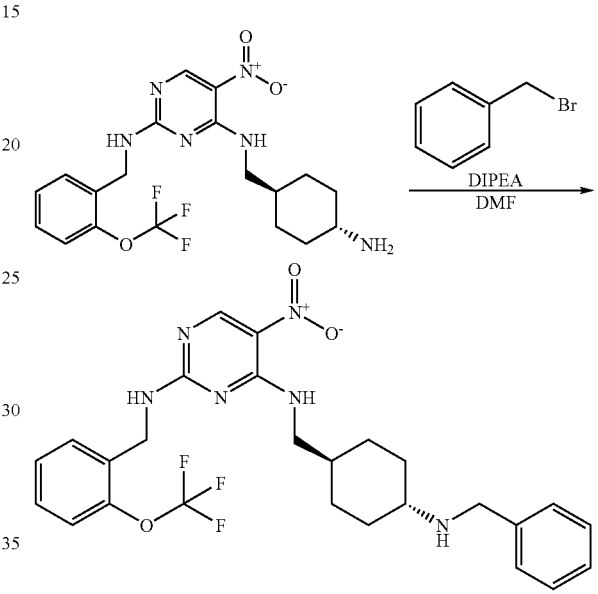

To a solution of $N^4$-[(trans-4-aminocyclohexyl)methyl]-5-nitro-$N^2$-[2-(trifluoromethoxy)benzyl]-pyrimidine-2,4-diamine (100 mg, 0.23 mmol) in DMF (3 mL) were added benzyl bromide (39 mg, 0.23 mmol) followed by DIPEA (40 μL, 0.23 mmol). The reaction mixture was stirred at room temperature for 20 h. The reaction mixture was diluted with EtOAc and washed with water (×4). The organic phase was dried over anhydrous Na$_2$SO$_4$ and concentrated in vacuo. The resulting residue was purified by silica gel prep TLC using 10:1 CH$_2$Cl$_2$:MeOH as an eluent to afford 8 mg of the title compound, m/z 531.6 [M+1]$^+$.

The following compounds were prepared following similar procedures as described above.

5-nitro-$N^4$-({trans-4-[(pyridin-4-ylmethyl)amino]cyclohexyl}methyl)-$N^2$-[2-(trifluoromethoxy)-benzyl]pyrimidine-2,4-diamine, m/z 532.6 [M+1]$^+$ 5-nitro-$N^4$-({trans-4-[(pyridin-3-ylmethyl)amino]cyclohexyl}methyl)-$N^2$-[2-(trifluoromethoxy)-benzyl]pyrimidine-2,4-diamine, m/z 532.4 [M+1]$^+$ 2-[(trans-4-{[(5-nitro-2-{[2-(trifluoromethoxy)benzyl]amino}pyrimidin-4-yl)amino]methyl}-cyclohexyl)amino]ethanol, m/z 485.7 [M+1]$^+$ 2,2'-[(trans-4-{[(5-nitro-2-{[2-(trifluoromethoxy)benzyl]amino}pyrimidin-4-yl)amino]methyl}-cyclohexyl)imino]diethanol, m/z 529.7 [M+1]$^+$ $N^4$-{[trans-4-(dibenzylamino)cyclohexyl]methyl}-5-nitro-$N^2$-[2-(trifluoromethoxy)benzyl]pyrimidine-2,4-diamine, m/z 621.7 [M+1]$^+$ N$^4$-({trans-4-[bis(pyridin-2-ylmethyl)amino]cyclohexyl}methyl)-5-nitro-N$^2$-[2-(trifluoromethoxy)benzyl]pyrimidine-2,4-diamine, m/z 623.7 [M+1]$^+$ N$^2$-(trans-4-{[(5-nitro-2-{[2-(trifluoromethoxy)benzyl]amino}pyrimidin-4-yl)amino]methyl}-cyclohexyl)glycinamide, m/z 496.3 [M−1]$^+$ N$^2$-[trans-4-({[5-nitro-2-({[4-(trifluoromethyl)pyridin-3-yl]methyl}amino)pyrimidin-4-yl]amino}methyl)cyclohexyl]glycinamide, m/z 483.4 [M+1]$^+$

Example 10

4-{[(trans-4-aminocyclohexyl)methyl]amino}-2-{[2-(trifluoromethoxy)-benzyl]amino}pyrimidine-5-carbonitrile

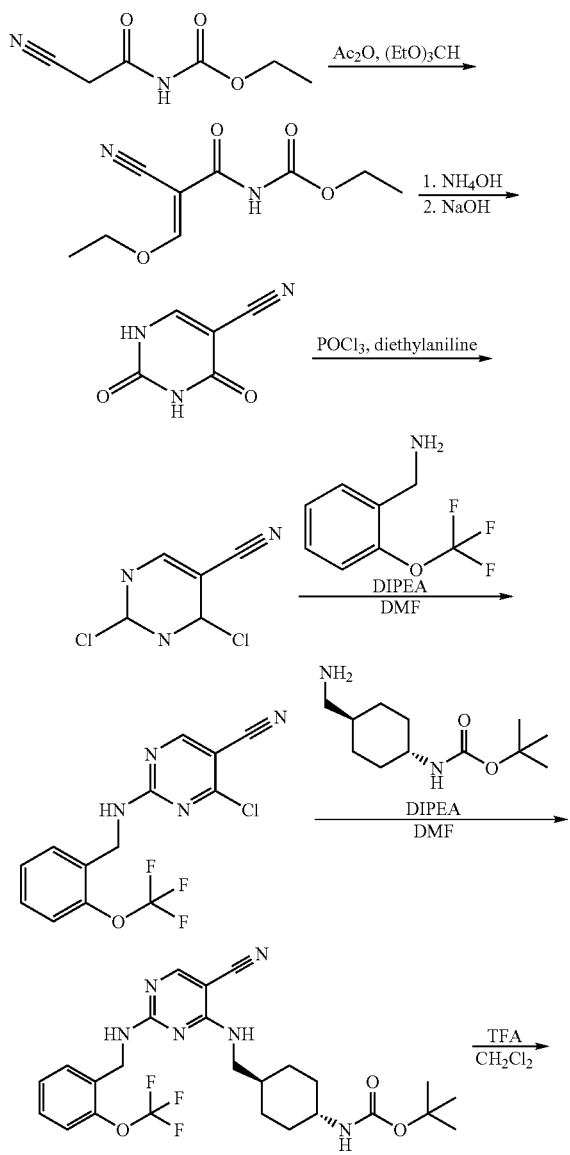

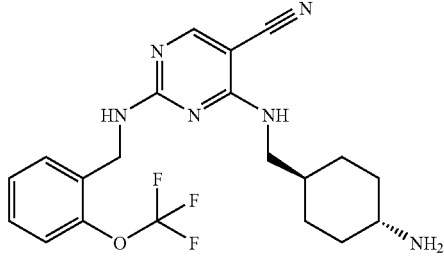

To a mixture of N-cyanoacetylurethane (100 g, 640.5 mmol) in acetic anhydride (160 mL) was added triethyl orthoformate (26.6 mL, 160 mmol). The mixture was stirred at reflux for 2.5 h; it was then cooled to 25° C. whereupon crystals formed. The reaction mixture was filtered and the collected solid was washed with hexanes and dried under vacuum to afford 21.4 g (67%) of the desired product.

Ammonium hydroxide (150 mL) was added to the above acrylamide (54.5 g, 258.29 mmol) in H$_2$O (150 mL) at 25° C. followed by NaOH (32 g) in H$_2$O (150 mL) dropwise over 10 min. The mixture was then heated at 70° C. with stirring for 1 h and then cooled to 25° C. The reaction mixture was filtered while basic, and then acidified to pH 4 with HCl and filtered to yield 25.4 g of uracil.

To a mixture of the above uracil (15.41 g, 112.5 mmol) and phosphorus oxychloride (157.4 mL, 1.69 mol) was added N,N-diethylaniline (34.2 mL, 225 mmol), cautiously, at 25° C. The reaction was then heated at 115° C. for 3 h after which the mixture was cooled to 40° C. and concentrated in vacuo to remove excess POCl$_3$. The remaining liquid was poured slowly onto ice-water with rapid stirring and the precipitated product was filtered. The aqueous layer was then extracted with chloroform and the extract was washed with 1 N HCl before concentrating in vacuo. This material was combined with the previously filtered material to afford 2,4-dichloropyrimidine-5-carbonitrile (15.36 g, 79%).

2,4-Dichloro-pyrimidine-5-carbonitrile (50 mg, 0.287 mmol) was dissolved in DMF (1 mL) and 2-(trifluoromethoxyl)benzylamine (57 mg, 0.287 mmol) was added to the solution followed by DIPEA (51 μL, 0.287 mmol). The reaction mixture was stirred at room temperature for 1 h. The solution was then diluted with EtOAc and washed with water (×4). The organic phase was then dried over anhydrous Na$_2$SO$_4$ and concentrated in vacuo. The residue was purified by silica gel prep TLC using CH$_2$Cl$_2$ as an eluent to afford 51 mg (54%) of (4-chloro-5-nitrile-pyrimidin-2-yl)-(2-trifluoromethoxy-benzyl)-amine as a white solid.

(4-Chloro-5-cyanopyrimidin-2-yl)-(2-trifluoromethoxy-benzyl)-amine (50 mg, 0.16 mmol) was dissolved in DMF (1 mL) and tert-butyl trans-4-aminomethylcyclohexylcarbamate (70 mg, 0.30 mmol) was added followed by DIPEA (53 μL, 0.30 mmol). The reaction mixture was stirred at room temperature for 16 h. The reaction mixture was then diluted with EtOAc and washed with water (×3). The organic phase was dried over anhydrous Na$_2$SO$_4$ and concentrated in vacuo. The resulting residue was purified by silica gel preparative TLC using 95:5 CH$_2$Cl$_2$:MeOH as an eluent to afford 76 mg (96%) of (4-{[5-cyano-2-(2-trifluoromethoxy-benzylamino)-pyrimidin-4-ylamino]-methyl}-cyclohexyl)-carbamic acid tert-butyl ester.

The above tert-butyl ester (75 mg, 0.14 mmol) was dissolved in CH$_2$Cl$_2$ (10 mL) and TFA (0.7 mL) was added to the solution. The reaction mixture was stirred at room temperature for 1 h and quenched with saturated NaHCO₃. The organic phase was separated from the aqueous phase which was then re-extracted with CH₂Cl₂ (×2). The combined organic phase was dried over anhydrous Na₂SO₄ and concentrated in vacuo. The resulting residue was purified by silica gel preparative TLC using 10:1:0.1 CH₂Cl₂:MeOH:NH₄OH as an eluent to afford 46 mg (77%) of the title compound, m/z 419.4 (M−1)⁺.

The following compounds were prepared using similar procedures as described above:

4-{[(trans-4-aminocyclohexyl)methyl]amino}-2-{[(2-chloropyridin-3-yl)methyl]amino}pyrimidine-5-carbonitrile, m/z 372.8 [M+1]⁺

4-{[(trans-4-aminocyclohexyl)methyl]amino}-2-{[(2-methoxypyridin-3-yl)methyl]amino}pyrimidine-5-carbonitrile, m/z 368.7 [M+1]⁺

4-{[(trans-4-aminocyclohexyl)methyl]amino}-2-{[(4-methoxypyridin-3-yl)methyl]amino}pyrimidine-5-carbonitrile m/z 368.6 [M+1]⁺

Example 11

4-({[trans-4-(dimethylamino)cyclohexyl]methyl}amino)-2-{[2-(trifluoromethoxy)benzyl]amino}pyrimidine-5-carbonitrile

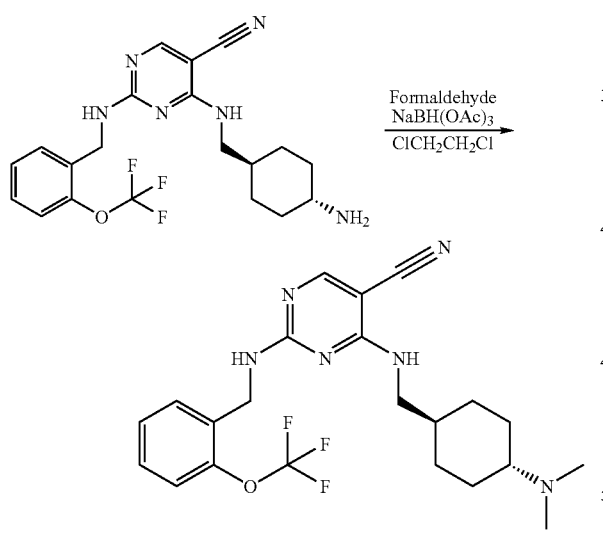

To a solution of 4-{[(trans-4-aminocyclohexyl)methyl]amino}-2-{[2-(trifluoromethoxy)benzyl]-amino}pyrimidine-5-carbonitrile (100 mg, 0.24 mmol) in dichloroethane (2 mL) were added 37% formaldehyde (100 mg, 1.2 mmol) and NaBH(OAc)₃ (151 mg, 0.71 mmol). The reaction mixture was stirred at room temperature for 2 h. The reaction mixture was then basified with a mixture of saturated NaHCO₃ and 1M Na₂CO₃ to pH 9. The organic phase was washed with water (×1), dried over anhydrous Na₂SO₄ and concentrated in vacuo. The resulting residue was purified by silica gel preparative TLC using 10:1:0.2 CH₂Cl₂:MeOH:NH₄OH as an eluent to afford 39 mg (36%) of the title compound as a while solid, m/z 449.5 (M+1)⁺.

Example 12

4-({[trans-4-(ethylamino)cyclohexyl]methyl}amino)-2-{[2-(trifluoromethoxy)benzyl]amino}pyrimidine-5-carbonitrile

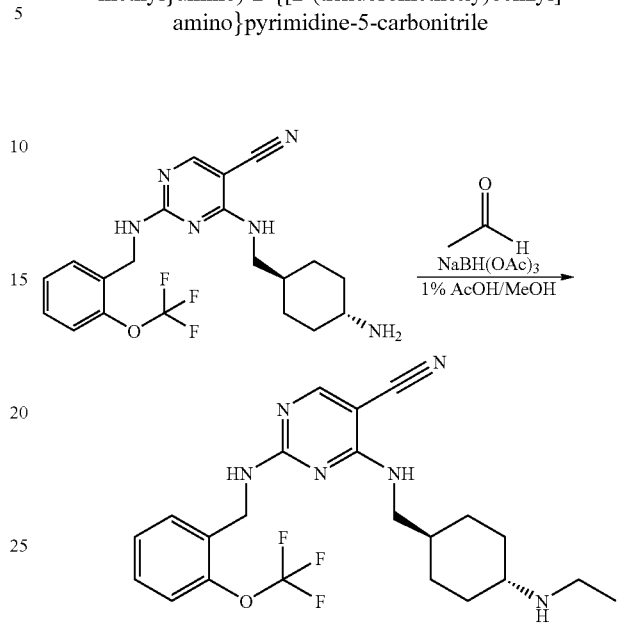

4-{[(trans-4-Aminocyclohexyl)methyl]amino}-2-{[2-(trifluoromethoxy)benzyl]amino}pyrimidine-5-carbonitrile (150 mg, 0.36 mmol) was dissolved in a solution of 1% AcOH in MeOH. The solution was cooled to 0° C. and to this cold solution were added NaBH(OAc)₃ and acetaldehyde. The reaction mixture was stirred at room temperature for 16 h. The reaction mixture was then treated with saturated NaHCO₃ and extracted with EtOAc. The organic phase was dried over anhydrous Na₂SO₄ and concentrated in vacuo. The resulting residue was purified by silica gel column chromatography using 9:1:0.1 CH₂Cl₂:MeOH:NH₄OH as an eluent to afford 24 mg (15%) of the title compound, m/z 449.4 (M+1)⁺.

The following compounds were prepared following similar procedures as described above.

4-({[trans-4-(diethylamino)cyclohexyl]methyl}amino)-2-{[2-(trifluoromethoxy)benzyl]amino}-pyrimidine-5-carbonitrile m/z 477.7 (M+1)⁺.

4-[({trans-4-[(pyridin-2-ylmethyl)amino]cyclohexyl}methyl)amino]-2-{[2-(trifluoromethoxy)benzyl]amino}pyrimidine-5-carbonitrile, m/z 510.7 [M−1]⁺.

4-[({trans-4-[(pyridin-3-ylmethyl)amino]cyclohexyl}methyl)amino]-2-{[2-(trifluoromethoxy)benzyl]amino}pyrimidine-5-carbonitrile, m/z 510.5 [M−1]⁺.

4-[({trans-4-[(pyridin-4-ylmethyl)amino]cyclohexyl}methyl)amino]-2-{[2-(trifluoromethoxy)benzyl]amino}pyrimidine-5-carbonitrile, m/z 510.4 [M−1]⁺.

4-[({trans-4-[(2,2-dimethylpropyl)amino]cyclohexyl}methyl)amino]-2-{[2-(trifluoromethoxy)benzyl]amino}pyrimidine-5-carbonitrile, m/z 489.4 [M−1]⁺.

4-[({trans-4-[(cyclopropylmethyl)amino]cyclohexyl}methyl)amino]-2-{[2-(trifluoromethoxy)benzyl]amino}pyrimidine-5-carbonitrile, m/z 475.7 [M−1]⁺.

4-({[trans-4-(isopropylamino)cyclohexyl]methyl}amino)-2-{[2-(trifluoromethoxy)benzyl]-amino}pyrimidine-5-carbonitrile, m/z 461.5 [M−1]⁺.

Example 13

4-{[(trans-4-azetidin-1-ylcyclohexyl)methyl]amino}-2-{[2-(trifluoromethoxy)benzyl]amino}pyrimidine-5-carbonitrile

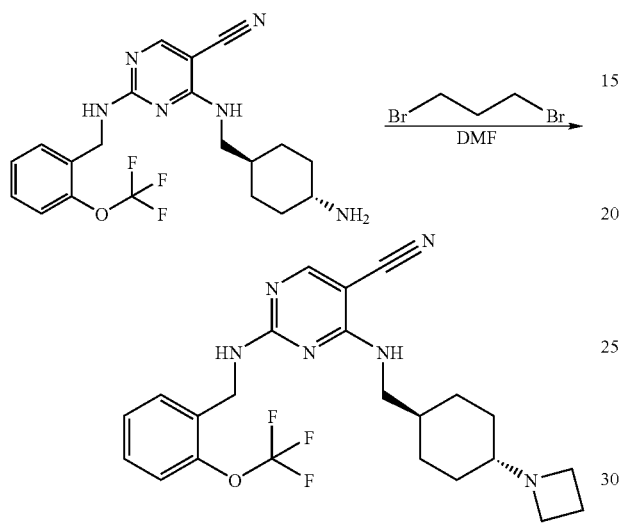

To a solution of 4-{[(trans-4-aminocyclohexyl)methyl]amino}-2-{[2-(trifluoromethoxy)benzyl]-amino}pyrimidine-5-carbonitrile (150 mg, 0.36 mmol) in DMF (1 mL) were added 1,3-dibromo-propane (86 mg, 0.43 mmol) and DIPEA (124 μL, 0.71 mmol). The reaction mixture was stirred at 50° C. for 24 h. The reaction mixture was then diluted with EtOAc and washed with NaHCO₃ (×1) and water (×4). The organic phase was dried over anhydrous Na₂SO₄ and concentrated in vacuo. The resulting residue was purified by silica gel preparative TLC using 10:1:0.2 CH₂Cl₂:MeOH:NH₄OH as an eluent to afford 54 mg (33%) of the title compound as a white solid, m/z 461.6 (M+1)⁺.

The following compounds were prepared using similar procedures described above:

4-{[(trans-4-pyrrolidin-1-ylcyclohexyl)methyl]amino}-2-{[2-(trifluoromethoxy)benzyl]amino}-pyrimidine-5-carbonitrile, m/z 473.4 (M−1)⁺

4-({[trans-4-(3-hydroxypyrrolidin-1-yl)cyclohexyl]methyl}amino)-2-{[2-(trifluoromethoxy)-benzyl]amino}pyrimidine-5-carbonitrile, m/z 489.2 (M−1)⁺

4-({[trans-4-(3-hydroxyazetidin-1-yl)cyclohexyl]methyl}amino)-2-{[2-(trifluoromethoxy)benzyl]-amino}pyrimidine-5-carbonitrile, m/z 475.4 [M−1]⁺

Example 14

N⁴-[(trans-4-aminocyclohexyl)methyl]-N²-{2-[(2-aminophenyl)thio]benzyl}-5-nitropyrimidine-2,4-diamine

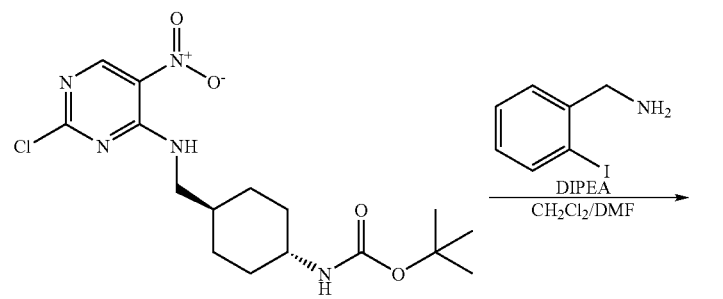

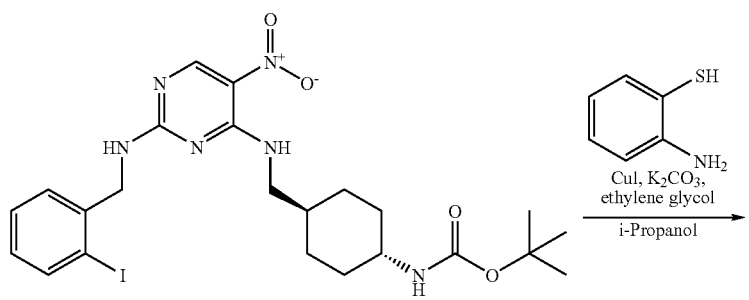

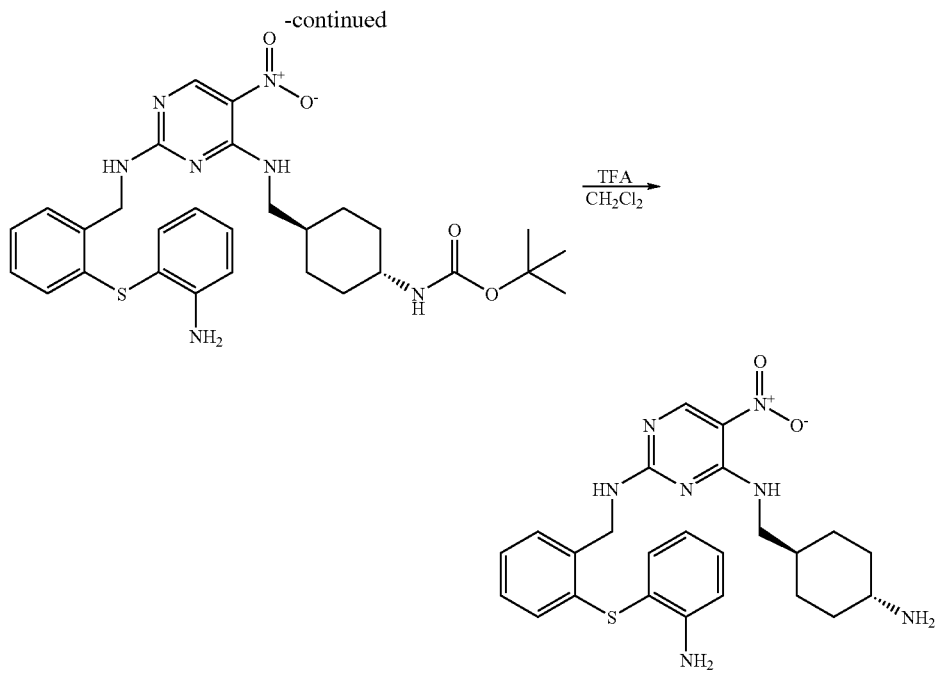

To a solution of {4-[(2-chloro-5-nitro-pyrimidin-4-ylamino)-methyl]-cyclohexyl}-carbamic acid tert-butyl ester (100 mg, 0.26 mmol) in a mixture of CH$_2$Cl$_2$ (2 mL) and DMF (1 mL) were added 2-iodobenzylamine (192 mg, 0.82 mmol) and DIPEA (135 μL, 1.04 mmoL). The reaction mixture was stirred at room temperature for 16 h and concentrated in vacuo. The resulting residue was diluted with EtOAc and washed with water (×3) and then with brine. The organic phase was dried over anhydrous Na$_2$SO$_4$ and concentrated in vacuo. The residue was purified by silica gel preparative TLC using 98:2 CH$_2$Cl$_2$:MeOH as an eluent to afford 97 mg (64%) of (4-{[2-(2-iodo-benzylamino)-5-nitro-pyrimidin-4-ylamino]-methyl}-cyclohexyl)-carbamic acid tert-butyl ester.

A mixture of the above (4-{[2-(2-iodo-benzylamino)-5-nitro-pyrimidin-4-ylamino]-methyl}-cyclohexyl)-carbamic acid tert-butyl ester (95 mg, 0.16 mmol), CuI (3 mg, 0.016 mmol), K$_2$CO$_3$ (50 mg, 0.36 mmol), ethylene glycol (27 μL, 0.49 mmol) in isopropanol (4 mL) was placed in a sealed tube and heated in a microwave at 150° C. for 2 h. The reaction mixture was treated with water (6 mL) and the organic layer was separated. The aqueous layer was extracted with EtOAc (×3). The combined organic layer was dried over anhydrous Na$_2$SO$_4$ and concentrated in vacuo. The resulting residue was purified by silica gel preparative TLC using 95:5 CH$_2$Cl$_2$:MeOH as an eluent to afford 35 mg (37%) of [4-({2-[2-(2-amino-phenylsulfanyl)-benzylamino]-5-nitro-pyrimidin-4-ylamino}-methyl)-cyclohexyl]-carbamic acid tert-butyl ester.

To a solution of the above [4-({2-[2-(2-amino-phenylsulfanyl)-benzylamino]-5-nitro-pyrimidin-4-ylamino}-methyl)-cyclohexyl]-carbamic acid tert-butyl ester (35 mg, 0.06 mmol) in CH$_2$Cl$_2$ (10 mL) was added TFA (1.2 mL). The reaction mixture was stirred at room temperature for 2 h. The reaction mixture was then treated with saturated NaHCO$_3$. During the work-up, some MeOH was added to solubilize the product in the organic phase. The organic phase was then dried over anhydrous Na$_2$SO$_4$ and concentrated in vacuo. The resulting residue was purified by silica gel preparative TLC using 10:1:0.1 CH$_2$Cl$_2$:MeOH:NH$_4$OH as an eluent to afford 20 mg 70%) of the title compound as an off-white solid, m/z 477.9 (M−1)$^+$.

Preparation of 2-iodobenzylamine:

To a solution of 2-iodobenzyl alcohol (6.0 g, 25.4 mmol) and DPPA (6.8 mL, 30.5 mmol) in toluene (65 mL) was added DBU (5.0 mL, 33.0 mmol). The reaction mixture was stirred at room temperature for 16 h. The reaction mixture was then diluted with 3M HCl (60 mL) and ether (150 mL). The organic phase was separated and the aqueous phase was extracted with ether (×3). The combined organic extracts were washed with water (×2) and and then with brine. The solution was dried over anhydrous Na$_2$SO$_4$ and concentrated in vacuo. Silica gel column chromatography using 95:5 hexanes:EtOAc afforded 6.1 g (93%) of 1-azidomethyl-2-iodobenzene.

To a solution of 1-azidomethyl-2-iodo-benzene (6.1 g, 23.4 mmol) in anhydrous THF (100 mL) was added triphenylphosphine (6.8 g, 25.7 mmol) at 0° C. The reaction mixture was slowly warmed up to room temperature and stirred for 16 h. The mixture was diluted with ammonium hydroxide (20 mL) and stirred for 3 h. The mixture was then treated with 2M NaOH (30 mL) and stirred for 1 h. The reaction mixture was acidified to pH 2 by adding 3 M HCl. The mixture was diluted with ether and the layers were separated. The aqueous layer was basified to pH 9 by adding 2 M NaOH and then extracted with CH$_2$Cl$_2$ (×3). The combined organic phase was dried over anhydrous Na$_2$SO$_4$ and concentrated in vacuo to yield an oily residue. The resulting residue was treated with ether and filtered. The filtrate was purified by silica gel column chromatography using 95:5 CH₂Cl₂:MeOH as an eluent to afford 5.4 g (80%) of 2-iodobenzylamine.

Example 15

N⁴-[(trans-4-aminocyclohexyl)methyl]-5-chloro-N²-[2-(trifluoromethoxy)benzyl]pyrimidine-2,4-diamine

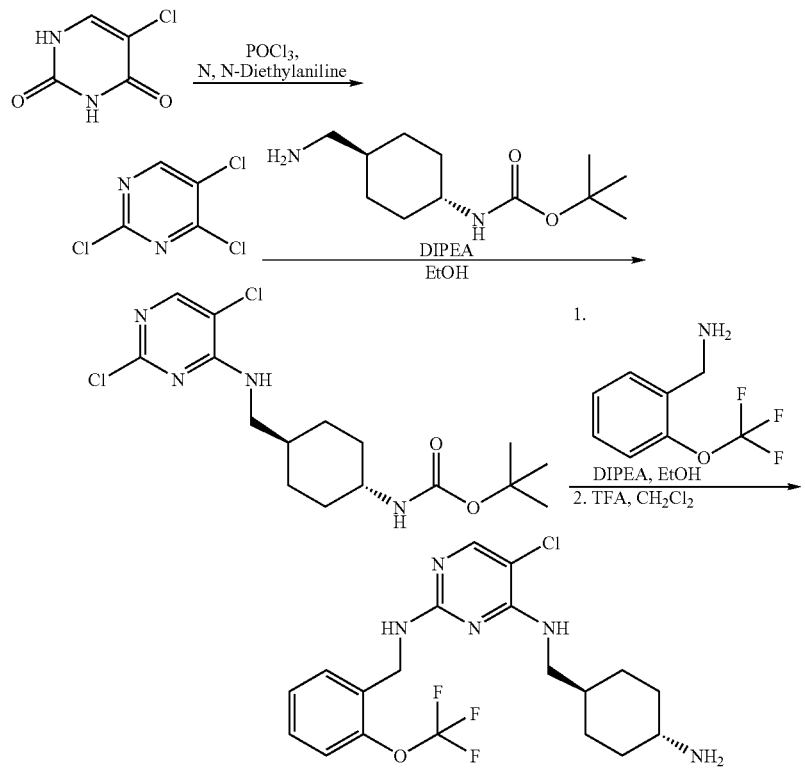

To a suspension of 5-chlorouracil (15.0 g, 102.4 mmol) in POCl₃ (50 mL, 326.1 mmol) was added N,N-diethylaniline (7.5 mL). The reaction mixture was heated at 110° C. for 24 h. The reaction mixture was cooled to room temperature and concentrated in vacuo to about 25 mL. The resulting residue was then poured into ice and stirred until all the ice melted. The aqueous layer was extracted with ether (×3). The combined organic phase was dried over anhydrous Na₂SO₄ and concentrated in vacuo. The resulting residue was distilled under vacuum at ~90° C. to afford 12.5 g (81%) of 5-chloro-2,4-dichloropyrimidine.

To a solution of the above 5-chloro-2,4-dichloropyrimidine (73 mg, 0.4 mmol) in EtOH (2 mL) were added tert-butyl trans-4-aminomethylcyclohexylcarbamate (100 mg, 0.44 mmol) and DIPEA (77 µL, 0.44 mmol). The reaction mixture was heated at 40° C. for 1 h. The reaction mixture was concentrated in vacuo and the resulting residue was diluted with EtOAc. The solution was washed with brine. The aqueous layer was re-extracted with EtOAc (×2). The combined organic phase was dried over anhydrous Na₂SO₄ and concentrated in vacuo to yield 148 mg (99%) of {4-[(2,5-dichloro-pyrimidin-4-ylamino)-methyl]-cyclohexyl}-carbamic acid tert-butyl ester.

The above {4-[(2,5-dichloro-pyrimidin-4-ylamino)-methyl]-cyclohexyl}-carbamic acid tert-butyl ester (97 mg, 0.26 mmol) was dissolved in 2-trifluoromethoxy-benzylamine (2.5 mL) and the mixture was heated to 180° C. for 20 min. The reaction mixture was diluted with EtOAc and poured into 1N HCl solution. The aqueous layer was separated and extracted with EtOAc (×2). The combined organic phase was dried over anhydrous Na₂SO₄ and concentrated in vacuo. The resulting residue was dissolved in CH₂Cl₂ (2.5 mL) and TFA (2.5 mL) was added. The reaction mixture was stirred at room temperature for 1 h. The mixture was then poured into 10% NaHCO₃ and the aqueous layer was extracted with EtOAc (×2). The combined organic phase was dried over anhydrous Na₂SO₄ and concentrated in vacuo. The resulting residue was purified by silica gel preparative TLC using 9:1:0.1 CH₂Cl₂:MeOH:NH₄OH as an eluent to afford 97 mg (87%) of the title compound, m/z 430.5 (M+1)⁺.

The following compounds were prepared using similar procedures as described above:

N⁴-[(cis-4-aminocyclohexyl)methyl]-5-chloro-N²-[2-(trifluoromethoxy)benzyl]pyrimidine-2,4-diamine, m/z 430.2 (M+1)⁺.

N⁴-[(trans-4-aminocyclohexyl)methyl]-N²-benzyl-5-chloropyrimidine-2,4-diamine, m/z 346.5 (M+1)⁺.

Example 16

N⁴-[(trans-4-aminocyclohexyl)methyl]-5-fluoro-N²-[2-(trifluoromethoxy)benzyl]pyrimidine-2,4-diamine

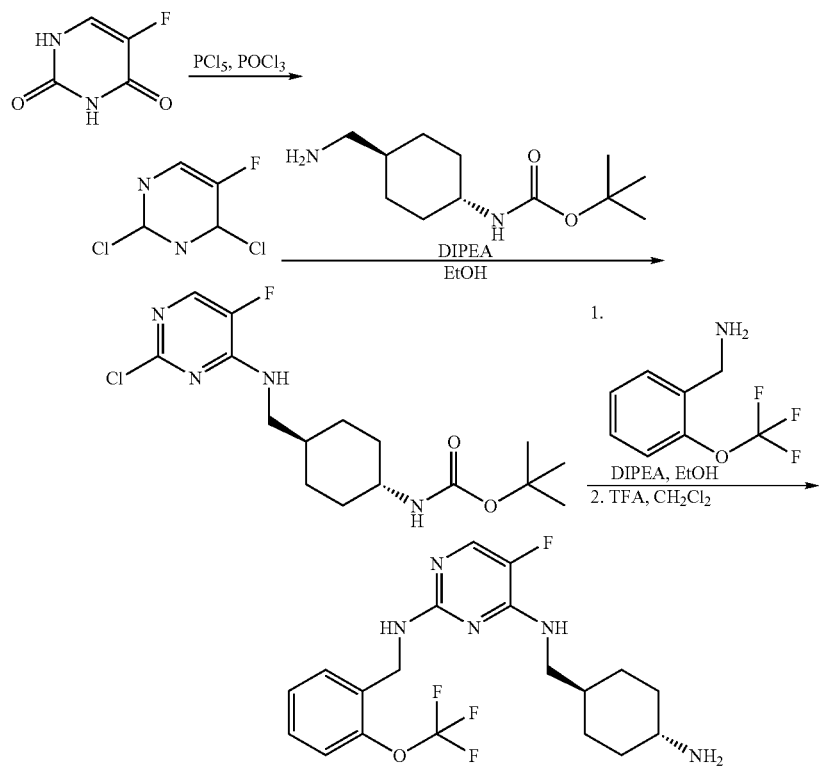

Phosphorous pentachloride (8.0 g, 38.4 mmol) was added to a mixture of 5-fluorouracil (10.0 g, 76.9 mmol) and phosphorous oxychloride (30 mL). The reaction mixture was heated at reflux, for 14 h, under $N_2$. The reaction mixture was cooled to room temperature and then poured into ice. The remaining residue from the flask was dissolved in saturated $Na_2CO_3$ and poured into the ice mixture. The mixture was extracted with EtOAc (×3) and the organic phase was dried over anhydrous $Na_2SO_4$. The solution was concentrated in vacuo to yield 9.1 g (71%) of 5-fluoro-2,4-dichloropyridine as a pale yellow oil.

To a solution of the above 5-fluoro-2,4-dichloropyridine (67 mg, 0.4 mol) in EtOH (2 mL) were added tert-butyl trans-4-aminomethylcyclohexylcarbamate (100 mg, 0.44 mmol) and DIPEA (77 µL, 0.44 mmol). The reaction mixture was heated at 40° C. for 1 h. The mixture was concentrated in vacuo and the resulting residue was dissolved in EtOAc and washed with brine. The aqueous layer was re-extracted with EtOAc (×2). The combined organic phase was dried over anhydrous $Na_2SO_4$ and concentrated in vacuo to yield 127 mg (89%) of {4-[(2-chloro-5-fluoro-pyrimidin-4-ylamino)-methyl]-cyclohexyl}-carbamic acid tert-butyl ester.

{4-[(2-Chloro-5-fluoro-pyrimidin-4-ylamino)-methyl]-cyclohexyl}-carbamic acid tert-butyl ester (127 mg, 0.35 mmol) was dissolved in 2-trifluoromethoxybenzylamine (2.5 mL) and heated at 180° C. for 20 min. The reaction mixture was diluted with EtOAc and poured into 1N HCl. The aqueous layer was separated and extracted with EtOAc (×2). The combined organic phase was dried over anhydrous $Na_2SO_4$ and concentrated in vacuo. The resulting residue was dissolved in $CH_2Cl_2$ (2.5 mL) and TFA (2.5 mL) was added. The reaction mixture was stirred at room temperature for 1 h. The reaction mixture was concentrated in vacuo and the resulting residue was diluted with EtOAc. The solution was poured into 10% $NaHCO_3$ and the aqueous layer was re-extracted with EtOAc. The combined organic phase was dried over anhydrous $Na_2SO_4$ and concentrated in vacuo. The resulting residue was purified by silica gel preparative TLC using 9:1:0.1 $CH_2Cl_2$:MeOH:$NH_4OH$ as an eluent to afford 22 mg (15%) of the title compound, m/z 414.6 (M+1)⁺.

Example 17

N⁴-[(trans-4-{[(1,5-dimethyl-1H-pyrazol-4-yl)methyl]amino}cyclohexyl)methyl]-5-nitro-N²-[2-(trifluoromethoxy)benzyl]pyrimidine-2,4-diamine

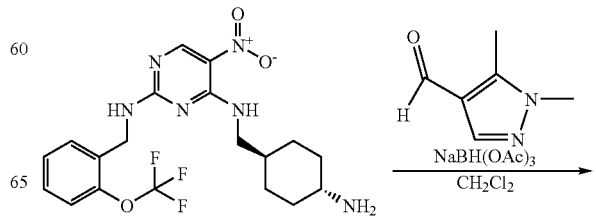

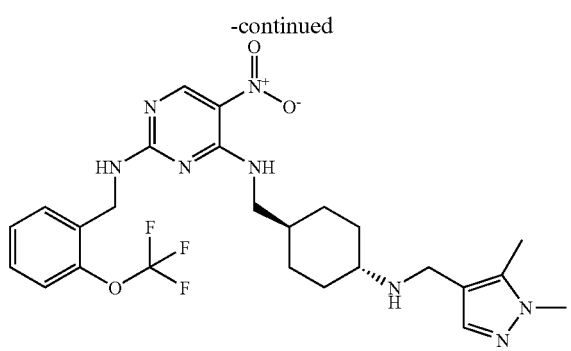

A mixture of $N^4$-[(trans-4-aminocyclohexyl)methyl]-5-nitro-$N^2$-[2-(trifluoromethoxy)benzyl]-pyrimidine-2,4-diamine (100 mg, 0.23 mmol) and 1,5-dimethyl-1H-pyrazole-4-carbaldehyde (23 mg, 0.19 mmol) in $CH_2Cl_2$ (15 mL) was stirred at room temperature for 1 h. $NaBH(OAc)_3$ (200 mg, 0.95 mmol) was then added to the reaction mixture and stirred for another 16 h. The reaction mixture was diluted with 1M $Na_2CO_3$ to pH 9-10 and the organic phase was separated. The aqueous phase was extracted with $CH_2Cl_2$. The combined organic phase was dried over $Na_2SO_4$ and concentrated. The resulting residue was purified by silica gel prep TLC using 98:2 $CH_2Cl_2$:MeOH as an eluent to afford 54 mg (52%) of the title compound as a pale yellow foam, m/z 549.7 [M+1]$^+$ The following compounds were prepared following similar procedures as described above:

$N^4$-[(trans-4-{[(3,5-dimethylisoxazol-4-yl)methyl]amino}cyclohexyl)methyl]-5-nitro-$N^2$-[2-(trifluoromethoxy)benzyl]pyrimidine-2,4-diamine, m/z 550.6 [M+1]$^+$ $N^4$-[(trans-4-{[(4-chloro-1-methyl-1H-pyrazol-3-yl)methyl]amino}cyclohexyl)methyl]-5-nitro-$N^2$-[2-(trifluoromethoxy)benzyl]pyrimidine-2,4-diamine, m/z 569.6 [M+1]$^+$ 5-nitro-$N^4$-({trans-4-[(pyrimidin-5-ylmethyl)amino]cyclohexyl}methyl)-$N^2$-[2-(trifluoromethoxy)-benzyl]pyrimidine-2,4-diamine, m/z 533.6 [M+1]$^+$ $N^4$-[(trans-4-{[(1,2-diethyl-1H-imidazol-4-yl)methyl]amino}cyclohexyl)methyl]-5-nitro-$N^2$-[2-(trifluoromethoxy)benzyl]pyrimidine-2,4-diamine, m/z 575.6 [M+1]$^+$ $N^4$-[(trans-4-{[(3,5-dichloropyridin-4-yl)methyl]amino}cyclohexyl)methyl]-5-nitro-$N^2$-[2-(trifluoromethoxy)benzyl]pyrimidine-2,4-diamine, m/z 600.6 [M+1]$^+$ 5-nitro-$N^2$-[2-(trifluoromethoxy)benzyl]-$N^4$-{[trans-4-({[6-(trifluoromethyl)pyridin-3-yl]methyl}-amino)cyclohexyl]methyl}pyrimidine-2,4-diamine, m/z 600.7 [M+1]$^+$ 5-nitro-$N^4$-({trans-4-[(quinolin-3-ylmethyl)amino]cyclohexyl}methyl)-$N^2$-[2-(trifluoromethoxy)-benzyl]pyrimidine-2,4-diamine, m/z 582.5 [M+1]$^+$ 5-nitro-$N^4$-({trans-4-[(pyridin-2-ylmethyl)amino]cyclohexyl}methyl)-$N^2$-[2-(trifluoromethoxy)-benzyl]pyrimidine-2,4-diamine, m/z 532.6 [M+1]$^+$ $N^4$-({trans-4-[(2-fluorobenzyl)amino]cyclohexyl}methyl)-5-nitro-$N^2$-[2-(trifluoromethoxy)-benzyl]pyrimidine-2,4-diamine, m/z 549.5 [M+1]$^+$ $N^4$-({trans-4-[(3-fluorobenzyl)amino]cyclohexyl}methyl)-5-nitro-$N^2$-[2-(trifluoromethoxy)-benzyl]pyrimidine-2,4-diamine, m/z 549.6 [M+1]$^+$ $N^4$-({trans-4-[(4-fluorobenzyl)amino]cyclohexyl}methyl)-5-nitro-$N^2$-[2-(trifluoromethoxy)-benzyl]pyrimidine-2,4-diamine, m/z 549.6 [M+1]$^+$ 5-nitro-$N^4$-({trans-4-[(quinolin-4-ylmethyl)amino]cyclohexyl}methyl)-$N^2$-[2-(trifluoromethoxy)-benzyl]pyrimidine-2,4-diamine, m/z 582.6 [M+1]$^+$ 5-nitro-$N^4$-({trans-4-[(2-phenylethyl)amino]cyclohexyl}methyl)-$N^2$-[2-(trifluoromethoxy)-benzyl]pyrimidine-2,4-diamine, m/z 545.6 [M+1]$^+$.

2-[(trans-4-{[(5-nitro-2-{[2-(trifluoromethoxy)benzyl]amino}pyrimidin-4-yl)amino]methyl}cyclohexyl)amino]propane-1,3-diol, m/z 515.8 [M+1]$^+$.

$N^4$-[(trans-4-{[(1-methyl-1H-pyrazol-4-yl)methyl]amino}cyclohexyl)methyl]-5-nitro-$N^2$-[2-(trifluoromethoxy)benzyl]pyrimidine-2,4-diamine, m/z 535.6 [M+1]$^+$.

$N^4$-[(trans-4-{[(1,3-dimethyl-1H-pyrazol-4-yl)methyl]amino}cyclohexyl)methyl]-5-nitro-$N^2$-[2-(trifluoromethoxy)benzyl]pyrimidine-2,4-diamine, m/z 549.6 [M+1]$^+$.

$N^4$-[(trans-4-{[(1,3-dimethyl-1H-pyrazol-5-yl)methyl]amino}cyclohexyl)methyl]-5-nitro-$N^2$-[2-(trifluoromethoxy)benzyl]pyrimidine-2,4-diamine, m/z 549.6 [M+1]$^+$.

$N^4$-[(trans-4-{[(1,5-dimethyl-1H-pyrazol-4-yl)methyl]amino}cyclohexyl)methyl]-5-nitro-$N^2$-{[4-(trifluoromethyl)pyridin-3-yl]methyl}pyrimidine-2,4-diamine, m/z 534.5 [M+1]$^+$ 2-{[(trans-4-{[(5-nitro-2-{[2-(trifluoromethoxy)benzyl]amino}pyrimidin-4-yl)amino]methyl}cyclohexyl)amino]methyl}benzoic acid, (BI0061120) m/z 575 [M+1]$^+$ Example 18

$N^4$-[(trans-4-azetidin-1-ylcyclohexyl)methyl]-5-chloro-$N^2$-[2-(trifluoromethoxy)benzyl]pyrimidine-2,4-diamine

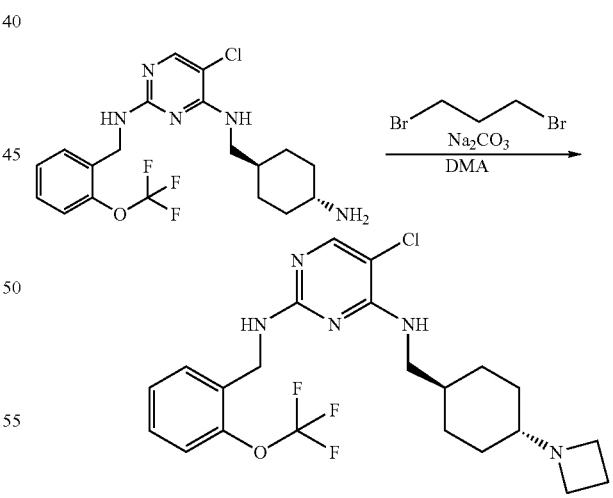

$N^4$-[(trans-4-aminocyclohexyl)methyl]-5-chloro-$N^2$-[2-(trifluoromethoxy)benzyl]pyrimidine-2,4-diamine (178 mg, 0.41 mmol) was dissolved in DMA (5 mL). To this solution was added 1,3-dibromopropane (208 μL, 2.01 mmol) and $NaCO_3$ (217 mg, 2.01 mmol). The reaction was heated in the microwave at 100° C. for 5 min. The volatiles were removed and the reaction was diluted with EtOAc and poured into $H_2O$. The aqueous phase was separated and extracted two more times with EtOAc. The organic layers were combined, dried (Na$_2$SO$_4$), decanted and concentrated. The crude product was purified on a 2000 micron SiO$_2$ preparative TLC plate, eluting with 10:1 CH$_2$Cl$_2$:MeOH (1% NH$_4$OH) to afford 102 mg (53%) of the title compound, m/z 470.5 [M+1]$^+$.

The following compounds were prepared following similar procedures as described above:

5-chloro-N$^4$-[(trans-4-pyrrolidin-1-ylcyclohexyl)methyl]-N$^2$-[2-(trifluoromethoxy)benzyl]pyrimidine-2,4-diamine, m/z 484.6 [M+1]$^+$ 1-(trans-4-{[(5-chloro-2-{[2-(trifluoromethoxy)benzyl]amino}pyrimidin-4-yl)amino]methyl}cyclohexyl)azetidin-3-ol, m/z 486.6 [M+1]$^+$ Example 19

5-fluoro-N$^4$-[(trans-4-pyrrolidin-1-ylcyclohexyl)methyl]-N$^2$-[2-(trifluoromethoxy)benzyl]pyrimidine-2,4-diamine

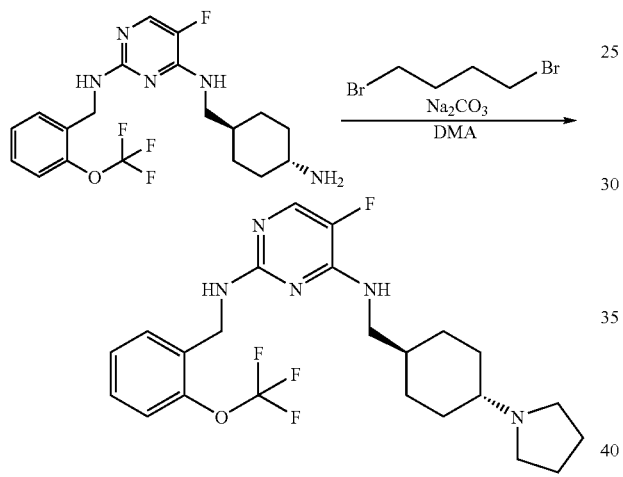

N$^4$-[(trans-4-aminocyclohexyl)methyl]-5-fluoro-N$^2$-[2-(trifluoromethoxy)benzyl]pyrimidine-2,4-diamine (71 mg, 0.17 mmol) was dissolved in DMA (2 mL). To this solution was added 1,4-dibromobutane (81 μL, 0.68 mmol) and NaCO$_3$ (72 mg, 0.68 mmol). The reaction was heated in the microwave at 100° C. for 20 min. The volatiles were removed and the reaction was diluted with EtOAc and poured into H$_2$O. The aqueous phase was separated and extracted two more times with EtOAc. The organic layers were combined, dried (Na$_2$SO$_4$), decanted and concentrated. The crude product was purified by twice running on a 1000 micron SiO$_2$ Prep TLC plate, eluting with 10:1 CH$_2$Cl$_2$:MeOH (1% NH$_4$OH) to afford 36 mg (45%) of the title compound, m/z 468.6 [M+1]$^+$.

The following compounds were prepared following similar procedures as described above:

N$^4$-[(trans-4-azetidin-1-ylcyclohexyl)methyl]-5-fluoro-N$^2$-[2-(trifluoromethoxy)benzyl]pyrimidine-2,4-diamine, m/z 454.5 [M+1]$^+$ 1-(trans-4-{[(5-fluoro-2-{[2-(trifluoromethoxy)benzyl]amino}pyrimidin-4-yl)amino]methyl}-cyclohexyl)azetidin-3-ol, m/z 470.5 [M+1]$^+$ 1-[trans-4-({[5-nitro-2-({[2-(2,2,2-trifluoroethoxy)pyridin-3-yl]methyl}amino)pyrimidin-4-yl]amino}methyl)cyclohexyl]azetidin-3-ol, m/z 512.5 [M+1]$^+$.

N$^4$-[(trans-4-azetidin-1-ylcyclohexyl)methyl]-5-nitro-N$^2$-{[2-(2,2,2-trifluoroethoxy)pyridin-3-yl]methyl}pyrimidine-2,4-diamine, m/z 496.5 [M+1]$^+$.

Example 20

N$^2$-[5-chloro-2-(trifluoromethoxy)benzyl]-5-nitro-N$^4$-[(trans-4-pyrrolidin-1-ylcyclohexyl)methyl]pyrimidine-2,4-diamine

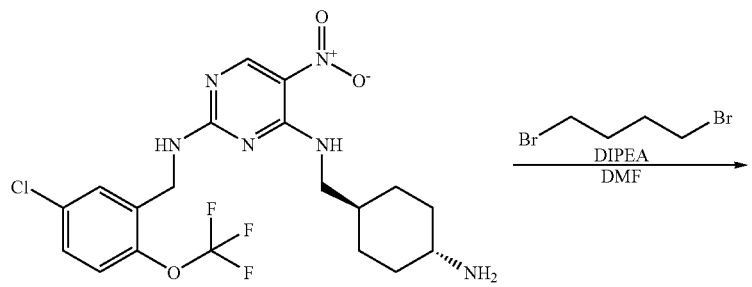

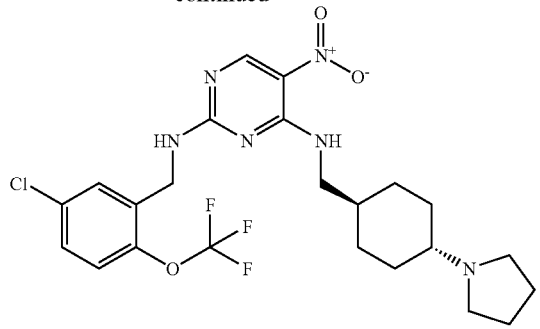

To a solution of N⁴-[(trans-4-aminocyclohexyl)methyl]-N²-[5-chloro-2-(trifluoromethoxy)benzyl]-5-nitropyrimidine-2,4-diamine (51 mg, 0.1 mmol) in DMF (0.5 mL) was added 1,4-dibromobutane (36 µL, 0.3 mmol) and DIPEA (104 µL, 0.6 mmol). The reaction mixture was stirred at 50° C. for 24 h and then 72 h at room temperature. The reaction mixture was then partitioned between EtOAc (20 mL) and saturated NaHCO₃ (less than 1 mL). The organic phase was washed with water (2×2 mL) and dried over Na₂SO₄. The resulting residue was purified by preparative HPLC to afford 13 mg (25%) of the title compound as a yellow oily solid, m/z 529.3 [M+1]⁺

Example 21

N²-(trans-4-{[(5-cyano-2-{[2-(trifluoromethoxy)benzyl]amino}pyrimidin-4-yl)amino]methyl}cyclohexyl)glycinamide

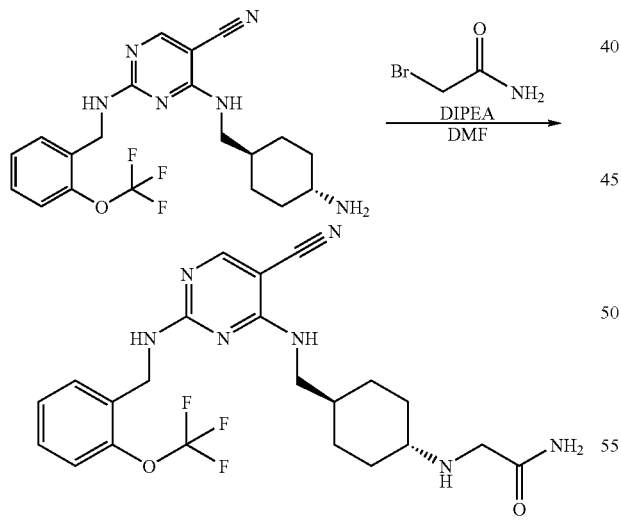

A mixture of 2-bromoacetamide (30 mg, 0.21 mmol), 4-{[(trans-4-aminocyclohexyl)methyl]amino}-2-{[2-(trifluoromethoxy)benzyl]amino}pyrimidine-5-carbonitrile (117 mg, 0.28 mmol) and DIPEA (74 mL, 0.43 mmol) in DMF (1 mL) was stirred at 50° C. for 4 h. The reaction mixture was then diluted with EtOAc (30 mL) and washed with water (3×3 mL) and brine. The organic phase was dried over Na₂SO₄ and concentrated. Silica gel preparative TLC of the crude product using 10:1:0.05 CH₂Cl₂:MeOH:NH₄OH as an eluent afforded 28 mg (27%) of the title compound as a white solid, m/z 476.5 [M−1]⁺

The following compound was prepared following similar procedures as described above:
N²-(2-amino-2-oxoethyl)-N²-(trans-4-{[(5-cyano-2-{[2-(trifluoromethoxy)benzyl]amino}pyrimidin-4-yl)amino]methyl}cyclohexyl)glycinamide, m/z 533.5 [M−1]⁺

Example 22

1-(trans-4-{[(5-nitro-2-{[2-(trifluoromethoxy)benzyl]amino}pyrimidin-4-yl)amino]methyl}cyclohexyl)azetidin-3-one

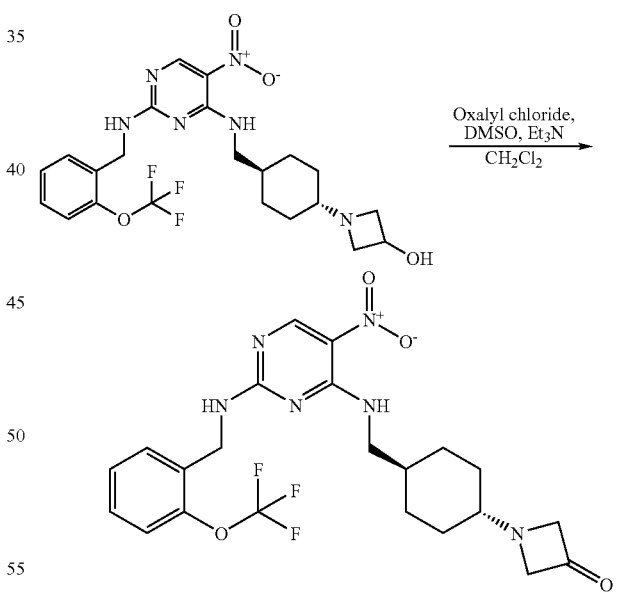

DMSO (170 µL, 2.4 mmol) was added dropwise to a solution of oxalyl chloride (105 µL, 1.2 mmol) in dry CH₂Cl₂ (10 mL) cooled in a dry ice/acetone bath. The reaction mixture was stirred with cooling for 30 min. A solution of 1-(trans-4-{[(5-nitro-2-{[2-(trifluoromethoxy)benzyl]amino}pyrimidin-4-yl)amino]methyl}cyclohexyl)azetidin-3-ol (200 mg, 0.4 mmol) in dry CH₂Cl₂ was added dropwise and the reaction was allowed to stir for 2 h. Et₃N (501 µL, 3.6 mmol) was then added and the reaction mixture was stirred for 16 h and allowed to slowly warm to room temperature.

The mixture was diluted with CH₂Cl₂ and poured into saturated aqueous Na₂SO₄. The aqueous phase was separated and extracted with CH₂Cl₂ (×2). The combined organic phase was dried over Na₂SO₄, decanted and concentrated. The crude product was purified by flash chromatography on a 120 g SiO₂ column, eluting with 90:9:1 CH₂Cl₂:MeOH:NH₄OH as an eluent to afford 147 mg (74%) of the title compound, m/z 495.6 [M+1]$^+$.

Example 23

1-(trans-4-{[(5-nitro-2-{[2-(trifluoromethoxy)benzyl]amino}pyrimidin-4-yl)amino]methyl}cyclohexyl)azetidin-3-yl acetate

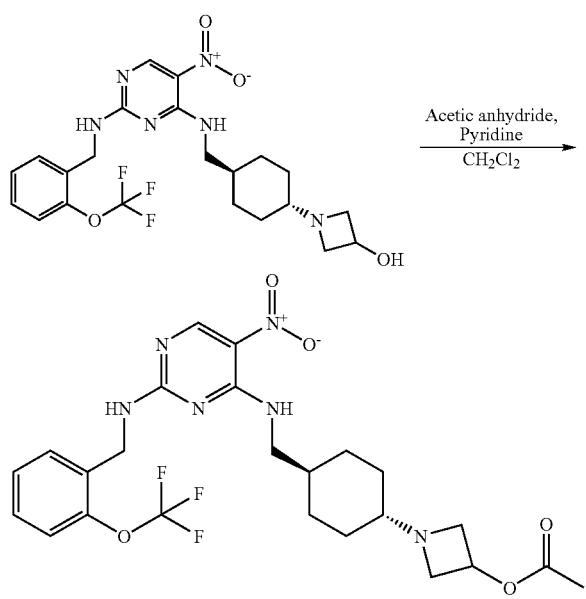

1-(trans-4-{[(5-Nitro-2-{[2-(trifluoromethoxy)benzyl]amino}pyrimidin-4-yl)amino]methyl}cyclohexyl)azetidin-3-ol (25 mg, 0.05 mmol) was dissolved in pyridine (12 µL, 0.15 mmol) and acetic anhydride (14 µL, 0.15 mmol) was added to the solution. The reaction was allowed to stir at 20° C. for 18 h. The volatiles were removed in vacuo and the crude product was purified by flash chromatography on a 12 g SiO₂ column, eluting with 90:9:1 CH₂Cl₂:MeOH:NH₄OH as an eluent to afford 5 mg of the title compound, m/z 539.6 [M+1]$^+$ Example 24

2-methyl-1-[(trans-4-{[(5-nitro-2-{[2-(trifluoromethoxy)benzyl]amino}pyrimidin-4-yl)amino]methyl}cyclohexyl)amino]propan-2-ol

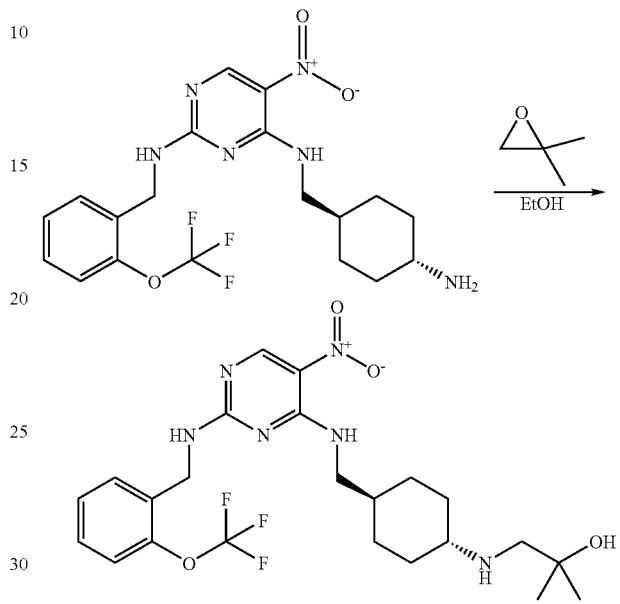

A reaction mixture of N⁴-[(trans-4-aminocyclohexyl)methyl]-5-nitro-N²-[2-(trifluoromethoxy)benzyl]pyrimidine-2,4-diamine (50 mg, 0.11 mmol) and 1,2-epoxy-2-methylpropanol (500 µL) in ethanol (1 mL) was heated to 100° C. for 1 h in a microwave. The reaction mixture was concentrated and the resulting residue was purified by silica gel preparative TLC using 10:1 CH₂Cl₂:MeOH as an eluent to afford 28 mg (47%) of the title compound as a white solid, m/z 513.5 [M+1]$^+$ Example 25

1-(trans-4-{[(5-nitro-2-{[2-(trifluoromethoxy)benzyl]amino}pyrimidin-4-yl)amino]methyl}cyclohexyl)azetidine-2-carboxamide

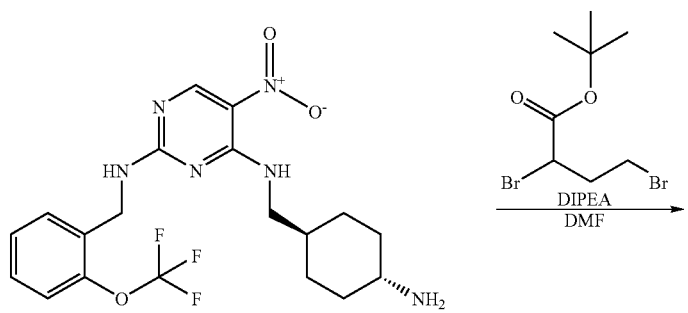

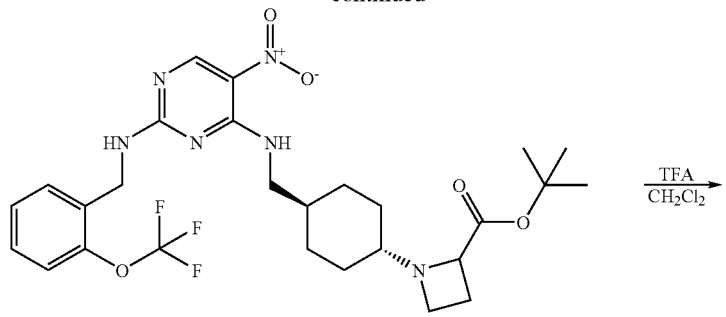

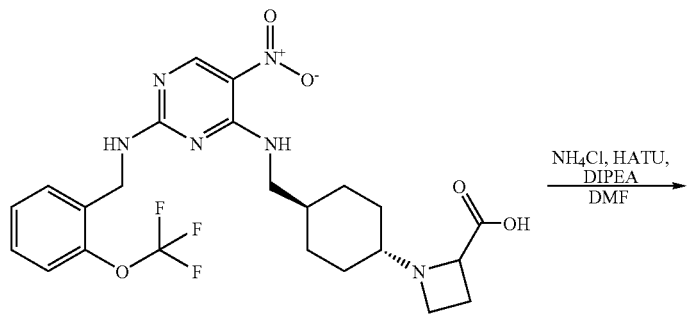

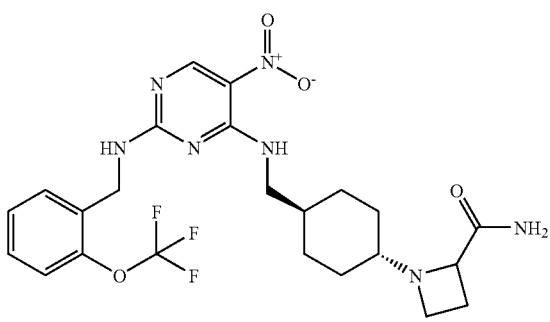

To a solution of N⁴-[(trans-4-aminocyclohexyl)methyl]-5-nitro-N²-[2-(trifluoromethoxy)benzyl]-pyrimidine-2,4-diamine (300 mg, 0.69 mmol) in DMF (3 mL) were added t-butyl 2,4-dibromobutyrate (322 μL, 1.5 mmol) and DIPEA (297 μL), 1.7 mmol). The reaction mixture was stirred at 60° C. for 9 h. The reaction mixture was then diluted with EtOAc and washed with 1M Na₂CO₃, water (×4) and brine. The organic phase was then dried over Na₂SO₄ and concentrated. The resulting residue was purified by silica gel preparative TLC using 98:2 CH₂Cl₂:MeOH as an eluent to afford 116 mg of 1-(trans-4-{[(5-nitro-2-{[2-(trifluoromethoxy)benzyl]amino}pyrimidin-4-yl)amino]methyl}cyclohexyl)azetidine-2-carboxylic acid tert-butyl ester.

To a solution of 1-(trans-4-{[(5-nitro-2-{[2-(trifluoromethoxy)benzyl]amino}pyrimidin-4-yl)amino]methyl}cyclohexyl)azetidine-2-carboxylic acid tert-butyl ester (110 mg, 0.19 mmol) in CH₂Cl₂ (5 mL) was added TFA (3 mL). The reaction mixture was stirred at room temperature for 16 h. The mixture was concentrated and the resulting residue was purified by silica gel preparative TLC using 4:1 CH₂Cl₂:MeOH as an eluent to afford the acid.

To a solution of 1-(trans-4-{[(5-nitro-2-{[2-(trifluoromethoxy)benzyl]amino}pyrimidin-4-yl)amino]methyl}cyclohexyl)azetidine-2-carboxylic acid (170 mg, 0.27 mmol) in DMF (1.5 mL) were added ammonium chloride (170 mg, 3.2 mmol), HATU (303 mg, 0.80 mmol) and DIPEA (370 μL, 2.1 mmol). The reaction mixture was stirred at room temperature for 16 h. The reaction mixture was diluted with EtOAc and washed with saturated NaHCO₃, water (×3) and brine. The organic phase was dried over Na₂SO₄ and concentrated. The resulting residue was purified by silica gel preparative TLC using 95:5 CH₂Cl₂:MeOH as an eluent to afford 7 mg of the title compound, m/z 522.6 [M−1]⁺

Example 26

4-[(trans-4-aminocyclohexyl)methoxy]-5-nitro-N-[2-(trifluoromethoxy)-benzyl]pyrimidin-2-amine

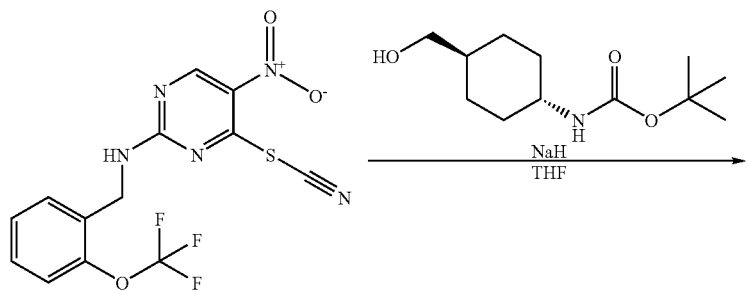

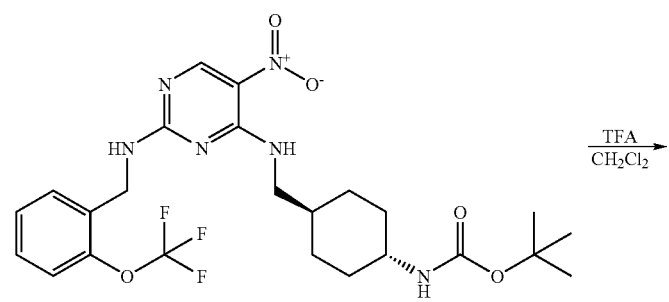

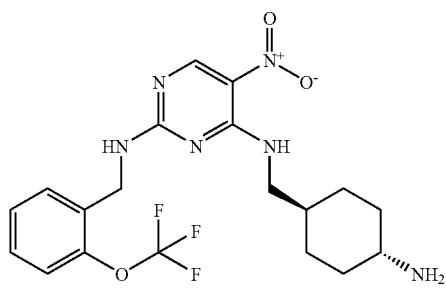

To a suspension of NaH (7 mg, 0.18 mmol, mineral oil was removed by triturating with hexanes) in THF (2 mL) at 0° C. was added a solution of the alcohol (37 mg, 0.16 mmol) in THF (1 mL) dropwise via syringe. The cloudy reaction mixture was stirred for 15 min, and the isocyanate (51 mg, 0.14 mmol) was added as a THF solution dropwise via syringe. The resulting clear orange reaction mixture was stirred at 0° C. for 2 h, then warmed to room temperature and stirred for an additional 18 h. The reaction mixture was partitioned between EtOAc (30 mL) and water (10 mL), and some NH$_4$Cl was added. The organic phase was washed with brine (10 mL), dried over Na$_2$SO$_4$, filtered and concentrated. The resulting orange oil was purified by flash chromatography (12 g of silica gel) eluting with 5-20% EtOAc/hexanes to give 20 mg (27%) of product as a yellow oil.

The above product was dissolved in CH$_2$Cl$_2$ (2 mL) and TFA (150 µL) was added. The reaction mixture was stirred at room temperature for 2 h and concentrated. The resulting residue was purified by silica gel preparative TLC using 9:1:0.1 CH$_2$Cl$_2$:MeOH:NH$_4$OH as an eluent to afford 5 mg (31%) of the title compound, m/z 442.6 [M+H]$^+$.

Example 27

N-(trans-4-{[(5-nitro-2-{[2-(trifluoromethoxy)benzyl]amino}pyrimidin-4-yl)amino]methyl}cyclohexyl)-2-pyridin-4-ylacetamide

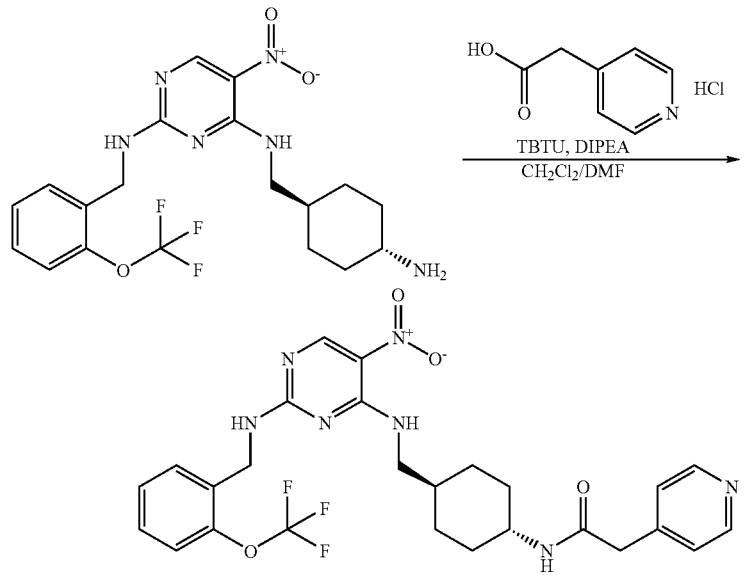

A mixture of $N^4$-[(trans-4-aminocyclohexyl)methyl]-5-nitro-$N^2$-[2-(trifluoromethoxy)benzyl]-pyrimidine-2,4-diamine (50 mg, 0.11 mmol), 4-pyridylacetic acid hydrochloride (30 mg, 0.17 mmol), TBTU (56 mg, 0.17 mmol), and DIPEA (69 µL, 0.40 mmol) in a mixture of $CH_2Cl_2$ (1 mL) and DMF (0.1 mL) was stirred at room temperature for 16 h. The reaction mixture was then diluted with $CH_2Cl_2$ and washed with 1M $Na_2CO_3$ and water. The organic phase was dried over $Na_2SO_4$ and concentrated. The resulting residue was purified by silica gel preparative TLC using 95:5 $CH_2Cl_2$:MeOH as an eluent to afford 35 mg (55%) of the title compound as a white solid after washing the obtained product with diethyl ether, m/z 558.4 $[M-1]^+$ The following compounds were prepared following similar procedures as described above:

N-(trans-4-{[(5-nitro-2-{[2-(trifluoromethoxy)benzyl]amino}pyrimidin-4-yl)amino]methyl}cyclohexyl)-2-pyridin-3-ylacetamide, m/z 558.6 $[M-1]^+$ N-(trans-4-{[(5-nitro-2-{[2-(trifluoromethoxy)benzyl]amino}pyrimidin-4-yl)amino]methyl}-cyclohexyl)-2-pyridin-2-ylacetamide, m/z 558.4 $[M-1]^+$ N-(trans-4-{[(5-nitro-2-{[2-(trifluoromethoxy)benzyl]amino}pyrimidin-4-yl)amino]methyl}-cyclohexyl)-2-phenylacetamide, m/z 559.5 $[M+1]^+$ N-(trans-4-{[(5-nitro-2-{[2-(trifluoromethoxy)benzyl]amino}pyrimidin-4-yl)amino]methyl}-cyclohexyl)acetamide, m/z 481.3 $[M-1]^+$ 2-Hydroxy-N-(trans-4-{[(5-nitro-2-{[2-(trifluoromethoxy)benzyl]amino}pyrimidin-4-yl)amino]-methyl}cyclohexyl)acetamide, m/z 497.7 $[M-1]^+$ N-(trans-4-{[(5-nitro-2-{[2-(trifluoromethoxy)benzyl]amino}pyrimidin-4-yl)amino]methyl}-cyclohexyl)benzamide, m/z 545.6 $[M+1]^+$ N-(trans-4-{[(5-nitro-2-{[2-(trifluoromethoxy)benzyl]amino}pyrimidin-4-yl)amino]methyl}-cyclohexyl)nicotinamide, m/z 544.5 $[M-1]^+$ N-(trans-4-{[(5-nitro-2-{[2-(trifluoromethoxy)benzyl]amino}pyrimidin-4-yl)amino]methyl}-cyclohexyl)isonicotinamide, m/z 544.5 $[M-1]^+$ N-(4-{[2-(3-Bromo-2-methyl-benzylamino)-5-nitro-pyrimidin-4-ylamino]-methyl}-cyclohexyl)-acetamide, m/z 492.4 $[M+1]^+$

Example 28

N-(trans-4-{[(5-nitro-2-{[2-(trifluoromethoxy)benzyl]amino}pyrimidin-4-yl)amino]methyl}cyclohexyl)methanesulfonamide

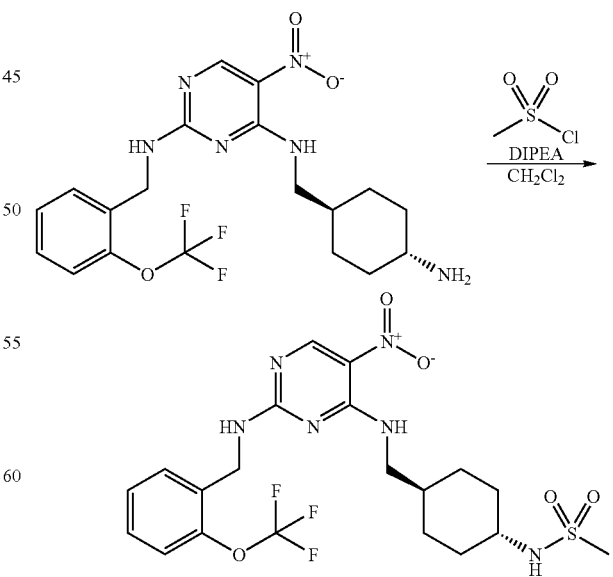

To a solution of $N^4$-[(trans-4-aminocyclohexyl)methyl]-5-nitro-$N^2$-[2-(trifluoromethoxy)benzyl]-pyrimidine-2,4-diamine (50 mg, 0.11 mmol) were added methanesulfonyl chloride (18 μL, 0.23 mmol) and DIPEA (59 μL, 0.34 mmol) in CH$_2$Cl$_2$ (2 mL). The reaction mixture was stirred at room temperature for 15 min and diluted with CH$_2$Cl$_2$. The organic phase was then washed with 1M Na$_2$CO$_3$ and water. The organic phase was dried over Na$_2$SO$_4$ and concentrated. The resulting residue was purified by silica gel preparative TLC using 98:2 CH$_2$Cl$_2$:MeOH as an eluent to afford 28 mg (47%) of the title compound, m/z 517.7 [M−1]$^+$ The following compounds were prepared following similar procedures as described above:

N-(trans-4-{[(5-nitro-2-{[2-(trifluoromethoxy)benzyl]amino}pyrimidin-4-yl)amino]methyl}-cyclohexyl)-1-phenylmethanesulfonamide, m/z 596.0 [M+1]$^+$ N-(trans-4-{[(5-nitro-2-{[2-(trifluoromethoxy)benzyl]amino}pyrimidin-4-yl)amino]methyl}-cyclohexyl)benzenesulfonamide, m/z 579.5 [M−1]$^+$ N-[1-(trans-4-{[(5-nitro-2-{[2-(trifluoromethoxy)benzyl]amino}pyrimidin-4-yl)amino]methyl}cyclohexyl)azetidin-3-yl]methanesulfonamide, m/z 574.3 [M+1]$^+$ N-{1-[trans-4-({[5-nitro-2-({[4-(trifluoromethyl)pyridin-3-yl]methyl}amino)pyrimidin-4-yl]amino}methyl)cyclohexyl]azetidin-3-yl}methanesulfonamide, m/z 559.63 (M+1)$^+$.

N-[1-(Trans-4-{[(5-nitro-2-{[2-(trifluoromethoxy)benzyl]amino}pyrimidin-4-yl)amino]methyl}cyclohexyl)azetidin-3-yl]benzenesulfonamide, m/z 636.37 (M+1)$^+$.

Example 29

N-ethyl-N'-(trans-4-{[(5-nitro-2-{[2-(trifluoromethoxy)benzyl]amino}pyrimidin-4-yl)amino]methyl}cyclohexyl)urea

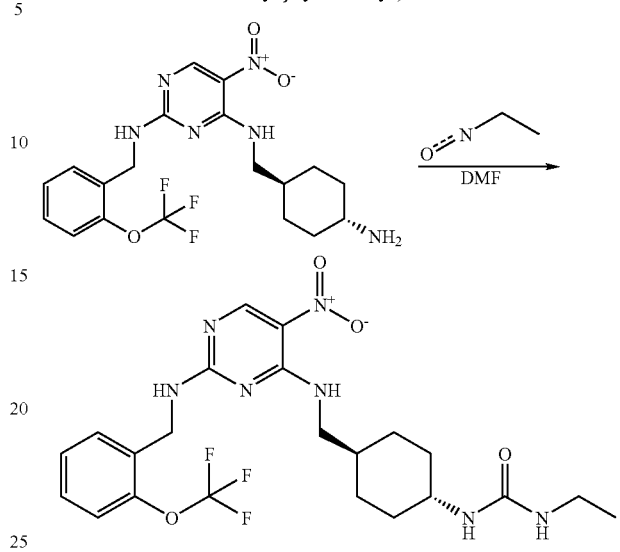

To a solution of N$^4$-[(trans-4-aminocyclohexyl)methyl]-5-nitro-N$^2$-[2-(trifluoromethoxy)benzyl]-pyrimidine-2,4-diamine (100 mg, 0.23 mmol) in DMF (2 mL) was added ethyl isocyanate (65 mg, 0.91 mmol). The reaction mixture was stirred at room temperature for 16 h. The resulting precipitate was filtered and triturated in MeOH. The solid was dried in a vacuum oven to afford 47 mg (41%) of the title compound, m/z 512.7 [M +1]$^+$

Example 30

N-(4-{[(4-{[(trans-4-aminocyclohexyl)methyl]amino}-5-nitropyrimidin-2-yl)amino]methyl}phenyl)acetamide,

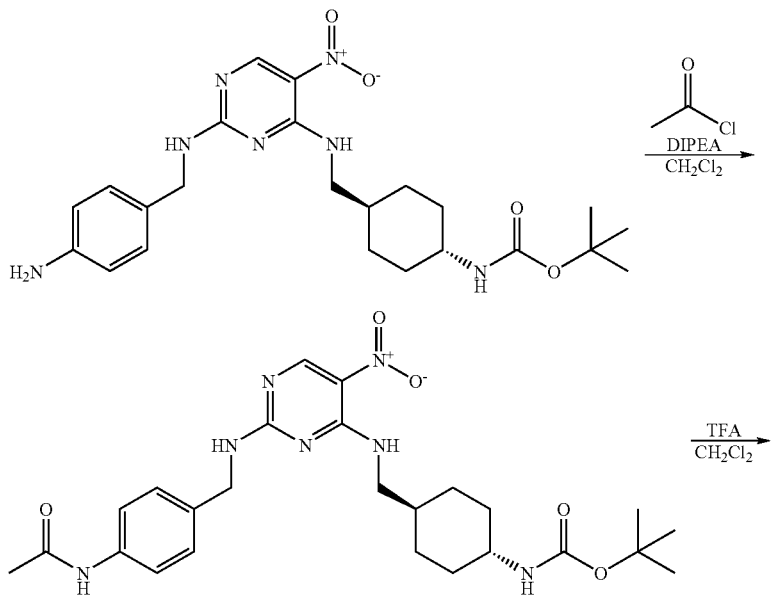

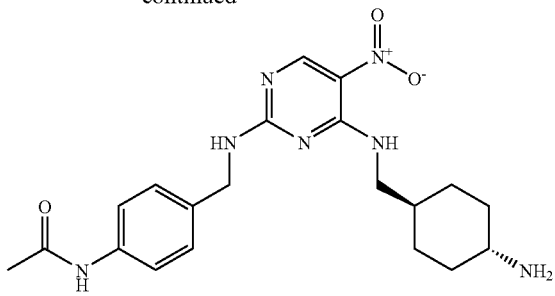

To a solution of {4-[(2-(4-aminobenzyl)-5-nitro-pyrimidin-4-ylamino)-methyl]-cyclohexyl}-carbamic acid tert-butyl ester (100 mg, 0.21 mmol) in CH$_2$Cl$_2$ (5 mL) was cooled to 0° C. To this solution were added acetyl chloride (18 mg, 0.23 mmol) and diisopropylethylamine (0.55 mL, 0.32 mmol). The reaction mixture was stirred at 0° C. for 10 min and an ice bath was removed. The reaction mixture was stirred for another 30 min. The reaction mixture was then washed with saturated NaHCO$_3$. The organic phase was dried over Na$_2$SO$_4$ and concentrated. The resulting residue was purified by silica gel prep TLC using 95:5 CH$_2$Cl$_2$:MeOH as an eluent to afford (4-{[2-(4-acetylamino-benzylamino)-5-nitro-pyrimidin-4-ylamino]-methyl}-cyclohexyl)-carbamic acid tert-butyl ester. This product was dissolved in CH$_2$Cl$_2$ (5 mL) and TFA (1 mL) was added. The reaction mixture was stirred at room temperature for 2 h and then treated with 1M Na$_2$CO$_3$. The mixture was then extracted with CH$_2$Cl$_2$. MeOH was added to the mixture during extraction to solubilize the product into the organic phase. The combined organic phase was dried over Na$_2$SO$_4$ and concentrated. The resulting residue was purified by silica gel prep TLC using 10:1:0.2 CH$_2$Cl$_2$:MeOH:NH$_4$OH as an eluent to afford 20 mg of the title compound as a pale yellow solid (21%), m/z 414.5 [M+1]$^+$.

Example 31

N$^4$-[(trans-4-aminocyclohexyl)methyl]-N$^2$-[(2-isopropoxypyridin-3-yl)methyl]-5-nitropyrimidine-2,4-diamine

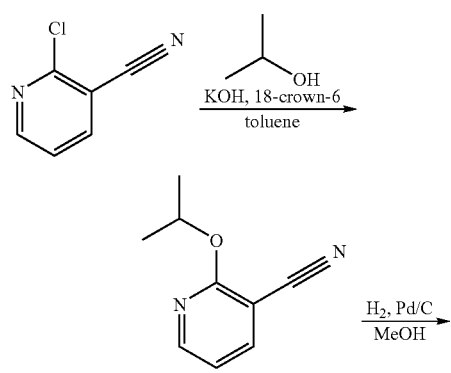

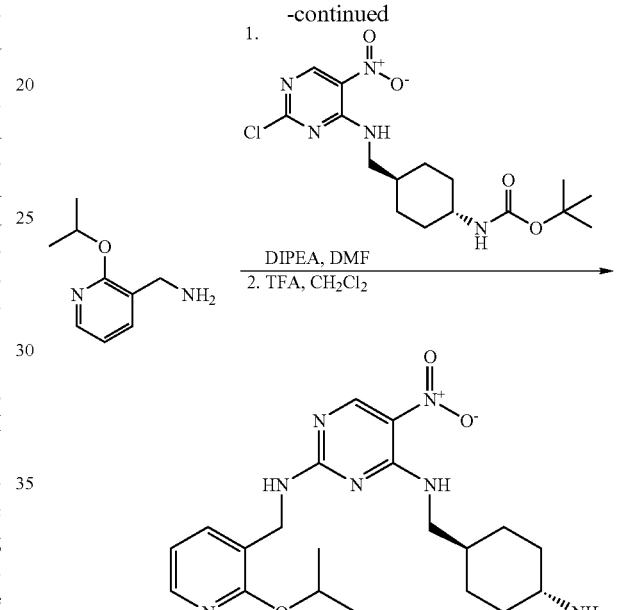

A mixture of 2-chloronicotinonitrile (1.0 g, 7.2 mmol), 2-propanol (0.87 g, 14.4 mmol), KOH (0.81 g, 14.4 mmol) and 18-crown-6 (1.8 g, 2.89 mmol) in toluene (30 mL) was stirred at 60° C. for 16 h. The reaction mixture was quenched with water and the organic phase was separated and then washed with water (×5). The organic phase was dried over Na$_2$SO$_4$ and concentrated to yield crude 2-isopropoxy-nicotinonitrile (1.1 g, 94%) which was used without further purification.

2-Isopropoxy-nicotinonitrile (200 mg, 1.2 mmol) obtained above was dissolved in MeOH (5 mL) and slurry of Pd/C (wet, 50% water content, 200 mg) in MeOH was added to the solution. The reaction mixture was degassed using in-house vacuum and saturated with H$_2$ balloon. The reaction mixture was stirred at room temperature for 6 h. The mixture was then filtered through a pad of celite and rinsed with MeOH. The filtrate was concentrated to yield crude (2-isopropoxy-pyridin-3-yl)-methylamine which was used in the next reaction without further purification (180 mg, 88%).

To a solution of {4-[(2-chloro-5-nitro-pyrimidin-4-ylamino)-methyl]-cyclohexyl}-carbamic acid tert-butyl ester (150 mg, 0.39 mmol) in DMF (1 mL) were added a solution of (2-isopropoxy-pyridin-3-yl)-methylamine (180 mg, 1.1 mmol) obtained above in DMF (1 mL) followed by DIPEA (135 μL, 0.78 mmol). The reaction mixture was stirred at room temperature for 30 min. The reaction mixture was diluted with ethyl acetate and washed with saturated NaHCO$_3$ and water (×4). The organic phase was dried over Na$_2$SO$_4$ and concentrated. The resulting residue was purified by silica gel prep TLC using 95:5 CH$_2$Cl$_2$:MeOH as an eluent to afford [4-({2-[(2-isopropoxy-pyridin-3-ylmethyl)-amino]-5-nitro-pyrimidin-4-ylamino}-methyl)-cyclohexyl]-carbamic acid tert-butyl ester which was dissolved in CH$_2$Cl$_2$ and TFA was added. The reaction mixture was stirred at room temperature for 2 h. The mixture was then treated with 1M Na$_2$CO$_3$ and extracted with CH$_2$Cl$_2$. MeOH was added to the mixture during the extraction to solublize the product into the organic phase. The combined organic phase was dried over Na$_2$SO$_4$ and concentrated. The resulting residue was purified by silica gel prep TLC using 10:1:0.2 CH$_2$Cl$_2$:MeOH:NH$_4$OH as an eluent to afford 75 mg of the title compound as a pale yellow solid (46%); m/z 416.4 [M+1]$^+$.

The following compounds were prepared using similar procedures as described above:

N$^4$-[(trans-4-aminocyclohexyl)methyl]-N$^2$-[(2-ethoxypyridin-3-yl)methyl]-5-nitropyrimidine-2,4-diamine, m/z 400.2 [M−1]$^+$.

N$^4$-[(trans-4-aminocyclohexyl)methyl]-5-nitro-N$^2$-{[2-(2,2,2-trifluoroethoxy)pyridin-3-yl]methyl}pyrimidine-2,4-diamine, m/z 456.4 [M+1]$^+$.

Example 32

N$^4$-[(trans-4-aminocyclohexyl)methyl]-N$^2$-[(5-fluoro-2-methoxypyridin-3-yl)methyl]-5-nitropyrimidine-2,4-diamine

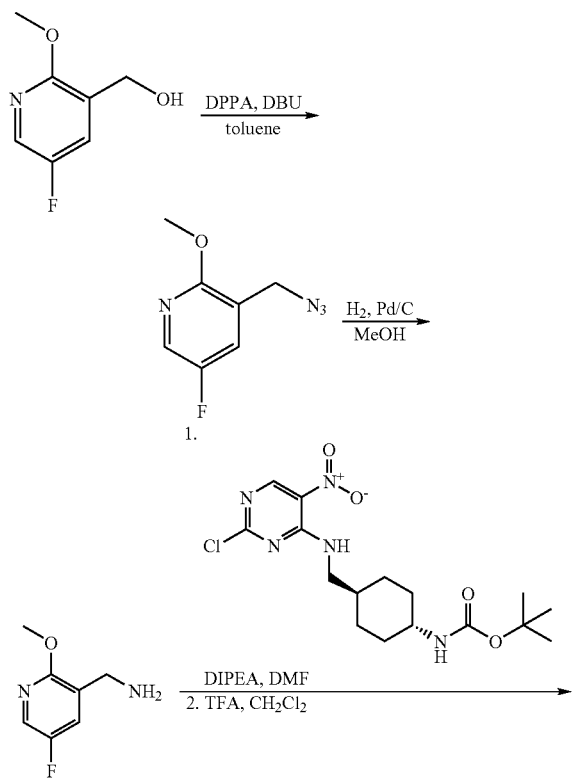

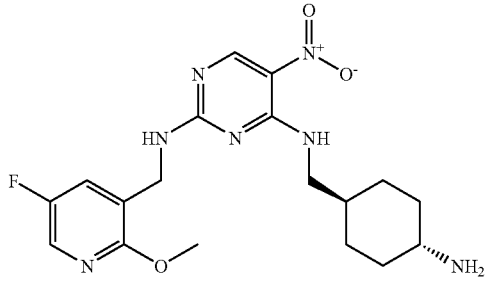

1,8-Diazabicyclo[5.4.0]undec-7-ene (630 mg, 4.1 mmol) was added to a solution of 5-fluoro-3-5 hydroxymethyl-2-methoxypyridine (500 mg, 3.2 mmol) and diphenylphosphoryl azide (1050 mg, 3.8 mmol) in toluene (10 mL) at room temperature. The reaction mixture was stirred at room temperature for 3 h. The reaction mixture was then diluted with 1M HCl and ether. The layers were separated and the aqueous layer was extracted with ether (×2). The combined organic phase was washed with water, brine and dried over Na$_2$SO$_4$. The resulting residue was purified by silica gel prep TLC using CH$_2$Cl$_2$ as an eluent to afford 320 mg of 3-azidomethyl-5-fluoro-2-methoxy-pyridine as colorless oil (55%).

To a solution of 3-azidomethyl-5-fluoro-2-methoxy-pyridine (320 mg, 1.8 mmol) in MeOH (8 mL) was added slurry of Pd/C (wet, 50% water content, 100 mg) in MeOH (2 mL). The reaction mixture was degassed using in-house vacuum for 5 min and then H$_2$ balloon was attached to the reaction flask. The reaction mixture was stirred at room temperature for 2 h. The mixture was then filtered through a pad of celite and the filtrated was concentrated to afford 280 mg of (5-fluoro-2-methoxy-pyridin-3-yl)-methylamine (100%). This product was used for the next reaction without further purification.

To a solution of {4-[(2-chloro-5-nitro-pyrimidin-4-ylamino)-methyl]-cyclohexyl}-carbamic acid tert-butyl ester (200 mg, 0.52 mmol) in DMF (2 mL) were added a solution of (5-fluoro-2-methoxy-pyridin-3-yl)-methylamine (120 mg, 0.78 mmol) in DMF (1 mL) followed by diisopropylethylamine (181 µL, 1.04 mmol). The reaction mixture was stirred at room temperature for 30 min. The reaction mixture was diluted with ethyl acetate and washed with saturated NaHCO$_3$ and water (×4). The organic phase was dried over Na$_2$SO$_4$, filtered and concentrated. The resulting residue was purified by silica gel prep TLC using 95:5 CH$_2$Cl$_2$:MeOH as an eluent to afford [4-({2-[(5-fluoro-2-methoxy-pyridin-3-ylmethyl)-amino]-5-nitro-pyrimidin-4-ylamino}-methyl)-cyclohexyl]-carbamic acid tert-butyl ester which was then dissolved in CH$_2$Cl$_2$ (5 mL) and TFA (1 mL) was added. The reaction mixture was stirred at room temperature for 2 h. The mixture was then treated with 1M Na$_2$CO$_3$ and extracted with CH$_2$Cl$_2$. MeOH was added to the mixture during the extraction to solublize the product into the organic phase. The combined organic phase was dried over Na$_2$SO$_4$ and concentrated. The resulting residue was purified by silica gel prep TLC using 10:1:0.2 CH$_2$Cl$_2$:MeOH:NH$_4$OH as an eluent to afford 156 mg of the title compound as a pale yellow solid (74%), m/z 406.4 [M+1]$^+$.

Example 33

N⁴-{[trans-4-(3-fluoroazetidin-1-yl)cyclohexyl]methyl}-5-nitro-N²-[2-(trifluoromethoxy)benzyl]pyrimidine-2,4-diamine

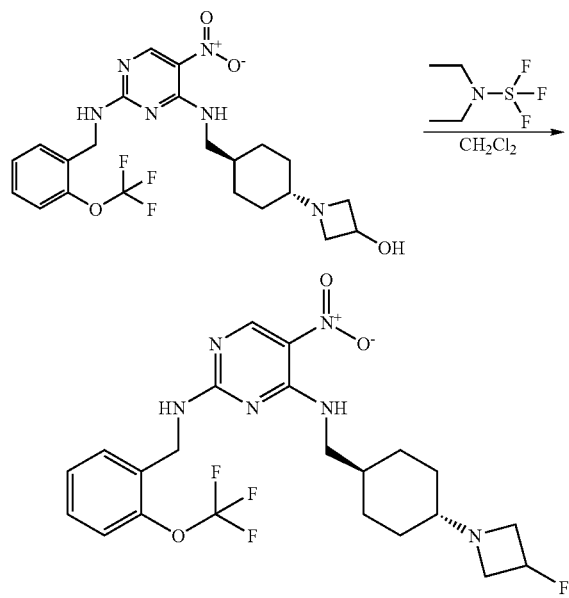

To a solution of 1-(trans-4-{[(5-nitro-2-{[2-(trifluoromethoxy)benzyl]amino}pyrimidin-4-yl)amino]methyl}cyclohexyl)azetidin-3-ol (100 mg, 0.20 mmol) in CH$_2$Cl$_2$ (25 mL) was added dropwise a solution of diethylaminosulfur trifluoride (32 µL, 0.24 mmol) in CH$_2$Cl$_2$ (0.5 mL) at room temperature over a period of 15 min. When the reaction was complete, the mixture was treated with saturated NaHCO$_3$ and stirred for 5 min. The organic phase was separated and washed with water. The organic phase was dried over Na$_2$SO$_4$ and concentrated. The resulting residue was purified by silica gel prep TLC using 95:5 CH$_2$Cl$_2$:MeOH as eluent to afford 26 mg of the title compound as a pale yellow solid (26%), m/z 499.1 [M+1]⁺.

Example 34

5-nitro-N⁴-({trans-4-[(2,2,2-trifluoroethyl)amino]cyclohexyl}methyl)-N²-[2-(trifluoromethoxy)benzyl]pyrimidine-2,4-diamine

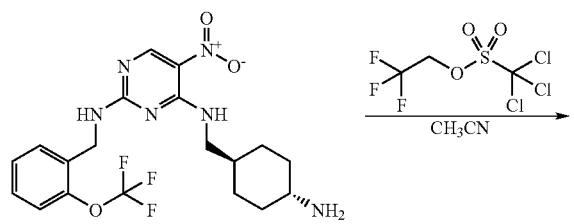

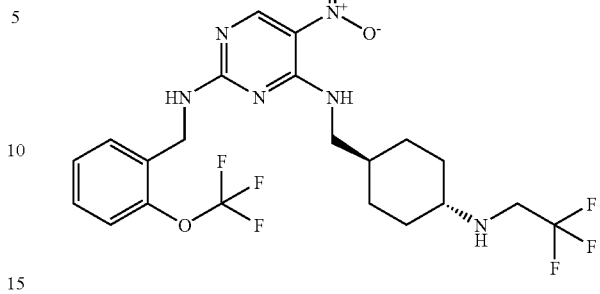

N⁴-[(trans-4-aminocyclohexyl)methyl]-5-nitro-N²-[2-(trifluoromethoxy)benzyl]pyrimidine-2,4-diamine (200 mg, 0.45 mmol) was suspended in CH$_3$CN (4 mL) and cooled to 0° C. 2,2,2-Trifluoroethyl trichloromethanesulphonate (66 mg, 0.23 mmol) in CH$_3$CN (1 mL) was added dropwise to the reaction mixture and the reaction mixture was heated to 90° C. for 5 h. The reaction mixture was concentrated and the resulting residue was diluted with ethyl acetate. The solution was treated with 1M Na$_2$CO$_3$ and the organic phase was separated. The aqueous phase was re-extracted with CH$_2$Cl$_2$. The combined organic phase was dried over Na$_2$SO$_4$ and concentrated. Silica gel prep TLC using 98:2 CH$_2$Cl$_2$:MeOH, then 7:3 Hexanes:ethyl acetate afforded 74 mg of the title compound, m/z 523.0 [M+1]⁺.

Example 35

(1S)-2-[(trans-4-{[(5-nitro-2-{[2-(trifluoromethoxy)benzyl]amino}pyrimidin-4-yl)amino]methyl}cyclohexyl)amino]-1-pyridin-3-ylethanol

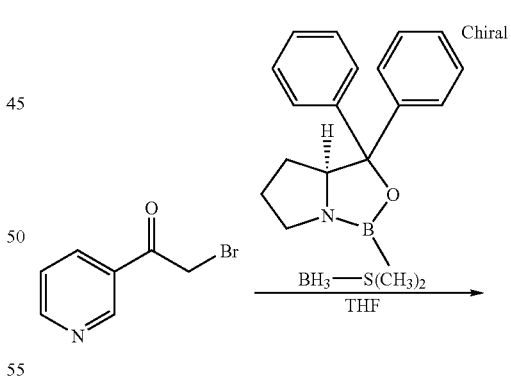

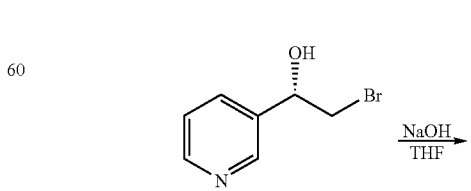

-continued

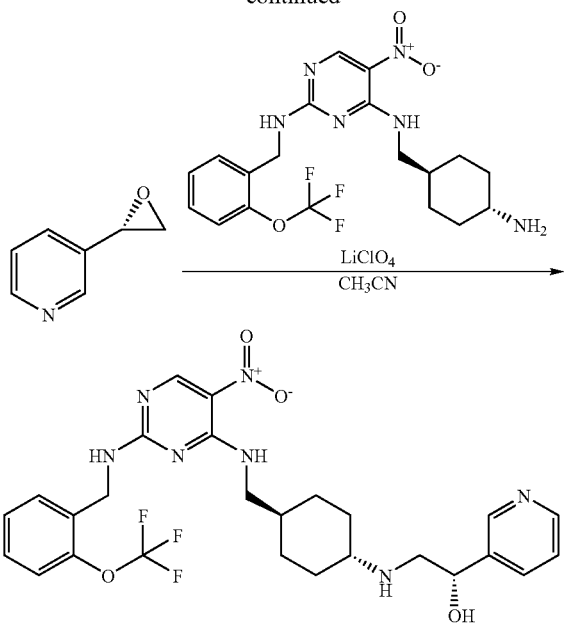

(S)-2-Methyl-CBS-oxazaborolidine (1M in toluene, 189 μL, 0.18 mmol) and borane-methyldisulfide complex (2M in toluene, 100 μL) in THF (11 mL) was allowed to stir at room temperature for 10 min. Then, the rest of $BH_3$—$S(CH_3)_2$ (2M in toluene, 1.33 mL, 2.85 mmol) was added to the reaction solution followed by a suspension of 3-(bromoacetyl)pyridine hydrochloride (0.5 g, 1.78 mmol) in THF (11 mL). The heterogeneous reaction mixture was stirred at room temperature for 16 h. The reaction mixture was then cooled to 0° C. and quenched with MeOH (1.5 mL). After 5 min of stirring, the solvent was removed and the resulting residue was diluted with $CH_2Cl_2$. The solution was treated with saturated $NaHCO_3$ and the organic phase was separated. The aqueous phase was re-extracted with $CH_2Cl_2$. The combined organic phase was dried over $Na_2SO_4$ and concentrated. The resulting residue was purified by silica gel prep TLC using 95:5 $CH_2Cl_2$:MeOH as an eluent to afford 0.24 g of (S)-2-bromo-1-pyridin-3-yl-ethanol as a colorless oil (66%).

To a solution of (S)-2-Bromo-1-pyridin-3-yl-ethanol (134 mg, 0.66 mmol) in THF (10 mL) was added 4N NaOH solution (8.3 mL). The reaction mixture was stirred at room temperature for 1 h. The organic phase was separated, dried over $Na_2SO_4$ and concentrated. Silica gel prep TLC of the resulting residue using 99:1 $CH_2Cl_2$:MeOH as an eluant afforded 34 mg of (S)-3-Oxiranyl-pyridine as a colorless oil (42%).

A mixture of $N^4$-[(trans-4-aminocyclohexyl)methyl]-5-nitro-$N^2$-[2-(trifluoromethoxy)benzyl]pyrimidine-2,4-diamine (124 mg, 0.28 mmol), (S)-3-oxiranyl-pyridine (34 mg, 0.28 mmol) and lithium perchlorate (60 mg, 0.56 mmol) in $CH_3CN$ was heated to 100° C. in a sealed tube and stirred for 1 h. The reaction mixture was concentrated and diluted with ethyl acetate. The solution was then treated with 1M $Na_2CO_3$ and the organic phase was separated. The aqueous phase was re-extracted with ethyl acetate (×2). The combined organic phase was dried over $Na_2SO_4$ and concentrated. The resulting residue was purified by silica gel prep TLC using 10:1:0.05 $CH_2Cl_2$:MeOH:$NH_4OH$ as an eluent to afford 15 mg of the title compound as an off-white solid (10%), m/z 562.7 $[M+1]^+$.

Example 36

5-nitro-$N^4$-{[trans-4-(pyridin-2-ylamino)cyclohexyl]methyl}-$N^2$-[2-(trifluoromethoxy)benzyl]pyrimidine-2,4-diamine

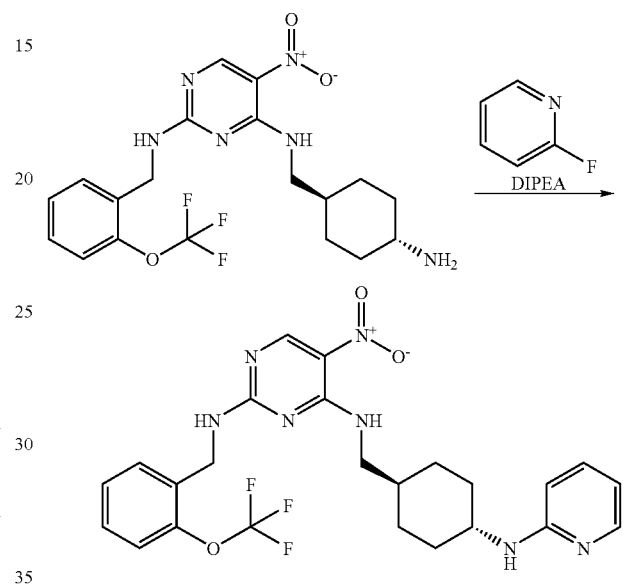

A mixture of $N^4$-[(trans-4-aminocyclohexyl)methyl]-5-nitro-$N^2$-[2-(trifluoromethoxy)benzyl]pyrimidine-2,4-diamine (100 mg, 0.23 mmol), 2-fluoropyridine (0.5 mL) and diisopropylethyl (0.2 mL) was placed in a microwave tube and heated to 150° C. in the Personal Chemistry Microwave for 1 h, 165° C. for 1 h, then 185° C. for another 2 h. The reaction mixture was concentrated and the resulting residue was diluted with ethyl acetate. The organic phase was washed with 10% citric acid and brine. The organic phase was dried over $Na_2SO_4$ and concentrated. The resulting residue was purified by silica gel prep TLC using 98:2 $CH_2Cl_2$:MeOH as an eluent to afford 29 mg of the title compound, m/z 518.9 $[M+1]^+$.

Example 37

$N^4$-[(trans-4-aminocyclohexyl)methyl]-$N^2$-(isoquinolin-1-ylmethyl)-5-nitropyrimidine-2,4-diamine

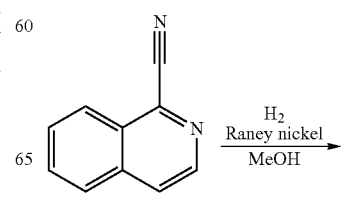

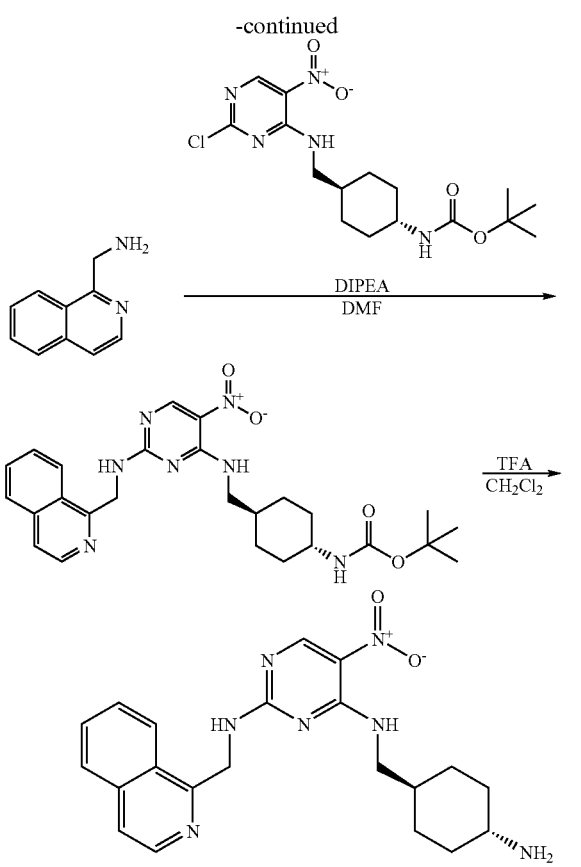

1-Isoquinolinecarbonitrile (2.0 g, 12.8 mmol) was dissolved in MeOH (160 mL). To this solution, was added 6 pasteur pipet full of Raney Nickel suspension in water. The reaction flask was degassed and backflushed with $N_2$ twice. The $N_2$ balloon was replaced with $H_2$ balloon and the flask was filled with $H_2$ after evacuation of $N_2$. The reaction mixture was stirred for 5 h and then filtered through a pad of celite under stream of $N_2$. The celite pad was flushed with MeOH. The combined organic solution was concentrated to afford 1.32 g of isoquinolin-1-yl-methylamine as brown oil (65%).

To a solution of isoquinolin-1-yl-methylamine (1.32 g, 8.35 mmol) and diisopropylethylamine (2.7 mL, 15.5 mmol) in DMF (20 mL) was added {4-[(2-chloro-5-nitro-pyrimidin-4-ylamino)-methyl]-cyclohexyl}-carbamic acid tert-butyl ester (1.5 g, 3.89 mmol). The reaction mixture was stirred at room temperature for 10 min. The solvent was removed and the resulting residue was diluted with a mixture of ethyl acetate (350 mL) and $CH_2Cl_2$ (100 mL). The solution was then washed with 1M $Na_2CO_3$ and water. The organic phase was dried over $Na_2SO_4$ and concentrated. The resulting solid was treated with ethyl acetate (poor solubility of the product in ethyl acetate) and the un-dissolved solid was filtered through a Buchner funnel. The white solid was dried in vacuo to yield 1.64 g of [4-({2-[(isoquinolin-1-ylmethyl)-amino]-5-nitro-pyrimidin-4-ylamino}-methyl)-cyclohexyl]-carbamic acid tert-butyl ester.

[4-({2-[(Isoquinolin-1-ylmethyl)-amino]-5-nitro-pyrimidin-4-ylamino}-methyl)-cyclohexyl]-carbamic acid tert-butyl ester (1.64 g, 3.24 mmol) was dissolved in $CH_2Cl_2$ (50 mL) and TFA (15 mL) was added. The reaction mixture was stirred at room temperature for 30 min. The reaction mixture was treated with 1M $Na_2CO_3$ and the organic phase was separated. The organic phase was dried over $Na_2SO_4$ and concentrated. Silica gel purification using a mixture of $CH_2Cl_2$:MeOH:$NH_4OH$ yielded 1.1 g of the title compound (84%), m/z 406.2 (M−1)$^+$.

The following compound was prepared using similar procedures as described above:

$N^4$-[(trans-4-aminocyclohexyl)methyl]-5-nitro-$N^2$-{[4-(trifluoromethyl)pyridin-3-yl]methyl}pyrimidine-2,4-diamine, m/z 426.4 (M+1)$^+$ Example 38

$N^4$-[(trans-4-aminocyclohexyl)methyl]-5-nitro-$N^2$-(quinolin-5-ylmethyl)pyrimidine-2,4-diamine

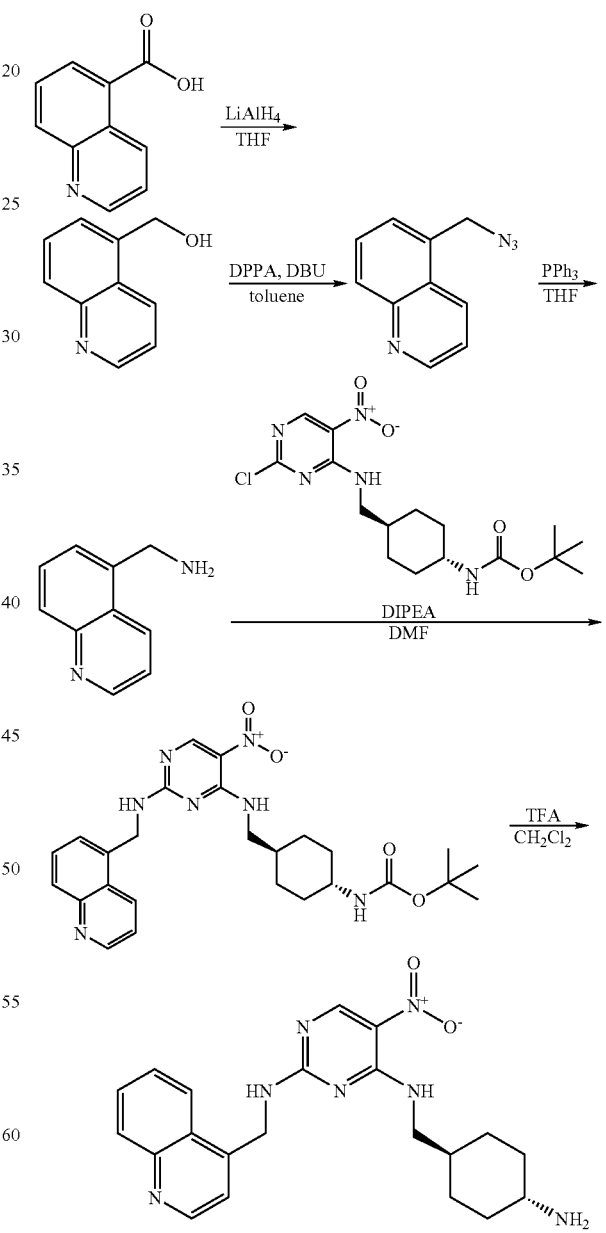

To a solution of quinoline-5-carboxylic acid (500 mg, 2.83 mmol) in THF (10 mL) was added slowly LiAlH$_4$ (1.0 M, THF) solution at 0° C. The resulting residue was heated to 70° C. for 3 h and stirred at room temperature for 16 h. The reaction mixture was cooled to 0° C. and quenched with water (1 mL) and 10% NaOH (1.5 mL) solution. The reaction mixture was stirred for 1 h. The solution was filtered through a pad of celite and rinsed with THF. The filtrate was concentrated and the resulting residue was purified by silica gel prep TLC using 95:5 $CH_2Cl_2$:MeOH as an eluent to afford 218 mg of quinolin-5-yl-methanol (48%).

To a solution of quinolin-5-yl-methanol (96 mg, 0.60 mmol) and DPPA (202 μL, 0.91 mmol) in toluene (2 mL) was added DBU (166 μL, 1.09 mmol) at room temperature. The reaction mixture was stirred at room temperature for 16 h. The reaction mixture was diluted with 3M HCl (1.7 mL) and ethyl acetate (5 mL). The organic phase was separated and the aqueous phase was re-extracted with ethyl acetate (×2). The combined organic phase was dried over $Na_2SO_4$ and concentrated. The resulting residue was purified by silica gel prep TLC using 98:2 $CH_2Cl_2$:MeOH as an eluent to afford 49 mg of 5-azidomethyl-quinoline as light brown oil (44%).

Triphenylphosphine (172 mg, 0.65 mmol) was added to the solution of 5-azidomethyl-quinoline (109 mg, 0.59 mmol) in THF (3 mL) at 0° C. After 5 min of stirring, the reaction mixture was warmed to room temperature and stirred at that temperature 16 h. The reaction mixture was diluted with ammonium hydroxide (0.55 mL) and stirred for 3 h. The mixture was then treated with 2M NaOH (0.8 mL) and stirred for another 1 h. The solution was diluted with ethyl acetate and the organic phase was separated, dried over $Na_2SO_4$, concentrated. The resulting residue was purified by silica gel prep TLC using 10:1:0.3 $CH_2Cl_2$:MeOH:$Et_3N$ as an eluant to afford 105 mg of quinolin-5-yl-methylamine as a colorless solid.

To a solution of quinolin-5-yl-methylamine 100 mg, 0.39 mmol) and diisopropylethylamine (140 μL, 0.78 mmol) in a mixture of DMF (2 mL) and acetonitrile (2 mL) was added {4-[(2-chloro-5-nitro-pyrimidin-4-ylamino)-methyl]-cyclohexyl}-carbamic acid tert-butyl ester (150 mg, 0.39 mmol). The reaction mixture was stirred at room temperature for 16 h. The reaction mixture was diluted with ethyl acetate and washed with water (×2). The combined organic phase was dried over $Na_2SO_4$ and concentrated. The resulting residue was purified by silica gel prep TLC using 95:5 $CH_2Cl_2$:MeOH as an eluent to afford 197 mg of [4-({5-nitro-2-[(quinolin-5-ylmethyl)-amino]-pyrimidin-4-ylamino}-methyl)-cyclohexyl]-carbamic acid tert-butyl ester as a light yellow solid (100%).

[4-({5-Nitro-2-[(quinolin-5-ylmethyl)-amino]-pyrimidin-4-ylamino}-methyl)-cyclohexyl]-carbamic acid tert-butyl ester (197 mg, 0.39 mmol) was dissolved in $CH_2Cl_2$ (10 mL) and TFA (2 mL) was added. The reaction mixture was stirred at room temperature for 1 h. The reaction mixture was treated with 3M $Na_2CO_3$ and the organic phase was separated. The organic phase was dried over $Na_2SO_4$ and concentrated. Silica gel purification using a mixture of 10:1:0.3 $CH_2Cl_2$:MeOH:$Et_3N$ yielded 120 mg of the title compound as a light yellow solid (79%), m/z 406.4 $[M-1]^+$.

The following compounds were prepared following similar procedures as described above:

$N^4$-[(trans-4-aminocyclohexyl)methyl]-$N^2$-[(3-chloropyridin-4-yl)methyl]-5-nitropyrimidine-2,4-diamine  m/z 392.5 $[M+1]^+$ $N^4$-[(trans-4-aminocyclohexyl)methyl]-$N^2$-[(2-methylpyridin-3-yl)methyl]-5-nitropyrimidine-2,4-diamine  m/z 372.6 $[M+1]^+$ Example 39

$N^4$-[(trans-4-aminocyclohexyl)methyl]-5-nitro-$N^2$-(2-oxo-2-piperidin-1-ylethyl)pyrimidine-2,4-diamine

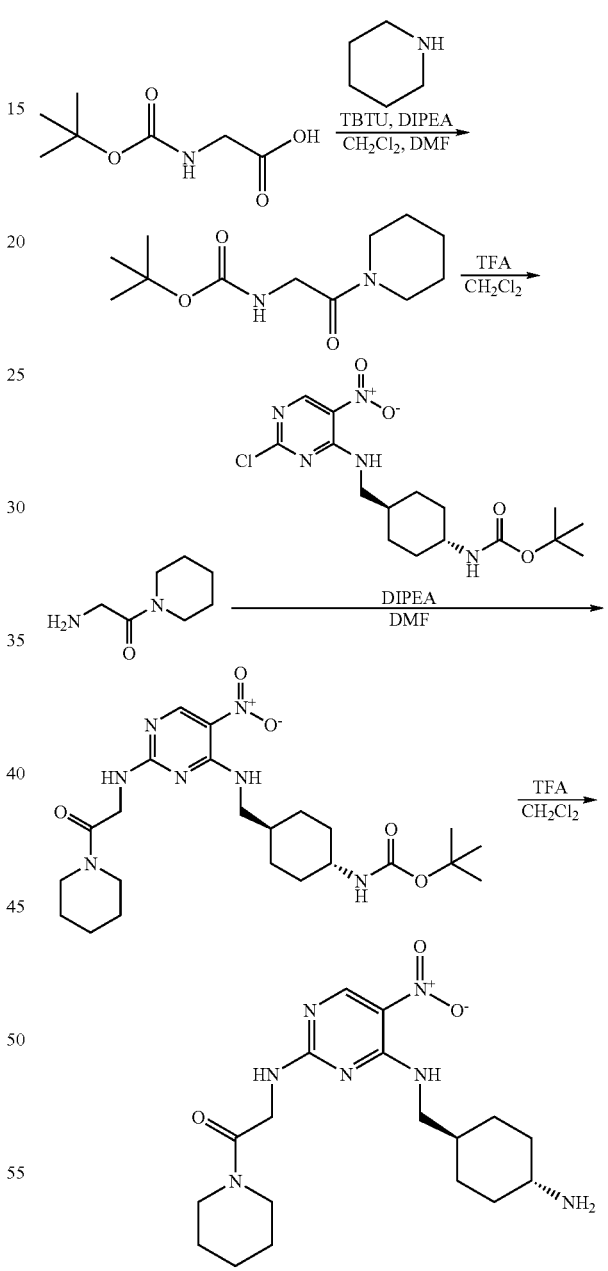

To a solution of N-(tert-butoxycarbonyl)glycine (500 mg, 2.8 mmol), piperidine (0.6 mL, 5.6 mmol) in a mixture of $CH_2Cl_2$ (10 mL) and DMF (1 mL) were added TBTU (1.4 g, 4.2 mmol) and diisopropylethylamine (970 μL). The reaction mixture was stirred at room temperature for 16 h. The reaction mixture was concentrated and the resulting residue was diluted with ethyl acetate.

The organic phase was washed with water (×3) and brine. The combined organic phase was dried over Na₂SO₄ and concentrated. Silica gel column chromatography using 98:2 CH₂Cl₂:MeOH as an eluent afforded 590 mg of (2-oxo-2-piperidin-1-yl-ethyl)-carbamic acid tert-butyl as a colorless solid (87%).

(2-Oxo-2-piperidin-1-yl-ethyl)-carbamic acid tert-butyl was dissolved in CH₂Cl₂ (10 mL) and TFA (3 mL) was added to the solution. The reaction mixture was stirred at room temperature for 16 h. The mixture was concentrated and the resulting residue of 2-amino-1-piperidin-1-yl-ethanone was used for the next reaction without further purification as a trifluoroacetic acid salt.

To a solution of {4-[(2-chloro-5-nitro-pyrimidin-4-ylamino)-methyl]-cyclohexyl}-carbamic acid tert-butyl ester (100 mg, 0.26 mmol) in DMF (3 mL) was added 2-amino-1-piperidin-1-yl-ethanone trifluoroacetic salt (200 mg, 0.78 mmol) and diisopropylethylamine (272 µL, 1.6 mmol). The reaction mixture was stirred at room temperature for 48 h. The mixture was diluted with ethyl acetate and washed with water (×3). The organic phase was dried over Na₂SO₄ and concentrated. The resulting residue was purified by silica gel prep TLC using 95:5 CH₂Cl₂:MeOH as an eluent to afford 36 mg of (4-{[5-nitro-2-(2-oxo-2-piperidin-1-yl-ethylamino)-pyrimidin-4-ylamino]-methyl}-cyclohexyl)-carbamic acid tert-butyl ester as an off-white solid (28%).

(4-{[5-Nitro-2-(2-oxo-2-piperidin-1-yl-ethylamino)-pyrimidin-4-ylamino]-methyl}-cyclohexyl)-carbamic acid tert-butyl ester (36 mg, 0.07 mmol) was dissolved in CH₂Cl₂ (10 mL) and TFA (1 mL) was added to the solution. The reaction mixture was stirred at room temperature for 16 h. The solution was treated with 3M Na₂CO₃ to pH 9 and the organic phase was separated. The aqueous phase was extracted with CH₂Cl₂ and the combined organic phase was dried over Na₂SO₄ and then concentrated. The resulting residue was purified by silica gel prep TLC using 10:1:0.3 CH₂Cl₂:MeOH:Et₃N as an eluent to afford 27 mg of the title compound as a yellow solid (93%), m/z 392.6 [M+1]⁺.

The following compounds were prepared using similar procedures as described above:

(3R)-1-[N-(4-{[(trans-4-aminocyclohexyl)methyl]amino}-5-nitropyrimidin-2-yl)glycyl]piperidin-3-ol, m/z 406.4 [M−1]⁺.

N⁴-[(trans-4-aminocyclohexyl)methyl]-N²-(2-morpholin-4-yl-2-oxoethyl)-5-nitropyrimidine-2,4-diamine, m/z 394.5 [M+1]⁺.

Example 40

N⁴-[(trans-4-aminocyclohexyl)methyl]-5-nitro-N²-(2-oxo-2-pyrrolidin-1-ylethyl)pyrimidine-2,4-diamine

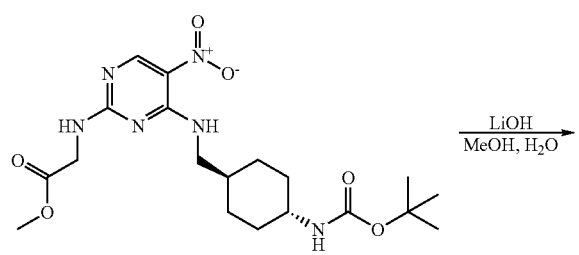

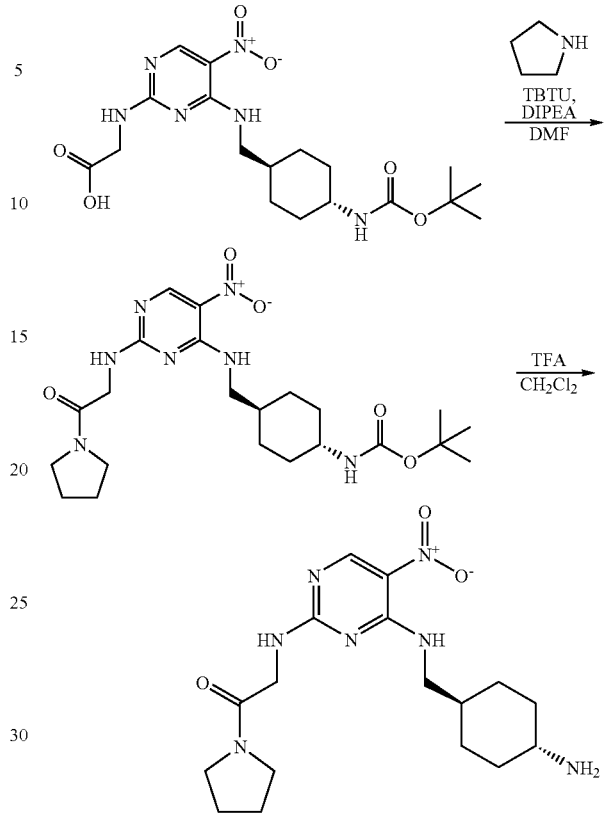

To a suspension of {4-[(4-tert-butoxycarbonylamino-cyclohexylmethyl)-amino]-5-nitro-pyrimidin-2-ylamino}-acetic acid methyl ester (845 mg, 1.9 mmol) in a mixture of MeOH (90 mL) and water (30 mL) was added lithium hydroxide monohydrate (404 mg, 9.6 mmol). The heterogeneous mixture was stirred at room temperature for 1 h. The mixture was concentrated and the resulting residue was acidified to pH 5 using 1M HCl. The product was extracted using ethyl acetate (×3). The combined organic phase was dried over Na₂SO₄ and concentrated to yield 1.0 g of the crude {4-[(4-tert-butoxycarbonylamino-cyclohexylmethyl)-amino]-5-nitro-pyrimidin-2-ylamino}-acetic acid as a white solid. This product was used for the next reaction without further purification.

To {4-[(4-tert-butoxycarbonylamino-cyclohexylmethyl)-amino]-5-nitro-pyrimidin-2-ylamino}-acetic acid (120 mg, 0.28 mmol) in DMF (1.5 mL) were added pyrrolidine (48 µL, 0.57 mmol), TBTU (141 mg, 0.43 mmol), and diisopropylethylamine (99 µL, 0.57 mmol). The reaction mixture was stirred at room temperature for 16 h. The mixture was diluted with ethyl acetate and washed with water (×2) and brine. The organic phase was dried over Na₂SO₄ and concentrated. The resulting residue was purified by silica gel prep TLC using 95:5 CH₂Cl₂:MeOH as an eluant to afford 19 mg of (4-{[5-nitro-2-(2-oxo-2-pyrrolidin-1-yl-ethylamino)-pyrimidin-4-ylamino]-methyl}-cyclohexyl)-carbamic acid tert-butyl ester as a light brown solid.

(4-{[5-Nitro-2-(2-oxo-2-pyrrolidin-1-yl-ethylamino)-pyrimidin-4-ylamino]-methyl}-cyclohexyl)-carbamic acid tert-butyl ester (19 mg, 0.04 mmol) was dissolved in CH₂Cl₂ (5 mL) and TFA (1 mL) was added. The reaction mixture was stirred at room temperature for 1 h. The solution was treated with saturated NaHCO$_3$ and the organic phase was separated. The aqueous phase was extracted with CH$_2$Cl$_2$ and the combined organic phase was dried over Na$_2$SO$_4$ and concentrated. The resulting residue was purified by silica gel prep TLC using 10:1:0.3 CH$_2$Cl$_2$:MeOH:Et$_3$N as an eluant to afford 13 mg of the title compound as a light yellow solid (83%), m/z 376.3 [M−1]$^+$.

The following compounds were prepared using similar procedures as described above:

1-[N-(4-{[(trans-4-aminocyclohexyl)methyl]amino}-5-nitropyrimidin-2-yl)glycyl]piperidin-4-ol, m/z 408.6 [M+1]$^+$.

N$^4$-[(trans-4-aminocyclohexyl)methyl]-5-nitro-N$^2$-(2-oxo-2-piperazin-1-ylethyl)pyrimidine-2,4-diamine, m/z 393.6 [M+1]$^+$.

(3R)-1-[N-(4-{[(trans-4-aminocyclohexyl)methyl]amino}-5-nitropyrimidin-2-yl)glycyl]pyrrolidin-3-ol, m/z 394.6 [M+1]$^+$.

1-[N-(4-{[(trans-4-aminocyclohexyl)methyl]amino}-5-nitropyrimidin-2-yl)glycyl]piperidine-4-carboxamide, m/z 433.3 [M−1]$^+$.

(3S)-1-[N-(4-{[(trans-4-aminocyclohexyl)methyl]amino}-5-nitropyrimidin-2-yl)glycyl]pyrrolidin-3-ol, m/z 392.3 [M−1]$^+$.

N$^4$-[(trans-4-aminocyclohexyl)methyl]-N$^2$-(2-azetidin-1-yl-2-oxoethyl)-5-nitropyrimidine-2,4-diamine, m/z 364.6 [M+1]$^+$.

N$^4$-[(trans-4-aminocyclohexyl)methyl]-5-nitro-N$^2$-[(1S)-2-oxo-1-phenyl-2-piperidin-1-ylethyl]pyrimidine-2,4-diamine, m/z 468.5 [M+1]$^+$.

N$^4$-[(trans-4-aminocyclohexyl)methyl]-5-nitro-N$^2$-[(1R)-2-oxo-1-phenyl-2-piperidin-1-ylethyl]pyrimidine-2,4-diamine, m/z 468.5 [M+1]$^+$.

Example 41

N$^4$-{[trans-4-(3-aminoazetidin-1-yl)cyclohexyl]methyl}-5-nitro-N$^2$-[2-(trifluoromethoxy)benzyl]pyrimidine-2,4-diamine

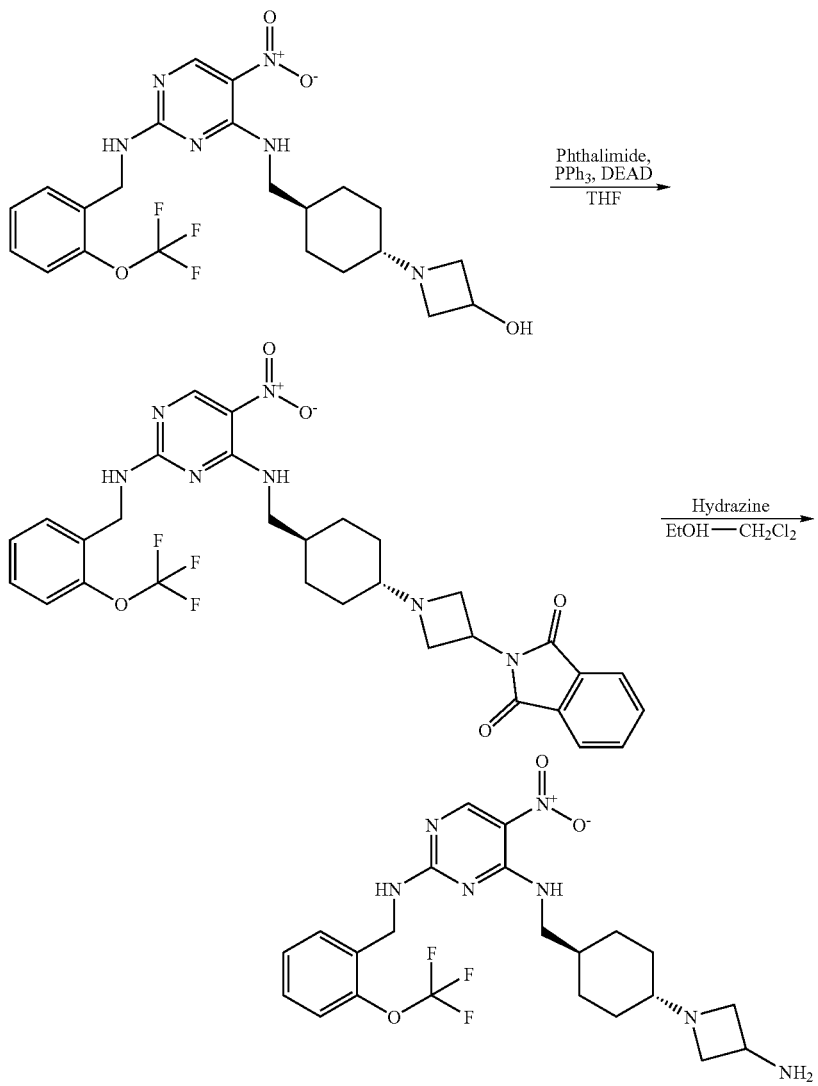

1-(trans-4-{[(5-nitro-2-{[2-(trifluoromethoxy)benzyl]amino}pyrimidin-4-yl)amino]methyl}-cyclohexyl)azetidin-3-ol (111 mg, 0.22 mmol, see Example 7), phthalimide (50 mg, 0.33 mmol) and PPh$_3$ (127 mg, 0.48 mmol) were combined in THF (5 mL). To this mixture was added DEAD (61 mg, 0.35 mmol) and the reaction was allowed to stir at 25° C. for 18 h. The reaction was diluted with EtOAc and poured into 10% aqueous NaHCO$_3$. The aqueous phase was separated and extracted two more times with EtOAc. The organic layers were combined, dried (Na$_2$SO$_4$), decanted and concentrated. The crude was purified via flash chromatography (SiO$_2$, 1:9:90-NH$_4$OH:CH$_3$OH:CH$_2$Cl$_2$) to afford 92 mg (67%) of 2-[1-(4-{[5-nitro-2-(2-trifluoromethoxy-benzylamino)-pyrimidin-4-ylamino]-methyl}-cyclohexyl)-azetidin-3-yl]-isoindole-1,3-dione.

2-[1-(4-{[5-Nitro-2-(2-trifluoromethoxy-benzylamino)-pyrimidin-4-ylamino]-methyl}-cyclohexyl)-azetidin-3-yl]-isoindole-1,3-dione (92 mg, 0.15 mmol) was dissolved in EtOH-CH$_2$Cl$_2$ (3 mL, 2:1). With stirring, hydrazine monohydrate (11.3 mg, 0.23 mmol) was added and the reaction was stirred at 25° C. for 3 h. The volatiles were removed in vacuo and the crude residue was purified via flash chromatography (SiO$_2$, 1:9:90-NH$_4$OH:CH$_3$OH:CH$_2$Cl$_2$) to afford 46 mg (62%) of the target compound, m/z 496.35 [M+1]$^+$.

Example 42

N-[1-(trans-4-{[(5-nitro-2-{[2-(trifluoromethoxy)benzyl]amino}pyrimidin-4-yl)amino]methyl}cyclohexyl)azetidin-3-yl]acetamide CH$_2$Cl$_2$ and extracted with 10% aqueous NaHCO$_3$. The aqueous phase was separated and extracted two more times with CH$_2$Cl$_2$. The organic layers were combined, dried (Na$_2$SO$_4$), decanted and concentrated. The resultant residue was purified via flash chromatography (SiO$_2$, 10-30% (2:18:80, NH$_4$OH:CH$_3$OH:CH$_2$Cl$_2$)—CH$_2$Cl$_2$) to afford 16 mg (74%) of the target compound, m/z 538.46 (M+1)$^+$.

Example 43

N-[1-(trans-4-{[(5-nitro-2-{[2-(trifluoromethoxy)benzyl]amino}pyrimidin-4-yl)amino]methyl}cyclohexyl)azetidin-3-yl]benzamide

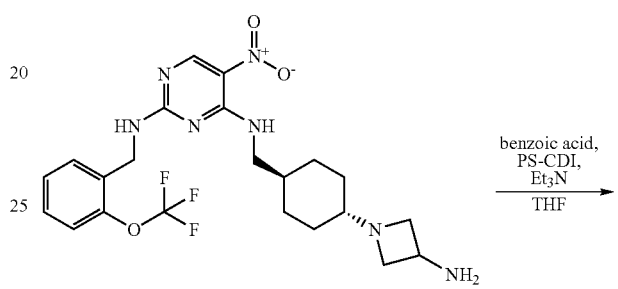

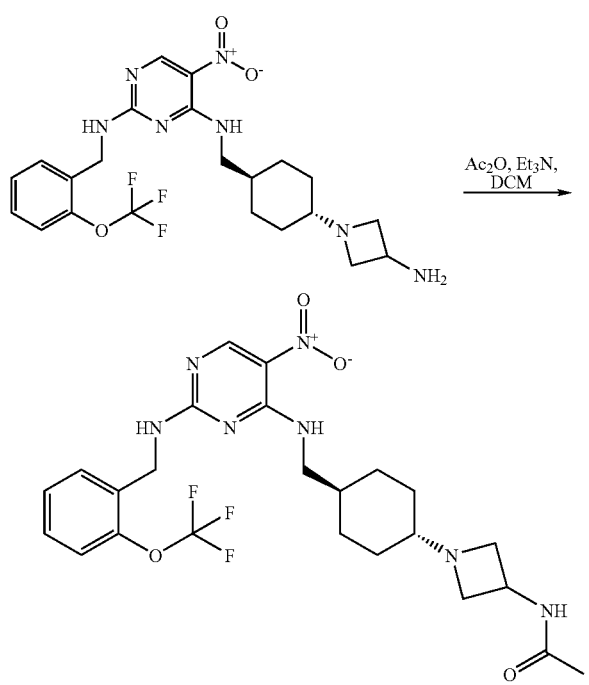

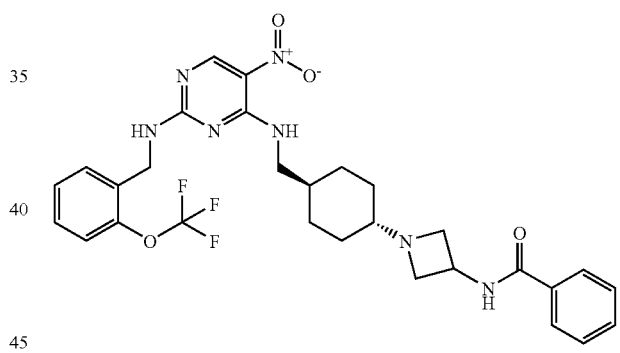

N$^4$-{[Trans-4-(3-aminoazetidin-1-yl)cyclohexyl]methyl}-5-nitro-N$^2$-[2-(trifluoromethoxy)benzyl]pyrimidine-2,4-diamine (20 mg, 0.04 mmol) was dissolved in CH$_2$Cl$_2$ (1.0 mL). To this solution was added acetic anhydride (0.057 mL, 0.06 mmol) followed by triethylamine (0.084 mL, 0.06 mmol). The reaction was allowed to stir at 25° C. for 18 h. The volatiles were removed and the crude was redissolved in N$^4$-{[Trans-4-(3-aminoazetidin-1-yl)cyclohexyl]methyl}-5-nitro-N$^2$-[2-(trifluoromethoxy)benzyl]pyrimidine-2,4-diamine (20 mg, 0.04 mmol) was dissolved in THF (1.0 mL). To this solution was added benzoic acid (7.3 mg, 0.06 mmol), Polystyrene-linked Carbodiimide (PS-CDI) (47 mg, 0.06 mmol) followed by triethylamine (0.084 mL, 0.06 mmol). The reaction was allowed to stir at 25° C. for 18 h. The reaction was filtered to remove the PS-CDI and the volatiles were removed in vacuo. The crude was redissolved in CH$_2$Cl$_2$ and extracted with 10% aqueous NaHCO$_3$. The aqueous phase was separated and extracted two more times with CH$_2$Cl$_2$. The organic layers were combined, dried (Na$_2$SO$_4$), decanted and concentrated. The resultant residue was purified via flash chromatography (SiO$_2$, 10-30% (2:18:80, NH$_4$OH:CH$_3$OH:CH$_2$Cl$_2$)—CH$_2$Cl$_2$) to afford 18 mg (74%) of the target compound, m/z 600.34 (M+1)$^+$.

Example 44

N⁴-[(trans-4-aminocyclohexyl)methyl]-5-nitro-N²-[(1-oxidopyridin-2-yl)methyl]pyrimidine-2,4-diamine

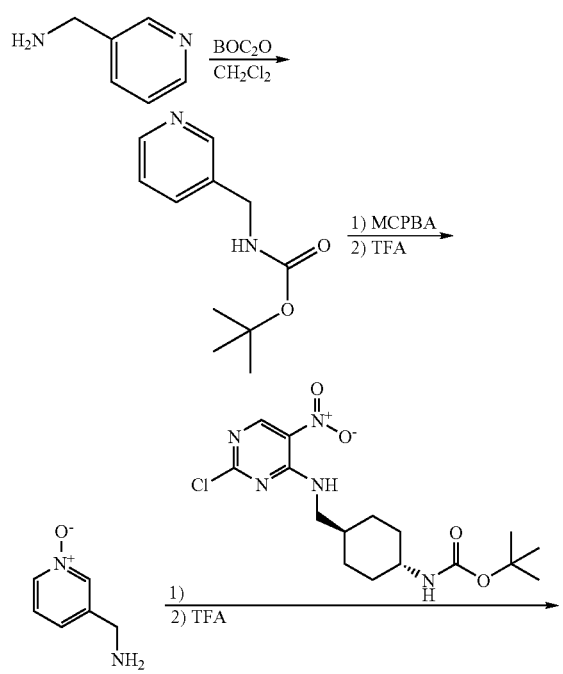

3-Aminomethylpyridine (2.5 g, 23 mmol), di-tert-butyl dicarbonate (7.72 g, 35.4 mmol) and diisopropylethyl amine (6.2 mL, 35.4 mmole) were combined in $CH_2Cl_2$ (50 mL). The reaction was allowed to stir for 18 h. The reaction was worked up by removal of the solvent in vacuo. The resultant residue was dissolved in EtOAc and poured into 10% aqueous $NaHCO_3$. The aqueous phase was separated and extracted two more times with EtOAc. The organic layers were combined, dried ($Na_2SO_4$), decanted and the concentrated. The crude was purified via flash chromatography ($SiO_2$, 2-5% MeOH—$CH_2Cl_2$) to afford 3.9 g (81%) of pyridin-3-ylmethyl-carbamic acid tert-butyl ester.

To pyridin-3-ylmethyl-carbamic acid tert-butyl ester (3.89 g, 18.7 mmol) dissolved in EtOH (50 mL), was added 3-chloroperoxybenzoic acid (4.7 g, 27.4 mmol). After 4 hours the volatiles were removed in vacuo and the crude was redissolved in $CH_2Cl_2$ (25 mL). To this solution was added TFA (25 mL) and the reaction was stirred at 25° C. for 2 h then the volatiles were removed in vacuo. The crude was redissolved in $CH_2Cl_2$ and evaporated. This procedure was done twice more. (1-Oxy-pyridin-3-yl)-methylamine was obtained with contamination of 3-chlorobenzoic acid, but carried further without any additional purification (2.74 g).

{trans-4-[(2-Chloro-5-nitro-pyrimidin-4-ylamino)-methyl]-cyclohexyl}-carbamic acid tert-butyl ester (105 mg, 0.27 mmol) was dissolved in DMA (5 mL). To this solution was added the (1-oxy-pyridin-3-yl)-methylamine (98 mg, 0.79 mmol), followed by DIEA (0.14 mL, 0.79 mmol). The reaction was allowed to stir at 25° C. for 18 h. The volatiles were removed in vacuo and the crude was purified via flash chromatography ($SiO_2$, 2-8% MeOH—$CH_2Cl_2$). [4-({5-Nitro-2-[(1-oxy-pyridin-3-ylmethyl)-amino]-pyrimidin-4-ylamino}-methyl)-cyclohexyl]-carbamic acid tert-butyl ester was obtained pure and was resuspended in $CH_2Cl_2$ (2.5 mL) To this suspension was added TFA (2.5 mL) and the reaction was stirred for 2 h. The volatiles were removed in vacuo and the crude was purified via flash chromatography ($SiO_2$, 25-100% (2:18:80-$NH_4OH$:MeOH:$CH_2Cl_2$)—$CH_2Cl_2$) to afford 107 mg (36%) of the target compound, m/z 374.41 $[M+1]^+$.

The following compound was prepared following a procedure similar to that described above:

N⁴-[(trans-4-aminocyclohexyl)methyl]-5-nitro-N²-[(1-oxidopyridin-2-yl)methyl]pyrimidine-2,4-diamine, m/z 374.59 $[M+1]^+$.

Example 45

N⁴-[(trans-4-aminocyclohexyl)methyl]-5-bromo-N²-[2-(trifluoromethoxy)benzyl]pyrimidine-2,4-diamine

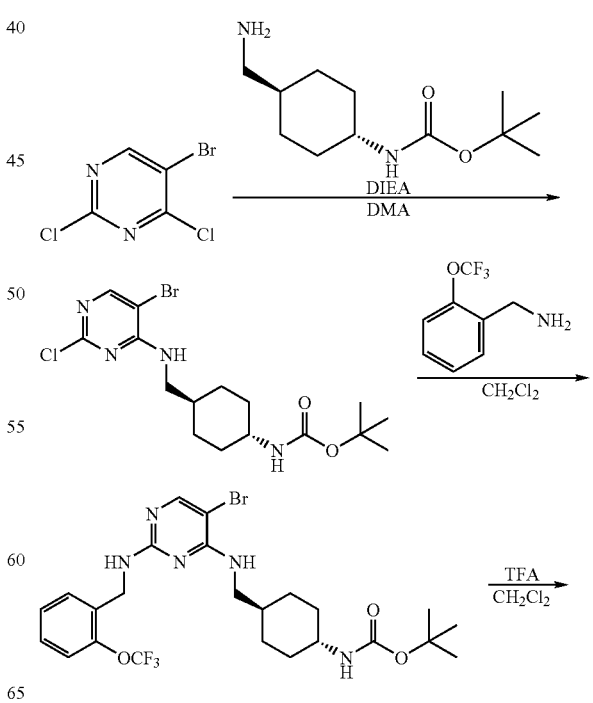

-continued

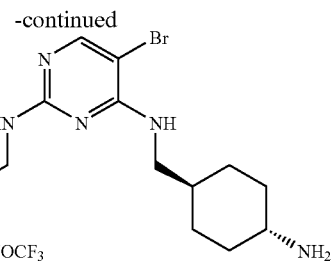

5-Bromo-2,4-dichloropyrimidine (1.1 g, 4.83 mmol) was dissolved in DMA (25 mL). To this solution was added tert-butyl-trans-4-aminomethylcyclohexylcarbamate hydrochloride (1.54 g, 5.80 mmol), followed by DIEA (1.98 mL, 11.4 mmol). The reaction was stirred at 25° C. for 18 h. The reaction was worked up by removal of the volatiles in vacuo. The crude was purified via flash chromatography (SiO$_2$, 10-25% EtOAc-Hexanes) to afford 1.32 g (65%) of {4-[(5-bromo-2-chloro-pyrimidin-4-ylamino)-methyl]-cyclohexyl}-carbamic acid tert-butyl ester.

{4-[(2-chloro-5-nitro-pyrimidin-4-ylamino)-methyl]-cyclohexyl}-carbamic acid tert-butyl ester (1.32 g, 3.14 mmol) was dissolved in 2-trifluoromethoxybenzyl amine (4.0 g, 20.9 mmol). The reaction was heated, in two separate iterations, to 140° C. for 10 min in a Smith Synthesizer Microwave Reactor. The reaction was diluted with CH$_2$Cl$_2$ and poured into 1 M aqueous HCl. The aqueous phase was separated and extracted two more times with CH$_2$Cl$_2$. The organic layers were combined, dried (Na$_2$SO$_4$), decanted and concentrated. The crude was diluted with minimal THF:MeOH:Hexane: EtOAc (25:1:49:25) and purified via flash chromatography (SiO$_2$, 15-25% EtOAc-Hexanes) to afford 103 g (57%) of (4-{[5-bromo-2-(2-trifluoromethoxy-benzylamino)-pyrimidin-4-ylamino]-methyl}-cyclohexyl)-carbamic acid tert-butyl ester.

(4-{[5-Bromo-2-(2-trifluoromethoxy-benzylamino)-pyrimidin-4-ylamino]-methyl}-cyclohexyl)-carbamic acid tert-butyl ester (75 mg, 0.13 mmol) was dissolved in CH$_2$Cl$_2$ (2 mL). To this solution was added TFA (2 mL) and the reaction was stirred at 25° C. for 1 h. The volatiles were removed in vacuo. The crude was redissolved in CH$_2$Cl$_2$ and poured into 10% aqueous NaHCO$_3$. The aqueous phase was separated and extracted two more times with CH$_2$Cl$_2$. The organic layers were combined, dried (Na$_2$SO$_4$), decanted and concentrated. The crude was purified via flash chromatography (SiO$_2$, 2-10% (NH$_4$OH:CH$_3$OH:CH$_2$Cl$_2$—CH$_2$Cl$_2$)) to afford 45 mg (73%) of the target compound, m/z 474.38 [M+1]$^+$.

Example 46

N$^4$-[(trans-4-aminocyclohexyl)methyl]-5-(phenylethynyl)-N$^2$-[2-(trifluoromethoxy)benzyl]pyrimidine-2,4-diamine

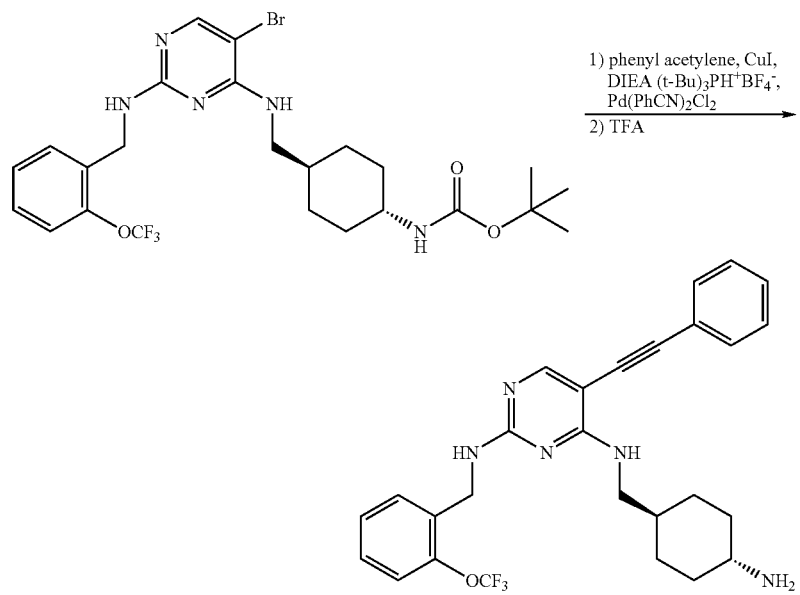

(trans-4-{[5-Bromo-2-(2-trifluoromethoxy-benzylamino)-pyrimidin-4-ylamino]-methyl}-cyclohexyl)-carbamic acid tert-butyl ester (100 mg, 0.174 mmol), CuI (0.97 mg, 0.005 mmol), and Pd(PhCN)$_2$Cl$_2$ (1.96 mg, 0.005 mmol) were dissolved in degassed dioxane (0.5 mmol). To this solution was added tri-(tert)-butylphosphine tetrafluoroborate (2.4 mg, 0.010 mmol) followed by diisopropylamine (0.029 mL, 0.2 mmol) and phenylacetylene (0.022 mL, 0.2 mmol). The reaction was stirred at 25° C. for 18 h. The reaction was worked up by the addition of EtOAc and filtered through a plug of SiO$_2$. The filtrate was concentrated and purified via flash chromatography (SiO$_2$, 25% EtOAc-Hexanes) to yield (4-{[5-phenylethynyl-2-(2-trifluoromethoxy-benzylamino)-pyrimidin-4-ylamino]-methyl}-cyclohexyl)-carbamic acid tert-butyl ester. (4-{[5-Phenylethynyl-2-(2-trifluoromethoxy-benzylamino)-pyrimidin-4-ylamino]-methyl}-cyclohexyl)-carbamic acid tert-butyl ester was dissolved in CH$_2$Cl$_2$ (0.5 mL) and TFA (0.5 mL) was added. The solution was stirred for 2 h and the volatiles were removed and the crude residue was purified via preparative thin layer chromatography (SiO$_2$, 2000 micron thickness, 1:9:90 NH$_4$OH: CH$_3$OH:CH$_2$Cl$_2$) to afford 49 mg (57%) of N$^4$-[(trans-4-aminocyclohexyl)methyl]-5-(phenylethynyl)-N$^2$-[2-(trifluoromethoxy)benzyl]pyrimidine-2,4-diamine, m/z 496.58 [M+1]$^+$.

The following compounds were prepared following a procedures similar to that described above:

N$^4$-[(trans-4-aminocyclohexyl)methyl]-5-pent-1-yn-1-yl-N$^2$-[2-(trifluoromethoxy)benzyl]pyrimidine-2,4-diamine, m/z 462.39 [M+1]$^+$.

N$^4$-[(trans-4-aminocyclohexyl)methyl]-N$^2$-[2-(trifluoromethoxy)benzyl]-5-{[3-(trifluoromethyl)phenyl]ethynyl}pyrimidine-2,4-diamine, m/z 564.59 [M+1]$^+$.

N$^4$-[(trans-4-aminocyclohexyl)methyl]-5-[(2-fluorophenyl)ethynyl]-N$^2$-[2-(trifluoromethoxy)benzyl]pyrimidine-2,4-diamine, m/z 513.91 [M+1]$^+$.

N$^4$-[(trans-4-aminocyclohexyl)methyl]-N$^2$-[2-(trifluoromethoxy)benzyl]-5-{[2-(trifluoromethyl)phenyl]ethynyl}pyrimidine-2,4-diamine, m/z 564.62 [M+1]$^+$.

N$^4$-[(trans-4-aminocyclohexyl)methyl]-5-[(3-methylphenyl)ethynyl]-N$^2$-[2-(trifluoromethoxy)benzyl]pyrimidine-2,4-diamine, m/z 510.04 [M+1]$^+$.

N$^4$-[(trans-4-aminocyclohexyl)methyl]-5-[(4-methylphenyl)ethynyl]-N$^2$-[2-(trifluoromethoxy)benzyl]pyrimidine-2,4-diamine, m/z 510.03 [M+1]$^+$.

Example 47

N$^4$-[(trans-4-aminocyclohexyl)methyl]-5-nitro-N$^2$-(3-piperidin-1-ylbenzyl)pyrimidine-2,4-diamine

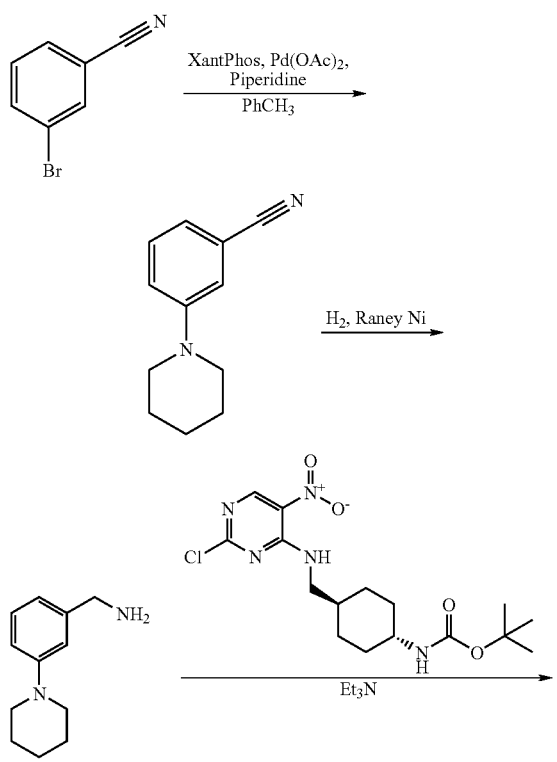

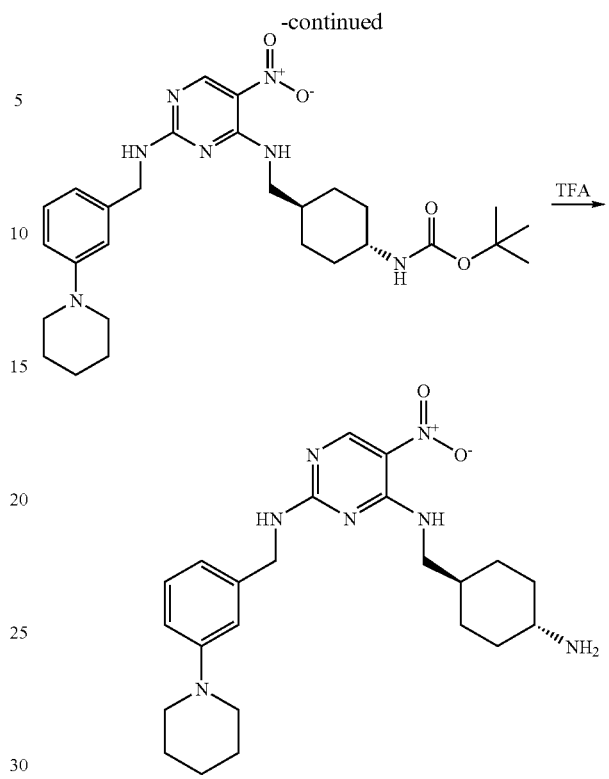

Palladium (II) acetate (12.3 mg, 0.055 mmol) and 4,5-bis(diphenylphosphino)-9,9-dimethylxanthene (47.7 mg, 0.082 mmol, Xantphos) were combined and the flask was evacuated and flushed three times with N$_2$. Degassed PhCH$_3$ (25 mL) was added and the solution was stirred for 5 min. 3-Bromobenzonitrile (1.0 g, 5.49 mmol) and piperidine (561 mg, 6.59 mmol) were added and the reaction was stirred for another 5 min. Cs$_2$CO$_3$ (2.15 g, 6.59 mmol) was added and the flasked was flushed with N$_2$ for 1 min then heated to 70° C. for 48 h. The volatiles were removed and the crude 3-piperidin-1-yl-benzonitrile (965 mg) was carried further without purification 3-Piperidin-1-yl-benzonitrile (965 mg, 5.18 mmol) was dissolved in MeOH (125 mL). To this solution was added about 1.5 mL of Raney Nickel suspension in H$_2$O. The flask was evacuated and backflushed with N$_2$. A balloon was filled with H$_2$ and the reaction flask was evacuated, filled with H$_2$, and maintained under atmospheric pressure. The reaction was stirred vigorously for 2 h, then filtered through a 2 cm thick pad of Celite under a stream of N$_2$. The volatiles were removed and the desired 3-piperidin-1-yl-benzylamine (993 mg) was carried further without purification.

{trans-4-[(2-Chloro-5-nitro-pyrimidin-4-ylamino)-methyl]-cyclohexyl}-carbamic acid tert-butyl ester (200 mg, 0.52 mmol) was dissolved in CH$_2$Cl$_2$ (10 mL) and Et$_3$N (0.289 mL, 2.07 mmol) was added. 3-Piperidin-1-yl-benzylamine (197 mg, 1.04 mmol) was dissolved in DMA:EtOH (2 mL, 1:1) and added to the reaction solution. The reaction was stirred at room temperature for 18 h. The volatiles were removed in vacuo and the crude was purified via flash chromatography (SiO$_2$, 25-50% EtOAc:Hexanes then 5% MeOH:CH$_2$Cl$_2$) to afford 176 mg (63%) of (4-{[5-nitro-2-(3-piperidin-1-yl-benzylamino)-pyrimidin-4-ylamino]-methyl}-cyclohexyl)-carbamic acid tert-butyl ester (4-{[5-Nitro-2-(3-piperidin-1-yl-benzylamino)-pyrimidin-4-ylamino]-methyl}-cyclohexyl)-carbamic acid tert-butyl ester (176 mg, 0.33 mmol) was dissolved in CH$_2$Cl$_2$ (6 mL). To this solution was added TFA (3 mL) and the reaction was stirred for 1 h. The volatiles were removed and the crude was re-dissolved in 90:9:1 (CH$_2$Cl$_2$:CH$_3$OH:NH$_4$OH), then concentrated again to afford a solid. The resultant solid was purified via flash chromatography (SiO$_2$, 10-75% CH$_2$Cl$_2$-(90:9:1-CH$_2$Cl$_2$:CH$_3$OH:NH$_4$OH)) to afford 131 mg (91%) of the target compound, m/z 440.72 [M+1]$^+$.

The following compounds were prepared following a procedure similar to that described above:

N$^4$-[(trans-4-aminocyclohexyl)methyl]-5-nitro-N$^2$-(3-pyrrolidin-1-ylbenzyl)pyrimidine-2,4-diamine, m/z 426.68 [M+1]$^+$.

N$^4$-[(trans-4-aminocyclohexyl)methyl]-N$^2$-(3-azepan-1-ylbenzyl)-5-nitropyrimidine-2,4-diamine, m/z 454.72 [M+1]$^+$.

Example 48

N-(4-{[2-(3-Bromo-2-methyl-benzylamino)-5-nitropyrimidin-4-ylamino]-methyl}-cyclohexyl)-2,2,2-trifluoro-acetamide

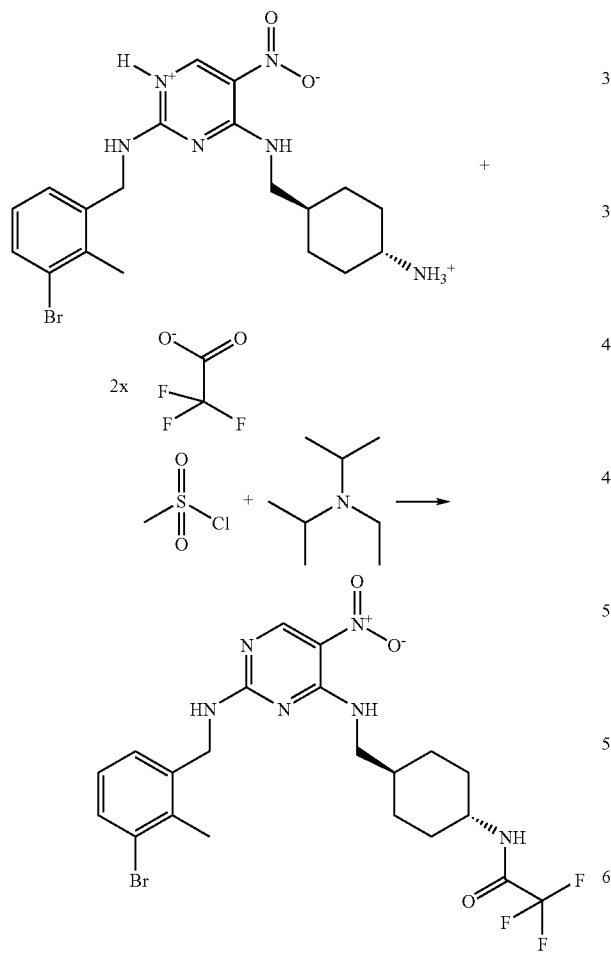

To a solution of the N$^4$-(4-Amino-cyclohexylmethyl)-N$^2$-(3-bromo-2-methyl-benzyl)-5-nitro-pyrimidine-2,4-diamine bis-trifluoroacetate salt (185 mg, 0.273 mmol) in dichloromethane (1.5 mL) was added the methanesulfonyl chloride (43 μL, 0.546 mmol) and diisopropylethylamine (143 μL, 0.819 mmol) and the solution was stirred for 1 hour. The reaction mixture was diluted with dichloromethane (2 mL) and saturated aqueous NaHCO$_3$ (2 mL) was added. The phases were separated and the aqueous phase was extracted with dichloromethane (3 mL). The organic phases were combined, dried over Na$_2$SO$_4$, and concentrated to afford 87.2 mg (59%) of the target compound, m/z 546.4 [M+1]$^+$ Example 49

3-{[(4-{[(trans-4-aminocyclohexyl)methyl]amino}-5-nitropyrimidin-2-yl)amino]methyl}pyridin-2(1H)-one

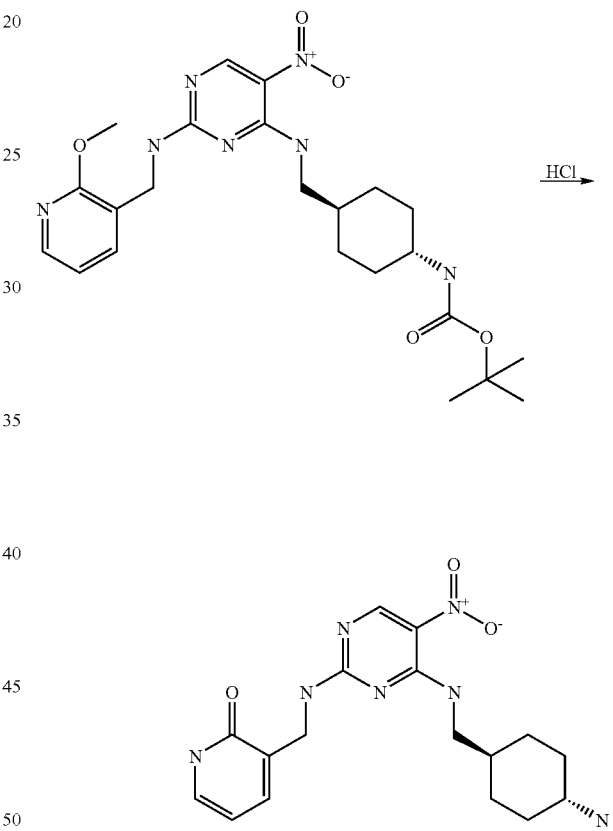

[trans-4-({2-[(2-Methoxy-pyridin-3-ylmethyl)-amino]-5-nitro-pyrimidin-4-ylamino}-methyl)-cyclohexyl]-carbamic acid tert-butyl ester (100 mg, 0.205 mmol) was dissolved in dioxane (2 mL) and treated with HCl in dioxane (0.85 mL, 4 mmol/mL, 3.40 mmol). After stirring overnight, an oil was seen at the bottom of the solution. The solvent was taken out and the residue dried to give an oily solid. The crude solid was purified with prep TLC (1:9:90 NH3:MeOH:DCM) to give the title product (20.5 mg, 0.055 mmol, 26.8%) as a yellow solid, m/z 374.5 (M+1)$^+$

Example 50

N-methyl-N-[1-(trans-4-{[(5-nitro-2-{[2-(trifluoromethoxy)benzyl]amino}pyrimidin-4-yl)amino]methyl}cyclohexyl)pyrrolidin-3-yl]acetamide

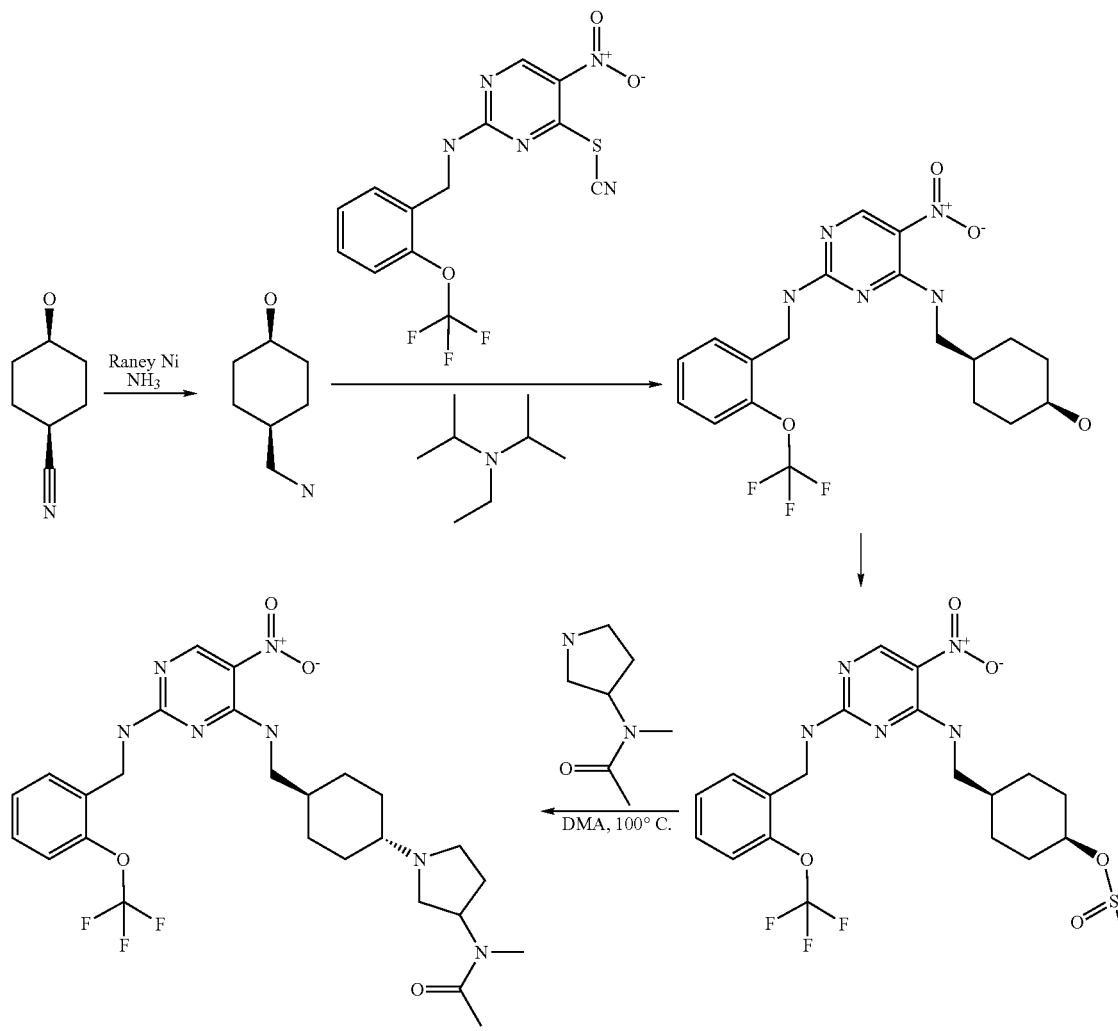

cis-4-Hydroxy-cyclohexanecarbonitrile was made according to literature procedures (Noyce, D. S. et al.; *J. Org. Chem.* 1969; 34, 1247).

To a 2 N solution of $NH_3$ in MeOH (40 mL) in a high pressure autoclave was added cis-4-hydroxy-cyclohexanecarbonitrile (6.6 g, 52.7 mmol) and Raney Ni (1.0 g, 17 mmol, 0.3 equiv.) The mixture was placed under 45 psi H2 and shaken overnight. The pressure was released and the reaction filtered through a pad of Celite. The filter pad was washed with EtOAc and the mixture was concentrated under reduced pressure to provide a yellow oil as cis-4-aminomethyl-cyclohexanol (6.3 5g, 49.1 mmol, 93.2%).

(5-Nitro-4-thiocyanato-pyrimidin-2-yl)-(2-trifluoromethoxy-benzyl)-amine (10 g, 26.9 mmol) was dissolved in DCM (100 ml). cis-4-aminomethyl-cyclohexanol (3.48 g, 26.9 mmol) and diisopropylethylamine (10 mL, 53.8 mmol) were added to the solution and stirred overnight. The reaction mixture was evaporated in-vacuo and purified by column chromatography (1% MeOH/99% CH2Cl2). The resulting solid was washed with cold methanol to give a pale yellow solid as cis-4-{[5-nitro-2-(2-trifluoromethoxy-benzylamino)-pyrimidin-4-ylamino]-methyl}-cyclohexanol (11.3 g, 25.6 mmol, 95.1%).

cis-4-{[5-Nitro-2-(2-trifluoromethoxy-benzylamino)-pyrimidin-4-ylamino]-methyl}-cyclohexanol (3.6 g, 8.16 mmol) was dissolved in dry DCM (150 mL) and cooled to 5° C. Methanesulfonyl chloride (0.94 ml, 12.2 mmol) and diisopropylethylamine (4.26 ml, 24.4 mmol) were added sequentially. After 2 h, the reaction was quenched with cold water (10 mL) and warmed to room temperature. The solution was partitioned between DCM (100 mL) and water (50 mL). The layers were separated and the aqueous layer was extracted with DCM (2×100 mL). The combined organic layers were washed with brine, dried over MgSO4, filtered and concentrated in vacuo to yield a yellow solid. The residue was then chromatographed (silica, 100:1 DCM/MeOH) and washed with cold methanol to yield a pale yellow solid as methanesulfonic acid cis-4-{[5-nitro-2-(2-trifluoromethoxy-benzylamino)-pyrimidin-4-ylamino]-methyl}-cyclohexyl ester (3.90 g, 7.50 mmol, 92%).

Methanesulfonic acid 4-{[5-nitro-2-(2-trifluoromethoxybenzylamino)-pyrimidin-4-ylamino]-methyl}-cyclohexyl ester (100 mg, 0.19 mmol) and N-Methyl-N-pyrrolidin-3-yl-acetamide (137 mg, 0.96 mmol) were combined with DMA (0.4 mL) and heated at 100 degrees overnight. The reaction mixture was then dissolved in methanol and purified by preparatory HPLC. The pure HPLC fractions were lyophilized to give the title compound (30 mg, 28%), m/z 566.6 [M+1]$^+$.

The following compounds were prepared following a procedure similar to that described above:

$N^4$-{[trans-4-(1,1-dioxidothiomorpholin-4-yl)cyclohexyl]methyl}-5-nitro-$N^2$-[2-(trifluoromethoxy)benzyl]pyrimidine-2,4-diamine, (BI00612608) m/z 559.2 [M+1]$^+$.

$N^4$-{[trans-4-(3,3-difluoropyrrolidin-1-yl)cyclohexyl]methyl}-5-nitro-$N^2$-[2-(trifluoromethoxy)benzyl]pyrimidine-2,4-diamine, m/z 531.1 [M+1]$^+$ 4-(trans-4-{[(5-nitro-2-{[2-(trifluoromethoxy)benzyl]amino}pyrimidin-4-yl)amino]methyl}cyclohexyl)piperazin-2-one, m/z 524.1 [M+1]$^+$ $N^4$-({trans-4-[4-(methylsulfonyl)piperazin-1-yl]cyclohexyl}methyl)-5-nitro-$N^2$-[2-(trifluoromethoxy)benzyl]pyrimidine-2,4-diamine, m/z 588.1 [M+1]$^+$ $N^4$-{[trans-4-(4-acetylpiperazin-1-yl)cyclohexyl]methyl}-5-nitro-$N^2$-[2-(trifluoromethoxy)benzyl]pyrimidine-2,4-diamine, m/z 552.1 [M+1]$^+$ $N^4$-({trans-4-[3-(methylsulfonyl)pyrrolidin-1-yl]cyclohexyl}methyl)-5-nitro-$N^2$-[2-(trifluoromethoxy)benzyl]pyrimidine-2,4-diamine, m/z 573.1 [M+1]$^+$ 1-(trans-4-{[(5-nitro-2-{[2-(trifluoromethoxy)benzyl]amino}pyrimidin-4-yl)amino]methyl}cyclohexyl)-1,4-diazepan-5-one, m/z 538.1 [M+1]$^+$ N-[(3S)-1-(trans-4-{[(5-nitro-2-{[2-(trifluoromethoxy)benzyl]amino}pyrimidin-4-yl)amino]methyl}cyclohexyl)pyrrolidin-3-yl]acetamide, m/z 552.2 [M+1]$^+$ N-[(3R)-1-(trans-4-{[(5-nitro-2-{[2-(trifluoromethoxy)benzyl]amino}pyrimidin-4-yl)amino]methyl}cyclohexyl)pyrrolidin-3-yl]acetamide, m/z 552.2 [M+1]$^+$ $N^4$-({trans-4-[(3R)-3-(dimethylamino)pyrrolidin-1-yl]cyclohexyl}methyl)-5-nitro-$N^2$-[2-(trifluoromethoxy)benzyl]pyrimidine-2,4-diamine, m/z 538.2 [M+1]$^+$ 1-(trans-4-{[(5-nitro-2-{[2-(trifluoromethoxy)benzyl]amino}pyrimidin-4-yl)amino]methyl}cyclohexyl)-L-prolinamide, m/z 538.2 [M+1]$^+$ 1-(trans-4-{[(5-nitro-2-{[2-(trifluoromethoxy)benzyl]amino}pyrimidin-4-yl)amino]methyl}cyclohexyl)-D-prolinamide, m/z 538.1 [M+1]$^+$ 1-(trans-4-{[(5-nitro-2-{[2-(trifluoromethoxy)benzyl]amino}pyrimidin-4-yl)amino]methyl}cyclohexyl)piperidine-3-carboxamide, m/z 552.2 [M+1]$^+$ 1-(trans-4-{[(5-nitro-2-{[2-(trifluoromethoxy)benzyl]amino}pyrimidin-4-yl)amino]methyl}cyclohexyl)piperidin-3-ol, m/z 525.1 [M+1]$^+$ 1-(trans-4-{[(5-nitro-2-{[2-(trifluoromethoxy)benzyl]amino}pyrimidin-4-yl)amino]methyl}cyclohexyl)piperidin-4-ol, m/z 525.2 [M+1]$^+$ 5-nitro-$N^4$-[(trans-4-piperazin-1-ylcyclohexyl)methyl]-$N^2$-[2-(trifluoromethoxy)benzyl]pyrimidine-2,4-diamine m/z 510.6 [M+1]$^+$ $N^4$-{[trans-4-(4-methylpiperazin-1-yl)cyclohexyl]methyl}-5-nitro-$N^2$-[2-(trifluoromethoxy)benzyl]pyrimidine-2,4-diamine, m/z 524.6 [M+1]$^+$ ethyl 4-(trans-4-{[(5-nitro-2-{[2-(trifluoromethoxy)benzyl]amino}pyrimidin-4-yl)amino]methyl}cyclohexyl)piperazine-1-carboxylate, m/z 582.6 [M+1]$^+$ 2-[methyl(trans-4-{[(5-nitro-2-{[2-(trifluoromethoxy)benzyl]amino}pyrimidin-4-yl)amino]methyl}cyclohexyl)amino]ethanol, m/z 499.6 [M+1]$^+$ N-{2-[(trans-4-{[(5-nitro-2-{[2-(trifluoromethoxy)benzyl]amino}pyrimidin-4-yl)amino]methyl}cyclohexyl)amino]ethyl}acetamide, m/z 526.6 [M+1]$^+$ $N^4$-{[trans-4-(1,4-diazepan-1-yl)cyclohexyl]methyl}-5-nitro-$N^2$-[2-(trifluoromethoxy)benzyl]pyrimidine-2,4-diamine, m/z 524.7 [M+1]$^+$ $N^4$-{[trans-4-(4-methyl-1,4-diazepan-1-yl)cyclohexyl]methyl}-5-nitro-$N^2$-[2-(trifluoromethoxy)benzyl]pyrimidine-2,4-diamine, m/z 538.6 [M+1]$^+$ $N^4$-{[trans-4-(4-acetyl-1,4-diazepan-1-yl)cyclohexyl]methyl}-5-nitro-$N^2$-[2-(trifluoromethoxy)benzyl]pyrimidine-2,4-diamine, m/z 566.6 [M+1]$^+$ $N^4$-{[trans-4-(3-fluoropyrrolidin-1-yl)cyclohexyl]methyl}-5-nitro-$N^2$-[2-(trifluoromethoxy)benzyl]pyrimidine-2,4-diamine, m/z 513.1 [M+1]$^+$ N,N-dimethyl-4-(trans-4-{[(5-nitro-2-{[2-(trifluoromethoxy)benzyl]amino}pyrimidin-4-yl)amino]methyl}cyclohexyl)piperazine-1-carboxamide, m/z 581.2 [M+1]$^+$ (2R)-1-[(trans-4-{[(5-nitro-2-{[2-(trifluoromethoxy)benzyl]amino}pyrimidin-4-yl)amino]methyl}cyclohexyl)amino]propan-2-ol, m/z 499.6 [M+1]$^+$ (2S)-1-[(trans-4-{[(5-nitro-2-{[2-(trifluoromethoxy)benzyl]amino}pyrimidin-4-yl)amino]methyl}cyclohexyl)amino]propan-2-ol, m/z 499.6 [M+1]$^+$ 3-[(trans-4-{[(5-nitro-2-{[2-(trifluoromethoxy)benzyl]amino}pyrimidin-4-yl)amino]methyl}cyclohexyl)amino]propan-1-ol, m/z 499.2 [M+1]$^+$ $N^4$-({trans-4-[(3-aminopropyl)amino]cyclohexyl}methyl)-5-nitro-$N^2$-[2-(trifluoromethoxy)benzyl]pyrimidine-2,4-diamine, m/z 498.1 [M+1]$^+$ (2R)-2-[(trans-4-{[(5-nitro-2-{[2-(trifluoromethoxy)benzyl]amino}pyrimidin-4-yl)amino]methyl}cyclohexyl)amino]propan-1-ol, m/z 499.1 [M+1]$^+$ (2S)-2-[(trans-4-{[(5-nitro-2-{[2-(trifluoromethoxy)benzyl]amino}pyrimidin-4-yl)amino]methyl}cyclohexyl)amino]propan-1-ol, m/z 499.1 [M+1]$^+$ (2R)-2-[(trans-4-{[(5-nitro-2-{[2-(trifluoromethoxy)benzyl]amino}pyrimidin-4-yl)amino]methyl}cyclohexyl)amino]-3-phenylpropan-1-ol, m/z 575.6[M+1]$^+$ (2S)-2-[(trans-4-{[(5-nitro-2-{[2-(trifluoromethoxy)benzyl]amino}pyrimidin-4-yl)amino]methyl}cyclohexyl)amino]-3-phenylpropan-1-ol, m/z 575.6 [M+1]$^+$ Nα-(trans-4-{[(5-nitro-2-{[2-(trifluoromethoxy)benzyl]amino}pyrimidin-4-yl)amino]methyl}cyclohexyl)-L-phenylalaninamide, m/z 588.6 [M+1]$^+$ Nα-(trans-4-{[(5-nitro-2-{[2-(trifluoromethoxy)benzyl]amino}pyrimidin-4-yl)amino]methyl}cyclohexyl)-D-phenylalaninamide, m/z 588.6 [M+1]$^+$ N,N-dimethyl-1-(trans-4-{[(5-nitro-2-{[2-(trifluoromethoxy)benzyl]amino}pyrimidin-4-yl)amino]methyl}cyclohexyl)-L-prolinamide, m/z 566.1 [M+1]$^+$

Example 51

N⁴-{[trans-4-(1H-imidazol-1-yl)cyclohexyl]methyl}-5-nitro-N²-[2-(trifluoromethoxy)benzyl]pyrimidine-2,4-diamine

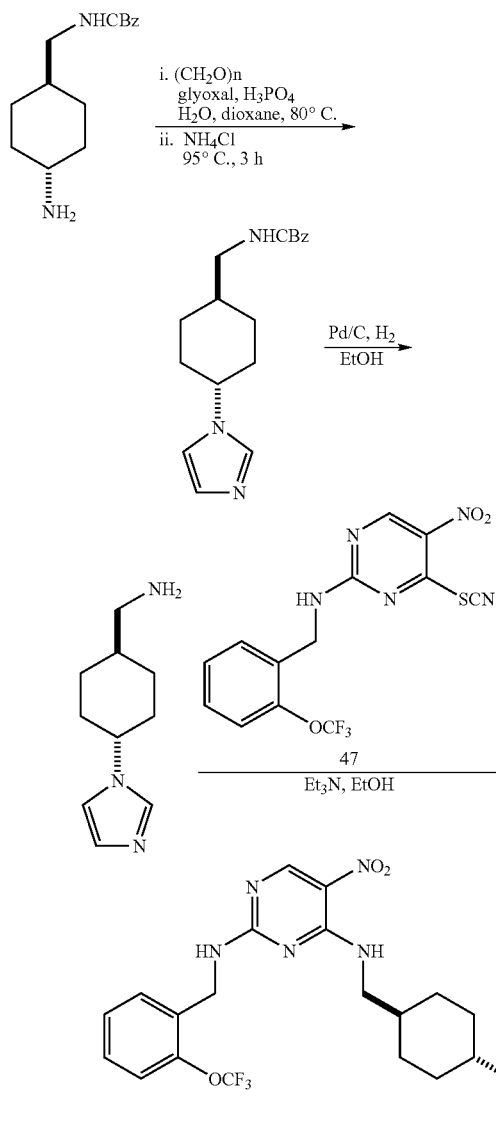

A stirred mixture of (4-amino-cyclohexylmethyl)-carbamic acid benzyl ester (285 mg, 1.09 mmol) in dioxane (1 mL) and water (2.5 mL) was acidified (pH 1-2) with a few drops of phosphoric acid. Paraformaldehyde (34 mg) and 40% aqueous glyoxal solution (150 μL, 1.09 mmol) were added before heating at 80° C. for 20 min. NH₄Cl (58 mg, 1.09 mmol) was then added and the mixture heated at 100° C. for a further 3 h. After cooling to room temperature 2 N NaOH was added until the reaction mixture attained pH 12. The aqueous phase was extracted with EtOAc (2×20 mL) and the combined extracts dried over Na₂SO₄ before concentrating in vacuo. The residue was purified by column chromatography using a 12 g ISCO combi-flash cartridge (silica gel, 95:4.75:0.25 DCM/MeOH/NH₄OH to obtain (4-imidazol-1-yl-cyclo-hexylmethyl)-carbamic acid benzyl ester (60 mg, 17%) as a colorless oil that solidified on standin.

To a solution of (4-imidazol-1-yl-cyclohexylmethyl)-carbamic acid benzyl ester (57 mg, 0.18 mmol) in EtOH (4 mL) under N₂ was added 10% Pd/C (200 mg). The reaction flask was flushed with H₂ via balloon and stirred at room temperature for 4 h whereupon TLC analysis (95:4.75:0.25 DCM/MeOH/NH₄OH) showed complete consumption of starting material. The reaction mixture was filtered through a plug of celite and the filtrate concentrated in vacuo to afford crude (4-imidazol-1-yl-cyclohexyl)-methylamine (32 mg, 95%). This material was used directly in the next reaction.

To a solution of (4-imidazol-1-yl-cyclohexyl)-methylamine (32 mg, 0.18 mmol) and Et₃N (76 μL, 0.54 mmol) in EtOH (1 mL) was added (5-Nitro-4-thiocyanato-pyrimidin-2-yl)-(2-trifluoromethoxy-benzyl)-amine (71 mg, 0.19 mmol). The mixture was stirred at room temperature for 14 h before concentrating in vacuo. The residue was partially purified by column chromatography using a 12 g ISCO combi-flash cartridge (silica gel, 95:4.75:0.25 DCM/MeOH/NH₄OH) then re-purified by semi-preparative HPLC. The isolated TFA salt was converted to the free base by partitioning between sat. NaHCO₃ and EtOAc. Concentration of the organic layer in vacuo afforded 29 mg of the title compound as an off-white solid, m/z 492 [M+1]⁺

Example 52

N²-[3-(aminomethyl)benzyl]-5-nitro-N⁴-[(trans-4-pyrrolidin-1-ylcyclohexyl)methyl]pyrimidine-2,4-diamine

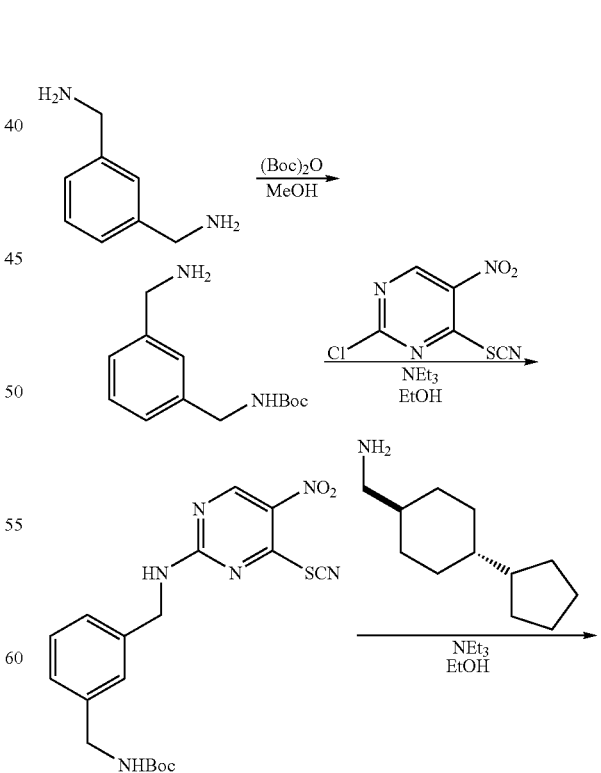

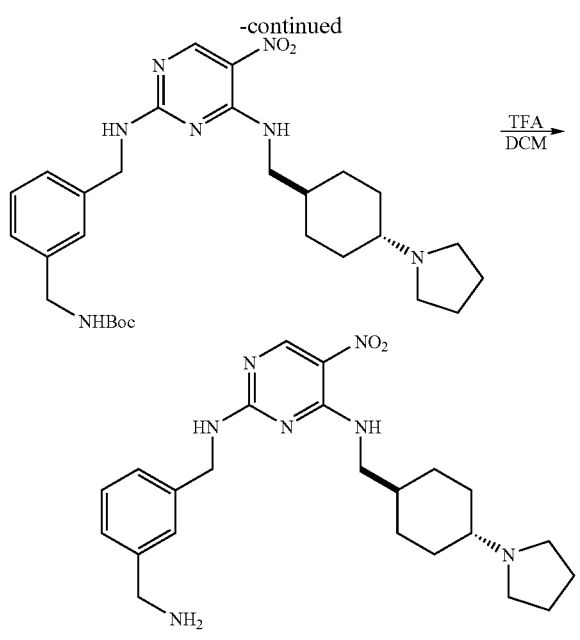

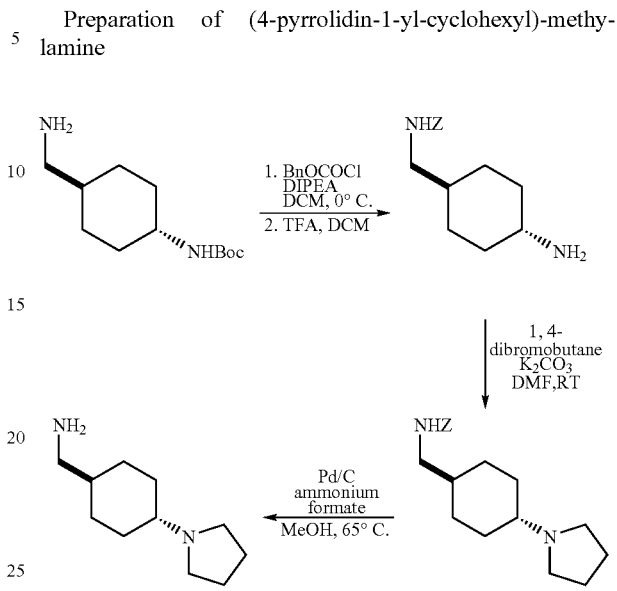

tography (silica gel, 96:4 to 93:7 DCM/10% NH$_4$OH in MeOH) to afford the title compound (25 mg), m/z 440 (M+1)$^+$.

Preparation of (4-pyrrolidin-1-yl-cyclohexyl)-methylamine

To a solution of m-xylylenediamine (5.00 g, 36.70 mmol) in MeOH (65 mL) was added a solution of Boc$_2$O (2.00 g, 9.16 mmol) in MeOH (35 mL) dropwise over 45 min. The reaction mixture was allowed to stir at room temperature overnight before concentrating in vacuo. The residue was purified by column chromatography (silica gel, DCM to 80:19:1 DCM/MeOH/NH$_4$OH) to afford (3-aminomethyl-benzyl)-carbamic acid tert-butyl ester (1.43 g, 67%).

To a solution of 2-chloro-5-nitro-4-thiocyanato-pyrimidine (1.31 g, 6.05 mmol) in EtOH (10 mL) at 0° C. was added a solution of (3-aminomethyl-benzyl)-carbamic acid tert-butyl ester (1.43 g, 6.05 mmol) dropwise over 45 min. The reaction was allowed to stir at room temperature overnight and the resulting precipitate filtered and washed with EtOH. The crude material was purified by column chromatography (silica gel, 10:90 to 12:88 EtOAc/hexane) to afford {3-[(5-nitro-4-thiocyanato-pyrimidin-2-ylamino)-methyl]-benzyl}-carbamic acid tert-butyl ester (1.43 g, 56%) as a yellow solid.

To a solution of (4-pyrrolidin-1-yl-cyclohexyl)-methylamine(32 mg, 0.18 mmol) and Et$_3$N (26 µL, 0.18 mmol) in EtOH (2 mL) was added {3-[(5-nitro-4-thiocyanato-pyrimidin-2-ylamino)-methyl]-benzyl}-carbamic acid tert-butyl ester (74 mg, 0.18 mmol). The reaction mixture was stirred at room temperature overnight before concentrating in vacuo. The residue was purified by chromatography using an ISCO combi-flash cartridge (silica gel, 50:50 to 0:100 DCM/80:18:2 DCM/MeOH/NH$_4$OH) to afford impure [3-({5-nitro-4-[(4-pyrrolidin-1-yl-cyclohexylmethyl)-amino]-pyrimidin-2-ylamino}-methyl)-benzyl]-carbamic acid tert-butyl ester (132 mg), m/z 540 (M+1)$^+$ To a solution of [3-({5-nitro-4-[(4-pyrrolidin-1-yl-cyclohexylmethyl)-amino]-pyrimidin-2-ylamino}-methyl)-benzyl]-carbamic acid tert-butyl ester (132 mg, 0.25 mmol) in DCM (1 mL) was added TFA (2 mL). After 20 min the reaction mixture was concentrated in vacuo and the resulting oil taken up in EtOAc and the solution washed with sat. NaHCO$_3$. The aqueous layer was then extracted with 90:10 CHCl$_3$/i-PrOH. The combined organic layers were concentrated in vacuo and the residue purified by column chroma- To a stirred slurry of (4-aminomethyl-cyclohexyl)-carbamic acid tert-butyl ester (500 mg, 2.19 mmol) and N,N-diisopropylethylamine (382 µL, 2.63 mmol) in DCM (8 mL) at 0° C. under N$_2$ was added benzylchloroformate (311 µL, 2.41 mmol) dropwise via syringe. After 30 min the reaction was allowed to warm to room temperature and stirred for a further 2 h before diluting with DCM (50 mL). The solution was washed successively with 1 N HCl, sat. NaHCO$_3$ and brine before drying over Na$_2$SO$_4$. Residual chloroformate was removed by chromatography using a 12 g ISCO combi-flash cartridge (silica gel, 90:10 to 50:50 hexane/EtOAc) to afford the di-protected intermediate which was treated directly with DCM (2 mL) and TFA (2 mL). After 1 h the volatiles were removed in vacuo and the residue partitioned between sat. NaHCO$_3$ and EtOAc. Concentration of the organic layer in vacuo afforded (4-amino-cyclohexylmethyl)-carbamic acid benzyl ester (517 mg, 90%) as a white solid.

To a solution of (4-amino-cyclohexylmethyl)-carbamic acid benzyl ester (350 mg, 1.34 mmol) in DMF (5 mL) was added K$_2$CO$_3$ (924 mg, 6.70 mmol) and 1,4-dibromobutane (160 mL, 1.34 mmol). The reaction mixture was stirred at room temperature for 14 h before diluting with EtOAc (100 mL). The reaction solution was washed with water (2×100 mL) and brine before concentrating in vacuo. The residue was purified by chromatography using a 12 g ISCO combi-flash cartridge (silica gel, 95:4.75:0.25 DCM/MeOH/NH$_4$OH) to afford (4-pyrrolidin-1-yl-cyclohexylmethyl)-carbamic acid benzyl ester (351 mg, 83%) as an off-white solid.

To a solution of (4-pyrrolidin-1-yl-cyclohexylmethyl)-carbamic acid benzyl ester (292 mg, 0.92 mmol) in MeOH (5 mL) was added ammonium formate (0.58 g, 9.20 mmol). The reaction flask was flushed with N$_2$ prior to addition of 10% Pd/C (300 mg). The mixture was heated at 65° C. for 2 h whereupon TLC analysis (silica gel, 95:4.75:0.25 DCM/MeOH/NH$_4$OH) showed complete consumption of 57. After cooling to room temperature the reaction mixture was filtered through a plug of celite in order to remove the Pd catalyst. The filtrate contained (4-pyrrolidin-1-yl-cyclohexyl)-methylamine which was used without further purification in the next step.

Example 53

3-{[(trans-4-{[(5-nitro-2-{[2-(trifluoromethoxy)benzyl]amino}pyrimidin-4-yl)amino]methyl}cyclohexyl)amino]methyl}benzoic acid

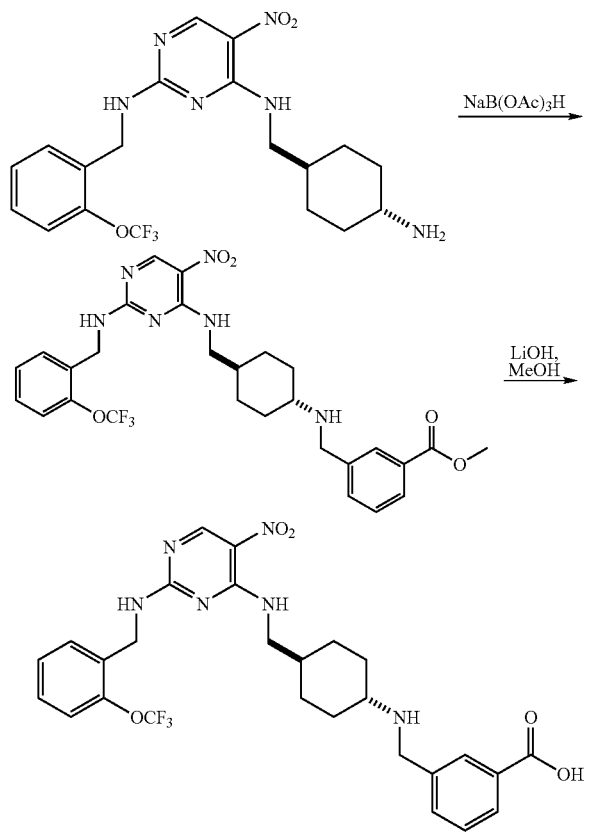

To a mixture of $N^4$-(4-amino-cyclohexylmethyl)-5-nitro-$N^2$-(2-trifluoromethoxy-benzyl)-pyrimidine-2,4-diamine (100 mg, 0.23 mmol) and 3-formyl-benzoic acid methyl ester (41 mg, 0.25 mmol) in DCM (1 mL) was added sodium triacetoxyborohydride (58 mg, 0.27 mmol). The mixture was stirred at room temperature for 18 h then quenched with excess water. The mixture was diluted with DCM and the organic layer separated and dried over $Na_2SO_4$. The solvent was removed in vacuo and the residue purified by column chromatography using an ISCO combi-flash cartridge (silica gel, DCM/MeOH) to afford 3-[(4-{[5-nitro-2-(2-trifluoromethoxy-benzylamino)-pyrimidin-4-ylamino]-methyl}-cyclohexylamino)-methyl]-benzoic acid methyl ester (76 mg, 57%), m/z 589 $(M+1)^+$.

A mixture of 3-[(4-{[5-nitro-2-(2-trifluoromethoxy-benzylamino)-pyrimidin-4-ylamino]-methyl}-cyclohexylamino)-methyl]-benzoic acid methyl ester (75 mg, 0.13 mmol), LiOH (30 mg, 1.29 mmol) and water (3 drops) in MeOH (2 mL) was heated at 50° C. for 18 h. The reaction mixture was concentrated in vacuo then taken up in water and EtOAc. Dilute HCl was added until the aqueous phase reached pH 6. The solid that precipitated was isolated by filtration to afford the target compound (20 mg, 30%) as a white solid, m/z 575 $(M+1)^+$.

The following compound was prepared following a procedure similar to that described above:

4-{[(trans-4-{[(5-nitro-2-{[2-(trifluoromethoxy)benzyl]amino}pyrimidin-4-yl)amino]methyl}cyclohexyl)amino]methyl}benzoic acid, m/z 575 $(M+1)^+$.

Example 54

N-(trans-4-{[(5-nitro-2-{[2-(trifluoromethoxy)benzyl]amino}pyrimidin-4-yl)amino]methyl}cyclohexyl)glycine

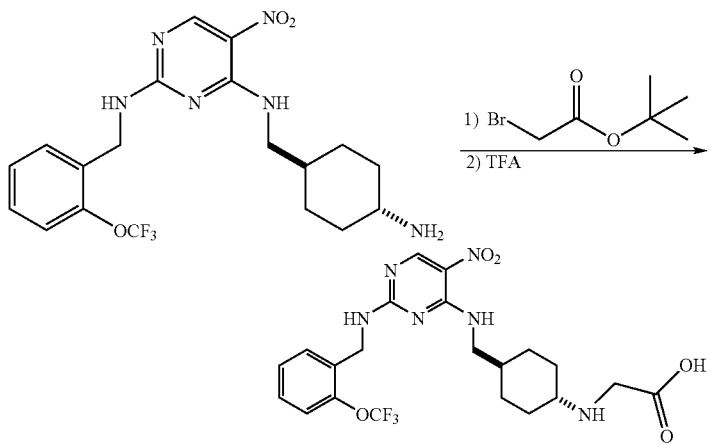

To a solution of N⁴-(4-amino-cyclohexylmethyl)-5-nitro-N²-(2-trifluoromethoxy-benzyl)-pyrimidine-2,4-diamine (88 mg, 0.20 mmol) in 2:1 DMF/DMSO (0.6 mL) was added N,N-diisopropylethylamine (35 µL, 0.30 mmol) followed by tert-butyl bromoacetate (22 µL, 0.15 mmol). The mixture was stirred at room temperature overnight then partitioned with EtOAc (15 mL) and water (5 mL). The layers were separated and the organics washed with water (2×5 mL) and brine. After concentration in vacuo, the residue was purified by column chromatography (silica gel, 97:3 DCM/MeOH) to afford (4-{[5-nitro-2-(2-trifluoromethoxy-benzylamino)-pyrimidin-4-ylamino]-methyl}-cyclohexylamino)-acetic acid tert-butyl ester (51 mg, 61%) as a colorless oil, m/z 555 [M+1]⁺.

To a solution of (4-{[5-nitro-2-(2-trifluoromethoxy-benzylamino)-pyrimidin-4-ylamino]-methyl}-cyclohexylamino)-acetic acid tert-butyl ester (60 mg, 0.108 mmol) in DCM (1 mL) was added TFA (1 mL). The solution was allowed to stand at room temperature for 16 h before the solvent was removed in vacuo. The residue was taken up in water (1 mL) and 2 N NaOH added until the mixture reached pH 5. The mixture was diluted with water (3 mL) and filtered. The filtered solid was washed with water and Et₂O before drying in vacuo to afford the target compound (46 mg, 85%) as a white solid, m/z 499 [M+1]⁺.

The following compound was prepared following similar procedures as described above:

N-(trans-4-{[(5-nitro-2-{[2-(trifluoromethoxy)benzyl]amino}pyrimidin-4-yl)amino]methyl}-cyclohexyl)-beta-alanine, m/z 513 (M+1)⁺.

Example 55

4-[(trans-4-{[(5-nitro-2-{[2-(trifluoromethoxy)benzyl]amino}pyrimidin-4-yl)amino]methyl}cyclohexyl)amino]butanoic acid

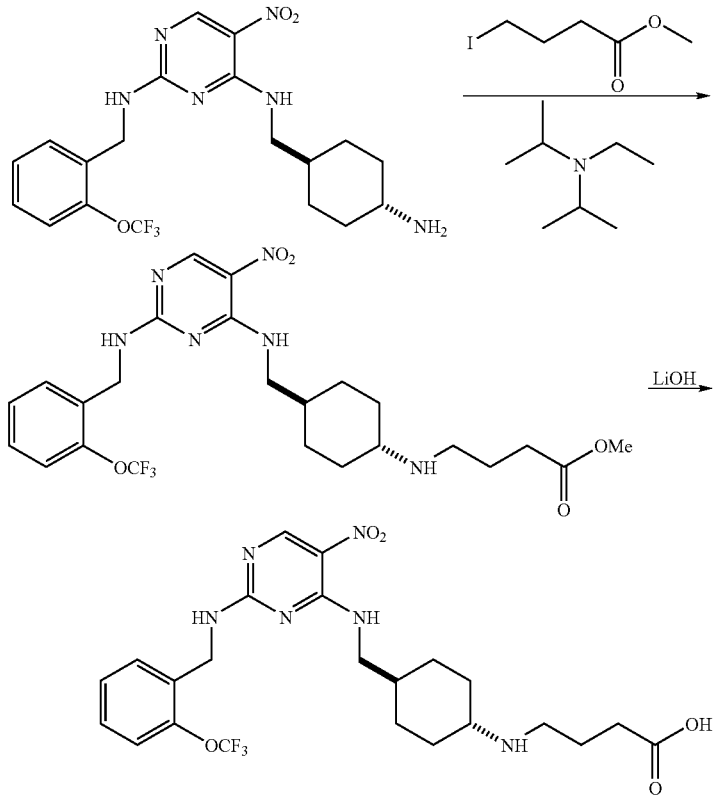

To a solution of N⁴-(4-amino-cyclohexylmethyl)-5-nitro-N²-(2-trifluoromethoxy-benzyl)-pyrimidine-2,4-diamine (80 mg, 0.182 mmol) in 2:1 DMF/DMSO (0.6 mL) was added N,N-diisopropylethylamine (32 µL, 0.272 mmol) followed by methyl-4-iodobutyrate (19 µL, 0.136 mmol). The mixture was stirred at room temperature overnight then partitioned with EtOAc (15 mL) and water (10 mL). The layers were separated and the organics dried over Na₂SO₄. After concentration in vacuo, the residue was purified by column chromatography using a 12 g ISCO combi-flash cartridge (silica gel, 100:0 to 90:10 DCM/MeOH) to afford 4-(4-{[5-nitro-2-(2-trifluoromethoxy-benzylamino)-pyrimidin-4-ylamino]-methyl}-cyclohexylamino)-butyric acid methyl ester (39 mg, 53%) as a white solid: m/z 541 [M+1]⁺.

To a solution of 4-(4-{[5-nitro-2-(2-trifluoromethoxy-benzylamino)-pyrimidin-4-ylamino]-methyl}-cyclohexylamino)-butyric acid methyl ester (39 mg, 0.072 mmol) in 6:1 MeOH/water (0.7 mL) was added LiOH (9 mg, 0.375 mmol) and the mixture stirred at room temperature overnight. The resulting suspension was diluted with MeOH (1 mL) and stirred at room temperature for a further 2 h. The reaction mixture was concentrated in vacuo and the remaining aqueous residue treated with 2 N HCl until the mixture reached pH 5-6. The resulting solid was filtered and washed with water. The material was subjected to semi-preparative to separate the title compound [7 mg, 13%, m/z 527 (M+1)$^+$] and 1-(trans-4-{[(5-nitro-2-{[2-(trifluoromethoxy)benzyl]amino}pyrimidin-4-yl)amino]methyl}cyclohexyl)pyrrolidin-2-one [15 mg, 41%, m/z 509 (M+1)$^+$].

Example 56

4-{[(4-{1(trans-4-aminocyclohexyl)methyl]amino}-5-nitropyrimidin-2-yl)amino]methyl}-5-chloropyridin-2(1H)-one

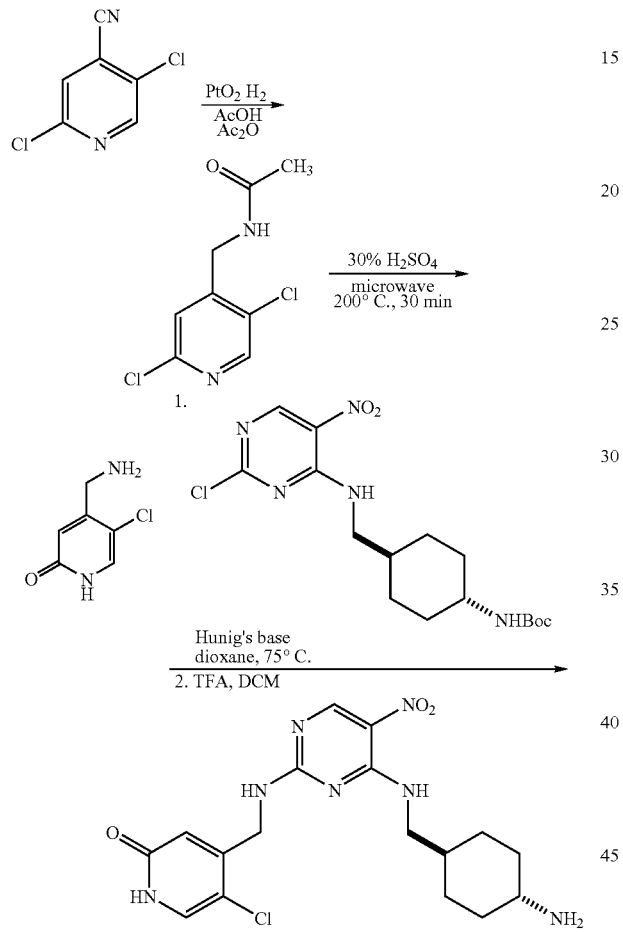

A mixture of 3,6-dichloro-4-cyanopyridine (prepared according to WO 9633975) (3.40 g, 19.65 mmol) and PtO$_2$ (0.40 g) in 1:1 Ac$_2$O/AcOH (60 mL) was shaken in a Parr hydrogenation apparatus at 30 psi H$_2$ for 6 h. The reaction mixture was filtered through a pad a celite and the filtered solids washed with EtOAc. The combined filtrate and washings were concentrated in vacuo and the resulting white solid purified by column chromatography on a 120 g ISCO combi-flash cartridge (silica gel, 20:80 to 100:0 EtOAc/hexane) to afford N-(2,5-Dichloro-pyridin-4-ylmethyl)-acetamide (1.73 g, 40%) as a white solid.

Compound N-(2,5-dichloro-pyridin-4-ylmethyl)-acetamide (250 mg, 1.14 mmol) was added to 33% H$_2$SO$_4$ (3 mL) and the mixture heated in a CEM microwave reactor at 200° C. for 30 min. After cooling to room temperature, the reaction mixture was diluted with water (20 mL) and basified with excess concentrated NH$_4$OH. The reaction mixture was then frozen using a dry ice/acetone bath and evaporated to dryness in vacuo overnight in a freeze-dry apparatus. The solids were purified by column chromatography using a 12 g ISCO combi-flash column and dry-loading cartridge (silica gel, 100:0 to 50:50 DCM:DCM/MeOH/NH$_4$OH 6:3:1) to afford N-(5-chloro-2-oxo-1,2-dihydro-pyridin-4-ylmethyl)-acetamide (246 mg, quant.) as an off-white solid. This material was directly in the next step.

A mixture of N-(5-chloro-2-oxo-1,2-dihydro-pyridin-4-ylmethyl)-acetamide (100 mg, 0.62 mmol), {4-[(2-chloro-5-nitro-pyrimidin-4-ylamino)-methyl]-cyclohexyl}-carbamic acid tert-butyl ester (146 mg, 0.38 mmol) and diisopropylethylamine (188 µL, 1.14 mmol) in i-PrOH (2 mL) was heated in a CEM microwave reactor at 120° C. for 30 min. After cooling the reaction mixture was concentrated in vacuo and the residue treated with TFA (10 mL). After 30 min the solution was concentrated in vacuo and basified with excess 6:3:1 DCM/MeOH/NH$_4$OH. Concentration in vacuo afforded a residue which was purified by column chromatography using a 12 g ISCO combi-flash cartridge (silica gel, 50:50 to 0:100 DCM/(6:3:1 DCM/MeOH/NH$_4$OH). The material obtained after chromatography was then suspended in EtOAc (20 mL) and the flask placed in a sonicator bath for 5 min. The insoluble material was removed by filtration and the filtrate concentrated in vacuo to afford the target compound (148 mg, 96%) as a white solid, m/z 408 [M+1]$^+$.

The following compound was prepared following similar procedures as described above:

4-{[(4-{[(trans-4-aminocyclohexyl)methyl]amino}-5-nitro-pyrimidin-2-yl)amino]methyl}pyridin-2(1H)-one, m/z 374 [M+1]$^+$.

Example 57

(1S)-2-[(trans-4-{[(5-nitro-2-{[2-(trifluoromethoxy)benzyl]amino}pyrimidin-4-yl)amino]methyl}cyclohexyl)amino]-1-phenylethanol and (2R)-2-[(trans-4-{1[(5-nitro-2-{[2-(trifluoromethoxy)benzyl]amino}pyrimidin-4-yl)amino]methyl}cyclohexyl)amino]-2-phenylethanol

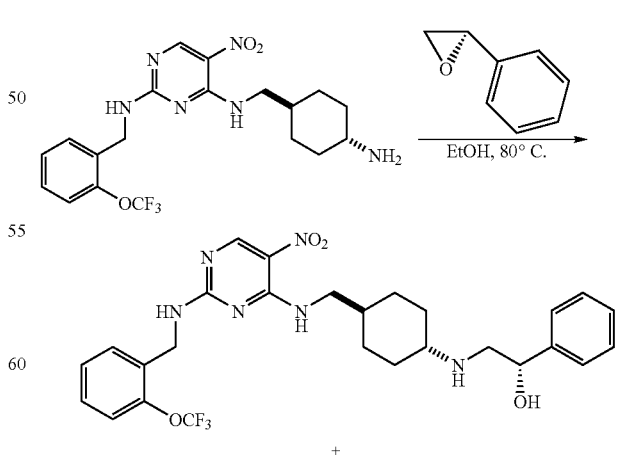

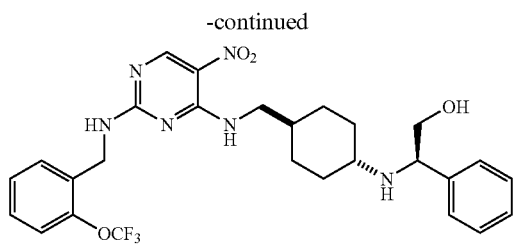

A solution of N⁴-trans-(4-amino-cyclohexylmethyl)-5-nitro-N²-(2-trifluoromethoxy-benzyl)-pyrimidine-2,4-diamine (400 mg, 0.91 mmol) and (S)-styrene oxide (109 mg, 0.91 mmol) in EtOH (5 mL) was stirred at 80° C. for 72 h. After concentration in vacuo, the residue was purified by preparative TLC (silica gel, 90:10 DCM/MeOH) to afford (1S)-2-[(trans-4-{[(5-nitro-2-{[2-(trifluoromethoxy)benzyl]amino}pyrimidin-4-yl)amino]methyl}cyclohexyl)amino]-1-phenylethanol, [52 mg, m/z 562 (M+1)⁺] and (2R)-2-[(trans-4-{[(5-nitro-2-{[2-(trifluoromethoxy)benzyl]amino}-pyrimidin-4-yl)amino]methyl}cyclohexyl)amino]-2-phenylethanol [6 mg, m/z 561 (M+1)⁺] as off-white solids.

The following compounds were prepared following similar procedures as described above:

(1R)-2-[(trans-4-{[(5-nitro-2-{[2-(trifluoromethoxy)benzyl]amino}pyrimidin-4-yl)amino]methyl}cyclohexyl)amino]-1-phenylethanol, m/z 562 [M+1]⁺.

(2S)-2-[(trans-4-{[(5-nitro-2-{[2-(trifluoromethoxy)benzyl]amino}pyrimidin-4-yl)amino]methyl}cyclohexyl)amino]-2-phenylethanol, m/z 562[M+1]⁺.

Example 58

N⁴-[(trans-4-amino-4-methylcyclohexyl)methyl]-5-nitro-N²-[2-(trifluoromethoxy)benzyl]pyrimidine-2,4-diamine

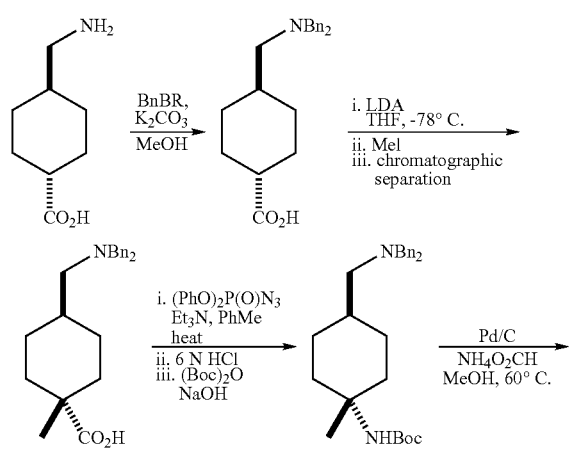

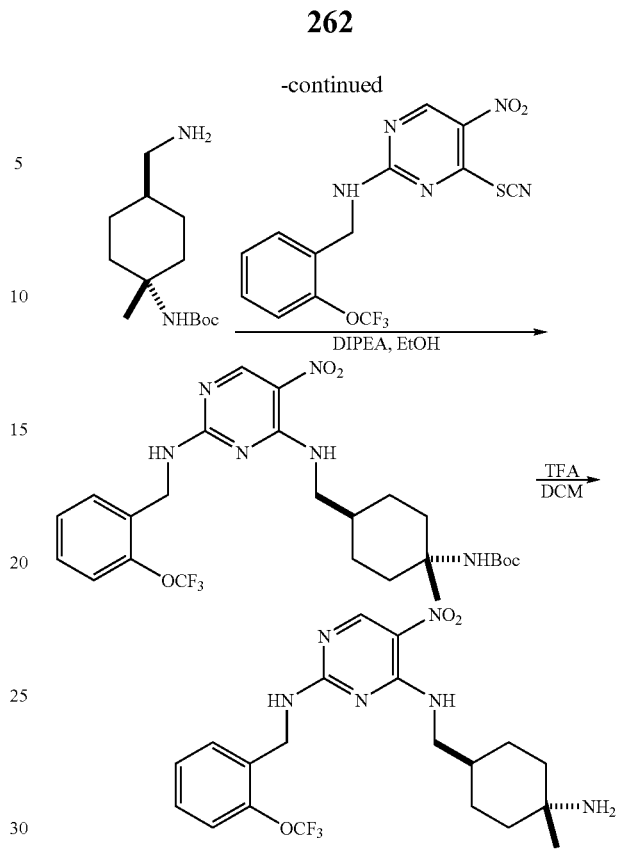

To a stirred slurry of trans-4-aminomethyl-cyclohexanecarboxylic acid (5.00 g, 31.8 mmol) and K₂CO₃ (4.40 g, 127.2 mmol) in MeOH (100 mL) cooled to 0° C. was added benzyl bromide (7.94 mL, 66.8 mmol). The reaction mixture was allowed to warm to room temperature and stirred overnight. Most of the volatiles were removed in vacuo before addition of water (100 mL). The aqueous mixture was extracted with Et₂O (2×200 mL) before adjusting to pH 5-6 by addition of 2 N HCl. The aqueous phase was extracted with DCM (3×200 mL) and the combined DCM extracts dried over Na₂SO₄ before concentrating in vacuo to afford trans-4-[(dibenzylamino)-methyl]-cyclohexanecarboxylic acid (3.22 g, 43%) as an off-white solid, m/z 338 [M+1]⁺.

To a solution of diisopropylamine (0.95 g, 9.4 mmol) in THF (40 mL) under N₂ at −78° C. was added n-BuLi (3.75 mL of a 2.5 M solution in hexanes, 9.38 mmol) dropwise via syringe. After 20 min a solution of trans-4-[(dibenzylamino)-methyl]-cyclohexanecarboxylic acid (1.58 g, 4.7 mmol) in THF (10 mL) was added dropwise. The reaction mixture was stirred at −78° C. for a further 20 min before it was allowed to warm to room temperature and stirred for a further 3 h. The reaction mixture was cooled to −78° C. and methyl iodide (0.32 mL, 5.2 mmol) added dropwise. The reaction was then allowed to warm slowly to room temperature and stirred overnight before quenching with water (10 mL). The mixture was treated with 6 N HCl until it reached pH 6 and was then concentrated in vacuo to remove most of the THF. The aqueous phase was extracted with EtOAc (2×60 mL) and the combined extracts washed with brine, dried (Na₂SO₄) and concentrated in vacuo. The residue was purified by column chromatography (silica gel, 1:1 hexane/Et₂O) to afford trans-4-[(dibenzylamino)-methyl]-1-methyl-cyclohexanecarboxylic acid (375 mg, 23%), m/z 352 (M+1)⁺.

To a solution of trans-4-[(dibenzylamino)-methyl]-1-methyl-cyclohexanecarboxylic acid (375 mg, 1.07 mmol) and Et$_3$N (317 μL, 2.28 mmol) in toluene (3.6 mL) under N$_2$ was added diphenylphosphoryl azide (250 μL, 1.16 mmol). The reaction was stirred at room temperature for 1 h before heating at 100° C. for 4 h. The reaction mixture was concentrated to about half volume then a solution of Boc$_2$O (0.70 g, 3.20 mmol) in THF (4 mL) added followed by Et$_3$N (0.60 mL, 4.30 mmol) and water (0.2 mL). After stirring at room temperature for 2 h, little or no reaction was observed and the intermediate isocyanate remained unchanged. The solvent was evaporated in vacuo before the residue was dissolved in 1:1 THF/6 N HCl (4 mL) and stirred at room temperature overnight. NaOH pellets were added until the reaction mixture reached pH 11 and Boc$_2$O (0.70 g, 3.20 mmol) added. After stirring at room temperature for 3 h the reaction mixture was extracted with EtOAc (2×30 mL) and the combined extracts dried over Na$_2$SO$_4$. After concentration in vacuo the residue was purified by column chromatography using a 12 g ISCO combi-flash cartridge (silica gel, 90:10 to 50:50 hexane/EtOAc) to afford trans-{4-[(dibenzylamino)-methyl]-1-methyl-cyclohexyl}-carbamic acid tert-butyl ester (221 mg, 50%) as a colorless oil, m/z 423 [M+1]$^+$.

To a mixture of trans-{4-[(dibenzylamino)-methyl]-1-methyl-cyclohexyl}-carbamic acid tert-butyl ester (221 mg, 0.52 mmol) and ammonium formate (330 mg, 5.23 mmol) in MeOH (5 mL) under N$_2$ was added 10% palladium on charcoal (300 mg). The reaction was heated at 60° C. for 1 h and allowed to cool to room temperature before filtering through celite. Concentration in vacuo afforded trans-(4-aminomethyl-1-methyl-cyclohexyl)-carbamic acid tert-butyl ester (126 mg, 100%) as a colorless oil, m/z 243 [M+1]$^+$.

A solution of trans-{4-[(dibenzylamino)-methyl]-1-methyl-cyclohexyl}-carbamic acid tert-butyl ester (62 mg, 0.26 mmol) was added to (5-nitro-4-thiocyanato-pyrimidin-2-yl)-(2-trifluoromethoxy-benzyl)-amine (95 mg, 0.26 mmol) followed by Et$_3$N (143 μL, 1.03 mmol). The mixture was stirred at room temperature for 3 h then concentrated in vacuo. The residue was purified by column chromatography using a 12 g ISCO combi-flash cartridge (silica gel, 90:10 to 70:30 hexane/EtOAc) to afford trans-(1-methyl-4-{[5-nitro-2-(2-trifluoromethoxy-benzylamino)-pyrimidin-4-ylamino]-methyl}-cyclohexyl)-carbamic acid tert-butyl ester (111 mg, 79%) as an off-white solid, m/z 555 [M+1]$^+$.

To a solution of trans-(1-methyl-4-{[5-nitro-2-(2-trifluoromethoxy-benzylamino)-pyrimidin-4-ylamino]-methyl}-cyclohexyl)-carbamic acid tert-butyl ester (110 mg, 0.20 mmol) in DCM (2 mL) at room temperature was added TFA (2 mL). After 1 h the reaction mixture was concentrated in vacuo and treated with sat. NaHCO$_3$ (5 mL) before extracting with EtOAc (2×25 mL). The combined organic layers were dried (Na$_2$SO$_4$) and concentrated in vacuo to afford the title compound (83 mg, 92%) as an off-white solid: m/z 455 [M+1]$^+$.

Example 59

N$^4$-[(trans-4-aminocyclohexyl)methyl]-N$^2$-(1,2-diphenylethyl)-5-nitropyrimidine-2,4-diamine

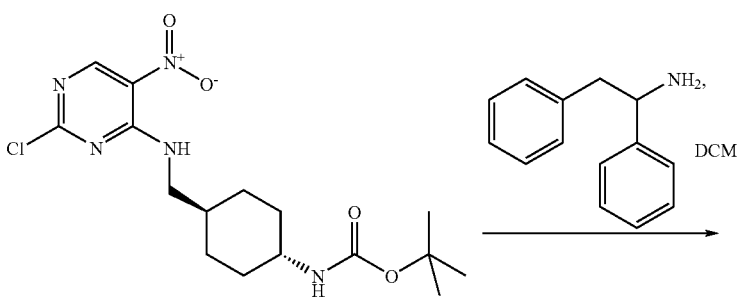

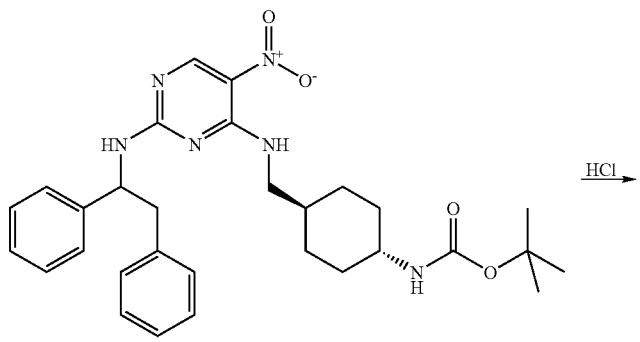

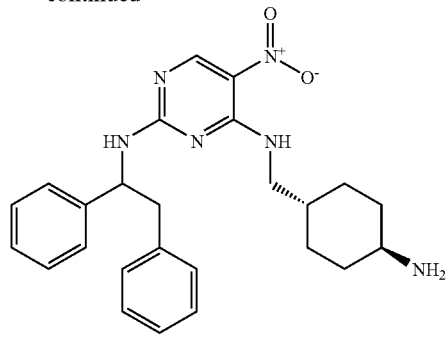

trans-{4-[(2-Chloro-5-nitro-pyrimidin-4-ylamino)-methyl]-cyclohexyl}-carbamic acid tert-butyl ester (100 mg, 0.26 mmol) was dissolved in DCM (5 mL). 1,2-Diphenyl-ethylamine (154 mg, 0.78 mmol) was added in one portion. After 18 h, the solution was partitioned between DCM (15 mL) and 2% AcOH (aq; 10 mL). The layers were separated and the aqueous layer was extracted with DCM (20 mL). The combined organic fraction were washed with saturated sodium carbonate (10 mL) and water, dried over MgSO$_4$, filtered and concentrated to yield a pale yellow solid. Chromatography (silica, 10%-50% Hex/EtOAc) yielded 110 mg of (4-{[2-(1,2-diphenyl-ethylamino)-5-nitro-pyrimidin-4-ylamino]-methyl}-cyclohexyl)-carbamic acid tert-butyl ester as a pale yellow solid, m/z 547.4 [M+1]$^+$.

(4-{[2-(1,2-Diphenyl-ethylamino)-5-nitro-pyrimidin-4-ylamino]-methyl}-cyclohexyl)-carbamic acid tert-butyl ester (105 mg, 0.19 mmol) was dissolved in dioxane (5 mL). An HCl solution (2 mL of a 4M solution) was added. After 18 h, an oil separated from the solvent. The solvent was decanted and the oil was dissolved in water and lyopholized yielding 57 mg of the title compound as a pale yellow solid, m/z 447.3 [M+1]$^+$.

The following compound was prepared following similar procedures as described above:

N$^4$-[(trans-4-aminocyclohexyl)methyl]-5-nitro-N$^2$-(2-piperidin-1-ylbenzyl)pyrimidine-2,4-diamine, m/z 440.6 [M+1]$^+$.

Example 60

N$^4$-[(trans-4-aminocyclohexyl)methyl]-n$^2$-[2-(methylsulfonyl)benzyl]-5-nitropyrimidine-2,4-diamine

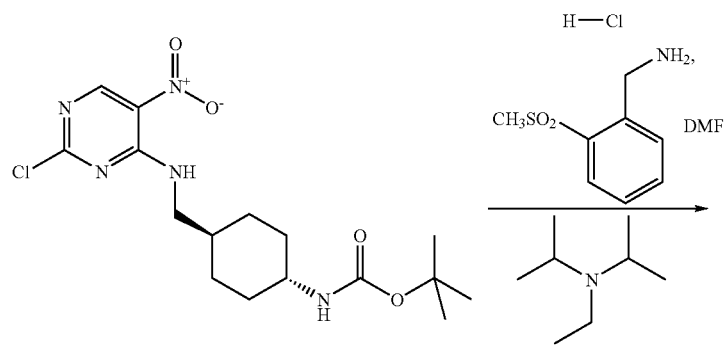

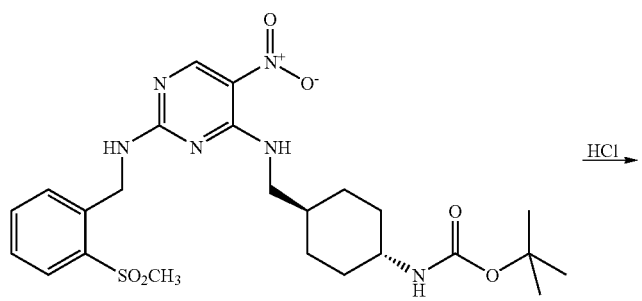

-continued

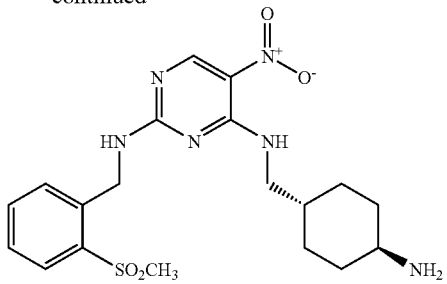

{4-[(2-Chloro-5-nitro-pyrimidin-4-ylamino)-methyl]-cyclohexyl}-carbamic acid tert-butyl ester (100 mg, 0.26 mmol) was dissolved in DMF (3 mL). 2-Methanesulfonyl-benzylamine hydrochloride (115 mg, 0.52 mmol) and diisopropylethylamine (0.14 mL, 0.78 mmol) were added sequentially. After 24 h, the reaction was partitioned between water (10 mL) and DCM (10 mL). The organic layer was washed with 5% AcOH (aq), saturated $Na_2CO_3$ and water, dried over $MgSO_4$, filtered and concentrated. Chromatography (silica, 0-15% MeOH in DCM; Rf=0.3 10% MeOH in DCM) yielded 96 mg of (4-{[2-(2-methanesulfonyl-benzylamino)-5-nitro-pyrimidin-4-ylamino]-methyl}-cyclohexyl)-carbamic acid tert-butyl ester as a pale yellow solid, m/z 535.7 $[M+1]^+$.

(4-{[2-(2-Methanesulfonyl-benzylamino)-5-nitro-pyrimidin-4-ylamino]-methyl}-cyclohexyl)-carbamic acid tert-butyl ester (96 mg, 0.18 mmol) was dissolved in warm dioxane (5 mL). HCl in dioxane (4M, 1.5 mL, 6.0 mmol) was added. After 18 h, the heterogeneous mixture was decanted and the solid was washed with dioxane and dried in-vacuo to yield 76 mg of the title compound as a white solid, m/z 435.5 $[M+1]^+$.

Preparation of 2-Methanesulfonyl-benzylamine intermediate:

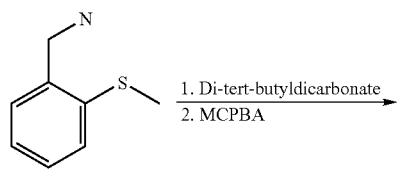

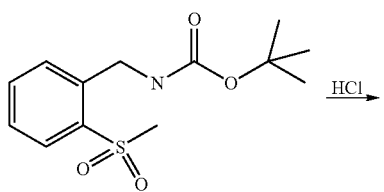

2-(Methylthio)benzyl amine (3 g, 19.6 mmol) was dissolved in DCM (100 mL). Di-tert-butyldicarbonate (4.27 g, 19.6 mmol) was added portionwise. After 8 h, the reaction was concentrated. Chromatography (silica, Hex/EtOAc 2%-15%) yielded 4.5 g of a (2-methylsulfanyl-benzyl)-carbamic acid tert-butyl ester as a colorless oil, m/z 254.4 $[M+1]^+$.

MCPBA (60%, 5.82 g, 20.2 mmol) was added to a solution of (2-methylsulfanyl-benzyl)-carbamic acid tert-butyl ester (2.5 g, 9.87 mmol) in DCM (100 mL) which was pre-cooled to 0 degrees C. After 5 h, 100 ml of a 10% aqueous solution of sodium sulfite (Na2SO3) was added to the reaction and the organic layers were collected, washed with saturated aqueous sodium carbonate (50 mL), dried over MgSO4, filtered and concentrated in-vacuo. Chromatography (silica, 0-15% MeOH in DCM) yielded 1.885 g of (2-methanesulfonyl-benzyl)-carbamic acid tert-butyl ester as an off-white solid.

(2-Methanesulfonyl-benzyl)-carbamic acid tert-butyl ester (1.55 g, 5.43 mmol) was dissolved in warm dioxane (50 mL) and cooled to room temperature. HCl solution (4M solution in dioxane, 20 ml, 80 mmol) was added. After 20 h, a white precipitate had formed. The reaction was diluted with $CHCl_3$ (50 mL) and filtered. The white solid was washed with $CHCl_3$ and dried in-vacuo to yield 1.075g of 2-methanesulfonyl-benzylamine hydrochloride as an off white solid, m/z 186.6 $(M+1)^+$.

The following compound was prepared following similar procedures as described above:

$N^4$-[(trans-4-aminocyclohexyl)methyl]-$N^2$-[5-chloro-2-(methylsulfonyl)benzyl]-5-nitropyrimidine-2,4-diamine, m/z 469.6 $(M+1)^+$.

The following intermediate was prepared following similar procedures as described above for 2-methanesulfonyl-benzylamine:

5-Chloro-2-methanesulfonyl-benzylamine, m/z 220.5 $(M+1)^+$.

Preparation of 5-chloro-2-methylsulfanyl-benzylamine intermediate:

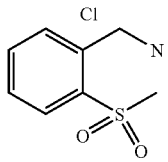

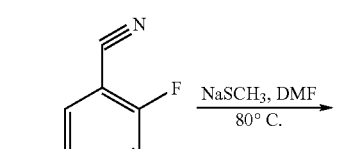

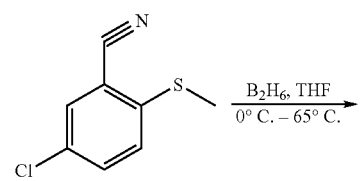

-continued

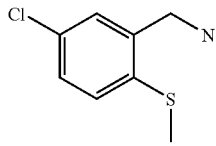

5-Chloro-2-fluorobenzonitrile (9.0 g, 57.9 mmol) was dissolved in DMF (200 mL). Sodium methanethiolate (4.86 g, 69.4 mmol) was added in one portion and the reaction was heated to 80 degrees C. After 72 h, the reaction was cooled to room temperature and partitioned between EtOAc (250 mL) and $H_2O$ (250 mL). The layers were separated and the aqueous layer was extracted with EtOAc (150 mL). The combined organic layers were washed with water (3×250 mL) and brine (50 mL), dried over $MgSO_4$, filtered and concentrated to yield 11 g of a yellow solid. Recrystallization from EtOH yielded 7.5 g (two batches) of 5-chloro-2-methylsulfanyl-benzonitrile as pale yellow crystals.

5-Chloro-2-methylsulfanyl-benzonitrile (3.9 g, 21.2 mmol) was dissolved in THF (42 mL) and cooled to 0 degrees C. Borane-THF complex (50 mL of a 1M THF solution) was added dropwise. After 10 minutes at 0 degrees C. the reaction was warmed to 65 degrees C. for 4 h. Methanol (approximately 30 mL) was added to the reaction at 0 degrees C. The reaction was warmed to room temperature and stirred for 10 minutes. The reaction solution was concentrated in-vacuo to yield a thick oil which was dissolved in 50% THF/MeOH (30 mL). 4M HCl (30 mL) was added slowly. After 10 minutes, the solution was partitioned between water (10 mL) and DCM (20 mL). The aqueous layer was extracted with DCM (30 mL) and the organic layers were discarded. The aqueous layer was neutralized to pH9 with 5M NaOH. The solution was extracted with DCM (3×70 mL). The combined organic layers were washed with brine, dried over $MgSO_4$, filtered and concentrated to yield 2.9 g of 5-chloro-2-methylsulfanyl-benzylamine as a pale yellow oil, $^1H$ NMR 400 MHz ($CDCl_3$) δ 7.33 (d, 1H, J=2.4 Hz), 7.22 (dd, 1H, J=2.4, 8.4 Hz), 7.13 (d, 1H, J=5 8.4 Hz), 3.89 (s, 2H), 2.48 (s, 3H).

Example 61 cis-2-amino-trans-5-{[(5-nitro-2-{[2-(trifluoromethoxy)benzyl]amino}pyrimidin-4-yl)amino]methyl}cyclohexanol

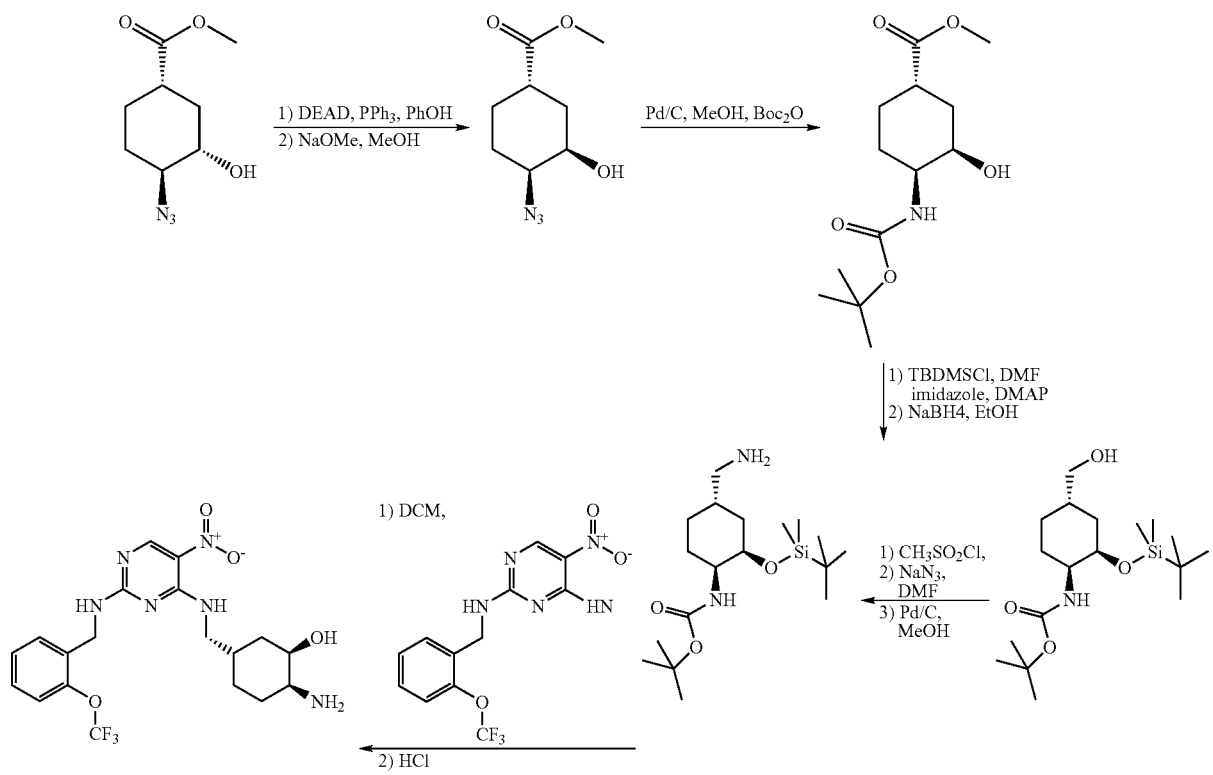

trans-4-Azido-cis-3-hydroxy-cyclohexanecarboxylic acid methyl ester (8.66 g, 43.5 mmol) was combined with $PPh_3$ (13.7 g, 52.2 mmol) and benzoic acid (6.4 g, 52.2 mmol) and dissolved in THF (150 mL). The solution was cooled to 0 degrees C. and DEAD (8.2 mL, 52.2 mmol) was added dropwise over 20 minutes. The reaction was stirred at 0 degrees C. for 24 h. The reaction was then warmed to room temperature. After 6 h at room temperature, the reaction was partitioned between saturated $NaHCO_3$ (100 mL) and $Et_2O$ (300 mL). The layers were separated and the aqueous layer was extracted with $Et_2O$ (2×250 mL). The combined organic layers were washed with brine, dried over $MgSO_4$, filtered and concentrated to yield a colorless oil. The oil was dissolved in $Et_2O$ (approx. 200 mL) and the heterogeneous solution was filtered and the white solid was washed with $Et_2O$ (75 mL). The filtrate was concentrated in vacuo. The oil was then stirred with 5% EtOAc in Hex (500 mL) over 30 minutes. The heterogeneous solution was filtered and the filtrate was concentrated in vacuo. Chromatography (Combiflash, 120 g silica, 0-30% EtOAc in hexanes; Rf=0.4 (25% EtOAc in hex)) yielded 7.6 g of benzoic acid-cis-2-azido-trans-5-methoxy-carbonyl-cyclohexyl ester as a colorless oil. The impure solid from the previous Hex/EtOAc filtration was mixed with 10% EtOAc in Hex and heated to reflux. The heterogeneous solution was cooled to room temperature and the filtrate was concentrated in vacuo to yield 5 g of a pale yellow oil. Chromatography (Combiflash, 120 g silica, 0-30% EtOAc in hexanes; Rf=0.4 (25% EtOAc in hex)) yielded another 1.2 g of benzoic acid-cis-2-azido-trans-5-methoxycarbonyl-cyclohexyl ester as a pale yellow oil (8.8 g total, 67%).

Benzoic acid-cis-2-azido-trans-5-methoxycarbonyl-cyclohexyl ester (4.0 g, 13.2 mmol) was dissolved in MeOH (50 mL). 25% Sodium methoxide solution (1.51 mL, 6.6 mmol) was added dropwise over 5 minutes. After 3 h, amberlite IRC-50 (8 g, weakly acidic ion exchange resin) was added and the solution was shaken at room temperature. After 4 h, the heterogeneous solution was filtered and the resin was washed with MeOH (2×40 mL). The combined filtrates were dried in vacuo. Chromatography (Combiflash, 120 g silica, 5-50% EtOAc in hex) yielded 2.3 g of trans-4-azido-trans-3-hydroxy-cyclohexane-carboxylic acid methyl ester as a colorless oil, $^1$H NMR 400 MHz (CDCl$_3$) δ 4.05 (brs, 1H), 3.68 (s, 3H), 3.49 (m, 1H), 2.76 (m, 1H), 2.14 (m, 1H), 2.05 (m, 1H), 1.96, Brs, 1H), 1.88 m, 2H), 1.48-1.72 (m, 2H).

trans-4-Azido-trans-3-hydroxycyclohexane-carboxylic acid methyl ester (2.75 g, 13.8 mmol) was dissolved in MeOH (70 mL) and flushed with Ar. 10% Pd/C (0.37 g, 0.34 mmol) was added and the flask was flushed with H$_2$. After 18 h, the reaction was filtered and the catalyst was washed with MeOH (2×10 mL). The filtrate was concentrated and yielded a pale yellow solid which was dissolved in DCM (60 mL) and diluted with iPr$_2$NEt (2.65 mL, 15.2 mmol). Boc$_2$O (3.32 g, 15.2 mmol) was added in one portion. After 8 h, the reaction was concentrated in vacuo. Chromatography (Combiflash, 120 g silica, 0-10% MeOH in DCM; Rf=0.4 5% MeOH in DCM) yielded 3.75 g of trans-4-tert-butoxycarbonylamino-trans-3-hydroxy-cyclohexanecarboxylic acid methyl ester as a white solid, $^1$H NMR 400 MHz (CDCl$_3$) δ 4.82 (brs, 1H), 4.11H), 3.67 (s, 3H), 3.51 (brs, 1H), 2.70 (m, 1H), 2.10 (ddd, 1H, J=3.6, 6.2 and 14.1 Hz), 2.00 (m, 1H), 1.48-1.80 (m, 5H), 1.45 (s, 9 h).

trans-4-tert-Butoxycarbonylamino-trans-3-hydroxy-cyclohexanecarboxylic acid methyl ester (3.75 g, 13.7 mmol) was dissolved in DMF (20 mL) and TBSCl (2.481 g, 16.44 mmol), imidazole (2.8 g, 41.1 mmol) and DMAP (5.02 g, 41.1 mmol) were added sequentially. After 18 h, another portion of TBSCl (1.24 g, 8.25 mmol) was added. After 72 h, the reaction was partitioned between Et$_2$O (150 mL) and water (100 mL). The layers were separated and the aqueous layer was extracted with Et$_2$O (2×100 mL). The combined organic layers were washed with water (3×100 mL) and brine (50 mL), dried over MgSO$_4$, filtered and concentrated to yield 5.6 g of a pale brown oil. Chromatography (Combiflash, 120 g silica, 3-15% EtOAc in Hex; Rf 0.5 (10% EtOAc in Hex)) yielded 3.44 g of trans-4-tert-butoxycarbonylamino-trans-3-(tert-butyl-dimethyl-silanyloxy)-cyclohexanecarboxylic acid methyl ester as a colorless oil which slowly solidified.

trans-4-tert-Butoxycarbonylamino-trans-3-(tert-butyl-dimethyl-silanyloxy)-cyclohexanecarboxylic acid methyl ester (3.44 g, 8.88 mmol) was dissolved in EtOH (60 mL) and the solution was cooled to 0 degrees C. Sodium borohydride (336 mg, 8.88 mmol) was added in one portion. The reaction was allowed to warm to room temperature slowly overnight. After 18 h, more sodium borohydride (100 mg, 2.64 mmol) was added and the reaction was warmed to 40 degrees C. After another 18 h, the reaction was partitioned between Et$_2$O (200 mL) and water (100 mL). The layers were separated and the aqueous layer was extracted with Et$_2$O (2×150 mL). The combined organic layers were washed with brine, dried over MgSO4, filtered and concentrated to yield a colorless oil. Chromatography (Combiflash, silica, 3%-50% EtOAc in Hex) yielded 1.2 g of [cis-2-(tert-butyl-dimethyl-silanyloxy)-trans-4-hydroxymethyl-cyclohexyl]-carbamic acid tert-butyl ester as a colorless oil which solidifies, $^1$H NMR 400 MHz (CDCl$_3$) δ 4.55 (d, 1H, J=9.2 Hz), 3.98 (s, 1H), 3.39 (m, 3H), 1.68-1.85 (m, 3H), 1.44-1.62 (m, 3H), 1.37 (s, 9H), 1.12 (ddd, 1H, J=1.8, 13, 13 Hz), 0.97 (m, 1H), 0.85 (s, 9H), 0.00 (s, 6H).

[cis-2-(tert-Butyl-dimethyl-silanyloxy)-trans-4-hydroxymethyl-cyclohexyl]-carbamic acid tert-butyl ester (1.33 g, 3.7 mmol) was dissolved in dry DCM (20 mL) and cooled to 5 degrees C. Diisopropylethylamine (0.97 mL, 5.55 mmol) and methanesulfonyl chloride (0.344 mL, 4.44 mmol) were added sequentially. After 2 h, the reaction was quenched with cold water (10 mL) and warmed to room temperature. The solution was partitioned between DCM (100 mL) and water (50 mL). The layers were separated and the aqueous layer was extracted with DCM (2×100 mL). The combined organic layers were washed with brine, dried over MgSO$_4$, filtered and concentrated in vacuo to yield 1.6 g (99%) of methanesulfonic acid trans-4-tert-butoxycarbonylamino-trans-3-(tert-butyl-dimethyl-silanyloxy)-cyclohexylmethyl ester as a pale yellow oil. The material was used without further purification.

Methanesulfonic acid trans-4-tert-butoxycarbonylamino-trans-3-(tert-butyl-dimethyl-silanyloxy)-cyclohexylmethyl ester (1.6 g, 3.66 mmol) was dissolved in dry DMF and sodium azide (475 mg, 7.31 mmol) was added. The reaction was heated to 55 degrees C. After 8 h, the reaction was cooled to room temperature and another portion of sodium azide (119 mg, 1.83 mmol) was added. After 72 h, the reaction was partitioned between EtOAc (100 mL) and water (50 mL). The layers were separated and the aqueous layer was extracted with EtOAc (2×50 mL). The combined organic layers were washed with water (3×75 mL) and brine (15 mL), dried over MgSO$_4$, filtered and concentrated to yield a colorless oil. Chromatography (Combiflash, 40 g silica, 3-50% EtOAc in Hex) yielded 1.34 g (95%) of trans-4-azidomethyl-cis-2-(tert-butyl-dimethyl-silanyloxy)-cyclohexyl]-carbamic acid tert-butyl ester a colorless oil.

trans-4-Azidomethyl-cis-2-(tert-butyl-dimethyl-silanyloxy)-cyclohexyl]-carbamic acid tert-butyl ester (1.1 g, 2.86 mmol) was dissolved in MeOH (50 mL) and flushed with Ar. 10% Pd/C (200 mg, 0.18 mmol) was added and the reaction was flushed with H$_2$. After 18 h, the reaction was flushed with Ar and the heterogeneous solution was filtered. The catalyst was washed with MeOH (2×5 mL) and the solvent was removed in vacuo to yield 900 mg of [trans-4-aminomethyl-cis-2-(tert-butyl-dimethyl-silanyloxy)-cyclohexyl]-carbamic acid tert-butyl ester (approximately 80% pure), m/z 359.6 [M+1]$^+$. The product was used in subsequent steps without any further purification.

A solution of diisopropylethyl amine (0.07 mL, 0.4 mmol) and [trans-4-aminomethyl-cis-2-(tert-butyl-dimethyl-silanyloxy)-cyclohexyl]-carbamic acid tert-butyl ester (290 mg, 0.81 mmol) were dissolved in DCM (2 mL) and added to a solution of (5-nitro-4-thiocyanato-pyrimidin-2-yl)-(2-trifluoromethoxy-benzyl)-amine (in 3 mL of DCM). After 18 h, the reaction was partitioned between DCM (10 mL) and water (5 mL). The layers were separated and the water layer was extracted with DCM (2×5 mL). The combined organic layers were washed with water (5 mL) and brine (5 mL), dried over MgSO$_4$, filtered and concentrated to yield a colorless oil.

Chromatography (Combiflash, 12 g silica, 5%-40% EtOAc in Hex; Rf (product in 20% EtOAc in Hex) 0.3) yielded 226 mg of (cis-2-(tert-butyl-dimethyl-silanyloxy)-4-{[5-nitro-2-(2-trifluoromethoxy-benzylamino)-pyrimidin-trans-4-ylamino]-methyl}-cyclohexyl)-carbamic acid tert-butyl ester as a pale yellow foam, m/z 671.7 $[M+1]^+$.

(cis-2-(tert-Butyl-dimethyl-silanyloxy)-4-{[5-nitro-2-(2-trifluoromethoxy-benzylamino)-pyrimidin-trans-4-ylamino]-methyl}-cyclohexyl)-carbamic acid tert-butyl ester (116 mg, 0.17 mmol) was dissolved in dioxane (2 mL)/MeOH (1 mL) and 4M HCl solution (1.5 mL, 10 mmol) was added dropwise. After 18 h, another portion of MeOH (1 mL) and 4M HCl solution (1 mL, 4 mmol) were added. After a total of 48 h, the reaction was concentrated and the residue was triturated with DCM. Chromatography of the residue (silica, 12 g, 9:1:2% DCM:MeOH:$NH_4OH$) yielded 48 mg (79%) of the title compound as a pale yellow solid, m/z 457.5 $[M+1]^+$. trans-4-Azido-cis-3-hydroxy-cyclohexanecarboxylic acid methyl ester was synthesized as described previously (Krzysztof, K., *Tett. Asym.*, 2001, 12, 455).

Assessment of Biological Activity

PKC-theta Inhibition Assay

The ability of compounds to inhibit the kinase activity of PKC-theta was measured using a Kinase Glo Assay. This assay detects the enzymatic activity of protein kinase C-theta using a firefly-luciferase reagent (Kinase-Glo-Promega #V6714) to detect ATP levels remaining after incubation of the enzyme with ATP and it's acceptor substrate, [Ser25]-Protein Kinase C (19-31) (Anaspec #23020). Briefly, compounds are diluted in 100% DMSO at 100× the final desired assay concentration. Compounds are subsequently diluted 1:25 into complete assay buffer (50 mM HEPES/KOH, pH 7.5; 10 mM $MgCl_2$; 50 mM KCl; 0.01% CHAPS; 0.1% BSA; 200 µM TCEP). 10 µl of the 4×'4% DMSO stocks are transferred to 384-well white polystyrene plates (Greiner #781075). 10 µl of 4 nM PKC-theta are added to the compounds; followed by 20 µl of a mixture containing 10 µM peptide substrate and 2 µM ATP. Blank wells are defined by the addition of an equal volume of assay buffer in place of the PKC-theta. The complete reaction is allowed to incubate at room temperature for 90 minutes. Following this incubation period the reaction is terminated by the addition of 40 µl of the Kinase-Glo reagent. This condition is allowed to incubate for 15 minutes after which luminescence is quantified using an LJL Analyst.

All compounds in the synthetic examples and Tables above were evaluated in the PKC-theta assay above and were found to have $IC_{50}$'s less than 1 microM. Preferred compounds had $IC_{50}$'s equal to or less than 0.01 microM.

Many of the compounds in the synthetic examples and Tables above were also tested against Syk, Lyn, Veg-f and insulin receptor kinase to evaluate selectivity for PKC-theta inhibition. Some compounds were also tested against other kinases including CDK-2 and PLK. Many of the compounds demonstrated selectivity for the inhibition of PKC-theta as compared to one or more of the other kinases tested.

Assay conditions for testing against other kinases are generally known in the art. Examples of suitable assays that can be used are described below:

SYK Kinase Assay

Syk is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly Glu4: Tyr1 (PGTYR).

The kinase assay is performed in kinase assay buffer (50 mM HEPES, pH 7.0, 25 mM $MgCl_2$, 5 mM $MnCl_2$, 50 mM KCl, 100 µM $Na_3VO_4$, 0.2% BSA, 0.01% CHAPS, 200 µM TCEP). Test compounds initially dissolved in DMSO at 5 mg/mL, are pre-diluted for dose response (starting conc. 10 µM (or 5 µg/mL), 1 to 3 serial dilutions, 10 doses) with the assay buffer in 96-well polypropylene microtiter plates. A 40 µL volume of diluted enzyme (0.5 nM final conc.) in kinase buffer and a 20 µL aliquot of diluted compound are sequentially added to neutravidin coated 96-well white plate (PIERCE). The kinase reaction is started with a 40 µL volume of a mixture of substrates containing 0.75 µM ATP plus 4.5 ng/µL PGTYR-biotin (CIS Biointernational) in kinase buffer. Background wells are incubated with kinase plus buffer, and the reference inhibitor wells are incubated with 20 µL of 25 µM ADP instead of the compound. The assay plates are incubated for 30 min at room temperature. Following incubation, the assay plates are washed three times with 250 µL wash buffer (50 mM Tris-HCL, pH 7.4, 150 mM NaCl, 0.05% Tween 20, 0.2% BSA). A 100 µL aliquot of europium-labeled anti-phosphotyrosine (Eu3+-PT66, Wallac CR04-100) diluted in 50 mM Tris-HCl, pH 7.8, 150 mM NaCl, 10 µM DTPA, 0.05% Tween 40, 0.2% BSA, 0.05% BGG (1 nM final conc.) is added to each well and incubated for 30 min at room temperature. Upon completion of the incubation, the plate is washed four times with 250 µL of wash buffer and 100 µL of DELFIA Enhancement Solution (Wallac) is added to each well. After 15 min or longer, time-resolved fluorescence is measured on the LJL's Analyst (excitation at 360 nm, emission at 620 nm, EU 400 Dichroic Mirror) after a delay time of 250 µs.

LYN Kinase Assay

Lyn(Kd) is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly Glu4:Tyr1 (PG-TYR).

The kinase assay is performed in kinase assay buffer (50 mM HEPES, pH 7.0, 25 mM $MgCl_2$, 5 mM $MnCl_2$, 50 mM KCl, 100 µM $Na_3VO_4$, 0.2% BSA, 0.01% CHAPS, 200 µM TCEP). Test compounds initially dissolved in DMSO at 5 mg/mL, are pre-diluted for dose response (starting conc. 10 µM (or 5 µg/mL), 1 to 3 serial dilutions, 10 doses) with the assay buffer in 96-well polypropylene microtiter plates. A 40 µL volume of diluted enzyme (0.7 nM final conc.) in kinase buffer and a 20 µL aliquot of diluted compound are sequentially added to neutravidin coated 96-well white plate (PIERCE). The kinase reaction is started with a 40 µL volume of a mixture of substrates containing 1.25 µM ATP plus 4.5 ng/µL PGTYR-biotin (CIS Biointernational) in kinase buffer. Background wells are incubated with kinase plus buffer, and the reference inhibitor wells are incubated with 20 µL of 25 µM ADP instead of the compound. The assay plates are incubated for 30 min at room temperature. Following incubation, the assay plates are washed three times with 250 µL wash buffer (50 mM Tris-HCL, pH 7.4, 150 mM NaCl, 0.05% Tween 20, 0.2% BSA). A 100 µL aliquot of europium-labeled anti-phosphotyrosine (Eu3+-PT66, Wallac CR04-100) diluted in 50 mM Tris-HCl, pH 7.8, 150 mM NaCl, 10 µM DTPA, 0.05% Tween 40, 0.2% BSA, 0.05% BGG (1 nM final conc.) is added to each well and incubated for 30 min at room temperature. Upon completion of the incubation, the plate is washed four times with 250 µL of wash buffer and 100 µL of DELFIA Enhancement Solution (Wallac) is added to each well. After 15 min or longer, time-resolved fluorescence is measured on the LJL's Analyst (excitation at 360 nm, emission at 620 nm, EU 400 Dichroic Mirror) after a delay time of 250 µs.

Methods of Therapeutic Use

The compounds of the invention are effective inhibitors of PKC-theta activity, and therefore are useful to inhibit PKC-theta activity in a patient and treat a variety of diseases and disorders that are mediated or sustained through the activity of PKC-theta.

Without wishing to be bound by theory, the compounds of this invention would be expected to inhibit T cell activation via effective inhibition of PKC-theta, and are therefore useful to treat diseases and disorders associated with T cell activation. For example, the inhibition of T cell activation is therapeutically useful for selectively suppressing the immune function. Thus, the inhibition of PKC-theta with the compounds of this invention is an attractive means for treating a variety of immunological disorders, including inflammatory diseases, autoimmune diseases, organ and bone marrow transplant rejection and other disorders associated with T cell mediated immune response. In particular, the compounds of the invention may be used to treat acute or chronic inflammation, allergies, contact dermatitis, psoriasis, rheumatoid arthritis, multiple sclerosis, type I diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with T cell-mediated immune responses will be evident to those of ordinary skill in the art and can also be treated with the compounds and compositions of this invention.

In addition, PKC theta activation has been shown to be associated with insulin resistance in skeletal muscle. Therefore, the inhibition of PKC-theta with the compounds of this invention is also an attractive means for treating type II diabetes.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

We claim:

1. A compound of the following formula (I):

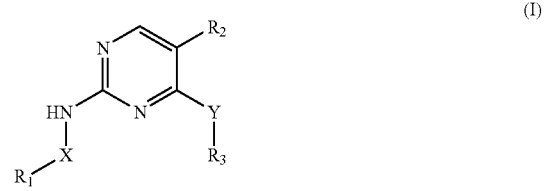

(I)

X is $C_{1-6}$ alkyl wherein one or two of the methylene units can be replaced by an oxygen or sulfur atom, and wherein the $C_{1-6}$alkyl group is optionally and independently substituted with:
(A) oxo,
(B) $C_{1-6}$alkyl which is optionally substituted with one or more of the following groups:
  (i) hydroxyl,
  (ii) $C_{1-3}$alkyloxy,
  (iii) halogen,
(C) $C_{1-6}$alkyloxy,
(D) $C_{1-6}$alkylthio,
(E) aryl
(F) —$COR_6$, wherein $R_6$ is:
  (i) $C_{1-6}$alkyl,
  (ii) $C_{1-6}$alkyloxy,
  (iii) —$NR_7R_8$, wherein $R_7$ and $R_8$ are each independently selected from:
    (a) hydrogen,
    (b) $C_{1-6}$alkyl,
    (c) aryl,
    (d) heteroaryl, (iv) —OH,
(G) halogen,
(H) —NR$_9$R$_{10}$, wherein R$_9$ and R$_{10}$ are each independently selected from:
  (i) hydrogen,
  (ii) C$_{1-6}$alkyl,
  (iii) C$_{1-6}$alkylcarbonyl,
  (iv) C$_{1-6}$alkylsylfonyl,
  (v) aryl,
  (vi) heteraoaryl;
Y is —NH—, —O— or —S—;
R$_1$ is:
(A) aryl or heteroaryl, each optionally and independently substituted with one or more of the following groups:
  (i) C$_{1-6}$alkyl, which is optionally substituted one or more of the following:
    (a) halogen,
    (b) NH$_2$
  (ii) C$_{1-6}$alkoxy, which is optionally substituted with halogen,
  (iii) C$_{1-6}$alkylthio, which is optionally substituted with halogen,
  (iv) C$_{1-6}$alkylsulfonyl,
  (v) cyano,
  (vi) halogen,
  (vii) hydroxyl,
  (viii) nitro,
  (ix) —COR$_{11}$, wherein R$_{11}$ is:
    (a) C$_{1-6}$alkyl,
    (b) C$_{1-6}$alkyloxy,
    (c) —OH,
    (d) —NR$_{12}$R$_{13}$, wherein R$_{12}$ and R$_{13}$ are each independently selected from:
      (I) hydrogen,
      (II) C$_{1-6}$alkyl,
      (III) aryl,
      (IV) heteroaryl,
  (x) —NR$_{14}$R$_{15}$, wherein R$_{14}$ and R$_{15}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
    or wherein R$_{14}$ and R$_{15}$ together constitute an alkylene bridge which together with the nitrogen atom between them forms a five to seven-membered ring,
  (xi) arylthio, arylsulfonyl or aryloxy, each optionally and independently substituted with one or more of the following groups:
    (a) C$_{1-6}$alkyl,
    (b) C$_{1-6}$alkoxy,
    (c) C$_{1-6}$alkylthio,
    (d) C$_{1-6}$alkylsulfonyl,
    (e) cyano,
    (f) halogen,
    (g) nitro,
    (h) —NR$_{16}$R$_{17}$, wherein R$_{16}$ and R$_{17}$ are each independently selected from:
      (I) hydrogen,
      (II) C$_{1-6}$alkyl,
      (III) C$_{1-6}$alkylcarbonyl,
      (IV) C$_{1-6}$alkylsulfonyl,
(B) C$_{3-6}$cycloalkyl which is optionally and independently substituted with one or more of the following groups:
  (i) C$_{1-6}$alkyl, which is optionally substituted with halogen,
  (ii) C$_{1-6}$alkoxy, which is optionally substituted with halogen,
  (iii) C$_{1-6}$alkylthio, which is optionally substituted with halogen,
  (iv) C$_{1-6}$alkylsulfonyl,
  (v) halogen,
  (vi) hydroxyl,
  (vii) —NR$_{18}$R$_{19}$, wherein R$_{18}$ and R$_{19}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
  (viii) —COR$_{20}$, wherein R$_{20}$ is:
    (a) C$_{1-6}$alkyl,
    (b) C$_{1-6}$alkyloxy,
    (c) —OH,
    (d) NR$_{21}$R$_{22}$, wherein R$_{21}$ and R$_{22}$ are each independently selected from:
      (I) hydrogen,
      (II) C$_{1-6}$alkyl,
(C) —COR$_{23}$, wherein R$_{23}$ is:
  (i) C$_{1-6}$alkyloxy,
  (ii) —NR$_{24}$R$_{25}$, wherein R$_{24}$ and R$_{25}$ are each independently selected from:
    (a) hydrogen,
    (b) C$_{1-6}$alkyl,
    or wherein R$_{24}$ and R$_{25}$ together constitute an alkylene bridge which together with the nitrogen atom between them forms a four to six-membered ring, wherein one of the methylene groups is optionally replaced by an oxygen, sulfur or NH group, and which ring is optionally and independently substituted with one or more of the following groups:
    (a) C$_{1-6}$alkyloxy,
    (b) C$_{1-6}$alkyl, which is optionally substituted with halogen,
    (c) hydroxyl,
    (d) halogen,
    (e) COR$_{26}$, wherein R$_{26}$ is:
      (I) C$_{1-6}$alkyloxy,
      (II) NR$_{27}$R$_{28}$, wherein R$_{27}$ and R$_{28}$ are each independently selected from:
        a. hydrogen,
        b. C$_{1-6}$alkyl,
        c. aryl,
        d. heteroaryl,
(D) is:

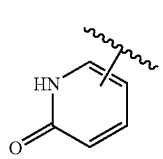

which is optionally substituted with halogen;

(E) is selected from the following:

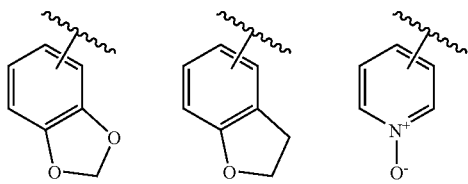

R$_2$ is selected from the following groups:
(A) CF$_3$,
(B) cyano,
(C) halogen,
(D) nitro,
(E) C$_{1-6}$alkylalkynyl,
(F) arylalkynyl which is optionally substituted with one or more of the following groups:
  (i) halogen,
  (ii) C$_{1-6}$alkyl, which is optionally substituted with halogen,
R$_3$ is selected from the following groups:

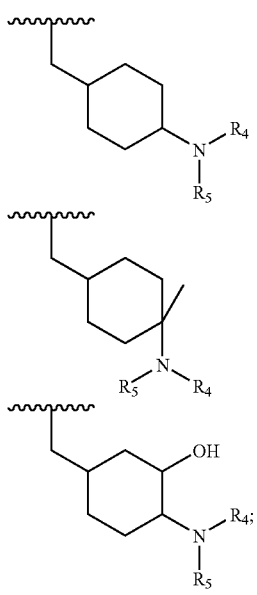

R$_4$ and R$_5$ are each independently selected from:
(A) hydrogen,
(B) C$_{1-6}$alkyl, optionally and independently substituted with one or more of the following groups:
  (i) oxo,
  (ii) C$_{3-6}$cycloalkyl,
  (iii) C$_{1-6}$alkyloxy,
  (iv) C$_{1-6}$alkylthio,
  (v) —COR$_{29}$, wherein R$_{29}$ is:
    (a) C$_{1-6}$alkyl,
    (b) C$_{1-6}$alkyloxy,
    (c) —OH,
  (vi) —CONR$_{30}$R$_{31}$, wherein R$_{30}$ and R$_{31}$ are each independently selected from:
    (a) hydrogen,
    (b) C$_{1-6}$alkyl,
    (c) aryl,
    (d) heteroaryl,
  (vii) halogen,
  (viii) hydroxyl,
  (ix) —NR$_{32}$R$_{33}$, wherein R$_{32}$ and R$_{33}$ are each independently selected from:
    (a) hydrogen,
    (b) C$_{1-6}$alkyl,
    (c) C$_{1-6}$alkylcarbonyl,
    (d) C$_{1-6}$alkylsulfonyl,
    (e) aryl,
    (f) heteroaryl,
  (x) aryl or heteroaryl, each optionally and independently substituted with one or more of the following groups:
    (a) C$_{1-6}$alkyl, which is optionally substituted with halogen,
    (b) C$_{1-6}$alkoxy, which is optionally substituted with halogen,
    (c) C$_{1-6}$alkylthio, which is optionally substituted with halogen,
    (d) C$_{1-6}$alkylsulfonyl,
    (e) cyano,
    (f) halogen,
    (g) nitro,
    (h) —NR$_{34}$R$_{35}$, wherein R$_{34}$ and R$_{35}$ are each independently selected from:
      (I) hydrogen,
      (II) C$_{1-6}$alkyl,
      (III) C$_{1-6}$alkylcarbonyl,
      (IV) C$_{1-6}$alkylsulfonyl,
    (i) —COR$_{36}$, wherein R$_{36}$ is:
      (I) C$_{1-6}$alkyl,
      (II) C$_{1-6}$alkyloxy,
      (III) —OH,
    (j) —CONR$_{37}$R$_{38}$, wherein R$_{37}$ and R$_{38}$ are each independently selected from:
      (I) hydrogen,
      (II) C$_{1-6}$alkyl,
      (III) aryl,
      (IV) heteroaryl,
(C) C$_{1-6}$alkylsulfonyl,
(D) arylsulfonyl,
(E) aryl-C$_{1-6}$alkylsulfonyl,
(F) heteroarylsulfonyl,
(G) C$_{1-6}$alkylcarbonyl,
(H) arylcarbonyl,
(I) aryl-C$_{1-6}$alkylcarbonyl,
(J) heteroarylcarbonyl,
(K) C$_{1-6}$alkylaminocarbonyl, or
(L) heteroaryl,
or wherein R$_4$ and R$_5$ together constitute an alkylene bridge which together with the nitrogen atom between them forms a four- to seven-membered ring, wherein one of the methylene groups is optionally replaced by an oxygen, sulfur or NH group, and which ring is optionally and independently substituted with one or more of the following groups:
(A) C$_{1-6}$alkyl, which is optionally substituted with halogen,
(B) C$_{1-6}$alkoxy, which is optionally substituted with halogen,
(C) C$_{1-6}$alkylthio, which is optionally substituted with halogen,
(D) C$_{1-6}$alkylsulfonyl,
(E) halogen,
(F) —NR$_{39}$R$_{40}$, wherein R$_{39}$ and R$_{40}$ are each independently selected from:
  (i) hydrogen,
  (ii) C$_{1-6}$alkyl, (iii) $C_{1-6}$alkylcarbonyl,
(iv) $C_{1-6}$alkylsulfonyl,
(v) arylcarbonyl,
(vi) arylsulfonyl
(vii) heteroarylcarbonyl,
(viii) heteroarylsulfonyl,
(G) —$COR_{41}$, wherein $R_{41}$ is:
(i) $C_{1-6}$alkyl,
(ii) $C_{1-6}$alkyloxy,
(iii) —$NR_{42}R_{43}$, wherein $R_{42}$ and $R_{43}$ are each independently selected from:
(a) hydrogen,
(b) $C_{1-6}$alkyl,
(c) aryl,
(d) heteroaryl,
(iv) hydroxyl,
(H) —$OR_{44}$, wherein $R_{44}$ is selected from:
(i) hydrogen,
(ii) $C_{1-6}$alkylcarbonyl,
(iii) $C_{1-6}$alkylsulfonyl
(I) oxo,
or wherein $NR_4R_5$ constitutes a 5-membered heteroaryl ring containing a total of 2 nitrogen hetero atoms in the ring;
or a tautomer or pharmaceutically acceptable salt thereof or a corresponding compound having at least one amine group protected by an amino-protecting group.

2. A compound of formula (I) according to claim 1, wherein:
X is $C_{1-3}$alkyl, optionally substituted with oxo,
Y is —NH— or —O—;
$R_1$ is:
(A) aryl or heteroaryl, each optionally and independently substituted with one or more of the following groups:
(i) $C_{1-3}$alkyl, which is optionally and independently substituted with fluorine,
(ii) $C_{1-3}$alkoxy, which is optionally and independently substituted with fluorine,
(iii) $C_{1-3}$alkylthio, which is optionally and independently substituted with fluorine,
(iv) arylthio, which is optionally substituted with —$NH_2$,
(v) halogen,
(vi) hydroxyl,
(vii) $C_{1-3}$alkylsulfonyl,
(viii) $CONH_2$,
(ix) —$NR_{14}R_{15}$, wherein $R_{14}$ and $R_{15}$ are each independently selected from:
(e) hydrogen,
(f) $C_{1-6}$alkyl
(B) $C_{1-6}$alkylcarbonyl,
(C) $C_{1-6}$alkylsulfonyl,
or wherein $R_{14}$ and $R_{15}$ together constitute an alkylene bridge which together with the nitrogen atom between them forms a five to seven-membered ring,
(B) cyclohexyl, which is optionally and independently substituted with:
(i) $C_{1-3}$alkyl,
(ii) hydroxyl;
(C) —$COR_{23}$, wherein $R_{23}$ is:
(i) —$NR_{24}R_{25}$, wherein $R_{24}$ and $R_{25}$ are each independently selected from:
(a) $C_{1-6}$alkyl;
or wherein $R_{24}$ and $R_{25}$ together constitute a alkylene bridge which together with the nitrogen atom between them forms a five to six-membered ring, wherein one of the methylene groups is optionally replaced by an oxygen atom and which ring is optionally and independently substituted with one or more of the following groups:
(i) hydroxyl,
(ii) —$CONH_2$,
(D) is:

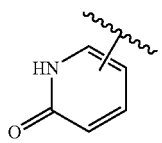

which is optionally substituted with halogen;
(E) is selected from the following:

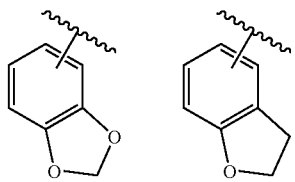

$R_2$ is:
(A) $CF_3$,
(B) cyano,
(C) halogen, or
(D) nitro,
$R_3$ is selected from the following:

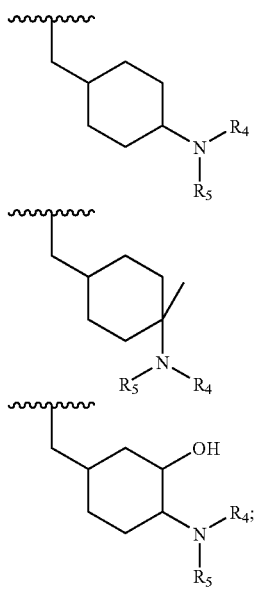

$R_4$ and $R_5$ are each independently selected from:
(A) hydrogen,
(B) $C_{1-6}$alkyl, which is optionally and independently substituted with one or more of the following groups:
(i) oxo,
(ii) $C_{3-5}$cycloalkyl, (iii) aryl or heteroaryl, each of which is optionally and independently substituted with one or more of the following groups:
(g) $C_{1-3}$alkyl which is optionally substituted with fluorine,
(h) —$CO_2H$
(i) halogen,
(iv) $NH_2$
(v) hydroxyl,
(vi) —$CONH_2$,
(vii) fluorine,
(viii) $NHCOCH_3$
or $R_4$ and $R_5$ together constitute an alkylene bridge which together with the nitrogen atom between them forms a four- to seven-membered ring, wherein one of the methylene groups is optionally replaced by an NH or oxygen atom and which ring is optionally and independently substituted with one or more of the following groups:
(A) —$CONH_2$,
(B) $NR_{39}R_{40}$ wherein $R_{39}$ and $R_{40}$ are optionally and independently selected from:
(i) $C_{1-5}$alkylcarbonyl
(ii) $C_{1-5}$alkylsulfonyl
(iii) arylcarbonyl
(iv) arylsulfonyl
(C) —$OR_{44}$, wherein $R_{44}$ is selected from:
(ix) hydrogen,
(x) $C_{1-5}$alkylcarbonyl
(D) oxo, or
(E) fluorine
or wherein $NR_4R_5$ constitute a 5-membered heteroaryl ring containing a total of 2 nitrogen hetero atoms in the ring,
or a tautomer or pharmaceutically acceptable salt thereof or a corresponding compound having at least one amine group protected by an amino-protecting group.

3. A compound of formula (I) according to claim 1, wherein:
X is —$CH_2$—, —$CH_2CH_2$— or —$CH_2CO$—,
Y is —NH— or —O—;
$R_1$ is:
(A) phenyl, pyridyl, naphthyl, quinolinyl or benzothienyl, each of which is optionally and independently substituted with one or more of the following groups:
(i) $C_{1-3}$alkyl, which is optionally substituted with fluorine,
(ii) $C_{1-3}$alkoxy, which is optionally substituted with fluorine,
(iii) methylthio, which is optionally substituted with fluorine,
(iv) arylthio, optionally substituted with $NH_2$,
(v) F, Cl or Br,
(vi) hydroxyl,
(vii) $NH_2$ or $N(CH_3)_2$,
(viii) $SO_2CH_3$
(B) cyclohexyl, optionally substituted with hydroxyl,
$R_2$ is:
(A) $CF_3$,
(B) cyano,
(C) F, Cl, Br or
(D) nitro, $R_3$ is:

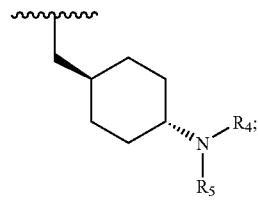

$R_4$, $R_5$ are each independently selected from:
(A) hydrogen,
(B) $C_{1-4}$alkyl, which is optionally and independently substituted with one or more of the following groups:
(i) oxo,
(ii) cyclopropyl,
(iii) aryl or heteroayl selected from phenyl, pyridyl, pyrimidyl, pyrazolyl and oxazolyl, each of which is optionally and independently substituted with one or more of the following groups:
(j) $C_{1-2}$alkyl,
(k) fluorine or chlorine,
(iv) —$CONH_2$
(v) hydroxyl,
(vi) fluorine,
(vii) $NHCOCH_3$
or $R_4$ and $R_5$ together constitute an alkylene bridge which together with the nitrogen atom between them forms a four- to seven-membered ring, wherein one of the methylene groups is optionally replaced by an NH, and which ring is optionally and independently substituted with one or more of the following groups:
(A) $CONH_2$,
(B) hydroxyl,
(C) $C_{1-5}$alkylcarbonyloxy,
(D) oxo,
(E) fluorine,
(F) $NR_{39}R_{40}$ wherein $R_{39}$ and $R_{40}$ are optionally and independently selected from:
(i) hydrogen
(ii) $C_{1-5}$alkylcarbonyl
(iii) $C_{1-5}$alkylsulfonyl
(iv) Phenylcarbonyl, or
(v) phenylsulfonyl,
or a tautomer or pharmaceutically acceptable salt thereof or a corresponding compound having at least one amine group protected by an amino-protecting group.

4. A compound of formula (I) according to claim 1, wherein:
X is —$CH_2$—,
Y is —NH—,
$R_1$ is:
(A) phenyl or pyridyl optionally and independently substituted with one or more of the following groups:
(i) methyl,
(ii) $CF_3$,
(iii) $OCF_3$,
(iv) $OCF_2H$
(v) $OCH_3$,
(vi) $OCH(CH_3)_2$
(vii) $SCF_3$,
(viii) arylthio substituted with $NH_2$,
(ix) F or Cl, (x) N(CH$_3$)$_2$,
(xi) OCH$_2$CF$_3$
(xii) SO$_2$CH$_3$
(B) naphthyl,
R$_2$ is:
(A) cyano,
(B) Cl, or
(C) nitro;
R$_3$ is:

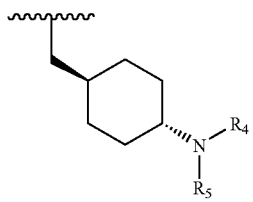

R$_4$ and R$_5$ are each independently selected from:
(A) hydrogen,
(B) C$_{1-3}$alkyl, optionally substituted with one or more of the following groups:
(i) hydroxyl,
(ii) pyridyl,
(iii) 1-methyl-1H-pyrazole,
(iv) 1,5-dimethyl-1H-pyrazole,
(v) —CONH$_2$,
or R$_4$ and R$_5$ together constitute an alkylene bridge which together with the nitrogen atom between them forms a four or five-membered ring, each optionally and independently substituted with one or more of the following:
(A) hydroxyl,
(B) amino
(C) fluorine
(D) oxo
(E) —NHSO$_2$CH$_3$
(F) —NHCOCH$_3$
or a tautomer or pharmaceutically acceptable salt thereof or a corresponding compound having at least one amine group protected by an amino-protecting group.

5. A compound of formula (I) according to claim 1, wherein:
X is —CH$_2$—,
Y is —NH—,
R$_1$ is:
(A) phenyl, optionally and independently substituted with one or more of the following groups:
(i) methyl,
(ii) CF$_3$,
(iii) OCF$_3$,
(iv) OCH$_3$,
(v) SCF$_3$,
(vi) arylthio substituted with NH$_2$,
(vii) F or Cl;
(B) naphthyl,
R$_2$ is:
(A) cyano,
(B) Cl, or
(C) nitro;

R$_3$ is:

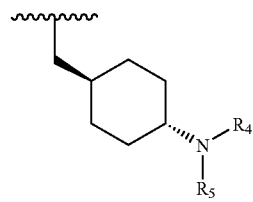

R$_4$ and R$_5$ are each independently selected from:
(A) hydrogen,
(B) C$_{1-2}$alkyl, optionally substituted with one or more of the following groups:
(i) hydroxyl,
(ii) pyridyl,
(iii) 1,5-dimethyl-1H-pyrazole,
(iv) CONH$_2$,
or R$_4$ and R$_5$ together constitute an alkylene bridge which together with the nitrogen atom between them forms a four or five-membered ring, each optionally and independently substituted with one or more hydroxyl or oxo;
or a tautomer or pharmaceutically acceptable salt thereof or a corresponding compound having at least one amine group protected by an amino-protecting group.

6. A compound of the formula (I) of claim 1, which is one of the following compounds:
N$^4$-[(trans-4-aminocyclohexyl)methyl]-N$^2$-[2-fluoro-3-(trifluoromethl)benzyl]-5-nitropyrimidine-2,4-diamine;
N$^4$-[(trans-4-aminocyclohexyl)methyl]-N$^2$-[(2-chloro-6-fluoro-3-methylbenzyl)-5-nitropyrimidine-2,4-diamine;
N$^4$-[(trans-4-aminocyclohexyl)methyl]-N$^2$-(1-naphthyl-methyl)-5-nitropyrimidine-2,4-diamine;
N$^4$-[(trans-4-aminocyclohexyl)methyl]-5-nitro-N$^2$-{2-[(trifluoromethyl)thio]benzyl}pyrimidine-2,4-diamine;
N$^4$-[(trans-4-aminocyclohexyl)methyl]-5-chloro-N$^2$-[2-(trifluoromethoxy)benzyl]pyrimidine-2,4-diamine;
1-(trans-4-{[(5-nitro-2-{(2-(trifluoromethoxy)benzyl]amino}pyrimidin-4-yl)amino]methyl}-cyclohexyl)azetidin-3-one;
N$^4$-{[trans-4-(3-aminoazetidin-1-yl)cyclohexyl]methyl}-5-nitro-N$^2$-[2-(trifluoromethoxy)benzyl]-pyrimidine-2,4-diamine;
N-[1-(trans-4-{[(5-nitro-2-{[2-(trifluoromethoxy)benzyl]amino}pyrimidin-4-yl)amino]methyl}-cyclohexyl)azetidin-3-yl]methanesulfonamide;
N-[1-(trans-4-{[(5-nitro-2-{[2-(trifluoromethoxy)benzxyl]amino}pyrimidin-4-yl)amino]methyl}-cyclohexyl)azetidin-3-yl]acetamide;
N$^4$-[(trans-4-aminocyclohexyl)methyl]-5-nitro-N$^2$-[2-(trifluoromethoxy)benzyl]pyrimidine-2,4-diamine;
4-{[(trans-4-aminocyclohexyl)methyl]amino}-2-{[2-(trifluoromethoxy)benzyl]amino}pyrimidine-5-carbonitrile;
N$^4$-[(trans-4-aminocyclohexyl)methyl]-N$^2$-{2-[(2-aminopheny)thio]benzyl}-5-nitropyrimidine-2,4-diamine;
5-nitro-N$^4$-[(trans-4-pyrrolidin-1-ylcyclohexyl)methyl}-N$^2$-(trifluoromethoxy)benzyl}pyrimidine-2,4-diamine;
1-(trans-4-{[(5-nitro-2-{[2-(trifluoromethoxy)benzyl]amino}pyrimidin-4-yl)amino]methyl}-cyclohexyl)pyrrolidin-3-ol;

$N^4$-[(trans-4-azetidin-1-ylcyclohexyl)methyl}-5-nitro-$N^2$-[2-(trifluoromethoxy)benzyl]pyrimidine-2,4-diamine;

$N^4$-{[trans-4-(dimethylamino)cyclohexyl]methyl}-5-nitro-$N^2$-[2-(trifluoromethoxy)benzyl]pyrimidine-2,4-diamine;

4-({[[trans-4-(dimethylamino)cyclohexyl)]methyl}amino)-2-{[2-(trifluoromethoxy)benzyl]amino}pyrimidine-5-carbonitrile;

5-nitro-$N^4$-({trans-4-[(pyridin-3-ylmethyl)amino]cyclohexyl}methyl)-$N^2$-[2-(trifluoromethoxy)benzyl]pyrimidine-2,4-diamine;

5-nitro-$N^4$-({trans-4-[(pyridin-4-ylmethyl)amino]cyclohexyl}methyl)-$N^2$-[2-(trifluoromethoxy)benzyl]pyrimidine-2,4-diamine;

2-[(trans-4-{[(5-nitro-2-{[2-(trifluoromethoxy)benzyl]amino}pyrimidin-4-yl)amino]methyl}-cyclohexyl)amino]ethanol;

1-(trans-4-{[(5-nitro-2-{[2(trifluoromethoxy)benzyl]amino}pyrimidin-4-yl)amino]methyl}-cyclohexyl)azetidin-3-ol;

5-nitro-$N^4$-({trans-4-[(pyridin-2-ylmethyl)amino]cyclohexyl}methyl)-$N^2$-[2-(trifluoromethoxy)benzyl]pyrimidine-2,4-diamine;

$N^2$-(trans-4-{[(5-nitro-2-{[2-(trifluoromethoxy)benzyl]amino}pyrimidin-4-yl)amino]methyl}-cyclohexyl)glycinamide;

$N^4$-[(trans-4-{[(1,5-dimethyl-1H-pyrazol-4-yl)methyl]amino}cyclohexyl)methyl]-5-nitro-$N^2$-[2-(trifluoromethoxy)benzyl]pyrimidine-2,4-diamine;

$N^4$-[(trans-4-{[(1-methyl-1H-pyrazol-4-yl)methyl]amino}cyclohexyl)methyl]-5-nitro-$N^2$-[2-(trifluoromethoxy)benzyl]pyrimidine-2,4-dlamine;

$N^4$-[(trans-4-aminocyclohexyl)methyl]-$N^2$-[(2-isopropoxypyridin-3-yl)methyl]-5-nitropyrimidine-2,4-diamine;

$N^4$-[trans-4-aminocyclohexyL)methyl]-5-nitro-$N^2$-{[2-(2,2,2-trifluoroethoxy)pyridin-3-yl]methyl}pyrimidine-2,4-diamine; $N^4$-[(trans-4-aminocyclohexyl)methyl]-$N^2$-[(5-fluoro-2-methoxypyridin-3-yl)methyl]-5-nitropyrimidine-2,4-diamine;

$N^4$-[(trans-4-aminocyclohexyl)methyl]-$N^2$-[2-(difluoromethoxy)benzyl]-5-nitropyrimidine-2,4-diamine;

$N^4$-[(trans-4-aminocyclohexyl)methyl]-$N^2$-(2-Chlorobenzyl)-5-nitropyrimidine-2,4-diamine;

$N^4$-[(trans-4-azetidin-1-ylcyclohexyl)methyl]-5-nitro-$N^2$-{[2-(2,2,2-trifluoroethoxy)pyridin-3-yl]methyl}pyrimidine-2,4-diamine;

$N^4$-{[(trans-4-(3-fluoroazetidin-1-yl)cyclohexyl]methyl}-5-nitro-$N^2$-[2-(trifluoromethoxy)benzyl]pyrimidine-2,4-diamine;

$N^4$-{[trans-4-(ethylamino)cyclohexyl]methyl}-5-nitro-$N^2$-[2-(trifluoromethoxy)benzyl]pyrimidine-2,4-diamine;

$N^4$-[(trans-4-aminocyclohexyl)methyl]$N^2$[2-chloro-3-(dimethylamino)benzyl]-5-nitropyrimidine-2,4-diamine;

1-(trans-4-{[(2-{[2-chloro-3-(dimethylamino)benzyl]amino}-5-nitropyrimidin-4-yl)amino]methyl}cyclohexyl)azetidin-3-ol;

$N^4$-[(trans-4-aminocyclohexyl)methyl[-$N^2$-(5-chloro-2-methoxybenzyl)-5-nitropyrimidine-2,4-diamine;

$N^4$-[(trans-4-aminocyclohexyl)methyl]-$N^2$-(2-methocybenzyl)-5-nitropyrimidine-2,4-diamine;

$N^4$-[(trans-4-aminocyclohexyl)methyl]-$N^2$-[5 -chloro-2-(trifluoromethoxy)benzyl]-5-nitropyrimidine-2,4-diamine;

$N^2$-[5-chloro-2-(trifluoromethoxy)benzyl]-5-nitro-$N^4$-[(trans-4-pyrrolidin-1ylcyclohexyl)-methyl]pyrimidine-2,4-diamine;

$N^4$-[(trans-4-aminocyclohexyl)methyl]-$N^2$-[(2-methoxypyridin-3-yl)methyl]-5-nitropyrimidine -2,4-diamine;

$N^4$-[(trans-4-aminocyclohexyl)methyl]-5-nitro-$N^2$-{[4-(trifluoromethyl)pyridin-3-yl]methyl}pyrimidine-2,4-diamine;

$N^4$-[(trans-4-aminocyclohexyl)methyl]-$N^2$-[5-chloro-2-(methylsulfonyl)benzyl]-5-nitropyrimidine-2,4-diamine;

$N^4$-[(trans-4-azetidin-1-ylcyclohexyl)methyl]-$N^2$4[(4-chloropyridin-3-yl)methyl]-5-nitropyrimidine-2,4-diamine;

$N^4$-[(trans-4-azetidin-1-ylcyclohexyl)methyl]-5-nitro-$N^2$-{[4-(trifluoromethyl)pyridin-3-yl]methyl}pyrimidine-2,4-diamine;

1-[(trans-4-({[5-nitro-2-({[4-(trifluoromethyl)pyridin-3-yl]methyl}amino)pyrimidin-4-yl]amino}methyl)cyclohexyl]azetidin-3-ol;

(2R)-1-[(trans-4-{[(5-nitro-2-{[2-(trifluoromethoxy)benzyl]amino}pyrimidin-4-yl)amino]methyl}cyclohexyl)amino]propan-2-ol;

(2S)-1-[(trans-4-{[(5-nitro-2-{[2-(trifluoromethoxy)benzyl]amino}pyrimidin-4-yl)amino]methyl}]cyclohexyl)amino]propan-2-ol;

3-[(trans-4-{[(5-nitro-2-{[2-(trifluoromethoxy)benzyl]amino}pyrimidin-4-yl)amino]methyl}cyclohexyl)amino]propan-1-ol;

(2R)-2-[(trans-4-{[(5-nitro-2-{[2-(trifluoromethoxy)benzyl]amino}pyrimidin-4-yl)amino]methyl}cyclohexyl)amino]propan-1-ol; or (2S)-2-[(trans-4-{[(5-nitro-2-{[2-(trifluoromethoxy)benzyl]amino}pyrimidin-4-yl)amino]methyl}cyclohexyl)amino]propan-1-ol.

7. A compound of the formula (I) of claim 1, which is one of the following compounds:

2-[(4-{[(trans-4-aminocyclohexyl)methyl]amino}-5-nitropyrimidin-2-yl)amino[-1- phenylethanone $N^4$-[(trans-4-aminocyclohexyl)methyl]-5-nitro-$N^2$-(2-phenylethyl)pyrimidine-2,4-diamine $N^4$-[(trans-4-aminocyclohexyl)methyl]-$N^2$-[2-(3-chlorophenyl)ethyl]-5 -nitropyrimidine- 2,4-diamine $N^4$-[(trans-4-aminocyclohexyl)methyl]-$N^2$-[2-fluoro-3-(trifluoromethyl)benzyl]-5- nitropyrimidine-2,4-diamine $N^4$-[(trans-4-aminocyclohexyl)methyl]-$N^2$-(2-chloro-6-fluoro-3-methylbenzyl)-5- nitropyrimidine-2,4-diamine $N^4$-[(trans-4-aminocyclohexyl)methyl]-$N^2$ -(1 -naphthylmethyl)-5-nitropyrimidine-2,4- diamine $N^4$-[(trans-4-aminocyclohexyl)methyl]-5-nitro-$N^2$-{2-[(trifluoromethyl)thio]benzyl}pyrimidine-2,4-diamine 4-{2-[(4-{[(trans-4-aminocyclohexyl)methyl]amino}-5-nitropyrimidin-2- yl)amino]ethyl}phenol $N^4$-[(trans-4-aminocyclohexyl)methyl]-$N^2$-(3-bromo-2-methylbenzyl)-5 -nitropyrimidine- 2,4-diamine N-{trans-4-[({2-[(3-bromo-2-methylbenzyl)amino]-5-nitropyrimidin-4- yl}amino)methyl]cyclohexyl}acetamide N-{trans-4-[({2-[(3-bromo-2-methylbenzyl)amino]-5-nitropyrimidin-4- yl}amino)methyl]cyclohexyl }-2,2,2-trifluoroacetamide N-{trans-4-[({2-[(3-bromo-2-methylbenzyl)amino]-5-nitropyrimidin-4-yl}amino)methyl]cyclohexyl}methanesulfonamide N-[(cis-4-aminocyclohexyl)methyl]-5-chloro-$N^2$-[2-(trifluoromethoxy)benzyl]pyrimidine-2,4-diamine N4-[(trans-4-aminocyclohexyl)methyl]-5-fluoro-$N^2$-[2-(trifluoromethoxy)benzyl]pyrimidine-2,4-diamine $N^4$-[(trans-4-aminocyclohexyl)methyl]-5-chloro-$N^2$-[2-(trifluoromethoxy)benzyl]pyrimidine-2,4-diamine 5-fluoro-$N^4$-[(trans-4-pyrrolidin-1-ylcyclohexyl)methyl]-$N^2$-[2-(trifluoromethoxy)benzyl]pyrimidine-2,4-diamine 5-chloro-$N^4$-[(trans-4-pyrrolidin-1-ylcyclohexyl)methyl]-$N^2$-[2-(trifluoromethoxy)benzyl]pyrimidine-2,4-diamine $N^4$-[(trans-4-azetidin-1-ylcyclohexyl)methyl]-5-chloro-$N^2$-[2-(trifluoromethoxy)benzyl]pyrimidine-2,4-diamine $N^4$-[(trans-4-azetidin-1-ylcyclohexyl)methyl]-5-fluoro-$N^2$-[2-(trifluoromethoxy)benzyl]pyrimidine-2,4-diamine 1-(trans-4-{[(5-chloro-2-{[2-(trifluoromethoxy)benzyl]amino}pyrimidin-4-yl)amino]methyl}cyclohexyl)azetidin-3-ol 1-(trans-4-{[(5-fluoro-2-{[2-(trifluoromethoxy)benzyl]amino}pyrimidin-4-yl)amino]methyl}cyclohexyl)azetidin-3-ol 1-(trans-4-{[(5-nitro-2-{[2-(trifluoromethoxy)benzyl]amino}pyrimidin-4-yl)amino]methyl}cyclohexyl)azetidin-3-one 1-(trans-4-{[(5-nitro-2-{[2-(trifluoromethoxy)benzyl]amino}pyrimidin-4-yl)amino]methyl}cyclohexyl)azetidin-3-yl acetate $N^4$-{[trans-4-(3-aminoazetidin-1-yl)cyclohexyl]methyl}-5-nitro-$N^2$-[2-(trifluoromethoxy)benzyl]pyrimidine-2,4-diamine N-[1-(trans-4-{[(5-nitro-2-{[2-(trifluoromethoxy)benzyl]amino}pyrimidin-4-yl)amino]methyl}cyclohexyl)azetidin-3-yl]methanesulfonamide N-[1-(trans-4-{[(5-nitro-2-{[2-(trifluoromethoxy)benzyl]amino}pyrimidin-4-yl)amino]methyl}cyclohexyl)azetidin-3-yl]acetamide N-[1-(trans-4-{[(5-nitro-2-{[2-(trifluoromethoxy)benzyl]amino}pyrimidin-4-yl)amino]methyl}cyclohexyl)azetidin-3-yl]benzamide N-[1-(trans-4-{[(5-nitro-2-{[2-(trifluoromethoxy)benzyl]amino}pyrimidin-4-yl)amino]methyl}cyclohexyl)azetidin-3-yl]benzenesulfonamide $N^4$-[(trans-4-aminocyclohexyl)methyl]-5-nitro-$N^2$-[(1-oxidopyridin-2-yl)methyl]pyrimidine-2,4-diamine $N^4$-[(trans-4-aminocyclohexyl)methyl]-5-nitro-$N^2$-[(1-oxidopyridin-3-yl)methyl]pyrimidine-2,4-diamine $N^4$-[(trans-4-aminocyclohexyl)methyl]-5-bromo-$N^2$-[2-(trifluoromethoxy)-benzyl]pyrimidine-2,4-diamine $N^4$-[(trans-4-aminocyclohexyl)methyl]-5-(phenylethynyl)-$N^2$-[2-(trifluoromethoxy)benzyl]pyrimidine-2,4-diamine $N^4$-[(trans-4-aminocyclohexyl)methyl]-5-pent-1-yn-1-yl-$N^2$-[2-(trifluoromethoxy)benzyl]pyrimidine-2,4-diamine $N^4$-[(trans-4-aminocyclohexyl)methyl]-5-nitro-$N^2$-(3-piperidin-1-ylbenzyl)pyrimidine-2,4-diamine $N^4$-[(trans-4-aminocyclohexyl)methyl]-5-nitro-N2-(3-pyrrolidin-1-ylbenzyl)pyrimidine-2,4-diamine $N^4$-[(trans-4-aminocyclohexyl)methyl]-$N^2$-(3-azepan-1-ylbenzyl)-5-nitropyrimidine-2,4-diamine N-{1-[trans-4-({[5-nitro-2-({[4-(trifluoromethyl)pyridin-3-yl]methyl}amino)pyrimidin-4-yl]amino}methyl)cyclohexyl]azetidin-3-yl}methanesulfonamide $N^4$-[(trans-4-aminocyclohexyl)methyl]-$N^2$-[2-(trifluoromethoxy)benzyl]-5-{[3-(trifluoromethyl)phenyl]ethynyl}pyrimidine-2,4-diamine $N^4$-[(trans-4-aminocyclohexyl)methyl]-5-[(2-fluorophenyl)ethynyl]-N2-[2-(trifluoromethoxy)benzyl]pyrimidine-2,4-diamine $N^4$-[(trans-4-aminocyclohexyl)methyl]-$N^2$-[2-(trifluoromethoxy)benzyl]-5-{[2-(trifluoromethyl)phenyl]ethynyl}pyrimidine-2,4-diamine $N^4$-[(trans-4-aminocyclohexyl)methyl]-5-[(3-methylphenyl)ethynyl]-$N^2$-[2-(trifluoromethoxy)benzyl]pyrimidine-2,4-diamine $N^4$-[(trans-4-aminocyclohexyl)methyl]-5-[(4-methylphenyl)ethynyl]-$N^2$-[2-(trifluoromethoxy)benzyl]pyrimidine-2,4-diamine $N^4$-[(trans-4-aminocyclohexyl)methyl]-$N^2$-(cyclohexylmethyl)-5-nitropyrimidine-2,4-diamine $N^4$-[(trans-4-aminocyclohexyl)methyl]-5-nitro-$N^2$-[2-(trifluoromethoxy)benzyl]pyrimidine-2,4-diamine $N^4$-[(cis-4-aminocyclohexyl)methyl]-5-nitro-$N^2$-[2-(trifluoromethoxy)benzyl]pyrimidine-2,4-diamine 4-{[(trans-4-aminocyclohexyl)methyl]amino}-2-{[2-(trifluoromethoxy)benzyl]amino}pyrimidine-5-carbonitrile $N^4$-[(trans-4-aminocyclohexyl)methyl]-$N^2$-[2-(trifluoromethoxy)benzyl]-5-(trifluoromethyl)pyrimidine-2,4-diamine $N^4$-[(trans-4-aminocyclohexyl)methyl]-$N^2$-{2-[(2-aminophenyl)thio]benzyl}-5-nitropyrimidine-2,4-diamine 5-nitro-$N^4$-[(trans-4-pynolidin-1-ylcyclohexyl)methyl]-$N^2$-[2-(trifluoromethoxy)benzyl]pyrimidine-2,4-diamine 1-(trans-4-{[(5-nitro-2-{[2-(trifluoromethoxy)benzyl]amino}pyrimidin-4-yl)amino]methyl}cyclohexyl)pymolidin-3-ol $N^4$-[(trans-4-morpholin-4-ylcyclohexyl)methyl]-5-nitro-$N^2$-[2-(trifluoromethoxy)benzyl]pyrimidine-2,4-diamine 5-nitro-$N^4$-[(trans-4-piperidin-1-ylcyclohexyl)methyl]-$N^2$-[2-(trifluoromethoxy)benzyl]pyrimidine-2,4-diamine $N^4$-[(trans-4-azetidin-1-ylcyclohexyl)methyl]-5-nitro-$N^2$-[2-(trifluoromethoxy)benzyl]pyrimidine-2,4-diamine $N^4$-[(trans-4-pynolidin-1-ylcyclohexyl)methyl]-$N^2$-[2-(trifluoromethoxy)benzyl]-5-(trifluoromethyl)pyrimidine-2,4-diamine 4-{[(trans-4-pynolidin-1-ylcyclohexyl)methyl]amino}-2-{[2-(trifluoromethoxy)benzyl]amino}pyrimidine-5-carbonitrile $N^4$-{[trans-4-(dimethylamino)cyclohexyl]methyl}-5-nitro-$N^2$-[2-(trifluoromethoxy)benzyl]pyrimidine-2,4-diamine 4-({[trans-4-(dimethylamino)cyclohexyl]methyl}amino)-2-{[2-(trifluoromethoxy)benzyl]amino}pyrimidine-5-carbonitrile 4-{[(trans-4-azetidin-1-ylcyclohexyl)methyl]amino1-2-{[2-(trifluoromethoxy)benzyl]amino}pyrimidine-5-carbonitrile $N^4$-{[trans-4-(dibenzylamino)cyclohexyl]methyl1-5-nitro-$N^2$-[2-(trifluoromethoxy)benzyl]pyrimidine-2,4-diamine N$^4$-{[trans-4-(benzylamino)cyclohexyl]methyl}-5-nitro-N$^2$-[2-(trifluoromethoxy)benzyl]pyrimidine-2,4-diamine 5-nitro-N$^4$-({trans-4-[(pyridin-3-ylmethyl)amino]cyclohexyl}methyl)-N$^2$-[2-(trifluoromethoxy)benzyl]pyrimidine-2,4-diamine N$^4$-({trans-4-[bis(pyridin-2-ylmethyl)amino]cyclohexyl}methyl)-5-nitro-N$^2$-[2-(trifluoromethoxy)benzyl]pyrimidine-2,4-diamine 5-nitro-N$^4$-({trans-4-[(pyridin-4-ylmethyl)amino]cyclohexyl}methyl)-N$^2$-[2-(trifluoromethoxy)benzyl]pyrimidine-2,4-diamine 4-({[trans-4-(3-hydroxyazetidin-1-yl)cyclohexyl]methyl}amino)-2-{[2-(trifluoromethoxy)benzyl]amino}pyrimidine-5-carbonitrile 4-({[trans-4-(3-hydroxypyrrolidin-1-yl)cyclohexyl]methyl}amino)-2-{[2-(trifluoromethoxy)benzyl]amino}pyrimidine-5-carbonitrile 4-[({trans-4-[(pyridin-2-ylmethyl)amino]cyclohexyl}methyl)amino]-2-{[2-(trifluoromethoxy)benzyl]amino}pyrimidine-5-carbonitrile 2,2'-[(trans-4-{[(5-nitro-2-{[2-(trifluoromethoxy)benzyl]amino}pyrimidin-4-yl)amino]methyl}cyclohexyl)imino]diethanol 2-[(trans-4-{[(5-nitro-2-{[2-(trifluoromethoxy)benzyl]amino}pyrimidin-4-yl)amino]methyl}cyclohexyl)amino]ethanol 4-[({trans-4-[(2,2-dimethylpropyl)amino]cyclohexyl}methyl)amino]-2-{[2-(trifluoromethoxy)benzyl]amino}pyrimidine-5-carbonitrile 1-(trans-4-{[(5-nitro-2-{[2-(trifluoromethoxy)benzyl]amino}pyrimidin-4-yl)amino]methyl}cyclohexyl)azetidin-3-ol 5-nitro-N$^4$-({trans-4-[(quinolin-3-ylmethyl)amino]cyclohexyl}methyl)-N2-112-(trifluoromethoxy)benzyl]pyrimidine-2,4-diamine 5-nitro-N$^4$-({trans-4-[(pyridin-2-ylmethyl)amino]cyclohexyl}methyl)-N$^2$-[2-(trifluoromethoxy)benzyl]pyrimidine-2,4-diamine N$^4$-({trans-4-[(2-fluorobenzyl)amino]cyclohexyl}methyl)-5-nitro-N$^2$-[2-(trifluoromethoxy)benzyl]pyrimidine-2,4-diamine N$^4$-({trans-4-[(3-fluorobenzyl)amino]cyclohexyl}methyl)-5-nitro-N$^2$-[2-(trifluoromethoxy)benzyl]pyrimidine-2,4-diamine N$^4$-({trans-4-[(4-fluorobenzyl)amino]cyclohexyl}methyl)-5-nitro-N$^2$-[2-(trifluoromethoxy)benzyl]pyrimidine-2,4-diamine 5-nitro-N$^4$-({trans-4-[(quinolin-4-ylmethyl)amino]cyclohexyl}methyl)-N$^2$-[2-(trifluoromethoxy)benzyl]pyrimidine-2,4-diamine N$^2$-(trans-4-{[5-cyano-2-{[2-(trifluoromethoxy)benzyl]amino}pyrimidin-4-yl)amino]methyl}cyclohexyl)glycinamide N$^2$-(2-amino-2-oxoethyl)-N$^2$-(trans-4-{[(5-cyano-2-{[2-(trifluoromethoxy)benzyl]amino}pyrimidin-4-yl)amino]methyl}cyclohexyl)glycinamide 4-({[trans-4-(isopropylamino)cyclohexyl]methyl}amino)-2-{[2-(trifluoromethoxy)benzyl]amino}pyrimidine-5-carbonitrile 4-[({trans-4-[(pyridin-4-ylmethyl)amino]cyclohexyl}methyl)amino]-2-{[2-(trifluoromethoxy)benzyl]amino}-pyrimidine-5-carbonitrile 4-[({trans-4-[(cyclopropylmethyl)amino]cyclohexyl}methyl)amino]-2-{[2-(trifluoromethoxy)benzyl]amino}-pyrimidine-5-carbonitrile 4-[({trans-4-[(pyridin-3-ylmethyl)amino]cyclohexyl}methyl)amino]-2-{[2-(trifluoromethoxy)benzyl]amino}-pyrimidine-5-carbonitrile N$^4$-[(trans-4-{[(4-chloro-1-methyl-1H-pyrazol-3-yl)methyl]amino}cyclohexyl)methyl]-5-nitro-N$^2$-[2-(trifluoromethoxy)benzyl]pyrimidine-2,4-diamine N$^4$-[(trans-4-{[(3,5-dichloropyridin-4-yl)methyl]amino}cyclohexyl)methyl]-5-nitro-N$^2$-[2-(trifluoromethoxy)benzyl]pyrimidine-2,4-diamine 5-nitro-N$^2$-[2-(trifluoromethoxy)benzyl]-N$^4$-{[trans-4-({[6-(trifluoromethyl)pyridin-3-yl]methyl}amino)cyclohexyl]-methyl}pyrimidine-2,4-diamine N$^2$-(trans-4-{[(5-nitro-2-{[2-(trifluoromethoxy)benzyl]amino}pyrimidin-4-yl)amino]methyl}cyclohexyl)glycinamide N$^4$-[(trans-4-{[(3,5-dimethylisoxazol-4-yl)methyl]amino}cyclohexyl)methyl]-5-nitro-N$^2$-[2-(trifluoromethoxy)benzyl]pyrimidine-2,4-diamine N$^4$-[(trans-4-{[(1,5-dimethyl-1H-pyrazol-4-yl)methyl]amino}cyclohexyl)methyl]-5-nitro-N$^2$-[2-(trifluoromethoxy)benzyl]pyrimidine-2,4-diamine 5-nitro-N$^4$-({trans-4-[(pyrimidin-5-ylmethyl)amino]cyclohexyl}methyl)-N$^2$-[2-(trifluoromethoxy)benzyl]pyrimidine-2,4-diamine N$^4$-[(trans-4-{[(1,2-diethyl-1H-imidazol-4-yl)methyl]amino}cyclohexyl)methyl]-5-nitro-N$^2$-[2-(trifluoromethoxy)benzyl]pyrimidine-2,4-diamine N-(trans-4-{[(5-nitro-2-{[2-(trifluoromethoxy)benzyl]amino}pyrimidin-4-yl)amino]methyl}cyclohexyl)-1-phenylmethanesulfonamide 5-nitro-N4-({trans-4-[2-phenylethyl)amino]cyclohexyl}-methyl)-N2-[2-(trifluoromethoxy)benzyl]pyrimidine-2,4-diamine 2-hydroxy-N-(trans-4-{[(5-nitro-2-{[2-(trifluoromethoxy)-benzyl]amino}pyrimidin-4-yl)amino]methyl}cyclohexyl)-acetamide N-(trans-4-{[(5-nitro-2-{[2-(trifluoromethoxy)benzyl]amino}pyrimidin-4-yl)amino]methyl}cyclohexyl)benzamide N-(trans-4-{[(5-nitro-2-{[2-(trifluoromethoxy)benzyl]amino}pyrimidin-4-yl)amino]methyl}cyclohexyl)nicotinamide N-(trans-4-{[(5-nitro-2-{[2-(trifluoromethoxy)benzyl]amino}pyrimidin-4-yl)amino]methyl}cyclohexyl)benzenesulfonamide N-(trans-4-{[(5-nitro-2-{[2-(trifluoromethoxy)benzyl]amino}pyrimidin-4-yl)amino]methyl}cyclohexyl)-2-phenylacetamide N-(trans-4-{[(5-nitro-2-{[2-(trifluoromethoxy)benzyl]amino}pyrimidin-4-yl)amino]methyl}cyclohexyl)acetamide N-(trans-4-{[(5-nitro-2-{[2-(trifluoromethoxy)benzyl]amino}pyrimidin-4-yl)amino]methyl}cyclohexyl)isonicotinamide N-(trans-4-{[(5-nitro-2-{[2-(trifluoromethoxy)benzyl]amino}pyrimidin-4-yl)amino]methyl}cyclohexyl)-2-pyridin-4-ylacetamide N-(trans-4-{[(5-nitro-2-{[2-(trifluoromethoxy)benzyl]amino}pyrimidin-4-yl)amino]methyl}cyclohexyl)-2-pyridin-3-ylacetamide N-(trans-4-{[(5-nitro-2-{[2-(trifluoromethoxy)benzyl]amino}pyrimidin-4-yl)amino]methyl}cyclohexyl)-2-pyridin-2-ylacetamide 2-methyl-1-[(trans-4-{[(5-nitro-2-{[2-(trifluoromethoxy)benzyl]amino}pyrimidin-4-yl)amino]methyl}cyclohexyl)amino]propan-2-ol 1-(trans-4-{[(5-nitro-2-{[2-(trifluoromethoxy)benzyl]amino}pyrimidin-4-yl)amino]methyl}cyclohexyl)azetidine-2-carboxamide N-(trans-4-{[(5-nitro-2-{[2-(trifluoromethoxy)benzyl]amino}pyrimidin-4-yl)amino]methyl}cyclohexyl)methanesulfonamide 2-[(trans-4-{[(5-nitro-2-{[2-(trifluoromethoxy)benzyl]amino}pyrimidin-4-yl)amino]methyl}cyclohexyl)amino]propane-1,3-diol $N^4$-[(trans-4-aminocyclohexyl)methyl]-$N^2$-[2-(2-fluorophenyl)ethyl]-5-nitropyrimidine-2,4-diamine $N^4$-[(trans-4-aminocyclohexyl)methyl]-$N^2$-[2-(3-fluorophenyl)ethyl]-5-nitropyrimidine-2,4-diamine $N^4$-[(trans-4-aminocyclohexyl)methyl]-$N^2$-[2-(4-fluorophenyl)ethyl]-5-nitropyrimidine-2,4-diamine $N^4$-[(trans-4-aminocyclohexyl)methyl]-$N^2$-[2-(1H-indol-3-yl)ethyl]-5-nitropyrimidine-2,4-diamine $N^4$-[(trans-4-aminocyclohexyl)methyl]-5-nitro-$N^2$-(2-pyridin-2-ylethyl)pyrimidine-2,4-diamine $N^4$-[(trans-4-aminocyclohexyl)methyl]-5-nitro-$N^2$-(2-pyridin-3-ylethyl)pyrimidine-2,4-diamine $N^4$-[(trans-4-aminocyclohexyl)methyl]-5-nitro-$N^2$-(2-pyridin-4-ylethyl)pyrimidine-2,4-diamine $N^2$-(4-aminobenzyl)-$N^4$-[(trans-4-aminocyclohexyl)methyl]-5-nitropyrimidine-2,4-diamine $N^4$-[(trans-4-aminocyclohexyl)methyl]-5-nitro-Nhu 2-(pyridin-4-ylmethyl)pyrimidine-2,4-diamine 5-nitro-$N^4$-{[trans-4-(pyridin-2-ylamino)cyclohexyl]methyl}-$N^2$-[2-(trifluoromethoxy)benzyl]pyrimidine-2,4-diamine $N^4$-{[trans-4-(1H-imidazol-1-yl)cyclohexyl]methyl}-5-nitro-$N^2$-[2-(trifluoromethoxy)benzyl]pyrimidine-2,4-diamine $N^4$-[(trans-4-aminocyclohexyl)methyl]-5-nitro-$N^2$-(pyrazin-2-ylmethyl)pyrimidine-2,4-diamine (2R)-2-[(trans-4-{[(5-nitro-2-{[2-(trifluoromethoxy)benzyl]amino}pyrimidin-4-yl)amino]methyl}cyclohexyl)amino]-2-phenylethanol (1S)-2-[(trans-4-{[(5-nitro-2-{[2-(trifluoromethoxy)benzyl]amino}pyrimidin-4-yl)amino]methyl}cyclohexyl)amino]-1-phenylethanol (2S)-2-[(trans-4-{[(5-nitro-2-{[2-(trifluoromethoxy)benzyl]amino}pyrimidin-4-yl)amino]methyl}cyclohexyl)amino]-2-phenylethanol (1R)-2-[(trans-4-{[(5-nitro-2-{[2-(trifluoromethoxy)benzyl]amino}pyrimidin-4-yl)amino]methyl}cyclohexyl)amino]-1-phenylethanol $N^4$-[(trans-4-aminocyclohexyl)methyl]-5-nitro-$N^2$-(quinolin-4-ylmethyl)pyrimidine-2,4-diamine 4-{[(4-{[(trans-4-aminocyclohexyl)methyl]amino}-5-nitropyrimidin-2-yl)amino]methyl}benzene-1,2-dial $N^4$-[(trans-4-aminocyclohexyl)methyl]-$N^2$-(1,3-benzodioxol-5-ylmethyl)-5-nitropyrimidine-2,4-diamine 4-{[(4-{[(trans-4-aminocyclohexyl)methyl]amino}-5-nitropyrimidin-2-yl)amino]methyl1-2-methoxyphenol $N^4$-[(trans-4-aminocyclohexyl)methyl]-$N^2$-[2-(1H-benzimidazol-2-yl)ethyl]-5-nitropyrimidine-2,4-diamine $N^4$-[(trans-4-{[(1-methyl-1H-pyrazol-4-yl)methyl]amino}cyclohexyl)methyl]-5-nitro-N2-[2-(trifluoromethoxy)benzyl]pyrimidine-2,4-diamine $N^4$-[(trans-4-{[(1,3-dimethyl-1H-pyrazol-4-yl)methyl]amino}cyclohexyl)methyl]-5-nitro-$N^2$-[2-(trifluoromethoxy)benzyl]pyrimidine-2,4-diamine $N^4$-[(trans-4-{[(1,3-dimethyl-1H-pyrazol-5-yl)methyl]amino}cyclohexyl)methyl]-5-nitro-$N^2$-[2-(trifluoromethoxy)benzyl]pyrimidine-2,4-diamine $N^4$-[(trans-4-aminocyclohexyl)methyl]-$N^2$-(1-benzothien-3-ylmethyl)-5-nitropyrimidine-2,4-diamine $N^4$-[(trans-4-aminocyclohexyl)methyl]-$N^2$-[(5-chloro-1-benzothien-3-yl)methyl]-5-nitropyrimidine-2,4-diamine $N^2$-(4-amino-2-chlorobenzyl)-$N^4$-[(trans-4-aminocyclohexyl)methyl]-5-nitropyrimidine-2,4-diamine $N^4$-[(trans-4-aminocyclohexyl)methyl]-5-nitro-$N^2$-(2-oxo-2-piperidin-1-ylethyl)pyrimidine-2,4-diamine $N^2$-(4-{[(trans-4-aminocyclohexyl)methyl]amino}-5-nitropyrimidin-2-yl)-N,N-dimethylglycinamide $N^4$-[(trans-4-aminocyclohexyl)methyl]2-(isoquinolin-1-ylmethyl)-5-nitropyrimidine-2,4-diamine $N^4$-[(trans-4-aminocyclohexyl)methyl]-5-nitro-$N^2$-(quinolin-5-ylmethyl)pyrimidine-2,4-diamine methyl N-(4-{[(trans-4-aminocyclohexyl)methyl]amino}-5-nitropyrimidin-2-yl)-L-alaninate methyl (2S)-[(4-{[(trans-4-aminocyclohexyl)methyl]amino}-5-nitropyrimidin-2-yl)amino](phenyl)acetate methyl (2R)-[(4-{[(trans-4-aminocyclohexyl)methyl]amino}-5-nitropyrimidin-2-yl)amino](phenyl)acetate methyl N-(4-{[(trans-4-aminocyclohexyl)methyl]amino}-5-nitropyrimidin-2-yl)glycinate $N^4$-[(trans-4-aminocyclohexyl)methyl]-5-nitro-$N^2$-[(1S)-2-oxo-1-phenyl-2-piperidin-1-ylethyl]pyrimidine-2,4-diamine $N^4$-[(trans-4-aminocyclohexyl)methyl]-5-nitro-$N^2$-[(1R)-2-oxo-1-phenyl-2-piperidin-1-ylethyl]pyrimidine-2,4-diamine $N^4$-[(trans-4-aminocyclohexyl)methyl]-$N^2$-(2-morpholin-4-yl-2-oxoethyl)-5-nitropyrimidine-2,4-diamine $N^4$-[(trans-4-aminocyclohexyl)methyl]-5-nitro-$N^2$-(2-oxo-2-pyrrolidin-1-ylethyl)pyrimidine-2,4-diamine 1-[N-(4-{[(trans-4-aminocyclohexyl)methyl]amino}-5-nitropyrimidin-2-yl)glycyl]piperidin-4-ol $N^4$-[(trans-4-aminocyclohexyl)methyl]-5-nitro-$N^2$-(2-oxo-2-piperazin-1-ylethyl)pyrimidine-2,4-diamine (3R)-1-[N-(4-{[(trans-4-aminocyclohexyl)methyl]amino}-5-nitropyrimidin-2-yl)glycyl]pymolidin-3-ol 1-[N-(4-{[(trans-4-aminocyclohexyl)methyl]amino}-5-nitropyrimidin-2-yl)glycyl]piperidine-4-carboxamide (3S)-1-[N-(4-{[(trans-4-aminocyclohexyl)methyl]amino}-5-nitropyrimidin-2-yl)glycyl]pymolidin-3-ol $N^4$-[(trans-4-aminocyclohexyl)methyl]-$N^2$-(2-azetidin-1-yl-2-oxoethyl)-5-nitropyrimidine-2,4-diamine $N^4$-[(trans-4-aminocyclohexyl)methyl]-$N^2$-[4-(dimethylamino)benzyl]-5-nitropyrimidine-2,4-diamine (3R)-1-[N-(4-{[(trans-4-aminocyclohexyl)methyl]amino}-5-nitropyrimidin-2-yl)glycyl]piperidin-3-ol $N^2$-(4-{[(trans-4-aminocyclohexyl)methyl]amino}-5-nitropyrimidin-2-yl)-N-methylglycinamide N-(4-{[(4-{[(trans-4-aminocyclohexyl)methyl]amino}-5-nitropyrimidin-2-yl)amino]methyl}phenyl)acetamide $N^4$-[(trans-4-aminocyclohexyl)methyl]-$N^2$-1j2-ethoxypyridin-3-yl)methyl]-5-nitropyrimidine-2,4-diamine $N^4$-[(trans-4-aminocyclohexyl)methyl]-$N^2$-[(2-isopropoxypyridin-3-yl)methyl]-5-nitropyrimidine-2,4-diamine $N^4$-[(trans-4-aminocyclohexyl)methyl]-5-nitro-$N^2$-{[2-(2,2,2-trifluoroethoxy)pyridin-3-yl]methyl}pyrimidine-2,4-diamine $N^4$-[(trans-4-aminocyclohexyl)methyl]-$N^2$-[(5-fluoro-2-methoxypyridin-3-yl)methyl]-5-nitropyrimidine-2,4-diamine N4-[(trans-4-aminocyclohexyl)methyl]-N2-[2-(difluoromethoxy)benzyl]-5-nitropyrimidine-2,4-diamine $N^4$-[(trans-4-aminocyclohexyl)methyl]-$N^2$-(2-chlorobenzyl)-5-nitropyrimidine-2,4- diamine $N^4$-[(trans-4-azetidin-1-ylcyclohexyl)methyl]-5-nitro-$N^2$-{[2-(2,2,2- trifluoroethoxy)pyridin-3-yl]methyl}pyrimidine-2,4-diamine 5-nitro-$N^4$-({trans-4-[(2-pyridin-3-ylethyl)amino]cyclohexyl}methyl)-$N^2$-[2- (trifluoromethoxy)benzyl]pyrimidine-2,4-diamine 1-[trans-4-( {[5-nitro-2-({[2-(2,2,2-trifluoroethoxy)pyridin-3-yl]methyl}amino)pyrimidin- 4-yl]amino}methyl)cyclohexyl]azetidin-3-ol (1S)-2-[(trans-4-{[(5-nitro-2-{[2-(trifluoromethoxy)benzyl]amino}pyrimidin-4- yl)amino]methyl}cyclohexyl)amino]-1-pyridin-3-ylethanol $N^4$-({trans-4-[(2-fluoroethyl)amino]cyclohexyl}methyl)-5-nitro-$N^2$-2- (trifluoromethoxy)benzyl]pyrimidine-2,4-diamine $N^4$-{[trans-4-(3-fluoroazetidin- 1-yl)cyclohexyl]methyl}-5-nitro-$N^2$-[2- (trifluoromethoxy)benzyl]pyrimidine-2,4-diamine $N^4$-({trans-4-[(2,2-difluoroethyl)amino]cyclohexyl}methyl)-5-nitro-$N^2$-[2- (trifluoromethoxy)benzyl]pyrimidine-2,4-diamine 5-nitro-$N^4$-({trans-4-[(2,2,2-trifluoroethyl)amino]cyclohexyl}methyl)-$N^2$-[2- (trifluoromethoxy)benzyl]pyrimidine-2,4-diamine 4-[(trans-4-aminocyclohexyl)methoxy]-5-nitro-N-[2-(trifluoromethoxy)benzyl]pyrimidin- 2-amine $N^4$-[(trans-4-aminocyclohexyl)methyl]-5-nitro-$N^2$-(pyridin-2-ylmethyl)pyrimidine-2,4- diamine $N^4$-[(trans-4-aminocyclohexyl)methyl]-5-nitro-$N^2$-(1,3-thiazol-2-ylmethyl)pyrimidine- 2,4-diamine $N^4$-[(trans-4-aminocyclohexyl)methyl]-$N^2$-(1H-imidazol-2-ylmethyl)-5-nitropyrimidine- 2,4-diamine $N^4$-[(trans-4-aminocyclohexyl)methyl]-$N^2$-[(3-methylpyridin-2-yl)methyl]-5- nitropyrimidine-2,4-diamine $N^4$-[(trans-4-aminocyclohexyl)methyl]-$N^2$-[(6-methylpyridin-2-yl)methyl]-5- nitropyrimidine-2,4-diamine $N^4$-[(trans-4-aminocyclohexyl)methyl]-N2-[(6-methylpyridin-3-yl)methyl]-5- nitropyrimidine-2,4-diamine $N^4$-[(trans-4-aminocyclohexyl)methyl]-$N^2$-[(5-methylpyridin-3-yl)methyl]-5- nitropyrimidine-2,4-diamine $N^4$-[(trans-4-aminocyclohexyl)methyl]-Nhu 2-[(5-chloropyridin-2-yl)methyl]-5- nitropyrimidine-2,4-diamine $N^4$-[(trans-4-aminocyclohexyl)methyl]-$N^2$-(3-bromobenzyl)-5-nitropyrimidine-2,4- diamine $N^4$-[(trans-4-aminocyclohexyl)methyl]-$N^2$-[(5-methyl-1,3-oxazol-4-yl)methyl]-5- nitropyrimidine-2,4-diamine $N^4$-[(trans-4-aminocyclohexyl)methyl]-$N^2$-[(5-bromopyridin-3-yl)methyl]-5- nitropyrimidine-2,4-diamine 2,2'-({trans-4-[({2-[(3-bromo-2-methylbenzyl)amino]-5-nitropyrimidin-4- yl}amino)methyl]cyclohexyl}imino)diacetamide $N^2$-{trans-4-[({2-[(3-bromo-2-methylbenzyl)amino]-5-nitropyrimidin-4- yl}amino)methyl]cyclohexyl}glycinamide $N^2$-(3-bromo-2-methylbenzyl)-5-nitro-$N^4$-({trans-4-[(2,2,2- trifluoroethyl)amino]cyclohexyl}methyl)pyrimidine-2,4-diamine $N^2$-(3-bromo-2-methylbenzyl)-$N^4$-({trans-4-[(2,2- difluoroethyl)amino]cyclohexyl}methyl)-5-nitropyrimidine-2,4-diamine $N^4$-{[trans-4-(diethylamino)cyclohexyl]methyl}-5-nitro-$N^2$-[2- (trifluoromethoxy)benzyl]pyrimidine-2,4-diamine 4-({[trans-4-(ethylamino)cyclohexyl]methyl}amino)-2-{[2- (trifluoromethoxy)benzyl]amino}pyrimidine-5-carbonitrile 4-({[trans-4-(diethylamino)cyclohexyl]methyl}amino)-2-{[2- (trifluoromethoxy)benzyl]amino}pyrimidine-5-carbonitrile N-ethyl-N'-(trans-4-{[(5-nitro-2-{[2-(trifluoromethoxy)benzyl]amino}pyrimidin-4- yl)amino]methyl}cyclohexyl)urea $N^4$-{[trans-4-(ethylamino)cyclohexyl]methyl}-5-nitro-$N^2$-[2- (trifluoromethoxy)benzyl]pyrimidine-2,4-diamine N-(trans-4-{[(5-nitro-2-{[2-(trifluoromethoxy)benzyl]amino}pyrimidin-4- yl)amino]methyl}cyclohexyl)glycine N-(trans-4-{[(5-nitro-2-{[2-(trifluoromethoxy)benzyl]amino}pyrimidin-4- yl)amino]methyl}cyclohexyl)-beta-alanine 3-{[(trans-4-{[(5 -nitro-2-{[2-(trifluoromethoxy)benzyl]amino}pyrimidin-4- yl)amino]methyl}cyclohexyl)amino]methyl}benzoic acid 2-{[(trans-4-{[(5-nitro-2-{[2-(trifluoromethoxy)benzyl]amino}pyrimidin-4- yl)amino]methyl}cyclohexyl)amino]methyl}benzoic acid 1-(trans-4-{[(5-nitro-2-{[2-(trifluoromethoxy)benzyl]amino}pyrimidin-4- yl)amino]methyl}cyclohexyl)pyrmolidin-2-one 4-{[(trans-4-{[(5-nitro-2-{[2-(trifluoromethoxy)benzyl]amino}pyrimidin-4- yl)amino]methyl}cyclohexyl)amino]methyl}benzoic acid 4-{[(trans-4-{[(5-nitro-2-{[2-(trifluoromethoxy)benzyl]amino}pyrimidin-4- yl)amino]methyl}cyclohexyl)amino]butanoic acid $N^2$-[3-(aminomethyl)benzyl]-5-nitro-$N^4$-[(trans-4-pyrrolidin-1- ylcyclohexyl)methyl]pyrimidine-2,4-diamine $N^4$-[(trans-4-amino-4-methylcyclohexyl)methyl]-5-nitro-$N^2$-[2- (trifluoromethoxy)benzyl]pyrimidine-2,4-diamine $N^2$-(5-amino-2-chlorobenzyl)-$N^4$-[(trans-4-aminocyclohexyl)methyl]-5-nitropyrimidine- 2,4-diamine $N^2$-(3-aminobenzyl)-$N^4$-[(trans-4-aminocyclohexyl)methyl]-5-nitropyrimidine-2,4- diamine N-(3-{[(4-{[(trans-4-aminocyclohexyl)methyl]amino}-5-nitropyrimidin-2- yl)amino]methyl}phenyl)acetamide $N^4$-[(trans-4-aminocyclohexyl)methyl]-$N^2$-[3-(dimethylamino)benzyl]-5-nitropyrimidine- 2,4-diamine $N^4$-[(trans-4-aminocyclohexyl)methyl]-$N^2$-benzyl-5-nitropyrimidine-2,4-diamine $N^4$-[(trans-4-aminocyclohexyl)methyl]-$N^2$-[2-(dimethylamino)benzyl]-5-nitropyrimidine- 2,4-diamine $N^4$-[(trans-4-aminocyclohexyl)methyl]-$N^2$-[2-chloro-5-(dimethylamino)benzyl]-5- nitropyrimidine-2,4-diamine N-(3-{[(4-{[(trans-4-aminocyclohexyl)methyl]amino}-5-nitropyrimidin-2- yl)amino]methyl}phenyl)-N-methylacetamide $N^4$-[(trans-4-aminocyclohexyl)methyl]-$N^2$-[2-chloro-3-(dimethylamino)benzyl]-5- nitropyrimidine-2,4-diamine $N^4$-[(trans-4-aminocyclohexyl)methyl]-$N^2$-(2,3-dihydro-1-benzofuran-5-ylmethyl)-5- nitropyrimidine-2,4-diamine $N^4$-[(trans-4-aminocyclohexyl)methyl]-$N^2$-[3-(methylamino)benzyl]-5-nitropyrimidine- 2,4-diamine 1-(trans-4-{[(2-{[2-chloro-3-(dimethylamino)benzyl]amino}-5 -nitropyrimidin-4- yl)amino]methyl }cyclohexyl)azetidin-3-ol $N^4$-[(trans-4-aminocyclohexyl)methyl]-$N^2$-(2-methylbenzyl)-5-nitropyrimidine-2,4- diamine
$N^4$-[(trans-4-aminocyclohexyl)methyl]$N^2$-(2-fluorobenzyl)-5-nitropyrimidine-2,4- diamine
$N^4$-[(trans-4-aminocyclohexyl)methyl]$N^2$-(3-methylbenzyl)-5-nitropyrimidine-2,4- diamine
$N^4$-[(trans-4-aminocyclohexyl)methyl]-$N^2$-(3-chlorobenzyl)-5-nitropyrimidine-2,4- diamine
$N^4$-[(trans-4-aminocyclohexyl)methyl]-$N^2$-(3-fluorobenzyl)-5-nitropyrimidine-2,4- diamine
$N^4$-[(trans-4-aminocyclohexyl)methyl]-5-nitro-$N^2$-[3-(trifluoromethoxy)benzyl]pyrimidine-2,4-diamine
$N^4$-[(trans-4-aminocyclohexyl)methyl]-$N^2$-(2,3-dimethylbenzyl)-5-nitropyrimidine-2,4- diamine
$N^4$-[(trans-4-aminocyclohexyl)methyl]-$N^2$-(3-chloro-2-methylbenzyl)-5 -nitropyrimidine- 2,4-diamine
$N^4$-[(trans-4-aminocyclohexyl)methyl]-$N^2$-(3-chloro-2-fluorobenzyl)-5-nitropyrimidine- 2,4-diamine
$N^4$-[(trans-4-aminocyclohexyl)methyl]-$N^2$-(2,3-difluorobenzyl)-5-nitropyrimidine-2,4- diamine
$N^4$-[(trans-4-aminocyclohexyl)methyl]-$N^2$-(5-chloro-2-fluorobenzyl)-5-nitropyrimidine-2,4- diamine
$N^4$-[(trans-4-aminocyclohexyl)methyl]-$N^2$-(5-chloro-2-methylbenzyl)-5 -nitropyrimidine- 2,4-diamine
$N^4$-[(trans-4-aminocyclohexyl)methyl]-$N^2$-(3,4-difluorobenzyl)-5-nitropyrimidine-2,4- diamine
$N^4$-[(trans-4-aminocyclohexyl)methyl]-$N^2$-(3-chloro-4-fluorobenzyl)-5-nitropyrimidine- 2,4-diamine
$N^4$-[(trans-4-aminocyclohexyl)methyl]-$N^2$ -(3,5-difluorobenzyl)-5-nitropyrimidine-2,4- diamine
$N^4$-[(trans-4-aminocyclohexyl)methyl]-$N^2$-(2-chloro-4-fluorobenzyl)-5-nitropyrimidine- 2,4-diamine
$N^4$-[(trans-4-aminocyclohexyl)methyl]-$N^2$-(3,5-dichlorobenzyl)-5-nitropyrimidine-2,4- diamine
$N^4$-[(trans-4-aminocyclohexyl)methyl]-$N^2$-(4-chloro-2-fluorobenzyl)-5-nitropyrimidine- 2,4-diamine
$N^4$-[(trans-4-aminocyclohexyl)methyl]-$N^2$-(4-bromo-2-fluorobenzyl)-5-nitropyrimidine- 2,4-diamine
$N^4$-[(trans-4-aminocyclohexyl)methyl]-$N^2$-[4-fluoro-2-(trifluoromethyl)benzyl]-5- nitropyrimidine-2,4-diamine
$N^4$-[(trans-4-aminocyclohexyl)methyl]-$N^2$-(5-chloro-2-methoxybenzyl)-5 - nitropyrimidine-2,4-diamine
(1R,3S)-3-{[(4-{[(trans-4-aminocyclohexyl)methyl]amino}-5-nitropyrimidin-2- yl)amino]methyl}cyclohexanol
$N^4$-[(trans-4-aminocyclohexyl)methyl]-$N^2$-[(4-chloropyridin-3-yl)methyl]-5- nitropyrimidine-2,4-diamine
$N^4$-[(trans-4-aminocyclohexyl)methyl]-$N^2$-[(2-chloropyridin-3-yl)methyl]-5- nitropyrimidine-2,4-diamine
(1S ,3S)-3-{[(4-{[(trans-4-aminocyclohexyl)methyl]amino}-5-nitropyrimidin-2- yl)amino]methyl}cyclohexanol
$N^4$-[(trans-4-aminocyclohexyl)methyl]-$N^2$-(5-fluoro-2-methylbenzyl)-5-nitropyrimidine- 2,4-diamine
$N^4$-[(trans-4-aminocyclohexyl)methyl]-$N^2$-(2-methoxybenzyl)-5-nitropyrimidine-2,4- diamine
$N^4$-[(trans-4-aminocyclohexyl)methyl]-$N^2$-benzyl-5-chloropyrimidine-2,4-diamine
$N^4$-[(trans-4-aminocyclohexyl)methyl]-$N^2$-(4-chloro-2-methylbenzyl)-5-nitropyrimidine- 2,4-diamine
(1R,3R)-3-{[(4-{[(trans-4-aminocyclohexyl)methyl]amino}-5 -nitropyrimidin-2- yl)amino]methyl}-4,4-dimethylcyclohexanol
$N^4$-[(trans-4-aminocyclohexyl)methyl]-$N^2$-[5-chloro-2-(trifluoromethoxy)benzyl[9 -5- nitropyrimidine-2,4-diamine
$N^2$-[5-chloro-2-(trifluoromethoxy)benzyl]-5 -nitro-$N^4$-[(trans-4-pyrrolidin-1- ylcyclohexyl)methyl]pyrimidine-2,4-diamine
$N^4$-[(trans-4-aminocyclohexyl)methyl]-$N^2$-[(4-methoxypyridin-3-yl)methyl]-5- nitropyrimidine-2,4-diamine
$N^4$-[(trans-4-aminocyclohexyl)methyl]-$N^2$-[(2-methoxypyridin-3-yl)methyl]-5- nitropyrimidine-2,4-diamine
4-{[(4-{[(trans-4-aminocyclohexyl)methyl]amino}-5-nitropyrimidin-2-yl)amino]methyl}- 5-chloropyridin-2(1H)-one
4-{[(4-{[(trans-4-aminocyclohexyl)methyl]amino}-5 -nitropyrimidin-2- yl)amino]methyl}pyridin-2(1H)-one
$N^4$-[(trans-4-aminocyclohexyl)methyl]-$N^2$-(1,2-diphenylethyl)-5-nitropyrimidine-2,4- diamine
$N^4$-[(trans-4-aminocyclohexyl)methyl]-5-nitro-$N^2$-{[4-(trifluoromethyl)pyridin-3- yl]methyl}pyrimidine-2,4-diamine
4-{[(trans-4-aminocyclohexyl)methyl]aminol[-2-{[(2-chloropyridin-3- yl)methyl]amino}pyrimidine-5-carbonitrile
$N^4$-[(trans-4-aminocyclohexyl)methyl]-$N^2$-[(3-chloropyridin-4-yl)methyl]-5- nitropyrimidine-2,4-diamine
4-{[(trans-4-aminocyclohexyl)methyl]aminol}-2-{[(2-methoxypyridin-3- yl)methyl]amino}pyrimidine-5-carbonitrile
$N^4$-[(trans-4-aminocyclohexyl)methyl]-$N^2$-[2-(methylsulfonyl)benzyl]-5-nitropyrimidine- 2,4-diamine
$N^4$-[(trans-4-aminocyclohexyl)methyl]-5-nitro-$N^2$-(pyridin-3-ylmethyl)pyrimidine-2,4- diamine
$N^4$-[(trans-4-aminocyclohexyl)methyl]-5-nitro-$N^2$-{[6-(trifluoromethyl)pyridin-3- yl]methyl}pyrimidine-2,4- diamine
4-{[(trans-4-aminocyclohexyl)methyl]amino}-2-{[(4-methoxypyridin-3- yl)methyl]amino}pyrimidine-5-carbonitrile
$N^4$-[(trans-4-aminocyclohexyl)methyl]-$N^2$-[5-chloro-2-(methylsulfonyl)benzyl]-5- nitropyrimidine-2,4-diamine
1-(trans-4-{[(2-{[(4-chloropyridin-3-yl)methyl]amino}-5-nitropyrimidin-4- yl)amino]methyl}cyclohexyl)azetidin-3-ol
$N^4$-[(trans-4-azetidin-1-ylcyclohexyl)methyl]-$N^2$-[(2-methoxypyridin-3-yl)methyl]-5- nitropyrimidine-2,4- diamine
1-(trans-4-{[(2-{[(2-methoxypyridin-3-yl)methyl]amino}-5-nitropyrimidin-4- yl)amino]methyl}cyclohexyl)azetidin-3-ol
$N^4$-[(trans-4-azetidin-1-ylcyclohexyl)methyl]-$N^2$-[(4-chloropyridin-3-yl)methyl]-5- nitropyrimidine-2,4-diamine
$N^4$-[(trans-4-azetidin-1-ylcyclohexyl)methyl]-5-nitro-$N^2$-{[4-(trifluoromethyl)pyridin-3- yl]methyl}pyrimidine-2,4-diamine
1-[trans-4-({[5-nitro-2-({[4-(trifluoromethyl)pyridin-3-yl]methyl}amino)pyrimidin-4- yl]amino}methyl)cyclohexyl]azetidin-3-ol
$N^4$-[(trans-4-{[(1,5-dimethyl-1H-pyrazol-4-yl)methyl]amino}cyclohexyl)methyl]-5-nitro- $N^2$-{[4-(trifluoromethyl)pyridin-3-yl]methyl}pyrimidine-2,4-diamine
$N^2$-[trans-4-({[5-nitro-2-({[4-(trifluoromethyl)pyridin-3-yl]methyl}amino)pyrimidin-4- yl]amino}methyl)cyclohexyl]glycinamide
cis-2-amino-trans-5-{[(5-nitro-2-{[2-(trifluoromethoxy)benzyl]amino}pyrimidin-4- yl)amino]methyl}cyclohexanol
3-{[(4-{[(trans-4-aminocyclohexyl)methyl]amino}-5-nitropyrimidin-2- yl)amino]methyl}benzamide
$N^4$-[(trans-4-aminocyclohexyl)methyl]-5-nitro-$N^2$-(2-piperidin-1-ylbenzyl)pyrimidine- 2,4-diamine
cis-2-amino-trans-5-({[2-(benzylamino)-5-nitropyrimidin-4- yl]amino}methyl)cyclohexanol
3-{[(4-{[(trans-4-aminocyclohexyl)methyl]amino}-5-nitropyrimidin-2- yl)amino]methyl}pyridin-2(1H)-one N⁴-[(trans-4-aminocyclohexyl)methyl]-5-nitro-N2-{[2-(trifluoromethyl)pyridin-3- yl]methyl}pyrimidine-2,4-diamine N⁴-[(trans-4-aminocyclohexyl)methyl]-N²-[(3-chloropyridin-2-yl)methyl]-5- nitropyrimidine-2,4-diamine N⁴-[(trans-4-aminocyclohexyl)methyl]-N²-[(3-methoxypyridin-2-yl)methyl]-5- nitropyrimidine-2,4-diamine N-methyl-N-[1-(trans-4-{[(5 -nitro-2-{[2-(trifluoromethoxy)benzyl]amino}pyrimidin-4- yl)amino]methyl}cyclohexyl)pymolidin-3-yl]acetamide N⁴-[(trans-4-aminocyclohexyl)methyl]-N²-[(4,5-dichloropyridin-3-yl)methyl]-5- nitropyrimidine-2,4-diamine N⁴-{[trans-4-(1,1-dioxidothiomorpholin-4-yl)cyclohexyl]methyl}-5 -nitro-N²-[2- (trifluoromethoxy)benzyl]pyrimidine-2,4-diamine N⁴-{[trans-4-(3,3-difluoropyrrolidin-1-yl)cyclohexyl]methyl}-5-nitro-N²-[2- (trifluoromethoxy)benzyl]pyrimidine-2,4-diamine 4-(trans-4-{[(5 -nitro-2-{[2-(trifluoromethoxy)benzyl]amino}pyrimidin-4- yl)amino]methyl}cyclohexyl)piperazin-2-one N⁴-({trans-4-[4-(methylsulfonyl)piperazin-1-yl]cyclohexyl}methyl)-5-nitro-N²-[2- (trifluoromethoxy)benzyl]pyrimidine-2,4-diamine N⁴-{[trans-4-(4-acetylpiperazin-1-yl)cyclohexyl]methyl}-5-nitro-N²-[2- (trifluoromethoxy)benzyl]pyrimidine-2,4-diamine N⁴-({trans-4-[3-(methylsulfonyl)pyrrolidin-1-yl]cyclohexyl}methyl)-5-nitro-N2-[2- (trifluoromethoxy)benzyl]pyrimidine-2,4-diamine 1-(trans-4-{[(5-nitro-2-{[2-(trifluoromethoxy)benzyl]amino}pyrimidin-4- yl)amino]methyl}cyclohexyl)-1,4-diazepan-5-one N-[(3S)-1-(trans-4-{[(5-nitro-2-{[2-(trifluoromethoxy)benzyl]amino}pyrimidin-4- yl)amino]methyl}cyclohexyl)pymolidin-3-yl]acetamide N-[(3R)-1-(trans-4-{[(5-nitro-2-{[2-(trifluoromethoxy)benzyl]amino}pyrimidin-4- yl)amino]methyl}cyclohexyl)pymolidin-3-yl]acetamide N⁴-({trans-4-[(3R)-3-(dimethylamino)pyrrolidin-1-yl]cyclohexyl}methyl)-5-nitro-N²-[2- (trifluoromethoxy)benzyl]pyrimidine-2,4-diamine 1-(trans-4-{[(5-nitro-2-{[2-(trifluoromethoxy)benzyl]amino}pyrimidin-4- yl)amino]methyl}cyclohexyl)-L-prolinamide 1-(trans-4-{[(5-nitro-2-{[2-(trifluoromethoxy)benzyl]amino}pyrimidin-4- yl)amino]methyl}cyclohexyl)-D-prolinamide 1-(trans-4-{[(5-nitro-2-{[2-(trifluoromethoxy)benzyl]amino}pyrimidin-4- yl)amino]methyl}cyclohexyl)piperidine-3-carboxamide 1-(trans-4-{[(5-nitro-2-{[2-(trifluoromethoxy)benzyl]amino}pyrimidin-4- yl)amino]methyl}cyclohexyl)piperidin-3-ol 5-nitro-N⁴-[(trans-4-piperazin-1-ylcyclohexyl)methyl]-N²-[2- (trifluoromethoxy)benzyl]pyrimidine-2,4-diamine 1-(trans-4-{[(5-nitro-2-{[2-(trifluoromethoxy)benzyl]amino}pyrimidin-4- yl)amino]methyl}cyclohexyl)piperidin-4-ol N⁴-{[trans-4-(4-methylpiperazin-1-yl)cyclohexyl]methyl}-5-nitro-N²-[2- (trifluoromethoxy)benzyl]pyrimidine-2,4-diamine ethyl4-(trans-4-{[(5-nitro-2-{[2-(trifluoromethoxy)benzyl]amino}pyrimidin-4- yl)amino]methyl}cyclohexyl)piperazine-1-carboxylate 2-[methyl(trans-4-{[(5 -nitro-2-{[2-(trifluoromethoxy)benzyl]amino}pyrimidin-4- yl)amino]methyl}cyclohexyl)amino]ethanol N-{2-[(trans-4-{[(5-nitro-2-{[2-(trifluoromethoxy)benzyl]amino}pyrimidin-4- yl)amino]methyl}cyclohexyl)amino]ethyl}acetamide N⁴-{[trans-4-(1,4-diazepan-1-yl)cyclohexyl]methyl}-5-nitro-N²-[2- (trifluoromethoxy)benzyl]pyrimidine-2,4-diamine N⁴-{[trans-4-(4-methyl-1,4-diazepan-1-yl)cyclohexyl]methyl}-5-nitro-N² -[2- (trifluoromethoxy)benzyl]pyrimidine-2,4-diamine N⁴-{[trans-4-(4-acetyl-1,4-diazepan-1-yl)cyclohexyl]methyl}-5-nitro-N²-[2- (trifluoromethoxy)benzyl]pyrimidine-2,4-diamine N⁴-{[trans-4-(3-fluoropynolidin-1-yl)cyclohexyl]methyl}-5-nitro-N2-[2- (trifluoromethoxy)benzyl]pyrimidine-2,4-diamine N,N-dimethyl-4-(trans-4-{[(5-nitro-2-{[2-(trifluoromethoxy)benzyl]amino}pyrimidin-4- yl)amino]methyl56 cyclohexyl)piperazine-1-carboxamide (2R)-1-[(trans-4-{[(5-nitro-2-{[2-(trifluoromethoxy)benzyl]amino}pyrimidin-4- yl)amino]methyl}cyclohexyl)amino]propan-2-ol (2S)-1-[(trans-4-{[(5-nitro-2-{[2-(trifluoromethoxy)benzyl]amino}pyrimidin-4- yl)amino]methyl}cyclohexyl)amino]propan-2-ol 3-[(trans-4-{[(5-nitro-2-{[2-(trifluoromethoxy)benzyl]amino}pyrimidin-4- yl)amino]methyl}cyclohexyl)amino]propan-1-ol N⁴-({trans-4-[(3-aminopropyl)amino]cyclohexyl}methyl)-5-nitro-N²-[2- (trifluoromethoxy)benzyl]pyrimidine-2,4-diamine (2R)-2-[(trans-4-{[(5-nitro-2-{[2-(trifluoromethoxy)benzyl]amino}pyrimidin-4- yl)amino]methyl}cyclohexyl)amino]propan-1-ol (2S)-2-[(trans-4-{[(5-nitro-2-{[2-(trifluoromethoxy)benzyl]amino}pyrimidin-4- yl)amino]methyl}cyclohexyl)amino]propan-1-ol (2R)-2-[(trans-4-{[(5-nitro-2-{[2-(trifluoromethoxy)benzyl]amino}pyrimidin-4- yl)amino]methyl}cyclohexyl)amino]-3-phenyipropan-1-ol (2S)-2-[(trans-4-{[(5-nitro-2-{[2-(trifluoromethoxy)benzyl]amino}pyrimidin-4- yl)amino]methyl}cyclohexyl)amino]-3-phenyipropan-1-al Nα-(trans-4-{[(5 -nitro-2-{[2-(trifluoromethoxy)benzyl]amino}pyrimidin-4- yl)amino]methyl}cyclohexyl)-L-phenylalaninamide Nα-(trans-4-{[(5-nitro-2-{[2-(trifluoromethoxy)benzyl]amino}pyrimidin-4- yl)amino]methyl}cyclohexyl)-D-phenylalaninamide N,N-dimethyl-1-(trans-4-{[(5-nitro-2-{[2-(trifluoromethoxy)benzyl]amino}pyrimidin-4- yl)amino]methyl}cyclohexyl)-L-prolinamide N⁴-[(trans-4-aminocyclohexyl)methyl]-N²-[(2-methylpyridin-3-yl)methyl]-5- nitropyrimidine-2,4-diamine.

8. A pharmaceutical composition comprising a compound according to claim 1, and at least one pharmaceutically acceptable carrier or adjuvant.

9. A method of treating type I or type II diabetes in a patient comprising administering to said patient a therapeutically effective amount of a compound according to claim 1.

* * * * *